(12) United States Patent
Chen et al.

(10) Patent No.: US 10,059,687 B2
(45) Date of Patent: Aug. 28, 2018

(54) HISTONE DEMETHYLASE INHIBITORS

(71) Applicant: CELGENE QUANTICEL RESEARCH, INC., San Diego, CA (US)

(72) Inventors: Young K. Chen, San Marcos, CA (US); Michael Brennan Wallace, San Diego, CA (US)

(73) Assignee: Celgene Quanticel Research, Inc., San Diego, CA (US)

(*) Notice: Subject to any disclaimer, the term of this patent is extended or adjusted under 35 U.S.C. 154(b) by 0 days.

(21) Appl. No.: 15/391,773

(22) Filed: Dec. 27, 2016

(65) Prior Publication Data

US 2017/0183325 A1 Jun. 29, 2017

Related U.S. Application Data

(60) Provisional application No. 62/271,654, filed on Dec. 28, 2015, provisional application No. 62/438,435, filed on Dec. 22, 2016.

(51) Int. Cl.
| | | |
|---|---|---|
| *C07D 401/12* | (2006.01) | |
| *C07D 409/14* | (2006.01) | |
| *C07D 401/14* | (2006.01) | |
| *C07D 407/14* | (2006.01) | |
| *C12N 9/02* | (2006.01) | |

(52) U.S. Cl.
CPC ......... *C07D 401/12* (2013.01); *C07D 401/14* (2013.01); *C07D 407/14* (2013.01); *C07D 409/14* (2013.01); *C12N 9/0071* (2013.01); *C12Y 114/11027* (2013.01)

(58) Field of Classification Search
CPC .................................................. C07D 401/12
USPC .......................................................... 546/112
See application file for complete search history.

(56) References Cited

U.S. PATENT DOCUMENTS

| | | | |
|---|---|---|---|
| 2014/0171432 A1 | 6/2014 | Kanouni et al. | |
| 2015/0119397 A1 | 4/2015 | Chen et al. | |
| 2015/0376169 A1* | 12/2015 | Boloor | C07D 409/14 514/210.2 |

FOREIGN PATENT DOCUMENTS

WO 2013/143597 A1 10/2013

OTHER PUBLICATIONS

International Search Report and Written Opinion dated Mar. 29, 2017, in related International Application No. PCT/US2016/068767, filed Dec. 27, 2016.
International Preliminary Report on Patentability dated Jul. 12, 2018 in related International Application No. PCT/US2016/068767, filed Dec. 27, 2016.

* cited by examiner

*Primary Examiner* — Nizal S Chandrakumar
(74) *Attorney, Agent, or Firm* — Wiley Rein LLP

(57) ABSTRACT

The present disclosure relates generally to compositions and methods for treating cancer and neoplastic disease. Provided herein are substituted pyridine derivative compounds, and compositions (including pharmaceutical compositions) that include these compounds. The subject compounds and compositions are useful for inhibition of at least one histone demethylase. Furthermore, the subject compounds and compositions are useful for the treatment of cancer or neoplastic disease, such as prostate cancer, breast cancer, bladder cancer, lung cancer, melanoma, retinoblastoma, or multiple endocrine neoplasia type 1.

17 Claims, No Drawings

HISTONE DEMETHYLASE INHIBITORS

RELATED APPLICATIONS

This Application claims priority benefit of U.S. Provisional Applications No. 62/271,654, filed 28 Dec. 2015, and No. 62/438,435, filed Dec. 22, 2016; both of which are incorporated herein by reference in their entireties for all purposes.

FIELD OF INVENTION

This disclosure is related to histone demethylase inhibitors.

BACKGROUND

A need exists in the art for an effective treatment of cancer and neoplastic disease.

SUMMARY

The present embodiments provide substituted pyridine derivative compounds useful for inhibition of at least one histone demethylase, and pharmaceutical compositions comprising these compounds. Additionally, the subject compounds and compositions are useful for the treatment of cancer, such as prostate cancer, breast cancer, bladder cancer, lung cancer, melanoma, and the like. The substituted pyridine derivative compounds described herein are based upon a disubstituted pyridine ring bearing at the 4-position a carboxylic acid, a carboxylic acid ester, or a carboxylic acid bioisostere thereof, and bearing at the 3-position a substituted amino group.

At least one embodiment provides a compound having the structure of Formula 1:

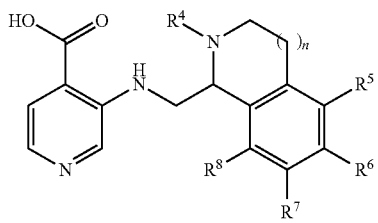

Formula 1 wherein a compound of Formula 1 includes isomers and pharmaceutically acceptable salts thereof, and wherein:
n is 0, 1, or 2;
$R^4$ is hydrogen or optionally substituted $C_1$-$C_6$ alkyl;
$R^6$ is hydrogen or X—Y, wherein
X is a bond, O, S, N(R), C(O), N(R)C(O), C(O)N(R), or optionally substituted $C_1$-$C_3$ alkyl, in which R is hydrogen or optionally substituted alkyl, and
Y is optionally substituted alkyl, cycloalkyl, heterocyclyl, aryl, or heteroaryl;
$R^5$, $R^7$, and $R^8$ are each independently selected from hydrogen, halogen, hydroxyl, cyanyl, $N(R^1)(R^2)$, or optionally substituted $C_1$-$C_6$ alkyl, $C_1$-$C_6$ alkynyl, $C_1$-$C_6$ alkenyl, $C_1$-$C_6$ alkoxy, $C_3$-$C_7$ carbocyclyl, $C_3$-$C_7$ carbocyclyloxy, $C_4$-$C_{12}$ carbocyclylalkyl, $C_4$-$C_{12}$ carbocyclylalkoxy, $C_6$-$C_{10}$ aryl, $C_6$-$C_{10}$ aryloxy, $C_6$-$C_{10}$ aryl-S, $C_6$-$C_{10}$ aryl-$SO_2$, $C_7$-$C_{14}$ aralkoxy, heteroaryl, heteroaryloxy, heterocyclyl, heterocyclyloxy, heterocyclylalkyl, heterocyclylalkoxy or heteroaryl-S, wherein
$R^1$ is hydrogen or optionally substituted alkyl, and
$R^2$ is optionally substituted alkyl, aryl, heteroaryl, heterocyclyl, cycloalkyl, cycloalkylalkyl, aryl-CO, heteroaryl-CO, cycloalkyl-CO, or alkyl-CO.

In at least one embodiment of a compound of Formula 1, n is 0. In at least one embodiment of a compound of Formula 1, n is 1. In at least one embodiment of a compound of Formula 1, $R^4$ is methyl. In one embodiment of the compound of Formula 1, each of $R^5$, $R^7$, and $R^8$ are hydrogen.

At least one embodiment provides a composition comprising a compound of Formula 1. In at least one embodiment, the composition is a pharmaceutical composition comprising at least one pharmaceutically acceptable excipient and a compound of Formula 1.

At least one embodiment provides a method of inhibiting a histone demethylase enzyme comprising contacting the histone demethylase enzyme with a compound of Formula 1 or a composition comprising a compound of Formula 1.

At least one embodiment provides a method of treating cancer in a subject in need thereof, comprising administering to the subject a pharmaceutical composition comprising a compound of Formula 1. Another embodiment provides use of a compound of Formula 1 in a medicament for treating cancer. A related embodiment provides use of a compound, composition, or pharmaceutical composition comprising the compound of Formula 1 in manufacture of a medicament for treating cancer or neoplastic disease, wherein the medicament is administered to a patient in need thereof. The cancer or neoplastic disease being treated, or for which the medicament is manufactured, may be prostate cancer, breast cancer, bladder cancer, lung cancer, melanoma, retinoblastoma, or multiple endocrine neoplasia type 1.

At least one embodiment provides a compound of Formula 2:

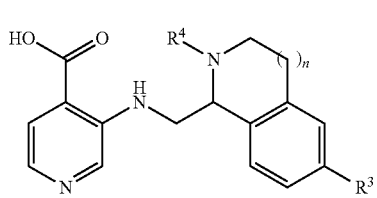

Formula 2 wherein a compound of Formula 2 includes isomers and pharmaceutically acceptable salts thereof, and wherein:
n is 0, 1, or 2;
$R^4$ is hydrogen or optionally substituted $C_1$-$C_6$ alkyl; and
$R^3$ is $N(R)(R^9)$, $N(R)C(O)$, $C(O)N(R)$, or optionally substituted $C_3$-$C_7$ carbocyclyl, $C_3$-$C_7$ carbocycly-loxy, $C_4$-$C_{12}$ carbocyclylalkyl, $C_4$-$C_{12}$ carbocyclylalkoxy, $C_6$-$C_{10}$ aryl, $C_6$-$C_{10}$ aryloxy, $C_6$-$C_{10}$ aryl-S, $C_6$-$C_{10}$ aryl-$SO_2$, $C_7$-$C_{14}$ aralkoxy, heteroaryl, heteroaryloxy, heterocyclyl, heterocyclyloxy, heterocyclylalkyl, heterocyclylalkoxy or heteroaryl-S, wherein
R is hydrogen or optionally substituted alkyl, and
$R^9$ is optionally substituted $C_3$-$C_7$ carbocyclyl, $C_3$-$C_7$ carbocyclyloxy, $C_4$-$C_{12}$ carbocyclylalkyl, $C_4$-$C_{12}$ carbocyclylalkoxy, $C_6$-$C_{10}$ aryl, $C_6$-$C_{10}$ aryloxy, $C_6$-$C_{10}$ aryl-S, $C_6$-$C_{10}$ aryl-$SO_2$, $C_7$-$C_{14}$ aralkoxy, heteroaryl, heteroaryloxy, heterocyclyl, heterocyclyloxy, heterocyclylalkyl, heterocyclylalkoxy or heteroaryl-S.

In at least one embodiment of a compound of Formula 2, n is 0. In at least one embodiment of a compound of Formula 2, n is 1.

In at least one embodiment of a compound of Formula 2, $R^4$ is methyl. In at least one embodiment of a compound of Formula 2, $R^4$ is hydrogen.

In at least one embodiment of a compound of Formula 2, $R^3$ is $N(R)(R^9)$. In some embodiments of a compound of Formula 2 in which $R^3$ is $N(R)(R^9)$, R is methyl.

In some embodiments of a compound of Formula 2 in which $R^3$ is $N(R)(R^9)$, $R^9$ is methylphenyl ("tolyl") or isopropylphenyl. In other embodiments of a compound of Formula 2, $R^3$ is $N(R)(R^9)$ wherein $R^9$ is trifluoroethoxyphenyl. In particular embodiments of a compound of Formula 2, $R^3$ is $N(R)(R^9)$, R is methyl, and $R^9$ is optionally substituted halophenyl, alkylphenyl, haloalkylphenyl, halo(alkyloxy)phenyl or haloalkyloxyphenyl. In particular embodiments of a compound of Formula 2, $R^3$ is $N(R)(R^9)$, R is methyl, and $R^9$ is optionally substituted methylphenyl. In particular embodiments of Formula 2, $R^3$ is $N(R)(R^9)$, R is methyl, and $R^9$ isopropylphenyl.

In some embodiments of a compound of Formula 2, $R^3$ is optionally substituted $C_6$-$C_{10}$ aryl. In some embodiments of a compound of Formula 2, $R^3$ is, for example, optionally substituted methylphenyl ("tolyl") (such as 2-toyl (o-toyl), or 4-tolyl (p-tolyl)), dimethylphenyl (such as 2,6-dimethyl propylphenyl), ethylphenyl (such as 2- or 4-ethylphenyl), propylphenyl, isopropylphenyl (such as 2- or 4-isopropylphenyl), n-propylphenyl, butylphenyl, pentylphenyl, propylmethylphenyl, cyclopropylphenyl, cyclopropyl-methylphenyl, cyclobutylphenyl.

In some embodiments of a compound of Formula 2, $R^3$ is optionally substituted halo-$C_6$-$C_{10}$ aryl, such as optionally substituted fluorophenyl, difluorophenyl, or fluro-chlorophenyl. In some embodiments, the optionally substituted halo-$C_6$-$C_{10}$ aryl is a halo-alkyloxyphenyl, such as fluoromethoxyphenyl.

In some embodiments, of a compound of Formula 2, $R^3$ is an optionally substituted alkyloxy-alkynyl; such as, for example, ethyloxy-methylphenyl, isopropoxy-methylphenyl, cyclopropylmethyloxy-methylphenyl. In some embodiments of a compound of Formula 2, $R^3$ is haloalkyloxy-alkylphenyl, such as a haloalkyloxy-methylphenyl; for example trifluoroethoxy-methylphenyl. In some embodiments of a compound of Formula 2, $R^3$ is haloalkyloxy-halophenyl, such as a haloalkyloxy-fluorophenyl; for example trifluoroethoxy-fluorophenyl. In some embodiments of a compound of Formula 2, $R^3$ is substituted cycloalkyloxyphenyl. In some embodiments of a compound of Formula 2, $R^3$ is substituted $C_4$-$C_{12}$ carbocyclylalkoxy, such as cycloalkyloxymethylphenyl, in particular (cyclopropylmethoxy)methylphenyl.

In some embodiments, $R^3$ is optionally substituted heterocyclyl, such as thoile (thiophen), pyrrolidinyl, benzylfuranyl, indolinyl, quinolin, or pyranyl. In some embodiments, $R^3$ is optionally substituted quinolinphenyl.

In particular embodiments of a compound of Formula 2, $R^3$ is selected from chlorophenyl, difluorophenyl, chlorofluorophenyl, (trifluoroethyl)phenyl, (trifluoropropyl)phenyl, methylphenyl ("tolyl"), dimethylphenyl, ethylphenyl, propylphenyl, butylphenyl, pentylphenyl, hexylphenyl, (cyclopropylethyl)phenyl, cyclopropylphenyl, cyclobutylphenyl, cyclopentylphenyl, cyclohexylphenyl, (cyclobutylmethyl)phenyl, propoxyphenyl, (propyl-methoxy)phenyl, (trifluoroethoxy)phenyl, (trifluoroethoxy)fluorophenyl, (trifluoroethoxy)dimethylphenyl, (propoxy)methylphenyl, (difluoromethoxy)methylphenyl, (quinolinyl)methylphenyl, (dihydroquinolinyl)methylphenyl, indolinylphenyl, dimethylaminophenyl, pyranylphenyl, methyldihydrobenzofuranyl, (indolinyl)methylphenyl, or (pyrrolidinyl)methyl-phenyl, or thiole.

In particular embodiments of a compound of Formula 2, $R^9$ is selected from chlorophenyl, difluorophenyl, chlorofluorophenyl, (trifluoroethyl)phenyl, (trifluoropropyl)phenyl, methylphenyl (tolyl), dimethylphenyl, ethylphenyl, propylphenyl, butylphenyl, pentylphenyl, hexylphenyl, (cyclopropylethyl)phenyl, cyclopropylphenyl, cyclobutylphenyl, cyclopentylphenyl, cyclohexylphenyl, (cyclobutylmethyl)phenyl, propoxyphenyl, (propylmethoxy)phenyl, (trifluoroethoxy)phenyl, (trifluoroethoxy)fluorophenyl, (trifluoroethoxy)dimethylphenyl, (propoxy)methylphenyl, (difluoromethoxy)methylphenyl, (quinolinyl)methylphenyl, (dihydroquinolinyl)methylphenyl, indolinylphenyl, dimethylaminophenyl, pyranyl-phenyl, methyldihydrobenzofuranyl, (indolinyl)methylphenyl, or (pyrrolidinyl)methylphenyl, or thiole.

At least one embodiment provides a composition comprising a compound of Formula 2. In at least one embodiment, the composition is a pharmaceutical composition, which comprises at least one pharmaceutically acceptable excipient and a compound of Formula 2.

At least one embodiment provides a method of inhibiting a histone demethylase enzyme comprising contacting the histone demethylase enzyme with a compound of Formula 2 or a composition comprising a compound of Formula 2.

At least one embodiment provides a method of treating cancer in a subject in need thereof, comprising administering to the subject a pharmaceutical composition comprising a compound of Formula 2. Another embodiment provides for use of a compound of Formula 2 in a medicament for treating cancer or neoplastic disease. A related embodiment provides use of a compound, composition, or pharmaceutical composition comprising the compound of Formula 2 in manufacture of a medicament for treating cancer or neoplastic disease, wherein the medicament is administered to a patient in need thereof. The cancer or neoplastic disease being treated, or for which the medicament is manufactured, may be prostate cancer, breast cancer, bladder cancer, lung cancer, melanoma, retinoblastoma, or multiple endocrine neoplasia type 1.

At least one embodiment provides a compound having the structure of Formula 3:

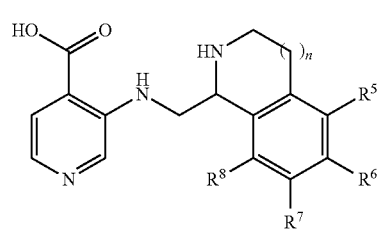

Formula 3 wherein a compound of Formula 3 includes isomers and pharmaceutically acceptable salts thereof, and wherein:
n is 0, 1, or 2;
$R^6$ is X—Y, wherein
   X is a bond, O, S, N(R), C(O), N(R)C(O), C(O)N(R), or optionally substituted $C_1$-$C_3$ alkyl,
   in which R is hydrogen or optionally substituted alkyl, and Y is optionally substituted alkyl, cycloalkyl, heterocyclyl, aryl, or heteroaryl; and $R^5$, $R^7$, and $R^8$ are each independently selected from hydrogen, halogen, hydroxyl, cyanyl, or $N(R^1)(R^2)$, or optionally substituted $C_1$-$C_6$ alkyl, $C_1$-$C_6$ alkynyl, $C_1$-$C_6$ alkenyl, $C_1$-$C_6$ alkoxy, $C_3$-$C_7$ carbocyclyl, $C_3$-$C_7$ carbocyclyloxy, $C_4$-$C_{12}$ carbocyclylalkyl, $C_4$-$C_{12}$ carbocyclylalkoxy, $C_6$-$C_{10}$ aryl, $C_6$-$C_{10}$ aryloxy, $C_6$-$C_{10}$ aryl-S, $C_6$-$C_{10}$ aryl-$SO_2$, $C_7$-$C_{14}$ aralkoxy, heteroaryl, heteroaryloxy, heterocyclyl, heterocyclyloxy, heterocyclylalkyl, heterocyclylalkoxy, or heteroaryl-S, in which
$R^1$ is hydrogen or optionally substituted alkyl, and
$R^2$ is optionally substituted alkyl, aryl, heteroaryl, heterocyclyl, cycloalkyl, cycloalkylalkyl, aryl-CO, heteroaryl-CO, cycloalkyl-CO, or alkyl-CO.

In one embodiment of a compound of Formula 3, n is 0. In one embodiment of a compound of Formula 3, n is 1. In one embodiment of the compound of Formula 3, each of $R^5$, $R^7$, and $R^8$ are hydrogen.

At least one embodiment provides a composition comprising a compound of Formula 3. In at least one embodiment, a composition comprising a compound of Formula 3 is a pharmaceutical composition, which includes at least one pharmaceutically acceptable excipient.

At least one embodiment provides a method of inhibiting a histone demethylase enzyme comprising contacting the histone demethylase enzyme with a compound of Formula 3 or a composition comprising Formula 3 that may be a pharmaceutical composition.

At least one embodiment provides a method of treating cancer in a subject in need thereof, comprising administering to the subject a pharmaceutical composition comprising a compound of Formula 3. Another embodiment provides for use of a compound of Formula 3 in a medicament for treating cancer or neoplastic disease. A related embodiment provides use of a compound, composition, or pharmaceutical composition comprising the compound of Formula 3 in manufacture of a medicament for treating cancer or neoplastic disease, wherein the medicament is administered to a patient in need thereof. The cancer or neoplastic disease being treated, or for which the medicament is manufactured, may be prostate cancer, breast cancer, bladder cancer, lung cancer, melanoma, retinoblastoma, or multiple endocrine neoplasia type 1.

At least one embodiment provides a compound of Formula 4:

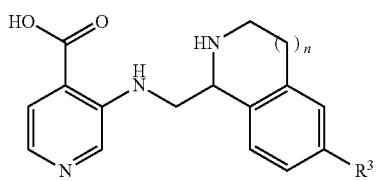

Formula 4 wherein a compound of Formula 4 includes isomers and pharmaceutically acceptable salts thereof, and wherein:
n is 0, 1, or 2; and
$R^3$ is $N(R)(R^9)$, $N(R)C(O)$, $C(O)N(R)$, or optionally substituted $C_3$-$C_7$ carbocyclyl, $C_3$-$C_7$ carbocyclyloxy, $C_4$-$C_{12}$ carbocyclylalkyl, $C_4$-$C_{12}$ carbocyclylalkoxy, $C_6$-$C_{10}$ aryl, $C_6$-$C_{10}$ aryloxy, $C_6$-$C_{10}$ aryl-S, $C_6$-$C_{10}$ aryl-$SO_2$, $C_7$-$C_{14}$ aralkoxy, heteroaryl, heteroaryloxy, heterocyclyl, heterocyclyloxy, heterocyclylalkyl, heterocyclylalkoxy, or heteroaryl-S,
wherein
R is hydrogen or optionally substituted $C_1$-$C_6$ alkyl, and
$R^9$ is optionally substituted $C_3$-$C_7$ carbocyclyl, $C_3$-$C_7$ carbocyclyloxy, $C_4$-$C_{12}$ carbocyclylalkyl, $C_4$-$C_{12}$ carbocyclylalkoxy, $C_6$-$C_{10}$ aryl, $C_6$-$C_{10}$ aryloxy, $C_6$-$C_{10}$ aryl-S—, $C_7$-$C_{14}$ aralkoxy, heteroaryl, heteroaryloxy, heterocyclyl, heterocyclyloxy, heterocyclylalkyl, heterocyclylalkoxy, $C_6$-$C_{10}$ aryl-$SO_2$, or heteroaryl-S.

In one embodiment of a compound of Formula 4, n is 0. In one embodiment of a compound of Formula 4, n is 1. In one embodiment of a compound of Formula 4, $R^3$ is $N(R)(R^9)$. In one embodiment of a compound of Formula 4, R is methyl. In one embodiment of a compound of Formula 4, $R^3$ is $N(R)(R^9)$, in which R is methyl, and $R^9$ is optionally substituted alkylphenyl or haloalkyloxyphenyl. In one embodiment of a compound of Formula 4, $R^9$ is methylphenyl (tolyl) or isopropylphenyl. In one embodiment of a compound of Formula 4, $R^3$ is $N(R)(R^9)$, in which R is methyl, and $R^9$ optionally substituted methylphenyl. In one embodiment of a compound of Formula 4, $R^3$ is $N(R)(R^9)$, in which R is methyl, and $R^9$ isopropylphenyl. In one embodiment of a compound of Formula 4, $R^9$ is trifluoroethoxyphenyl. In one embodiment of a compound of Formula 4, $R^3$ is substituted $C_6$-$C_{10}$ aryl. In one embodiment of a compound of Formula 4, $R^3$ is substituted methylphenyl. In one embodiment of a compound of Formula 4, $R^3$ is substituted cycloalkyloxyphenyl. In one embodiment of a compound of Formula 4, $R^3$ is substituted $C_4$-$C_{12}$ carbocyclylalkoxy. In one embodiment of a compound of Formula 4, $R^3$ is cycloalkyloxymethylphenyl. In one embodiment of a compound of Formula 4, $R^3$ is (cyclopropylmethoxy)methylphenyl.

At least one embodiment provides a composition comprising a compound of Formula 4. In at least one embodiment, the composition is a pharmaceutical composition comprising at least one pharmaceutically acceptable excipient and a compound of Formula 4.

At least one embodiment provides a method of inhibiting a histone demethylase enzyme comprising contacting the histone demethylase enzyme with a compound of Formula 4 or a composition comprising a compound of Formula 4.

At least one embodiment provides a method of treating cancer in a subject in need thereof, comprising administering to the subject a pharmaceutical composition comprising a compound of Formula 4. Another embodiment provides for use of a compound of Formula 4 in a medicament for treating cancer or neoplastic disease. A related embodiment provides use of a compound, composition, or pharmaceutical composition comprising the compound of Formula 4 in manufacture of a medicament for treating cancer or neoplastic disease, wherein the medicament is administered to a patient in need thereof. The cancer or neoplastic disease being treated, or for which the medicament is manufactured, may be prostate cancer, breast cancer, bladder cancer, lung cancer, melanoma, retinoblastoma, or multiple endocrine neoplasia type 1.

DETAILED DESCRIPTION

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

All patents and other publications identified are incorporated herein by reference for the purpose of describing and disclosing, for example, the methodologies described in such publications that might be used in connection with the present invention, but are not to provide definitions of terms inconsistent with those presented herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on information available to the applicants and do not constitute any admission as to the correctness of the dates or contents of these documents.

As used herein and in the claims, the singular forms "a," "an," and "the" include the plural reference unless the context clearly indicates otherwise. The term "or" is inclusive unless modified, for example, by "either." Thus, unless context indicates otherwise, the word "or" means a member of a particular list and any optional combination of members of that list. Throughout this specification, unless otherwise indicated, "comprise," "comprises" and "comprising" are used inclusively rather than exclusively, so that a stated integer or group of integers may include one or more other non-stated integers or groups of integers.

The term "about" when referring to a number or a numerical range means that the number or numerical range referred to is an approximation within experimental variability (or within statistical experimental error), and thus the number or numerical range may vary. "About" refers generally to ±1% of the designated value, but may allow for ±5% or ±10% of the designated value as accepted in the relevant context by one of skill in the art. Accordingly, numbers expressing quantities or reaction conditions used herein should be understood as modified in all instances by the term "about" unless stated to the contrary. When ranges are used herein for physical properties, such as molecular weight, or chemical properties, such as chemical formulae, all combinations and subcombinations of ranges and specific embodiments therein are intended to be included.

Definitions

As used in the specification and appended claims, unless specified otherwise, the following terms have the meaning indicated below:

"Amino" refers to the —$NH_2$ radical.
"Cyano" refers to the —CN radical.
"Nitro" refers to the —$NO_2$ radical.
"Oxa" refers to the —O-radical.
"Oxo" refers to the =O radical.
"Thioxo" refers to the =S radical.
"Imino" refers to the =N—H radical.
"Oximo" refers to the =N—OH radical.
"Hydrazino" refers to the =N—$NH_2$ radical.
"Alkyl" refers to a straight or branched hydrocarbon chain radical consisting solely of carbon and hydrogen atoms, containing no unsaturation, and typically having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl) (i.e., methyl, ethyl, or propyl). In other embodiments, an alkyl comprises one to two carbon atoms (e.g., $C_1$-$C_2$ alkyl) (i.e., methyl or ethyl). In other embodiments, an alkyl comprises one carbon atom (e.g., $C_1$ alky) (methyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises two to ten carbon atoms (e.g., $C_2$-$C_{10}$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethyl ethyl (tert-butyl), 1-pentyl (n-pentyl). The alkyl is attached to the rest of the molecule by a single bond. Unless stated otherwise, an alkyl group may be substituted (i.e. is optionally substituted) by one or more of the following substituents: halo, cyano, amino, nitro, oxo, thioxo, imino, oximo, trimethylsilanyl, $OR^a$, $SR^a$, OC(O)—$R^a$, $N(R^a)_2$, $C(O)R^a$, $C(O)OR^a$, $C(O)N(R^a)_2$, $N(R^a)C(O)OR^a$, OC(O)—$N(R^a)_2$, $N(R^a)C(O)R^a$, $N(R^a)S(O)_tR^a$, $S(O)_tOR^a$, $S(O)_tR^a$, or $S(O)_tN(R^a)_2$, where each t is independently 1 or 2, and each $R^a$ independently represents hydrogen, alkyl, fluoroalkyl, carbocyclyl, carbocyclylalkyl, aryl, aralkyl, heterocyclyl, heterocyclylalkyl, heteroaryl, or heteroarylalkyl.

"Alkenyl" refers to a straight or branched hydrocarbon chain radical group consisting solely of carbon and hydrogen atoms, containing at least one carbon-carbon double bond (C=C), and having from two to twelve carbon atoms. In certain embodiments, an alkenyl comprises two to eight carbon atoms (i.e., $C_2$-$C_8$ alkenyl). In other embodiments, an alkenyl comprises two to four carbon atoms (i.e., $C_2$-$C_4$ alkenyl). The alkenyl is typically attached to the rest of the molecule by a single bond, for example, ethenyl (i.e., vinyl), prop-1-enyl (i.e., allyl), but-1-enyl, pent-1-enyl, penta-1,4-dienyl, and the like. Unless specified otherwise herein, an alkenyl group is optionally substituted by one or more of the following substituents: halo, cyano, nitro, oxo, thioxo, imino, oximo, trimethylsilanyl, $OR^a$, $SR^a$, OC(O)—$R^a$, $N(R^a)_2$, $C(O)R^a$, $C(O)OR^a$, $C(O)N(R^a)_2$, $N(R^a)C(O)OR^a$, OC(O)—$N(R^a)_2$, $N(R^a)C(O)R^a$, $N(R^a)S(O)_tR^a$, $S(O)_tOR^a$, $S(O)_tR^a$, or $S(O)_tN(R^a)_2$, in which each t is independently 1 or 2, and each $R^a$ independently represents hydrogen, alkyl, fluoroalkyl, carbocyclyl, carbocyclylalkyl, aryl, aralkyl, heterocyclyl, heterocyclylalkyl, heteroaryl, or heteroarylalkyl.

"Alkynyl" refers to a straight or branched hydrocarbon chain radical group consisting solely of carbon and hydrogen atoms, containing at least one carbon-carbon triple bond (C≡C), having from two to twelve carbon atoms (i.e., $C_2$-$C_{12}$ alkynyl). In certain embodiments, an alkynyl comprises two to eight carbon atoms (i.e., $C_2$-$C_8$ alkynyl). In other embodiments, an alkynyl has two to four carbon atoms (i.e., $C_2$-$C_4$ alkynyl). The alkynyl is typically attached to the rest of the molecule by a single bond, for example, ethynyl, propynyl, butynyl, pentynyl, hexynyl, and the like. Unless specified otherwise herein, an alkynyl group is optionally substituted by one or more of the following substituents: halo, cyano, nitro, oxo, thioxo, imino, oximo, trimethylsilanyl, $OR^a$, $SR^a$, OC(O)—$R^a$, $N(R^a)_2$, $C(O)R^a$, $C(O)OR^a$, $C(O)N(R^a)_2$, $N(R^a)C(O)OR^a$, OC(O)—$N(R^a)_2$, $N(R^a)C(O)R^a$, $N(R^a)S(O)_tR^a$, $S(O)_tOR^a$, $S(O)_tR^a$, or $S(O)_tN(R^a)_2$, where each t is independently 1 or 2, and each $R^a$ independently represents hydrogen, alkyl, fluoroalkyl, carbocyclyl, carbocyclylalkyl, aryl, aralkyl, heterocyclyl, heterocyclylalkyl, heteroaryl, or heteroarylalkyl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin, and naphthalene. Unless stated otherwise specifically herein, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, or optionally substituted aryl, aralkyl, aralkenyl, aralkynyl, carbocyclyl, carbocyclylalkyl, heterocyclyl, heterocyclylalkyl, heteroaryl or heteroarylalkyl, or $R^b$—$OR^a$, $R^b$—$OC(O)$—$R^a$, $R^b$—$OC(O)$—$OR^a$, $R^b$—$OC(O)$—$N(R^a)_2$, $R^b$—$N(R^a)_2$, $R^b$—$C(O)R^a$, $R^b$—$C(O)OR^a$, $R^b$—$C(O)N(R^a)_2$, $R^b$—$O$—$R^c$—$C(O)N(R^a)_2$, $R^b$—$N(R^a)C(O)OR^a$, $R^b$—$N(R^a)C(O)R^a$, $R^b$—$N(R^a)S(O)_tR^a$, $R^b$—$S(O)_tR^a$, $R^b$—$S(O)_tOR^a$, or $R^b$—$S(O)_tN(R^a)_2$, wherein each t is independently 1 or 2, each $R^a$ independently represents hydrogen, alkyl, fluoroalkyl, cycloalkyl, cycloalkylalkyl, aryl (optionally substituted with one or more halo groups), aralkyl, heterocyclyl, heterocyclylalkyl, heteroaryl, or heteroarylalkyl, and each $R^b$ independently represents a direct bond, or a straight or branched alkyl or alkenyl chain, and $R^c$ is a straight or branched alkyl or alkyl, and where each of the above substituents may be substituted unless otherwise indicated.

"Aralkyl" refers to a radical of the formula $R^c$-aryl where $R^c$ is an alkyl as defined above, for example, methyl, ethyl, branched or straight chain, and the like. The alkyl part of the aralkyl radical is optionally substituted as described above for an alkyl chain. The aryl part of the aralkyl radical is optionally substituted as described above for an aryl group.

"Aralkenyl" refers to a radical of the formula $R^d$-aryl where $R^d$ is an alkenyl as defined above. The aryl part of the aralkenyl radical is optionally substituted as described above for an aryl group. The alkenyl chain part of the aralkenyl radical is optionally substituted as defined above for an alkenyl group.

"Aralkynyl" refers to a radical of the formula $R^e$-aryl, where $R^e$ is an alkynyl as defined above. The aryl part of the aralkynyl radical is optionally substituted as described above for an aryl group. The alkynyl part of the aralkynyl radical is optionally substituted as defined above for an alkynyl group.

"Aralkoxy" refers to a radical bonded through an oxygen atom of the formula O—$R^e$-aryl, where $R^c$ is an alkyl as defined above, for example, methyl, ethyl, straight or branched alyl chain, and the like. The alkyl part of the aralkoxy radical is optionally substituted as described above for an alkyl. The aryl part of the aralkoxy radical is optionally substituted as described above for an aryl group.

"Carbocyclyl" refers to a stable non-aromatic monocyclic or polycyclic hydrocarbon radical consisting solely of carbon and hydrogen atoms, which may include fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl may be saturated, (i.e., containing single C—C bonds only) or unsaturated (i.e., containing one or more double bonds or triple bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo(2.2.1)heptanyl), norbornenyl, decalinyl, 7,7-dimethyl-bicyclo(2.2.1)heptanyl, and the like. Unless otherwise specified herein, "carbocyclyl" includes carbocyclyl radicals that are optionally substituted by one or more substituents independently selected from alkyl, alkenyl, alkynyl, halo, fluoroalkyl, oxo, thioxo, cyano, nitro, or optionally substituted aryl, aralkyl, aralkenyl, aralkynyl, carbocyclyl, carbocyclylalkyl, heterocyclyl, heterocyclylalkyl, heteroaryl or heteroarylalkyl, or $R^b$—$OR^a$, $R^b$—$OC(O)$—$R^a$, $R^b$—$OC(O)$—$OR^a$, $R^b$—$OC(O)$—$N(R^a)_2$, $R^b$—$N(R^a)_2$, $R^b$—$C(O)R^a$, $R^b$—$C(O)OR^a$, $R^b$—$C(O)N(R^a)_2$, $R^b$—$O$—$R^c$—$C(O)N(R^a)_2$, $R^b$—$N(R^a)C(O)OR^a$, $R^b$—$N(R^a)C(O)R^a$, $R^b$—$N(R^a)S(O)_tR^a$, $R^b$—$S(O)_tR^a$, $R^b$—$S(O)_tOR^a$, or $R^b$—$S(O)_tN(R^a)_2$, wherein each t is independently 1 or 2, where each $R^a$ independently represents hydrogen, alkyl, fluoroalkyl, cycloalkyl, cycloalkylalkyl, aryl, aralkyl, heterocyclyl, heterocyclylalkyl, heteroaryl or heteroarylalkyl, and where each $R^b$ independently represents direct bond or a straight or branched alkyl or alkenyl chain, and $R^c$ is a straight or branched alkyl or alkenyl chain, and where each of the above substituents may be substituted unless otherwise indicated.

"Carbocyclylalkyl" refers to a radical of the formula $R^c$-carbocyclyl where $R^c$ is an alkyl chain as defined above. The alkyl chain and the carbocyclyl radical are optionally substituted as defined above.

"Carbocyclylalkoxy" refers to a radical bonded through an oxygen atom of the formula —O—$R^c$-carbocyclyl where $R^c$ is an alkyl chain as defined above. The alkyl chain and the carbocyclyl radical are optionally substituted as defined above.

"Halo" or "halogen" refers to bromo, chloro, fluoro, or iodo substituents.

"Fluoroalkyl" refers to an alkyl radical, as defined above (substituted by one or more fluoro radicals, as defined above), for example, trifluoromethyl, difluoromethyl, fluoromethyl, 2,2,2-trifluoroethyl, 1-fluoromethyl-2-fluoroethyl, and the like. The alkyl part of the fluoroalkyl radical may be optionally substituted as defined above for an alkyl group.

"Heterocyclyl" refers to a stable three- to eighteen-membered non-aromatic ring radical that comprises two to twelve carbon atoms and from one to six heteroatoms (i.e., atoms other than carbon) selected from nitrogen, oxygen, and sulfur. Unless specified otherwise, the heterocyclyl radical is typically a monocyclic, bicyclic, tricyclic, or tetracyclic ring system, that may include fused or bridged ring systems. The heteroatoms in the heterocyclyl radical may be optionally oxidized. One or more nitrogen atoms, if present, are optionally quaternized. The heterocyclyl radical may be partially or fully saturated. The heterocyclyl may be attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydro-pyranyl, thiomorpholinyl, thiamorpholinyl, 1-oxo-thio-morpholinyl, and 1,1-dioxothiomorpholinyl.

Unless stated otherwise, the term "heterocyclyl" includes heterocyclyl radicals as defined above that are optionally substituted by one or more substituents selected from alkyl, alkenyl, alkynyl, halo, fluoroalkyl, oxo, thioxo, cyano, nitro, optionally substituted aryl, aralkyl, aralkenyl, aralkynyl, carbocyclyl, carbocyclylalkyl, heterocyclyl, heterocyclylalkyl, heteroaryl or heteroarylalkyl, or $R^b$—$OR^a$, $R^b$—OC(O)—$R^a$, $R^b$—OC(O)—$OR^a$, $R^b$—OC(O)—$N(R^a)_2$, $R^b$—$N(R^a)_2$, $R^b$—$C(O)R^a$, $R^b$—$C(O)OR^a$, $R^b$—$C(O)N(R^a)_2$, $R^b$—O—$R^cC(O)N(R^a)_2$, $R^b$—$N(R^a)C(O)OR^a$, $R^b$—$N(R^a)C(O)R^a$, $R^b$—$N(R^a)S(O)_tR^a$, $R^b$—$S(O)_tR^a$, $R^b$—$S(O)_tOR^a$, or $R^b$—$S(O)_tN(R^a)_2$, in which each t is independently 1 or 2, wherein each $R^a$ independently represents hydrogen, alkyl, fluoroalkyl, cycloalkyl, cycloalkylalkyl, aryl, aralkyl, heterocyclyl, heterocyclylalkyl, heteroaryl, or heteroarylalkyl, and wherein each $R^b$ independently represents a direct bond or a straight or branched alkyl or alkenyl chain, and wherein $R^c$ is a straight or branched alkyl or alkenyl chain, and wherein each of the above substituents is unsubstituted unless otherwise indicated.

"N-heterocyclyl" or "N-attached heterocyclyl" refers to a heterocyclyl radical as defined above containing at least one nitrogen, and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include 2-morpholinyl, 2- or 3- or 4-piperi-dinyl, 2-piperazinyl, 2- or 3-pyrrolidinyl, and the like.

"Heterocyclylalkyl" refers to a radical of the formula $R^c$-heterocyclyl where $R^c$ represents an alkyl as defined above. If the heterocyclyl is a nitrogen-containing heterocyclyl, the heterocyclyl is optionally attached to the alkyl radical at the nitrogen atom. The alkyl of the heterocyclylalkyl radical is optionally substituted as defined above for an alkyl. The heterocyclyl part of the heterocyclylalkyl radical is optionally substituted as defined above for a heterocyclyl group.

"Heterocyclylalkoxy" refers to a radical bonded through an oxygen atom of the formula O—$R^c$-heterocyclyl where $R^c$ is an alkyl chain as defined above. If the heterocyclyl is a nitrogen-containing heterocyclyl, the heterocyclyl is optionally attached to the alkyl radical at the nitrogen atom. The alkyl of the heterocyclylalkoxy radical is optionally substituted as defined above for an alkyl. The heterocyclyl part of the heterocyclylalkoxy radical is optionally substituted as defined above for a heterocyclyl group.

"Heteroaryl" refers to a radical derived from a three- to eighteen-membered aromatic ring radical that comprises two to seventeen carbon atoms and from one to six heteroatoms typically nitrogen, oxygen, or sulfur. A heteroaryl radical may be a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Example heteroaryls include azepinyl, acridinyl, benzimidazolyl, benzindolyl, 1,3-benzodioxolyl, benzofuranyl, benzooxazolyl, benzo[d]thia-zolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzo-pyranonyl, benzofuranyl, benzofuranonyl, benzothienyl (benzothiophenyl), benzothieno[3,2-d] pyrimidinyl, benzotria-zolyl, benzo[4,6]imidazo[1,2-a]-pyridinyl, carbazolyl, cinnolinyl, cyclopenta[d]pyrimidinyl, 6,7-dihydro-5H-cyclopenta[4,5]-thieno[2,3-d]pyrimidinyl, 5,6-dihydro-benzo[h]quinazolinyl, 5,6-dihydrobenzo[h]cinnolinyl, 6,7-dihydro-5H-benzo[6,7]cyclohepta-[1,2-c]pyridazinyl, dibenzofuranyl, dibenzothiophenyl, furanyl, furanonyl, furo[3,2-c]pyridinyl, 5,6,7,8,9,10-hexa-hydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, inda-zolyl, iso-indolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoaze-pinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido-[3,2-d]pyrimidinyl, pyrido[3,4-d]pyr-imidinyl, pyrazinyl, pyrimidinyl, pyridazinyl, pyrrolyl, quinazolinyl, quinoxalinyl, quinolinyl, isoquino-linyl, tetrahydroquinolinyl, 5,6,7,8-tetrahydroquinazolinyl, 5,6,7,8-tetrahydrobenzo-[4,5]thieno-[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno-[2,3-d]pyrimidinyl, thieno[3,2-d]pyrimidinyl, thieno[2,3-c]pridinyl, and thiophenyl (i.e. thienyl). Unless specified otherwise herein, the term "heteroaryl" includes heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, aralkyl, aralkenyl, aralkynyl, carbocyclyl, carbocyclylalkyl, heterocyclyl, heterocyclylalkyl, heteroaryl or heteroarylalkyl, or $R^b$—$OR^a$, $R^b$—OC(O)—$R^a$, $R^b$—OC(O)—$OR^a$, $R^b$—OC(O)—$N(R^a)_2$, $R^b$—$N(R^a)_2$, $R^b$—$C(O)R^a$, $R^b$—$C(O)OR^a$, $R^b$—$C(O)N(R^a)_2$, $R^b$—O—$R^c$—$C(O)N(R^a)_2$, $R^b$—$N(R^a)C(O)OR^a$, $R^b$—$N(R^a)C(O)R^a$, $R^b$—$N(R^a)S(O)_tR^a$, $R^b$—$S(O)_tR^a$, $R^b$—$S(O)_tOR^a$, or $R^b$—$S(O)_tN(R^a)_2$, in which each t is independently 1 or 2, in which each $R^a$ independently represents hydrogen, alkyl, fluoroalkyl, cycloalkyl, cycloalkylalkyl, aryl, aralkyl, heterocyclyl, heterocyclylalkyl, heteroaryl or heteroarylalkyl, and in which each $R^b$ independently represents a direct bond or a straight or branched alkyl or alkenyl, and in which $R^c$ represents a straight or branched alkyl or alkenyl, and wherein unless otherwise indicated each of the above substituents may be substituted.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula $R^c$-heteroaryl, where $R^c$ is an alkyl as defined above. If the heteroaryl is a nitrogen-containing heteroaryl, the heteroaryl is optionally attached to the alkyl radical at the nitrogen atom. The alkyl of the heteroarylalkyl radical is optionally substituted as defined above for an alkyl chain. The heteroaryl part of the heteroarylalkyl radical is optionally substituted as defined above for a heteroaryl group.

"Heteroarylalkoxy" refers to a radical bonded through an oxygen atom of the formula O—$R^c$-heteroaryl, where $R^c$ is an alkyl as defined above. If the heteroaryl is a N-containing heteroaryl, the heteroaryl is optionally attached to the alkyl radical at the N atom. The alkyl of the heteroarylalkoxy radical is optionally substituted as defined above for an alkyl chain. The heteroaryl part of the heteroarylalkoxy radical is optionally substituted as defined above for a heteroaryl group.

As used herein, "carboxylic acid bioisostere" refers to a functional group or moiety that exhibits similar physical, biological or chemical properties as a carboxylic acid moiety. Examples of carboxylic acid bioisosteres include, but are not limited to,

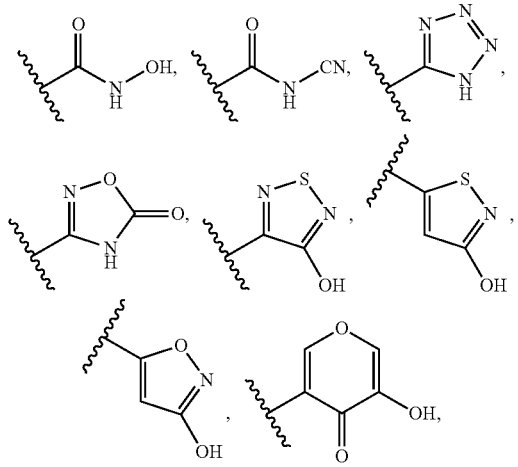

and the like.

The compounds described herein (which includes their pharmaceutically acceptable salts), in some instances contain one or more asymmetric centers and thus give rise to enantiomers, diastereomers, and other stereoisomeric forms that are defined, in terms of absolute stereochemistry, as (R) or (S). When the compounds described herein contain olefinic double bonds or other centers of geometric asymmetry, these compounds include both E and Z geometric isomers (e.g., cis or trans) unless specified otherwise; likewise, all possible isomers, as well as their racemic and optically pure forms, and all tautomeric forms are included in the compounds of the present embodiments unless specified otherwise. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "stereoisomer" refers to a compound made up of the same atoms bonded by the same bonds but having different three-dimensional structures, which are not interchangeable. The discussion provided herein encompasses the various stereoisomers and mixtures thereof, and includes "enantiomers," which refers to two stereoisomers whose molecular structures are nonsuperimposeable mirror images of one another.

A "tautomer" refers to a molecule wherein a proton shift from one atom of a molecule to another atom of the same molecule is possible. The compounds presented herein may, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

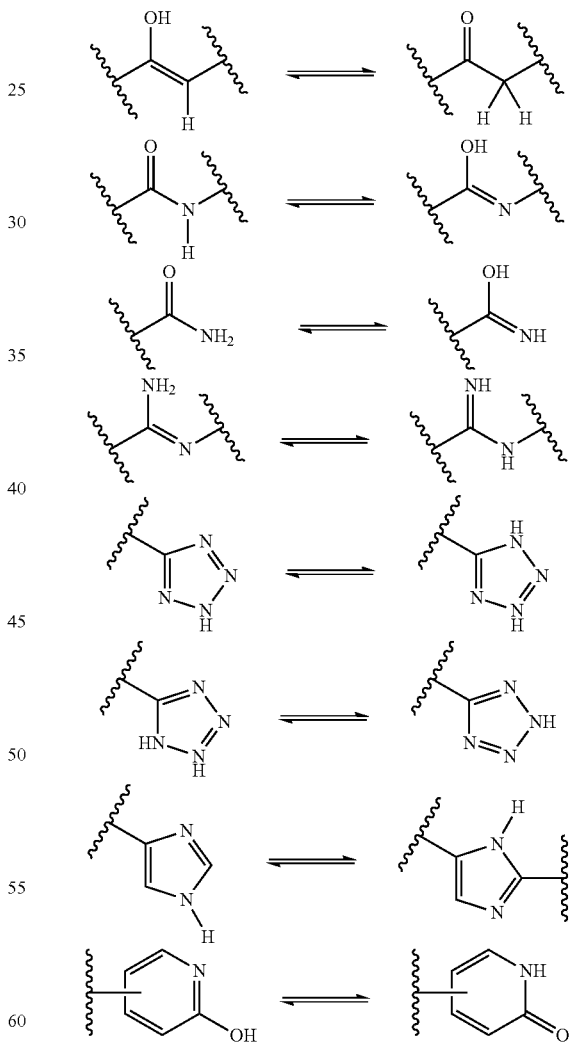

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution. In general as used herein, in a list of moieties, radicals, or substituents, the first instance of "optionally substituted" applies to all the members of the list as if the phrase were repeated with each member. Accordingly, "optionally substituted benzene or hydroquinoline," should be understood to mean "optionally substituted benzene or optionally substituted hydroquinoline."

A "pharmaceutically acceptable salt" of any one of the compounds described herein includes any and all pharmaceutically suitable salt forms. These pharmaceutically acceptable salts are pharmaceutically acceptable acid addition salts or pharmaceutically acceptable base addition salts. Standard references for the preparation and selection of pharmaceutical salts of the substituted pyridine and pyridazine derivative compounds are known in the art. See, e.g., Stahl & Wermuth, HANDBOOK PHARM. SALTS (Verlag Helvetica Chimica Acta, Zurich, 2002); Berge et al., *Pharmaceutical Salts,* 66 J. Pharm. Sci. 1-19 (1997).

A "pharmaceutically acceptable acid addition salt" retains the desirable biological effectiveness and properties of the free base, and is typically formed with inorganic acids such as hydrochloric acid, hydrobromic acid, sulfuric acid, nitric acid, phosphoric acid, hydroiodic acid, hydrofluoric acid, phosphorous acid, and the like. These include, for example, salts formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc.; and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfates, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. These salts also include salts of amino acids, such as arginates, gluconates, and galacturonates. Acid addition salts of basic compounds may be prepared by contacting the free base forms with a sufficient amount of the desired acid to produce the salt, according to methods and techniques well-known to those of skill in the art. See Berge et al., 1997.

A "pharmaceutically acceptable base addition salt" retains the desirable biological effectiveness and properties of the free acids, and is prepared from addition of an inorganic base or an organic base to the free acid. Pharmaceutically acceptable base addition salts may be formed with metals or amines, such as alkali and alkaline earth metals, or organic amines. Salts derived from inorganic bases include sodium, potassium, lithium, ammonium, calcium, magnesium, iron, zinc, copper, manganese, aluminum salts, and the like. Salts derived from organic bases include salts of primary, secondary, and tertiary amines, substituted amines including naturally occurring substituted amines, cyclic amines, and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methyl-glucamine, glucosamine, methylglucamine, theobromine, purines, piperazine, piperidine, N-ethyl-piperidine, polyamine resins and the like. See Berge et al., 1997.

The terms, "treatment," "treating," "palliating," or "ameliorating" are used interchangeably herein, and refer to an approach for obtaining beneficial or desired results including but not limited to therapeutic benefit or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder, such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

"Prodrug" indicates a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound may offer advantages of solubility, tissue compatibility, or delayed release in a mammalian organism. See, e.g., Bundgard, DESIGN OF PRODRUGS, 7-9, 21-24 (Elsevier, Amsterdam, 1985); Higuchi & Stella, *Pro-drugs as Novel Delivery Systems,* 14 A.C.S. Symposium Series in BIOREVERSIBLE CARRIERS IN DRUG DESIGN (Pergamon Press, 1987).

The term "prodrug" also includes any covalently bonded carriers that release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds comprising a hydroxy, amino or mercapto group bonded to any group that, when the prodrug of the active compound is administered to a mammalian subject, cleaves to form a free hydroxy, free amino, or free mercapto group, respectively. Examples of prodrugs include acetate, formate and benzoate derivatives of alcohol or amine functional groups in the active compounds.

Throughout the discussion of the present embodiments in this specification, and in the claims, reference to a compound of Formula 1, Formula 2, Formula 3, Formula 4, the compounds described herein, or provided by the embodiments hereof, and the like, includes by this incorporation unless context specifies otherwise: a pharmaceutically acceptable salt, stereoisomer, prodrug, hydrate, solvate, or N-oxide thereof. Accordingly, for example, reference to "compound of Formula 1," typically encompasses "compound of Formula 1 or a stereoisomer or pharmaceutically acceptable salt thereof" unless context requires otherwise.

Substituted Pyridine Derivative Compounds

The embodiments of substituted pyridine derivative compounds described herein inhibit at least one histone demethylase enzyme. These compounds, and compositions comprising these compounds, are useful for the treatment of cancer and neoplastic disease. For example, embodiments of the compounds described herein are useful for treating prostate cancer, breast cancer, bladder cancer, lung cancer, or melanoma, and the like.

At least one embodiment provides a compound having the structure of Formula 1:

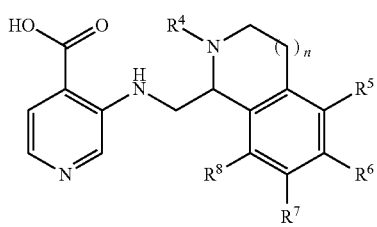

Formula 1 wherein a compound of Formula 1 includes isomers and pharmaceutically acceptable salts thereof, and wherein:

n is 0, 1, or 2;

$R^4$ is hydrogen or optionally substituted $C_1$-$C_6$ alkyl;

$R^6$ is hydrogen or X—Y, wherein
  X is a bond, O, S, N(R), C(O), N(R)C(O), C(O)N(R), or optionally substituted $C_1$-$C_3$ alkyl,
    in which R is hydrogen or optionally substituted $C_1$-$C_6$ alkyl, and
  Y is optionally substituted alkyl, cycloalkyl, heterocyclyl, aryl, or heteroaryl; and $R^5$, $R^7$, and $R^8$ are each independently selected from hydrogen, halogen, hydroxyl, cyanyl, $N(R^1)(R^2)$, or optionally substituted $C_1$-$C_6$ alkyl, $C_1$-$C_6$ alkynyl, $C_1$-$C_6$ alkenyl, $C_1$-$C_6$ alkoxy, $C_3$-$C_7$ carbocyclyl, $C_3$-$C_7$ carbocyclyloxy, $C_4$-$C_{12}$ carbocyclylalkyl, $C_4$-$C_{12}$ carbocyclylalkoxy, $C_6$-$C_{10}$ aryl, $C_6$-$C_{10}$ aryloxy, $C_6$-$C_{10}$ aryl-S, $C_6$-$C_{10}$ aryl-SO$_2$, $C_7$-$C_{14}$ aralkoxy, heteroaryl, heteroaryloxy, heterocyclyl, heterocyclyloxy, heterocyclylalkyl, heterocyclylalkoxy or heteroaryl-S, wherein $R^1$ is hydrogen or optionally substituted alkyl, and $R^2$ is optionally substituted alkyl, aryl, heteroaryl, heterocyclyl, cycloalkyl, alkylalkoxy, heteroarylalkoxy, cycloalkylalkoxy, cycloalkylalkyl, aryl-CO, heteroaryl-CO, cycloalkyl-CO, or alkyl-CO.

In at least one embodiment of a compound of Formula 1, n is 0. In at least one embodiment of a compound of Formula 1, n is 1. In at least one embodiment of a compound of Formula 1, n is 0. In at least one embodiment of a compound of Formula 1, n is 2.

At least one embodiment provides a compound of Formula 1 wherein $R^4$ is optionally substituted $C_1$-$C_6$ alkyl. In at least one embodiment of a compound of Formula 1, $R^4$ is methyl.

In at least one embodiment of the compound of Formula 1, each of $R^5$, $R^7$, and $R^8$ are hydrogen. Another embodiment provides the compound of Formula 1 wherein each $R^5$, $R^7$ and $R^8$ is independently hydrogen or halogen.

Another embodiment provides the compound of Formula 1 wherein X is a bond. Another embodiment provides the compound of Formula 1 wherein X is 0. Another embodiment provides the compound of Formula 1 wherein X is S. Another embodiment provides the compound of Formula 1 wherein X is N(R). Another embodiment provides the compound of Formula 1 wherein X is C(O). Another embodiment provides the compound of Formula 1 wherein X is N(R)C(O). Another embodiment provides the compound of Formula 1 wherein X is C(O)N(R). Another embodiment provides the compound of Formula 1 wherein X is optionally substituted $C_1$-$C_3$ alkyl.

At least one embodiment provides the compound of Formula 1 wherein R is hydrogen. Another embodiment provides the compound of Formula 1 wherein R is optionally substituted $C_1$-$C_6$ alkyl. Another embodiment provides the compound of Formula 1 wherein R is methyl.

Another embodiment provides the compound of Formula 1 wherein Y is optionally substituted alkyl. Another embodiment provides the compound of Formula 1 wherein Y is optionally substituted cycloalkyl. Another embodiment provides the compound of Formula 1 wherein Y is optionally substituted heterocyclyl. Another embodiment provides the compound of Formula 1 wherein Y is optionally substituted aryl. Another embodiment provides the compound of Formula 1 wherein Y is optionally substituted heteroaryl.

In at least one embodiment of a compound of Formula 1 Y is $N(R^1)(R^2)$. In at least one embodiment of a compound of Formula 1, X is a bond, and Y is $N(R^1)(R^2)$.

At least one embodiment provides the compound of Formula 1 wherein $R^1$ is hydrogen. Another embodiment provides the compound of Formula 1 wherein $R^1$ is optionally substituted alkyl. Another embodiment provides the compound of Formula 1 wherein $R^1$ is methyl. In at least one embodiment of a compound of Formula 1, X is a bond, and Y is $N(R^1)(R^2)$ in which $R^1$ is methyl and $R^2$ is substituted aryl.

In particular embodiments of compound Formula 1, n is 0, $R^4$ is methyl, and each of $R^5$, $R^7$, and $R^8$ are hydrogen. In some embodiments of a compound Formula 1, n is 1, $R^4$ is methyl, and each of $R^5$, $R^7$, and $R^8$ are hydrogen. In particular embodiments of compound of Formula 1 n is 0; $R^4$ is methyl; each of $R^5$, $R^7$, and $R^8$ is hydrogen; and $R^6$ is X—Y, wherein X is a bond, and Y is either (a) $N(R)(R^9)$ wherein R is methyl and $R^9$ is optionally substituted aryl or heterocyclyl, or (b) optionally substituted aryl, heterocyclyl, aryloxy, or aryl-S. In a particular embodiment in which Y is $(N(R^1)(R^9)$, R is methyl and $R^9$ is tolyl. Tolyl can be, for example, para-tolyl or ortho-tolyl. In other particular embodiments of compound Formula 1, n is 1; $R^4$ is hydrogen; each of $R^5$, $R^7$ and $R^8$ is hydrogen; and $R^6$ is X—Y in which X is a bond and Y is either (a) $N(R)(R^9)$ wherein $R^1$ is methyl and $R^9$ is optionally substituted aryl or heterocyclyl, or (b) optionally substituted aryl, heterocyclyl, aryloxy, or aryl-S.

An aspect of the present embodiments provides a composition comprising a compound of Formula 1. In at least one embodiment, the composition is a pharmaceutical composition comprising at least one pharmaceutically acceptable excipient and a compound of Formula 1.

Another aspect of the present embodiments provides a method of inhibiting a histone demethylase enzyme comprising contacting the histone demethylase enzyme with a compound of Formula 1 or a composition comprising a compound of Formula 1.

Another aspect of the present embodiments provides a method of treating cancer in a subject in need thereof, comprising administering to the subject a pharmaceutical composition comprising a compound of Formula 1. A related embodiment provides a method of treating cancer in a subject in need thereof, comprising administering to the subject a pharmaceutical composition comprising a compound of Formula 1. A related embodiment provides use of a compound, composition, or pharmaceutical composition comprising the compound of Formula 1 in manufacture of a medicament for treating cancer or neoplastic disease, wherein the medicament is administered to a patient in need thereof. The cancer or neoplastic disease being treated, or for which the medicament is manufactured, may be prostate cancer, breast cancer, bladder cancer, lung cancer, melanoma, retinoblastoma, or multiple endocrine neoplasia type 1.

At least one embodiment provides a compound of Formula 2:

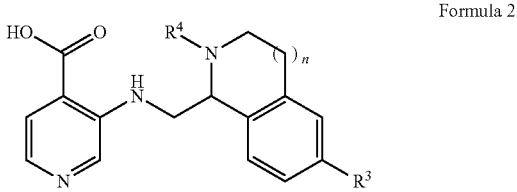

Formula 2 wherein a compound of Formula 2 includes isomers and pharmaceutically acceptable salts thereof, and wherein:
n is 0, 1, or 2;
$R^4$ is hydrogen or optionally substituted $C_1$-$C_6$ alkyl; and
$R^3$ is $N(R)(R^9)$, $N(R)C(O)$, $C(O)N(R)$, or optionally substituted $C_3$-$C_7$ carbocyclyl, $C_3$-$C_7$ carbocyclyloxy, $C_4$-$C_{12}$ carbocyclylalkyl, $C_4$-$C_{12}$ carbocyclylalkoxy, $C_6$-$C_{10}$ aryl, $C_6$-$C_{10}$ aryloxy, $C_6$-$C_{10}$ aryl-S, $C_6$-$C_{10}$ aryl-$SO_2$, $C_7$-$C_{14}$ aralkoxy, heteroaryl, heteroaryloxy, heterocyclyl, heterocyclyloxy, heterocyclylalkyl, heterocyclylalkoxy or heteroaryl-S, wherein
R is hydrogen or optionally substituted $C_1$-$C_6$ alkyl, and
$R^9$ is optionally substituted $C_3$-$C_7$ carbocyclyl, $C_3$-$C_7$ carbocyclyloxy, $C_4$-$C_{12}$ carbocyclylalkyl, $C_4$-$C_{12}$ carbocyclylalkoxy, $C_6$-$C_{10}$ aryl, $C_6$-$C_{10}$ aryloxy, $C_6$-$C_{10}$ aryl-S, $C_6$-$C_{10}$ aryl-$SO_2$, $C_7$-$C_{14}$ aralkoxy, heteroaryl, heteroaryloxy, heterocyclyl, heterocyclyloxy, heterocyclylalkyl, heterocyclylalkoxy or heteroaryl-S.

In at least one embodiment of a compound of Formula 2, n is 0. In at least one embodiment of a compound of Formula 2, n is 1.

In at least one embodiment of a compound of Formula 2, $R^4$ is methyl. In at least one embodiment of a compound of Formula 2, $R^4$ is H. In at least one embodiment of a compound of Formula 2, $R^4$ is $C_2$ alkyl. In at least one embodiment of a compound of Formula 2, $R^4$ is $C_3$ alkyl. In at least one embodiment of a compound of Formula 2, $R^4$ is $C_4$ alkyl.

In at least one embodiment of a compound of Formula 2, $R^3$ is $N(R)(R^9)$. In at least one embodiment of a compound of Formula 2 in which $R^3$ is $N(R)(R^9)$, R and $R^4$ are independently H or methyl.

In n some embodiments of a compound of Formula 2, $R^9$ is optionally substituted haloaryl, such as chlorophenyl, fluorophenyl, difluorophenyl, or fluorochlorophenyl. In some of these embodiments, R and $R^4$ may be chosen independently from hydrogen or methyl.

In some embodiments of a compound of Formula 2, $R^9$ is optionally substituted alkylaryl, such as methylphenyl ("tolyl"), ethylphenyl (such as 2-ethylphenyl), n-proplyphenyl (such as 4-n-propylphenyl), isopropylphenyl (such as 2- or 4-isopropylphenyl), pentylphenyl, hexylphenyl, cyclohexylphenyl, cyclobutylmethylphenyl, or cyclopropylmethylphenyl. In some embodiments of a compound of Formula 2, $R^9$ is optionally substituted 2-tolyl (o-tolyl), or 4-tolyl (p-tolyl). In some of these embodiments, R and $R^4$ may independently be chosen from hydrogen or methyl.

In some embodiments of a compound of Formula 2, $R^3$ is $N(R)(R^9)$ in which $R^9$ is optionally substituted alkyloxyphenyl, such as trifluoroethoxyphenyl. In some embodiments of a compound of Formula 2, $R^9$ is optionally substituted trifluoroethylphenyl or trifluoroethoxy-phenyl, such as trifluoroethoxy-methylphenyl or (trifluoroethoxy)fluorophenyl. In these embodiments, R and $R^4$ may independently be chosen from hydrogen or methyl.

In some embodiments in which $R^3$ is $N(R)(R^9)$, $R^9$ is heterocyclylaryl, such as pyranylphenyl. In some of these embodiments, R and $R^4$ may independently be chosen from hydrogen or methyl.

In at least one embodiment of a compound of Formula 2, $R^3$ is $N(R)(R^9)$ in which R is methyl and $R^9$ is propylphenyl or isopropylphenyl. In an embodiment of a compound of Formula 2, $R^3$ is $N(R)(R^9)$ in which R is methyl and $R^9$ is trifluoroethoxyphenyl. In particular embodiments of a compound of Formula 2, $R^3$ is $N(R)(R^9)$, R is methyl, and $R^9$ is optionally substituted methylphenyl. In particular embodiments of Formula 2, $R^3$ is $N(R)(R^9)$, R is methyl, and $R^9$ is isopropylphenyl. In particular embodiments of a compound of Formula 2, $R^3$ is $N(R)(R^9)$, R is methyl, and $R^9$ is optionally substituted halophenyl, alkylphenyl, haloalkylphenyl, halo(alkyloxy)phenyl, or haloalkyloxyphenyl. In an embodiment of a compound of Formula 2, $R^3$ is $N(R)(R^9)$, R is methyl, and $R^9$ is optionally substituted alkylphenyl or haloalkyloxyphenyl. In an embodiment of a compound of Formula 2, $R^3$ is $N(R)(R^9)$, R is methyl, and $R^9$ is tolyl. Tolyl, in particular embodiments of Formula 2, is p-tolyl or o-tolyl. In some of these embodiments, R and $R^4$ may independently be hydrogen or methyl.

In at least one embodiment, $R^3$ is optionally substituted aminophenyl. For example, the amino radical may be $N(R)_2$, wherein R is methyl. In some of these embodiments, R and $R^4$ may independently be hydrogen or methyl.

In particular embodiments of a compound of Formula 2 in which $R^3$ is $N(R)(R^9)$, $R^9$ is selected from chlorophenyl, difluorophenyl, chlorofluorophenyl, (trifluoroethyl)phenyl, (trifluoropropyl)phenyl, methylphenyl (tolyl), dimethylphenyl, ethylphenyl, propylphenyl, butylphenyl, pentylphenyl, hexylphenyl, (cyclopropylethyl)phenyl, cyclopropylphenyl, cyclobutylphenyl, cyclopentylphenyl, cyclohexylphenyl, (cyclobutylmethyl)phenyl, propoxyphenyl, (propylmethoxy)phenyl, (trifluoroethoxy)phenyl, (trifluoroethoxy)fluorophenyl, (trifluoroethoxy)dimethylphenyl, (propoxy)methylphenyl, (difluoromethoxy)methylphenyl, (quinolinyl)methyl-phenyl, (dihydroquinolinyl)methylphenyl, indolinylphenyl, dimethylaminophenyl, pyranylphenyl, methyldihydrobenzofuranyl, (indolinyl)methylphenyl, (pyrrolidinyl)methylphenyl, or thiole. In some of these embodiments, R and $R^4$ may be independently hydrogen or methyl.

In some embodiments of a compound of Formula 2 in which $R^3$ is $N(R)(R^9)$, R is optionally substituted $C_2$-$C_4$ alkyl; for example R may be ethyl, cyclopropylmethyl, or trifluroethyl. In such embodiments of a compound of Formula 2, $R^9$ may be any substituent as described herein for a compound of Formula 2. For example, when $R^3$ is $N(R)(R^9)$ and R is ethyl, cyclopropylmethyl or trifluroethyl, $R^9$ may be tolyl. In some of these embodiments, $R^4$ may be hydrogen or methyl.

In at least one embodiment of a compound of Formula 2, $R^3$ is optionally substituted aryl, alkylphenyl, alkoxyphenyl, cyclyloxyphenyl, aryloxyphenyl, heterocyclylphenyl, or heterocyclylalkylphenyl. In some of these embodiments, $R^4$ may be hydrogen or methyl.

For example, optionally substituted aryl can be optionally substituted haloaryl, such as optionally substituted fluorophenyl; or can be alklyaryl, such as optionally substituted methylphenyl. In some embodiments of a compound of Formula 2, $R^3$ is substituted $C_6$-$C_{10}$ aryl. In some embodiments of Formula 2, $R^3$ is optionally substituted mono-, di-, or tri-halophenyl. In some embodiments of Formula 2, $R^3$ is optionally substituted fluorophenyl, difluorophenyl (e.g., 2,4-difluorophenyl), chlorofluorophenyl, or chlorodifluorophenyl. In one embodiment of a compound of Formula 2, $R^3$ is (methoxy)fluorophenyl. In some embodiments of Formula 2, $R^3$ is an optionally substituted haloalkylaryl such as (trifluoroethyl)methylphenyl or (trifluoroethyl)-dimethylphenyl. In one embodiment of Formula 2, $R^3$ is an optionally substituted haloalkyloxyaryl such as (trifluoroethoxy)methylphenyl. In one embodiment of Formula 2, $R^3$ is (trifluoroethoxy)-halophenyl, such as (trifluoroethoxy)fluorophenyl. In some of these embodiments, $R^4$ may be hydrogen or methyl.

In at least one embodiment of a compound of Formula 2, $R^3$ is optionally substituted alkylphenyl. In some embodiments of a compound of Formula 2, $R^3$ is optionally substituted methylphenyl (such as 2- or 4-methylphenyl) or dimethylphenyl (such as 2,4-dimethylphenyl). In at least one embodiment of a compound of Formula 2, $R^3$ is ethylphenyl (such as 2- or 4-ethylphenyl) or propylphenyl (such as 2- or 4-iso- or cyclo-propylphenyl). In some embodiments of a compound of Formula 2, $R^3$ is (isopropyl)methylphenyl or (n-propyl)-methylphenyl. In some embodiments of a compound of Formula 2, $R^3$ is a substituted methylphenyl, such as (methoxy)methylphenyl, (ethoxy)methylphenyl, (propoxy)methylphenyl, (isopropoxy)methylphenyl, (trifluoroethoxy)methylphenyl, (phenoxy)methylphenyl, (pyrrolidin)methylphenyl. In some of these embodiments, $R^4$ may be hydrogen or methyl.

In some embodiments, $R^3$ is optionally substituted alkyloxyphenyl, such as methoxy-isopropylphenyl. In one embodiment of a compound of Formula 2, $R^3$ is optionally substituted (cycloalkyloxy)phenyl. In one embodiment of a compound of Formula 2, $R^3$ is substituted $C_4$-$C_{12}$ carbocyclylalkoxy, such as (cycloalkyloxy)methylphenyl, such as, for example, (cyclopropylmethoxy)methylphenyl, (cyclobutylmethoxy)methylphenyl, or (cyclopentylmethoxy)methylphenyl. In one embodiment of a compound of Formula 2, $R^3$ is substituted alkaryloxyaryl, such as (methylphenoxy)phenyl. In some of these embodiments, $R^4$ may be hydrogen or methyl.

In some embodiments of Formula 2, $R^3$ is optionally substituted heterocyclylalkylphenyl, such as (dihydroquinolinyl)methylphenyl, or (pyrrolidinyl)methyl-phenyl. In these embodiments, $R^4$ may be hydrogen or methyl.

In at least one embodiment of Formula 2, $R^3$ is optionally substituted heterocyclyl or heteroaryl. In some embodiments of Formula 2, $R^3$ is optionally substituted thiophenyl or thiole, indolinyl, or quinolinyl. Example embodiments of substituted lindolinyl are methylindolinyl and biisoquinolinyl. In some of Formula 2, $R^3$ is optionally substituted dihydrobenzofuranyl or methyldihydrobenzofuranyl. In some of these embodiments, $R^4$ may be hydrogen or methyl.

In at least one embodiment of Formula 2, $R^3$ is optionally substituted $C_6$-$C_{10}$ aryloxy, such as halophenoxy, for example fluorophenoxy (e.g., 2- or 4-fluorophenoxy); or $C_6$-$C_{10}$ alkylaryloxy, for example tolyloxy. In these embodiments, $R^4$ may be hydrogen or methyl.

In at least one embodiment, $R^3$ is heterocyclyl- or heterobicyclyl-methylphenyl; for example quinolin methylphenyl, in particular 6-(3,4-dihydroquinolin)methylphenyl, or 4(3,4-dihydroquinolin)-methylphenyl. In at least one embodiment, $R^3$ is heterocyclyloxy- or heterobicyclyloxymethylphenyl (e.g., phenoxyphenyl). In at least one embodiment, $R^3$ is (pyrrolidinyl)methylphenyl. In some of these embodiments, $R^4$ may be hydrogen or methyl.

In at least one embodiment of Formula 2, $R^3$ is optionally substituted $C_6$-$C_{10}$ aryl-S, such as an alkylaryl-S, for example tolylthio (e.g., p- or o-tolylthio). In at least one embodiment of Formula 2, $R^3$ is optionally substituted $C_6$-$C_{10}$ aryl-S, such as an haloaryl-S, for example 2- or 4-fluorophenylthio. In one embodiment of Formula 2, $R^3$ is optionally substituted $C_6$-$C_{10}$ arylsulfanyl, such as tolylthio (or tolylsulfanyl) or fluorophenylthio. In some of these embodiments, $R^4$ may be hydrogen or methyl.

In particular embodiments of a compound of Formula 2, $R^3$ is selected from chlorophenyl, difluorophenyl, chlorofluorophenyl, (trifluoroethyl)phenyl, (trifluoropropyl)-phenyl, methylphenyl ("tolyl"), dimethylphenyl, ethylphenyl, propylphenyl (such as isopropylphenyl), butylphenyl, pentylphenyl, hexylphenyl, cyclopropylphenyl, cyclobutylphenyl, cyclopentylphenyl, cyclohexylphenyl, (cyclopropylethyl)phenyl, (cyclobutylmethyl)phenyl, propoxyphenyl, (propylmethoxy)phenyl, (trifluoroethoxy)phenyl, (trifluoroethoxy)fluorophenyl, (trifluoroethoxy)dimethylphenyl, (propoxy)methylphenyl, (difluoromethoxy)methylphenyl, (quinolinyl)methylphenyl, (dihydroquinolinyl)methylphenyl, indolinylphenyl, dimethylaminophenyl, pyranylphenyl, methyldihydrobenzofuranyl, (indolinyl)methylphenyl, (pyrrolidinyl)methylphenyl, or thiole. In these embodiments, $R^4$ may be hydrogen or methyl.

In particular embodiments of the compound of Formula 2, the compound is (R) or (S) 3-[((6-[methyl(4-methylphenyl)amino]-1,2,3,4-tetrahydroisoquinolyl)methyl)amino]pyridine-4-carboxylic acid; (R) or (S) 3-([(6-(methyl[4-(methylethyl)phenyl]amino)-1,2,3,4-tetrahydroisoquinolyl)methyl]amino)pyridine-4-carboxylic acid; (R) or (S) 3-[((5-[methyl(4-methylphenyl)-amino]isoindolinyl)methyl)amino]pyridine-4-carboxylic acid; (R) or (S) 3-([(6-(methyl[4-(methylethyl)phenyl]amino)-1,2,3,4-tetrahydroisoquinolyl)methyl] amino) pyridine-4-carboxylic acid; (R) or (S) 3-(((2-methyl-5-(methyl(p-tolyl)amino)isoindolin-1-yl) methyl)amino)isonicotinic acid; (R) or (S) 3-(((2-methyl-6-(methyl(p-tolyl)amino)-1,2,3,4-tetra-hydroisoquinolin-1-yl)methyl)-amino)isonicotinic acid; (R) or (S) 3-(((6-((4-ethylphenyl)(methyl)amino)-2-methyl-1,2,3,4-tetrahydroisoquinolin-1-yl)methyl) amino)isonicotinic acid; (R) or (S) 3-(((6-(2-ethylphenyl)-2-methyl-1,2,3,4-tetrahydroiso-quinolin-1-yl)methyl)amino) isonicotinic acid; (R) or (S) 3-(((2-methyl-5-(methyl(p-tolyl)amino)isoindolin-1-yl)methyl) amino)isonicotinic acid; (R) or (S) 3-(((5-((4-ethyl-phenyl)(methyl)amino)-2-methylisoindolin-1-yl)methyl)amino)isonicotinic acid; (R) or (S) 3-(((2-methyl-5-(methyl(4-propylphenyl)amino) isoindolin-1-yl)methyl)amino)isonicotinic acid; (R) or (S) 3-(((2-methyl-5-(o-tolyl)iso-indolin-1-yl)methyl)amino)isonicotinic acid; or (R) or (S) 3-(((5-(2-ethylphenyl)-2-methyliso-indolin-1-yl)methyl)amino)isonicotinic acid. In these embodiments, $R^4$ may be hydrogen or methyl.

In some embodiments of Formula 2, n is 2. In some embodiments of Formula 2 wherein n is 2, $R^3$ and $R^4$ may be as described above. In some of these embodiments, R and $R^4$ may be independently hydrogen or methyl.

In at least one embodiment of a compound of Formula 2, $R^4$ is $C_2$ alkyl (ethyl). In at least one embodiment of a compound of Formula 2, $R^4$ is $C_3$ alkyl, such as n-propyl, isopropyl, or cyclopropyl. In at least one embodiment of a compound of Formula 2, $R^4$ is $C_4$ alkyl, such as cyclopropylmethyl. In embodiments, where $R^4$ is $C_2$-$C_4$ alkyl, $R^3$ may be any substitutent as described above for a compound of Formula 2. In particular embodiments, $R^4$ is ethyl and $R^3$ is tolyl or fluoro. In particular embodiments, $R^4$ is isopropanol or cyclopropyl and $R^3$ is tolyl or fluoro. In particular embodiments, $R^4$ is cyclopropylmethyl and $R^3$ is tolyl or fluoro.

At least one embodiment provides a composition comprising a compound of Formula 2. In at least one embodiment, the composition is a pharmaceutical composition, which comprises at least one pharmaceutically acceptable excipient and a compound of Formula 2.

At least one embodiment provides a method of inhibiting a histone demethylase enzyme comprising contacting the histone demethylase enzyme with a compound of Formula 2 or a composition comprising a compound of Formula 2.

At least one embodiment provides a method of treating cancer in a subject in need thereof, comprising administering to the subject a pharmaceutical composition comprising a compound of Formula 2. A related embodiment provides a method of treating cancer in a subject in need thereof, comprising administering to the subject a pharmaceutical composition comprising a compound of Formula 2. A related embodiment provides use of a compound, composition, or pharmaceutical composition comprising the compound of Formula 2 in manufacture of a medicament for treating cancer or neoplastic disease, wherein the medicament is administered to a patient in need thereof. The cancer or neoplastic disease being treated, or for which the medicament is manufactured, may be prostate cancer, breast cancer, bladder cancer, lung cancer, melanoma, retinoblastoma, or multiple endocrine neoplasia type 1.

At least one embodiment provides a compound having the structure of Formula 3:

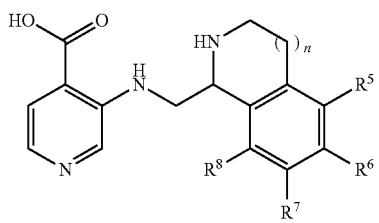

Formula 3 wherein a compound of Formula 2 includes isomers and pharmaceutically acceptable salts thereof, and wherein:
n is 0, 1, or 2;
$R^6$ is X—Y, wherein
  X is a bond, O, S, N(R), C(O), N(R)C(O), C(O)N(R), or optionally substituted $C_1$-$C_3$ alkyl,
  in which R is hydrogen or optionally substituted alkyl, and
  Y is optionally substituted alkyl, cycloalkyl, heterocyclyl, aryl, or heteroaryl; and
$R^5$, $R^7$, and $R^8$ are each independently selected from hydrogen, halogen, hydroxyl, cyanyl, or $N(R^1)(R^2)$, or optionally substituted $C_1$-$C_6$ alkyl, $C_1$-$C_6$ alkynyl, $C_1$-$C_6$ alkenyl, $C_1$-$C_6$ alkoxy, $C_3$-$C_7$ carbocyclyl, $C_3$-$C_7$ carbocyclyloxy, $C_4$-$C_{12}$ carbocyclylalkyl, $C_4$-$C_{12}$ carbocyclylalkoxy, $C_6$-$C_{10}$ aryl, $C_6$-$C_{10}$ aryloxy, $C_6$-$C_{10}$ aryl-S, $C_6$-$C_{10}$ aryl-$SO_2$, $C_7$-$C_{14}$ aralkoxy, heteroaryl, heteroaryloxy, heterocyclyl, heterocyclyloxy, heterocyclylalkyl, heterocyclylalkoxy, or heteroaryl-S, in which
  $R^1$ is hydrogen or optionally substituted alkyl, and
  $R^2$ is optionally substituted alkyl, aryl, heteroaryl, heterocyclyl, cycloalkyl, cycloalkylalkyl, aryl-CO, heteroaryl-CO, cycloalkyl-CO, or alkyl-CO.

In one embodiment of a compound of Formula 3, n is 0. In one embodiment of a compound of Formula 3, n is 1. In one embodiment of the compound of Formula 3, each of $R^5$, $R^7$, and $R^8$ are hydrogen.

At least one embodiment provides a composition comprising a compound of Formula 3. In at least one embodiment, a composition comprising a compound of Formula 3 is a pharmaceutical composition, which includes at least one pharmaceutically acceptable excipient.

At least one embodiment provides a method of inhibiting a histone demethylase enzyme comprising contacting the histone demethylase enzyme with a compound of Formula 3 or a composition comprising Formula 3 that may be a pharmaceutical composition.

At least one embodiment provides a method of treating cancer in a subject in need thereof, comprising administering to the subject a pharmaceutical composition comprising a compound of Formula 3. A related embodiment provides a method of treating cancer in a subject in need thereof, comprising administering to the subject a pharmaceutical composition comprising a compound of Formula 3. A related embodiment provides use of a compound, composition, or pharmaceutical composition comprising the compound of Formula 3 in manufacture of a medicament for treating cancer or neoplastic disease, wherein the medicament is administered to a patient in need thereof. The cancer or neoplastic disease being treated, or for which the medicament is manufactured, may be prostate cancer, breast cancer, bladder cancer, lung cancer, melanoma, retinoblastoma, or multiple endocrine neoplasia type 1.

At least one embodiment provides a compound of Formula 4:

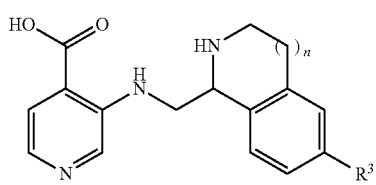

Formula 4 wherein a compound of Formula 4 includes isomers and pharmaceutically acceptable salts thereof, and wherein:
n is 0, 1, or 2; and
$R^3$ is $N(R)(R^9)$, N(R)C(O), C(O)N(R), or optionally substituted $C_3$-$C_7$ carbocyclyl, $C_3$-$C_7$ carbocyclyloxy, $C_4$-$C_{12}$ carbocyclylalkyl, $C_4$-$C_{12}$ carbocyclylalkoxy, $C_6$-$C_{10}$ aryl, $C_6$-$C_{10}$ aryloxy, $C_6$-$C_{10}$ aryl-S, $C_6$-$C_{10}$ aryl-$SO_2$, $C_7$-$C_{14}$ aralkoxy, heteroaryl, heteroaryloxy, heterocyclyl, heterocyclyloxy, heterocyclylalkyl, heterocyclylalkoxy, or heteroaryl-S, wherein
  R is hydrogen or optionally substituted $C_1$-$C_6$ alkyl, and
  $R^9$ is optionally substituted $C_3$-$C_7$ carbocyclyl, $C_3$-$C_7$ carbocyclyloxy, $C_4$-$C_{12}$ carbocyclylalkyl, $C_4$-$C_{12}$ carbocyclylalkoxy, $C_6$-$C_{10}$ aryl, $C_6$-$C_{10}$ aryloxy, $C_6$-$C_{10}$ aryl-S—, $C_7$-$C_{14}$ aralkoxy, heteroaryl, heteroaryloxy, heterocyclyl, heterocyclyloxy, heterocyclylalkyl, heterocyclylalkoxy, $C_6$-$C_{10}$ aryl-$SO_2$, or heteroaryl-S.

In one embodiment of a compound of Formula 4, n is 0. In one embodiment of a compound of Formula 4, n is 1. In one embodiment of a compound of Formula 4, $R^3$ is N(R)($R^9$). In one embodiment of a compound of Formula 4, R is methyl. In one embodiment of a compound of Formula 4, $R^3$ is N(R)($R^9$), in which R is methyl, and $R^9$ is optionally substituted alkylphenyl or haloalkyloxyphenyl. In one embodiment of a compound of Formula 4, $R^9$ is methylphenyl (tolyl) or isopropylphenyl. In one embodiment of a compound of Formula 4, $R^3$ is N(R)($R^9$), in which R is methyl, and $R^9$ optionally substituted methylphenyl. In one embodiment of a compound of Formula 4, $R^3$ is N(R)($R^9$), in which R is methyl, and $R^9$ isopropylphenyl. In one embodiment of a compound of Formula 4, $R^9$ is trifluoroethoxyphenyl. In one embodiment of a compound of Formula 4, $R^3$ is substituted $C_6$-$C_{10}$ aryl. In one embodiment of a compound of Formula 4, $R^3$ is substituted methylphenyl. In one embodiment of a compound of Formula 4, $R^3$ is substituted cycloalkyloxyphenyl. In one embodiment of a compound of Formula 4, $R^3$ is substituted $C_4$-$C_{12}$ carbocyclylalkoxy. In one embodiment of a compound of Formula 4, $R^3$ is cycloalkyloxymethylphenyl. In one embodiment of a compound of Formula 4, $R^3$ is (cyclopropylmethoxy)methylphenyl. Unless otherwise specified, the $R^3$ and $R^9$ substituents of a compound of Formula 4 include those described for Formula 2.

At least one embodiment provides a composition comprising a compound of Formula 4. In at least one embodiment, the composition is a pharmaceutical composition comprising at least one pharmaceutically acceptable excipient and a compound of Formula 4.

At least one embodiment provides a method of inhibiting a histone demethylase enzyme comprising contacting the histone demethylase enzyme with a compound of Formula 4 or a composition comprising a compound of Formula 4.

At least one embodiment provides a method of treating cancer in a subject in need thereof, comprising administering to the subject a pharmaceutical composition comprising a compound of Formula 4. A related embodiment provides a method of treating cancer in a subject in need thereof, comprising administering to the subject a pharmaceutical composition comprising a compound of Formula 4. A related embodiment provides use of a compound, composition, or pharmaceutical composition comprising the compound of Formula 4 in manufacture of a medicament for treating cancer or neoplastic disease, wherein the medicament is administered to a patient in need thereof. The cancer or neoplastic disease being treated, or for which the medicament is manufactured, may be prostate cancer, breast cancer, bladder cancer, lung cancer, melanoma, retinoblastoma, or multiple endocrine neoplasia type 1.

In some embodiments, the substituted pyridine derivative compound as described herein has the structure provided in Table 1, in which "Example" refers to the chemical synthesis example described in the Examples herein:

TABLE 1

| Example | Formula | Name |
| --- | --- | --- |
| 1A | | 3-[({(1S)-6-[methyl(4-methylphenyl)amino]-1,2,3,4-tetrahydroisoquinolyl}methyl)amino]pyridine-4-carboxylic acid |
| 1B | | 3-[({(1R)-6-[methyl(4-methylphenyl)amino]-1,2,3,4-tetrahydroisoquinolyl}methyl)amino]pyridine-4-carboxylic acid |
| 2A | | 3-[({(1S)-6-[2-methyl-4-(2,2,2-trifluoroethoxy)phenyl]-1,2,3,4-tetrahydroisoquinolyl}methyl)amino]pyridine-4-carboxylic acid |

TABLE 1-continued

| Example | Formula | Name |
|---|---|---|
| 2B | | 3-[({(1R)-6-[2-methyl-4-(2,2,2-trifluoroethoxy)phenyl]-1,2,3,4-tetrahydroisoquinolyl)methyl)amino]pyridine-4-carboxylic acid |
| 3A | | 3-{[((1S)-6-{methyl[4-isopropylphenyl]amino}-1,2,3,4-tetrahydroisoquinolyl)methyl]amino}pyridine-4-carboxylic acid |
| 3B | | 3-{[((1R)-6-{methyl[4-isopropylphenyl]amino}-1,2,3,4-tetrahydroisoquinolyl)methyl]amino}pyridine-4-carboxylic acid |
| 4A | | 3-[({(1S)-6-[4-(cyclopropylmethoxy)-2-methylphenyl]-1,2,3,4-tetrahydroisoquinolyl}methyl)amino]pyridine-4-carboxylic acid |
| 4B | | 3-[({(1R)-6-[4-(cyclopropylmethoxy)-2-methylphenyl]-1,2,3,4-tetrahydroisoquinolyl}methyl)amino]pyridine-4-carboxylic acid |
| 5A | | 3-[({(1S)-5-[methyl(4-tolyl)amino]isoindolinyl}methyl)amino]pyridine-4-carboxylic acid |

TABLE 1-continued

| Example | Formula | Name |
|---|---|---|
| 5B | | 3-[({(1R)-5-[methyl(4-tolyl)amino] isoindolinyl}methyl)amino] pyridine-4-carboxylic acid |
| 6A | | 3-{[((1S)-5-{methyl[4-isopropylphenyl] amino}isoindolinyl)methyl]amino}pyridine-4-carboxylic acid |
| 6B | | 3-{[((1R)-5-{methyl[4-isopropylphenyl] amino}isoindolinyl)methyl]amino}pyridine-4-carboxylic acid |
| 7A | | 3-[({(1S)-5-[2-methyl-4-(2,2,2-trifluoro-ethoxy)phenyl]isoindolinyl}methyl) amino]pyridine-4-carboxylic acid |
| 7B | | 3-[({(1R)-5-[2-methyl-4-(2,2,2-trifluoro-ethoxy)phenyl]isoindolinyl}methyl)amino] pyridine-4-carboxylic acid |
| 10A | | (R)-3-(((6-((4-ethylphenyl)(methyl)amino)-1,2,3,4-tetrahydroisoquinolin-1-yl)methyl)amino)isonicotinic acid |
| 10B | | (S)-3-(((6-((4-ethylphenyl)(methyl)amino)-1,2,3,4-tetrahydroisoquinolin-1-yl) methyl)amino)isonicotinic acid |

TABLE 1-continued

| Example | Formula | Name |
|---|---|---|
| 11A | | (R)-3-(((2-methyl-6-(methyl(p-tolyl)amino)-1,2,3,4-tetrahydroisoquinolin-1-yl)methyl)amino)isonicotinic acid |
| 11B | | (S)-3-(((2-methyl-6-(methyl(p-tolyl)amino)-1,2,3,4-tetrahydroisoquinolin-1-yl)methyl)amino)isonicotinic acid |
| 12A | | (R)-3-(((2-methyl-6-(o-tolyl)-1,2,3,4-tetrahydroisoquinolin-1-yl)methyl)amino)isonicotinic acid |
| 12B | | (S)-3-(((2-methyl-6-(o-tolyl)-1,2,3,4-tetrahydroisoquinolin-1-yl)methyl)amino)isonicotinic acid |
| 13A | | (R)-3-(((6-((4-ethylphenyl)(methyl)amino)-2-methyl-1,2,3,4-tetrahydro-isoquinolin-1-yl)methyl)amino)isonicotinic acid |
| 13B | | (S)-3-(((6-((4-ethylphenyl)(methyl)amino)-2-methyl-1,2,3,4-tetrahydro-isoquinolin-1-yl)methyl)amino)isonicotinic acid |
| 14A | | (R)-3-(((2-methyl-6-(methyl(4-propylphenyl)amino)-1,2,3,4-tetrahydroisoquinolin-1-yl)methyl)amino)isonicotinic acid |

TABLE 1-continued

| Example | Formula | Name |
|---|---|---|
| 14B | | (S)-3-(((2-methyl-6-(methyl (4-propylphenyl)amino)-1,2,3,4-tetrahydroisoquinolin-1-yl) methyl)amino)isonicotinic acid |
| 15A | | (R)-3-(((6-(2-ethylphenyl)-2-methyl-1,2,3,4-tetrahydroisoquinolin-1-yl) methyl)amino)isonicotinic acid |
| 15B | | (S)-3-(((6-(2-ethylphenyl)-2-methyl-1,2,3,4-tetrahydroisoquinolin-1-yl) methyl)amino)isonicotinic acid |
| 16A | | (R)-3-(((6-(2-isopropylphenyl))-2-methyl-1,2,3,4-tetrahydroisoquinolin-1-yl) methyl)amino)isonicotinic acid |
| 16B | | (S)-3-(((6-(2-isopropylphenyl))-2-methyl-1,2,3,4-tetrahydroisoquinolin-1-yl) methyl)amino)isonicotinic acid |
| 17A | | (R)-3-(((6-(2,6-dimethylphenyl)-2-methyl-1,2,3,4-tetrahydroisoquinolin-1-yl) methyl)amino)isonicotinic acid |

TABLE 1-continued

| Example | Formula | Name |
|---|---|---|
| 17B | | (S)-3-(((6-(2,6-dimethylphenyl)-2-methyl-1,2,3,4-tetrahydroisoquinolin-1-yl)methyl)amino)isonicotinic acid |
| 18A | | (R)-3-(((2-methyl-5-(methyl(p-tolyl)amino)isoindolin-1-yl)methyl)amino)isonicotinic acid |
| 18B | | (S)-3-(((2-methyl-5-(methyl(p-tolyl)amino)isoindolin-1-yl)methyl)amino)isonicotinic acid |
| 19A | | (R)-3-(((5-((4-ethylphenyl)(methyl)amino)-2-methylisoindolin-1-yl)methyl)amino)isonicotinic acid |
| 19B | | (S)-3-(((5-((4-ethylphenyl)(methyl)amino)-2-methylisoindolin-1-yl)methyl)amino)isonicotinic acid |
| 20A | | (R)-3-(((2-methyl-5-(methyl(4-propylphenyl)amino)isoindolin-1-yl)methyl)amino)isonicotinic acid |

TABLE 1-continued

| Example | Formula | Name |
| --- | --- | --- |
| 20B | | (S)-3-(((2-methyl-5-(methyl (4-propylphenyl)amino)isoindolin-1-yl) methyl)amino)isonicotinic acid |
| 21A | | (R)-3-(((2-methyl-5-(o-tolyl)isoindolin-1-yl) methyl)amino)isonicotinic acid |
| 21B | | (S)-3-(((2-methyl-5-(o-tolyl)isoindolin-1-yl) methyl)amino)isonicotinic acid |
| 22A | | (R)-3-(((5-(2-ethylphenyl)-2-methyl-isoindolin-1-yl)methyl)amino) isonicotinic acid |
| 22B | | (S)-3-(((5-(2-ethylphenyl)-2-methyl-isoindolin-1-yl)methyl)amino) isonicotinic acid |
| 23A | | 3-({[(1R)-6-(thiol-3-yl)-1,2,3,4-tetrahydroisoquinolin-1-yl]methyl}amino)pyridine-4-carboxylic acid |
| 23B | | 3-({[(1S)-6-(thiol-3-yl)-1,2,3,4-tetrahydroisoquinolin-1-yl]methyl}amino)pyridine-4-carboxylic acid |

TABLE 1-continued

| Example | Formula | Name |
|---|---|---|
| 24A | | 3-({[(1R)-6-[2-fluoro-4-(2,2,2-trifluoro-ethoxy)phenyl]-1,2,3,4-tetrahydroiso-quinolin-1-yl]methyl}amino)pyridine-4-carboxylic acid |
| 24B | | 3-({[(1S)-6-[2-fluoro-4-(2,2,2-trifluoro-ethoxy)phenyl]-1,2,3,4-tetrahydroiso-quinolin-1-yl]methyl}amino)pyridine-4-carboxylic acid |
| 25A | | 3-({[(1R)-6-(2,4-difluorophenyl)-1,2,3,4-tetrahydroisoquinolin-1-yl]methyl}amino)pyridine-4-carboxylic acid |
| 25B | | 3-({[(1S)-6-(2,4-difluorophenyl)-1,2,3,4-tetrahydroisoquinolin-1-yl]methyl}amino)pyridine-4-carboxylic acid |
| 26A | | (R)-3-(((6-(4-chloro-2-fluorophenyl)-1,2,3,4-tetrahydroisoquinolin-1-yl)methyl)amino)isonicotinic acid |
| 26B | | (S)-3-(((6-(4-chloro-2-fluorophenyl)-1,2,3,4-tetrahydroisoquinolin-1-yl)methyl)amino)isonicotinic acid |

TABLE 1-continued

| Example | Formula | Name |
|---------|---------|------|
| 27A | | (R)-3-(((6-(4-isopropoxy-2-methylphenyl)-1,2,3,4-tetrahydroisoquinolin-1-yl)methyl)amino)isonicotinic acid |
| 27B | | (S)-3-(((6-(4-isopropoxy-2-methylphenyl)-1,2,3,4-tetrahydroisoquinolin-1-yl)methyl)amino)isonicotinic acid |
| 28A | | (R)-3-(((6-(4-isopropyl-2-methylphenyl)-1,2,3,4-tetrahydroisoquinolin-1-yl)methyl)amino)isonicotinic acid |
| 28B | | (S)-3-(((6-(4-isopropyl-2-methylphenyl)-1,2,3,4-tetrahydroisoquinolin-1-yl)methyl)amino)isonicotinic acid |
| 29A | | (R)-3-(((6-(4-(difluoromethoxy)-2-methylphenyl)-1,2,3,4-tetrahydroisoquinolin-1-yl)methyl)amino)isonicotinic acid |
| 29B | | (S)-3-(((6-(4-(difluoromethoxy)-2-methylphenyl)-1,2,3,4-tetrahydroisoquinolin-1-yl)methyl)amino)isonicotinic acid |

TABLE 1-continued

| Example | Formula | Name |
|---|---|---|
| 30A | | (R)-3-(((6-(2-methyl-4-propoxyphenyl)-1,2,3,4-tetrahydroisoquinolin-1-yl)methyl)amino)isonicotinic acid |
| 30B | | (S)-3-(((6-(2-methyl-4-propoxyphenyl)-1,2,3,4-tetrahydroisoquinolin-1-yl)methyl)amino)isonicotinic acid |
| 31A | | (R)-3-(((6-(4-chloro-3-fluorophenyl)-1,2,3,4-tetrahydroisoquinolin-1-yl)methyl)amino)isonicotinic acid |
| 31B | | (S)-3-(((6-(4-chloro-3-fluorophenyl)-1,2,3,4-tetrahydroisoquinolin-1-yl)methyl)amino)isonicotinic acid |
| 32A | | (R)-3-(((6-(2-fluoro-6-methoxyphenyl)-1,2,3,4-tetrahydroisoquinolin-1-yl)methyl)amino)isonicotinic acid |
| 32B | | (S)-3-(((6-(2-fluoro-6-methoxyphenyl)-1,2,3,4-tetrahydroisoquinolin-1-yl)methyl)amino)isonicotinic acid |

TABLE 1-continued

| Example | Formula | Name |
|---|---|---|
| 33A | | (R)-3-(((6-(2-methyl-4-(3,4-dihydroquinolin-1(2H)-yl)phenyl)-1,2,3,4-tetrahydro-isoquinolin-1-yl)methyl)amino)isonicotinic acid |
| 33B | | (S)-3-(((6-(2-methyl-4-(3,4-dihydroquinolin-1(2H)-yl)phenyl)-1,2,3,4-tetrahydro-isoquinolin-1-yl)methyl)amino)isonicotinic acid |
| 34A | | (R)-3-(((6-(2-methyl-4-(3,4-dihydroisoquinolin-2(1H)-yl)phenyl)-1,2,3,4-tetrahydro-isoquinolin-1-yl)methyl)amino)isonicotinic acid |
| 34B | | (S)-3-(((6-(2-methyl-4-(3,4-dihydroisoquinolin-2(1H)-yl)phenyl)-1,2,3,4-tetrahydro-isoquinolin-1-yl)methyl)amino)isonicotinic acid |
| 35A | | (R)-3-(((6-(4-isopropyl-2-methoxy-phenyl)-1,2,3,4-tetrahydro-isoquinolin-1-yl)methyl)amino)isonicotinic acid |

TABLE 1-continued

| Example | Formula | Name |
|---|---|---|
| 35B | | (S)-3-(((6-(4-isopropyl-2-methoxy-phenyl)-1,2,3,4-tetrahydro-isoquinolin-1-yl)methyl)amino)isonicotinic acid |
| 36A | | (R)-3-(((6-(2-methyl-4-(6-methyl-indolin-1-yl)phenyl)-1,2,3,4-tetrahydroiso-quinolin-1-yl)methyl)amino)isonicotinic acid |
| 36B | | (S)-3-(((6-(2-methyl-4-(6-methyl-indolin-1-yl)phenyl)-1,2,3,4-tetrahydroiso-quinolin-1-yl)methyl)amino)isonicotinic acid |
| 37A | | (R)-3-(((6-((4-cyclopropylphenyl)(methyl)amino)-1,2,3,4-tetrahydroisoquinolin-1-yl)methyl)amino)isonicotinic acid |
| 37B | | (S)-3-(((6-((4-cyclopropylphenyl)(methyl)amino)-1,2,3,4-tetrahydroisoquinolin-1-yl)methyl)amino)isonicotinic acid |

TABLE 1-continued

| Example | Formula | Name |
|---|---|---|
| 38A | | (R)-3-(((6-(methyl(4-propylphenyl)amino)-1,2,3,4-tetrahydroisoquinolin-1-yl)methyl)amino)isonicotinic acid |
| 38B | | (S)-3-(((6-(methyl(4-propylphenyl)amino)-1,2,3,4-tetrahydroisoquinolin-1-yl)methyl)amino)isonicotinic acid |
| 39A | | (R)-3-(((6-((4-isobutylphenyl)(methyl)amino)-1,2,3,4-tetrahydroisoquinolin-1-yl)methyl)amino)isonicotinic acid |
| 39B | | (S)-3-(((6-((4-isobutylphenyl)(methyl)amino)-1,2,3,4-tetrahydroisoquinolin-1-yl)methyl)amino)isonicotinic acid |
| 40A | | (R)-3-(((6-((4-hexylphenyl)(methyl)amino)-1,2,3,4-tetrahydroisoquinolin-1-yl)methyl)amino)isonicotinic acid |
| 40B | | (S)-3-(((6-((4-hexylphenyl)(methyl)amino)-1,2,3,4-tetrahydroisoquinolin-1-yl)methyl)amino)isonicotinic acid |
| 41A | | (R)-3-(((6-((4-(cyclopropylmethyl)phenyl)(methyl)amino)-1,2,3,4-tetrahydroisoquinolin-1-yl)methyl)amino)isonicotinic acid |

TABLE 1-continued

| Example | Formula | Name |
|---|---|---|
| 41B | | (S)-3-(((6-((4-(cyclopropylmethyl)phenyl)(methyl)amino)-1,2,3,4-tetrahydroisoquinolin-1-yl)methyl)amino)isonicotinic acid |
| 42A | | (R)-3-(((6-(methyl(4-(2,2,2-trifluoroethoxy)phenyl)amino)-1,2,3,4-tetrahydroisoquinolin-1-yl)methyl)amino)isonicotinic acid |
| 42B | | (S)-3-(((6-(methyl(4-(2,2,2-trifluoroethoxy)phenyl)amino)-1,2,3,4-tetrahydroisoquinolin-1-yl)methyl)amino)isonicotinic acid |
| 43A | | (R)-3-(((6-(2-methyl-4-(pyrrolidin-1-yl)phenyl)-1,2,3,4-tetrahydroisoquinolin-1-yl)methyl)amino)isonicotinic acid |
| 43B | | (R)-3-(((6-(2-methyl-4-(pyrrolidin-1-yl)phenyl)-1,2,3,4-tetrahydroisoquinolin-1-yl)methyl)amino)isonicotinic acid |
| 44A | | (R)-3-(((6-((4-isopropoxyphenyl)(methyl)amino)-1,2,3,4-tetrahydroisoquinolin-1-yl)methyl)amino)isonicotinic acid |

TABLE 1-continued

| Example | Formula | Name |
|---|---|---|
| 44B | | (S)-3-(((6-((4-isopropoxyphenyl)(methyl)amino)-1,2,3,4-tetrahydroisoquinolin-1-yl)methyl)amino)isonicotinic acid |
| 45A | | (R)-3-(((6-(methyl(4-(2,2,2-trifluoroethyl)phenyl)amino)-1,2,3,4-tetrahydroisoquinolin-1-yl)methyl)amino)isonicotinic acid |
| 45B | | (S)-3-(((6-(methyl(4-(2,2,2-trifluoroethyl)phenyl)amino)-1,2,3,4-tetrahydroisoquinolin-1-yl)methyl)amino)isonicotinic acid |
| 46A | | (R)-3-(((6-((4-chlorophenyl)(methyl)amino)-1,2,3,4-tetrahydroisoquinolin-1-yl)methyl)amino)isonicotinic acid |
| 46B | | (S)-3-(((6-((4-chlorophenyl)(methyl)amino)-1,2,3,4-tetrahydroisoquinolin-1-yl)methyl)amino)isonicotinic acid |
| 47A | | (R)-3-(((6-(2-ethylphenyl)-1,2,3,4-tetrahydroisoquinolin-1-yl)methyl)amino)isonicotinic acid |
| 47B | | (S)-3-(((6-(2-ethylphenyl)-1,2,3,4-tetrahydroisoquinolin-1-yl)methyl)amino)isonicotinic acid |

TABLE 1-continued

| Example | Formula | Name |
|---|---|---|
| 48A | | (R)-3-(((6-(2-isopropylphenyl)-1,2,3,4-tetrahydroisoquinolin-1-yl)methyl)amino)isonicotinic acid |
| 48B | | (S)-3-(((6-(2-isopropylphenyl)-1,2,3,4-tetrahydroisoquinolin-1-yl)methyl)amino)isonicotinic acid |
| 49A | | (R)-3-(((6-(2,6-dimethyl-4-(2,2,2-trifluoroethoxy)phenyl)-1,2,3,4-tetrahydroisoquinolin-1-yl)methyl)amino)isonicotinic acid |
| 49B | | (S)-3-(((6-(2,6-dimethyl-4-(2,2,2-trifluoroethoxy)phenyl)-1,2,3,4-tetrahydroisoquinolin-1-yl)methyl)amino)isonicotinic acid |
| 50A | | (R)-3-(((6-(2-(2,2,2-trifluoroethoxy)phenyl)-1,2,3,4-tetrahydroisoquinolin-1-yl)methyl)amino)isonicotinic acid |
| 50B | | (S)-3-(((6-(2-(2,2,2-trifluoroethoxy)phenyl)-1,2,3,4-tetrahydroisoquinolin-1-yl)methyl)amino)isonicotinic acid |

TABLE 1-continued

| Example | Formula | Name |
|---|---|---|
| 51A | | (R)-3-(((6-(2,6-dimethylphenyl)-1,2,3,4-tetrahydroisoquinolin-1-yl)methyl)amino)isonicotinic acid |
| 51B | | (S)-3-(((6-(2,6-dimethylphenyl)-1,2,3,4-tetrahydroisoquinolin-1-yl)methyl)amino)isonicotinic acid |
| 52A | | (R)-3-(((6-(2-cyclopropylphenyl)-1,2,3,4-tetrahydroisoquinolin-1-yl)methyl)amino)isonicotinic acid |
| 52B | | (S)-3-(((6-(2-cyclopropylphenyl)-1,2,3,4-tetrahydroisoquinolin-1-yl)methyl)amino)isonicotinic acid |
| 53A | | (R)-3-(((6-((4-(dimethylamino)phenyl)(methyl)amino)-1,2,3,4-tetrahydroisoquinolin-1-yl)methyl)amino)isonicotinic acid |
| 53B | | (S)-3-(((6-((4-(dimethylamino)phenyl)(methyl)amino)-1,2,3,4-tetrahydroisoquinolin-1-yl)methyl)amino)isonicotinic acid |
| 54A | | (R)-3-(((6-((4-cyclohexylphenyl)(methyl)amino)-1,2,3,4-tetrahydroisoquinolin-1-yl)methyl)amino)isonicotinic acid |

TABLE 1-continued

| Example | Formula | Name |
|---|---|---|
| 54B | | (S)-3-(((6-((4-cyclohexylphenyl)(methyl)amino)-1,2,3,4-tetrahydroisoquinolin-1-yl)methyl)amino)isonicotinic acid |
| 55A | | (R)-3-(((6-(methyl(4-(tetrahydro-2H-pyran-4-yl)phenyl)amino)-1,2,3,4-tetrahydro-isoquinolin-1-yl)methyl)amino)isonicotinic acid |
| 55B | | (S)-3-(((6-(methyl(4-(tetrahydro-2H-pyran-4-yl)phenyl)amino)-1,2,3,4-tetra-hydroisoquinolin-1-yl)methyl)amino)isonicotinic acid |
| 56A | | (R)-3-(((6-(methyl(4-(3,3,3-trifluoropropyl)phenyl)amino)-1,2,3,4-tetrahydroisoquinolin-1-yl)methyl)amino)isonicotinic acid |
| 56B | | (S)-3-(((6-(methyl(4-(3,3,3-trifluoropropyl)phenyl)amino)-1,2,3,4-tetrahydroisoquinolin-1-yl)methyl)amino)isonicotinic acid |
| 57A | | (R)-3-(((6-((4-(2-cyclopropylethyl)phenyl)(methyl)amino)-1,2,3,4-tetrahydroisoquinolin-1-yl)methyl)amino)isonicotinic acid |
| 57B | | (S)-3-(((6-((4-(2-cyclopropylethyl)phenyl)(methyl)amino)-1,2,3,4-tetrahydroisoquinolin-1-yl)methyl)amino)isonicotinic acid |

TABLE 1-continued

| Example | Formula | Name |
|---|---|---|
| 58A | | (R)-3-(((6-((4-cyclobutylphenyl)(methyl)amino)-1,2,3,4-tetrahydroisoquinolin-1-yl)methyl)amino)isonicotinic acid |
| 58B | | (S)-3-(((6-((4-cyclobutylphenyl)(methyl)amino)-1,2,3,4-tetrahydroisoquinolin-1-yl)methyl)amino)isonicotinic acid |
| 59A | | (R)-3-(((6-((4-cyclopentylphenyl)(methyl)amino)-1,2,3,4-tetrahydro-isoquinolin-1-yl)methyl)amino)isonicotinic acid |
| 59B | | (S)-3-(((6-((4-cyclopentylphenyl)(methyl)amino)-1,2,3,4-tetrahydro-isoquinolin-1-yl)methyl)amino)isonicotinic acid |
| 60A | | (R)-3-(((6-((4-(cyclobutylmethyl)phenyl)(methyl)amino)-1,2,3,4-tetrahydro-isoquinolin-1-yl)methyl)amino)isonicotinic acid |
| 60B | | (S)-3-(((6-((4-(cyclobutylmethyl)phenyl)(methyl)amino)-1,2,3,4-tetrahydroisoquinolin-1-yl)methyl)amino)isonicotinic acid |

TABLE 1-continued

| Example | Formula | Name |
|---|---|---|
| 61A | | (R)-3-(((6-(6-methyl-2,3-dihydrobenzofuran-5-yl)-1,2,3,4-tetrahydroisoquinolin-1-yl)methyl)amino)isonicotinic acid |
| 61B | | (S)-3-(((6-(6-methyl-2,3-dihydrobenzofuran-5-yl)-1,2,3,4-tetrahydroisoquinolin-1-yl)methyl)amino)isonicotinic acid |
| 62A | | (R)-3-(((6-(5-methyl-2,3-dihydrobenzofuran-4-yl)-1,2,3,4-tetrahydroisoquinolin-1-yl)methyl)amino)isonicotinic acid |
| 62B | | (S)-3-(((6-(5-methyl-2,3-dihydrobenzofuran-4-yl)-1,2,3,4-tetrahydroisoquinolin-1-yl)methyl)amino)isonicotinic acid |
| 63A | | (R)-3-(((5-(2-fluoro-4-(2,2,2-trifluoroethoxy)phenyl)isoindolin-1-yl)methyl)amino)isonicotinic acid |
| 63B | | (S)-3-(((5-(2-fluoro-4-(2,2,2-trifluoroethoxy)phenyl)isoindolin-1-yl)methyl)amino)isonicotinic acid |

TABLE 1-continued

| Example | Formula | Name |
|---|---|---|
| 64A | | (R)-3-(((5-(o-tolyl)isoindolin-1-yl)methyl)amino)isonicotinic acid |
| 64B | | (S)-3-(((5-(o-tolyl)isoindolin-1-yl)methyl)amino)isonicotinic acid |
| 65A | | (R)-3-(((5-((4-isopropylphenyl)(methyl)amino)isoindolin-1-yl)methyl)amino)isonicotinic acid |
| 65B | | (S)-3-(((5-((4-isopropylphenyl)(methyl)amino)isoindolin-1-yl)methyl)amino)isonicotinic acid |
| 66A | | (R)-3-(((5-(4-isopropyl-2-methylphenyl)isoindolin-1-yl)methyl)amino)isonicotinic acid |
| 66B | | (S)-3-(((5-(4-isopropyl-2-methylphenyl)isoindolin-1-yl)methyl)amino)isonicotinic acid |
| 67A | | (R)-3-(((5-((4-cyclopropylphenyl)(methyl)amino)isoindolin-1-yl)methyl)amino)isonicotinic acid |

TABLE 1-continued

| Example | Formula | Name |
|---|---|---|
| 67B | | (S)-3-(((5-((4-cyclopropylphenyl)(methyl)amino)isoindolin-1-yl)methyl)amino)isonicotinic acid |
| 68A | | (R)-3-(((5-((4-ethylphenyl)(methyl)amino)isoindolin-1-yl)methyl)amino)isonicotinic acid |
| 68B | | (S)-3-(((5-((4-ethylphenyl)(methyl)amino)isoindolin-1-yl)methyl)amino)isonicotinic acid |
| 69A | | (R)-3-(((5-(methyl(4-propylphenyl)amino)isoindolin-1-yl)methyl)amino)isonicotinic acid |
| 69B | | (S)-3-(((5-(methyl(4-propylphenyl)amino)isoindolin-1-yl)methyl)amino)isonicotinic acid |
| 70A | | (R)-3-(((5-(2-methyl-4-(pyrrolidin-1-yl)phenyl)isoindolin-1-yl)methyl)amino)isonicotinic acid |
| 70B | | (S)-3-(((5-(2-methyl-4-(pyrrolidin-1-yl)phenyl)isoindolin-1-yl)methyl)amino)isonicotinic acid |

TABLE 1-continued

| Example | Formula | Name |
|---|---|---|
| 71A | | (R)-3-(((5-(2-ethylphenyl)isoindolin-1-yl)methyl)amino)isonicotinic acid |
| 71B | | (S)-3-(((5-(2-ethylphenyl)isoindolin-1-yl)methyl)amino)isonicotinic acid |
| 72A | | (R)-3-(((5-(2-isopropylphenyl)isoindolin-1-yl)methyl)amino)isonicotinic acid |
| 72B | | (S)-3-(((5-(2-isopropylphenyl)isoindolin-1-yl)methyl)amino)isonicotinic acid |
| 73A | | (R)-3-(((5-(2-cyclopropylphenyl)isoindolin-1-yl)methyl)amino)isonicotinic acid |
| 73B | | (S)-3-(((5-(2-cyclopropylphenyl)isoindolin-1-yl)methyl)amino)isonicotinic acid |

In some embodiments, the substituted pyridine derivative compound as described herein, or a stereoisomer or pharmaceutically acceptable salt thereof, has the structure provided in Table 2:

TABLE 2

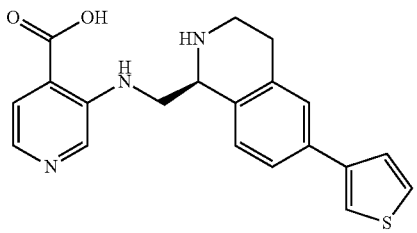 [SMILES: O=C(O)c1ccncc1NC[C@H]1NCCc2cc(-c3ccsc3)ccc21]

(S)-3-(((6-(thiol-3-yl)-1,2,3,4-tetrahydroisoquinolin-1-yl)methyl)amino)isonicotinic acid

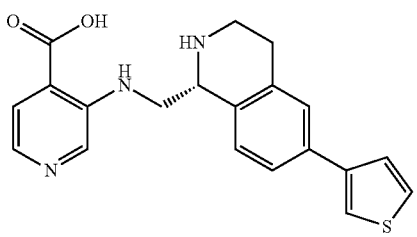 [SMILES: O=C(O)c1ccncc1NC[C@@H]1NCCc2cc(-c3ccsc3)ccc21]

(R)-3-(((6-(thiol-3-yl)-1,2,3,4-tetrahydroisoquinolin-1-yl)methyl)amino)isonicotinic acid

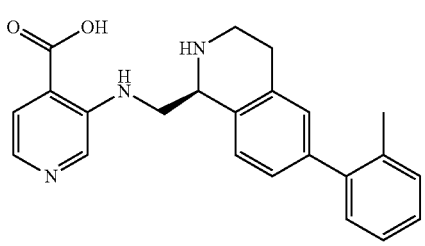 [SMILES: Cc1ccccc1-c1ccc2c(c1)CCN[C@@H]2CNc1cnccc1C(=O)O]

(S)-3-(((6-(o-tolyl)-1,2,3,4-tetrahydroisoquinolin-1-yl)methyl)amino)isonicotinic acid

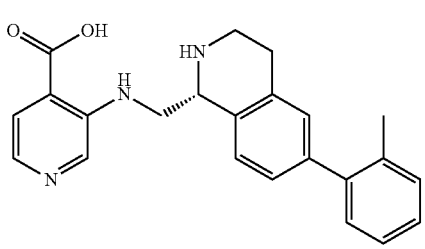 [SMILES: Cc1ccccc1-c1ccc2c(c1)CCN[C@H]2CNc1cnccc1C(=O)O]

(R)-3-(((6-(o-tolyl)-1,2,3,4-tetrahydroisoquinolin-1-yl)methyl)amino)isonicotinic acid TABLE 2-continued

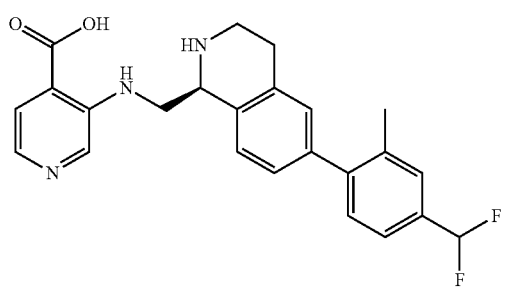 [SMILES: Cc1cc(C(F)F)ccc1-c1ccc2c(c1)CCN[C@@H]2CNc1cnccc1C(=O)O]

(S)-3-(((6-(4-(difluoromethyl)-2-methylphenyl)-1,2,3,4-tetrahydroisoquinolin-1-yl)methyl)amino) isonicotinic acid

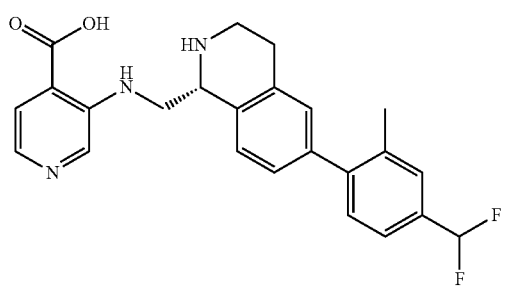 [SMILES: Cc1cc(C(F)F)ccc1-c1ccc2c(c1)CCN[C@H]2CNc1cnccc1C(=O)O]

(R)-3-(((6-(4-(difluoromethyl)-2-methyl-phenyl)-1,2,3,4-tetrahydroisoquinolin-1-yl)methyl)amino) isonicotinic acid

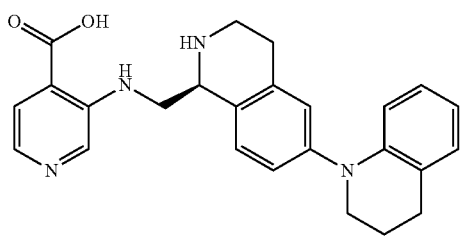 [SMILES: O=C(O)c1ccncc1NC[C@H]1NCCc2cc(N3CCCc4ccccc43)ccc21]

(S)-3-(((6-(3,4-dihydroquinolin-1(2H)-yl)-1,2,3,4-tetrahydroisoquinolin-1-yl)methyl)amino) isonicotinic acid

(R)-3-(((6-(3,4-dihydroquinolin-1(2H)-yl)-1,2,3,4-tetrahydroisoquinolin-1-yl)methyl)amino) isonicotinic acid TABLE 2-continued

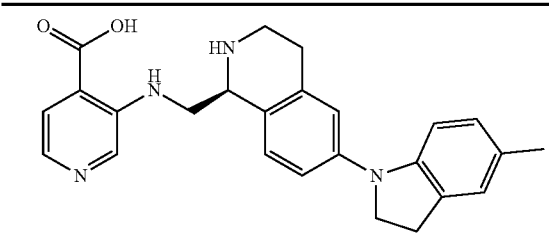

(S)-3-(((6-(5-methylindolin-1-yl)-1,2,3,4-tetrahydroisoquinolin-1-yl)methyl)amino)isonicotinic acid

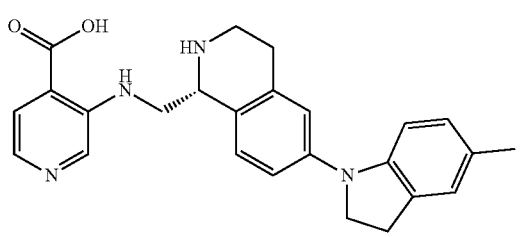 [SMILES: Cc1ccc2c(c1)CCN2c1ccc2c(c1)CCN[C@H]2CNc1cnccc1C(=O)O]

(R)-3-(((6-(5-methylindolin-1-yl)-1,2,3,4-tetrahydroisoquinolin-1-yl)methyl)amino)isonicotinic acid

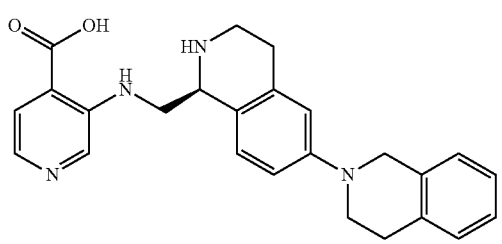 [SMILES: O=C(O)c1ccncc1NC[C@H]1NCCc2cc(N3CCc4ccccc4C3)ccc21]

(S)-3-(((1',2',3,3',4,4'-hexahydro-1H-[2,6'-bi-isoquinolin]-1'-yl)methyl)amino)isonicotinic acid

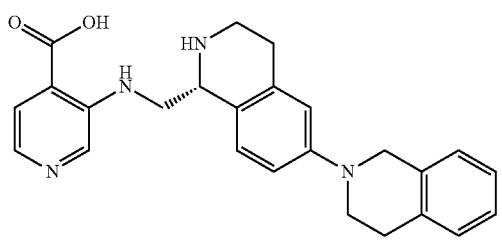 [SMILES: O=C(O)c1ccncc1NC[C@@H]1NCCc2cc(N3CCc4ccccc4C3)ccc21]

(R)-3-(((1',2',3,3',4,4'-hexahydro-1H-[2,6'-bi-isoquinolin]-1'-yl)methyl)amino)isonicotinic acid

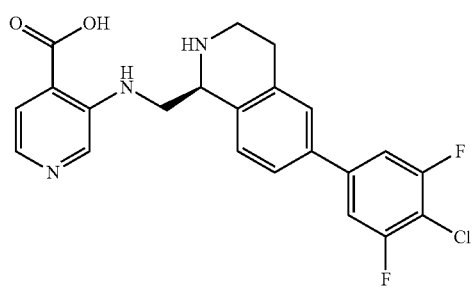 [SMILES: O=C(O)c1ccncc1NC[C@H]1NCCc2cc(-c3cc(F)c(Cl)c(F)c3)ccc21]

(S)-3-(((6-(4-chloro-3,5-difluorophenyl)-1,2,3,4-tetrahydroisoquinolin-1-yl)methyl)amino)isonicotinic acid TABLE 2-continued

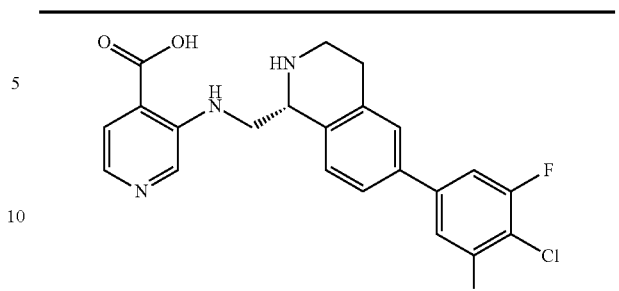

(R)-3-(((6-(4-chloro-3,5-difluorophenyl)-1,2,3,4-tetrahydroisoquinolin-1-yl)methyl)amino)isonicotinic acid

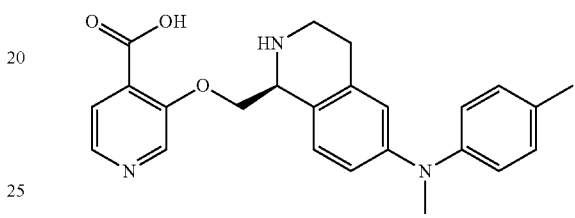

(S)-3-((6-(methyl(p-tolyl)amino)-1,2,3,4-tetrahydroisoquinolin-1-yl)methoxy)isonicotinic acid

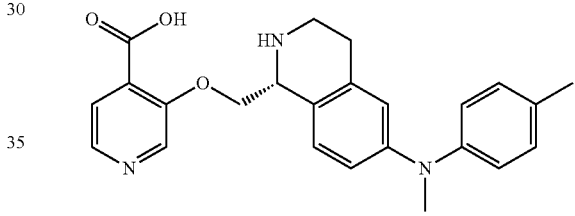

(R)-3-((6-(methyl(p-tolyl)amino)-1,2,3,4-tetrahydroisoquinolin-1-yl)methoxy)isonicotinic acid

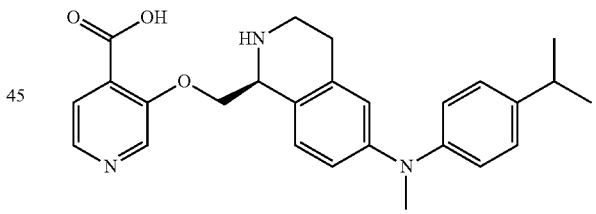

(S)-3-((6-((4-isopropylphenyl)(methyl)amino)-1,2,3,4-tetrahydroisoquinolin-1-yl)methoxy)isonicotinic acid

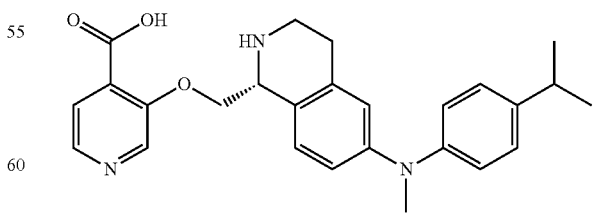

(R)-3-((6-((4-isopropylphenyl)(methyl)amino)-1,2,3,4-tetrahydroisoquinolin-1-yl)methoxy)isonicotinic acid TABLE 2-continued

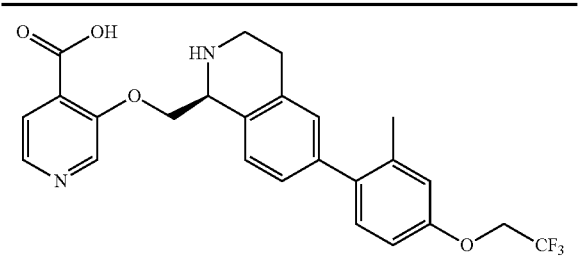

(S)-3-((6-(2-methyl-4-(2,2,2-trifluoroethoxy)
phenyl)-1,2,3,4-tetrahydroisoquinolin-1-yl)
methoxy)isonicotinic acid

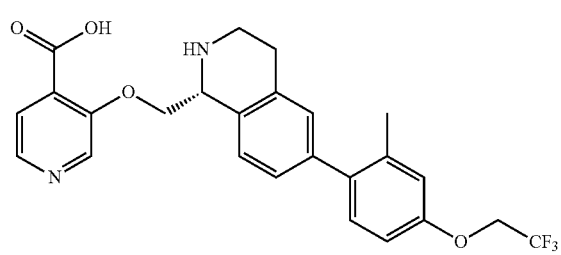 [SMILES: Cc1cc(OCC(F)(F)F)ccc1-c1ccc2c(c1)CCN[C@H]2COc1cnccc1C(=O)O]

(R)-3-((6-(2-methyl-4-(2,2,2-trifluoroethoxy)
phenyl)-1,2,3,4-tetrahydroisoquinolin-1-yl)
methoxy)isonicotinic acid

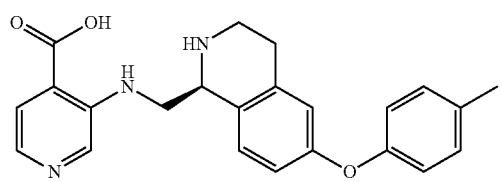 [SMILES: Cc1ccc(Oc2ccc3c(c2)CCN[C@@H]3CNc2cnccc2C(=O)O)cc1]

(S)-3-(((6-(p-tolyloxy)-1,2,3,4-tetrahydroiso-
quinolin-1-yl)methyl)amino)isonicotinic acid

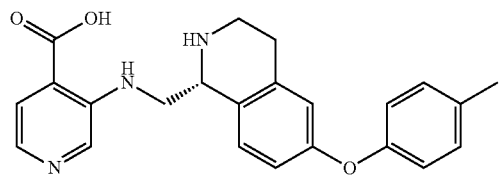 [SMILES: Cc1ccc(Oc2ccc3c(c2)CCN[C@H]3CNc2cnccc2C(=O)O)cc1]

(R)-3-(((6-(p-tolyloxy)-1,2,3,4-tetrahydroiso-
quinolin-1-yl)methyl)amino)isonicotinic acid

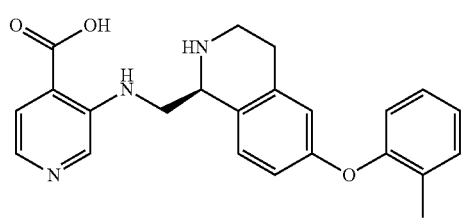 [SMILES: Cc1ccccc1Oc1ccc2c(c1)CCN[C@@H]2CNc1cnccc1C(=O)O]

(S)-3-(((6-(o-tolyloxy)-1,2,3,4-tetrahydroiso-
quinolin-1-yl)methyl)amino)isonicotinic acid TABLE 2-continued

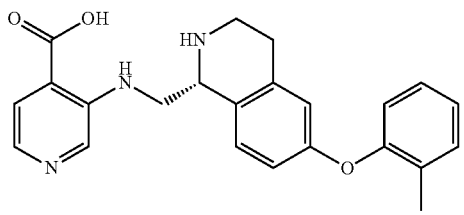 [SMILES: Cc1ccccc1Oc1ccc2c(c1)CCN[C@H]2CNc1cnccc1C(=O)O]

(R)-3-(((6-(o-tolyloxy)-1,2,3,4-tetrahydro-
isoquinolin-1-yl)methyl)amino)isonicotinic acid

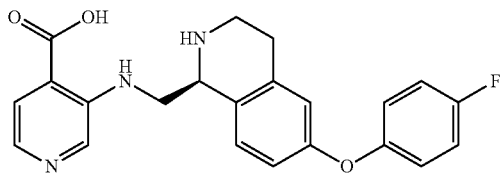 [SMILES: O=C(O)c1ccncc1NC[C@H]1NCCc2cc(Oc3ccc(F)cc3)ccc21]

(S)-3-(((6-(4-fluorophenoxy)-1,2,3,4-tetrahydro-
isoquinolin-1-yl)methyl)amino)isonicotinic acid

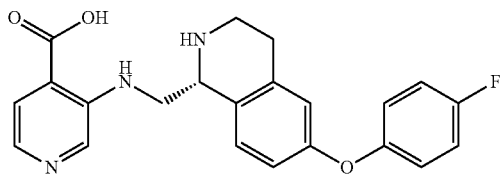 [SMILES: O=C(O)c1ccncc1NC[C@@H]1NCCc2cc(Oc3ccc(F)cc3)ccc21]

(R)-3-(((6-(4-fluorophenoxy)-1,2,3,4-tetrahydro-
isoquinolin-1-yl)methyl)amino)isonicotinic acid

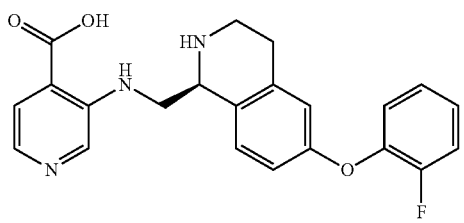 [SMILES: O=C(O)c1ccncc1NC[C@H]1NCCc2cc(Oc3ccccc3F)ccc21]

(S)-3-(((6-(2-fluorophenoxy)-1,2,3,4-tetrahydro-
isoquinolin-1-yl)methyl)amino)isonicotinic acid

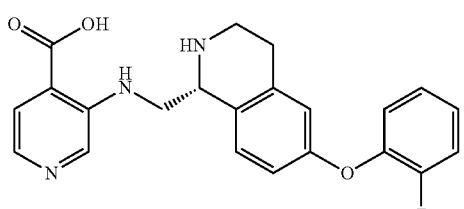

(R)-3-(((6-(2-fluorophenoxy)-1,2,3,4-tetrahydro-
isoquinolin-1-yl)methyl)amino)isonicotinic acid

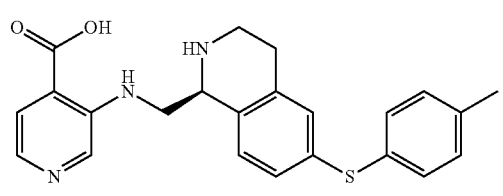 [SMILES: Cc1ccc(Sc2ccc3c(c2)CCN[C@@H]3CNc2cnccc2C(=O)O)cc1]

(S)-3-(((6-(p-tolylthio)-1,2,3,4-
tetrahydroisoquinolin-1-yl)
methyl)amino)isonicotinic acid TABLE 2-continued

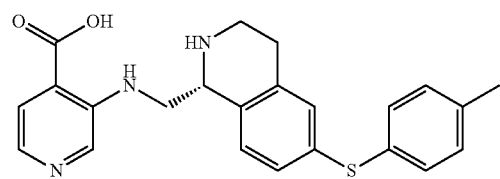 [SMILES: Cc1ccc(Sc2ccc3c(c2)CCN[C@H]3CNc2cnccc2C(=O)O)cc1]

(R)-3-(((6-(p-tolylthio)-1,2,3,4-
tetrahydroisoquinolin-1-yl)
methyl)amino)isonicotinic acid

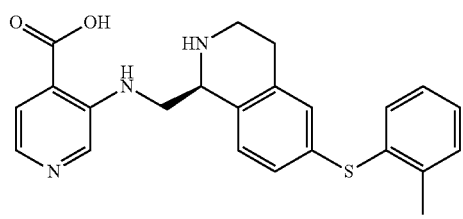 [SMILES: Cc1ccccc1Sc1ccc2c(c1)CCN[C@@H]2CNc1cnccc1C(=O)O]

(S)-3-(((6-(o-tolylthio)-1,2,3,4-tetrahydroiso-
quinolin-1-yl)methyl)amino)isonicotinic acid

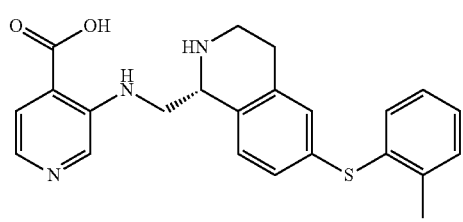 [SMILES: Cc1ccccc1Sc1ccc2c(c1)CCN[C@H]2CNc1cnccc1C(=O)O]

(R)-3-(((6-(o-tolylthio)-1,2,3,4-tetrahydroiso-
quinolin-1-yl)methyl)amino)isonicotinic acid

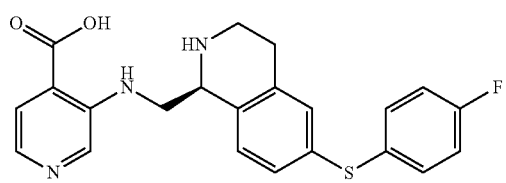 [SMILES: O=C(O)c1ccncc1NC[C@H]1NCCc2cc(Sc3ccc(F)cc3)ccc21]

(S)-3-(((6-((4-fluorophenyl)thio)-1,2,3,4-
tetrahydroisoquinolin-1-yl)methyl)amino)
isonicotinic acid

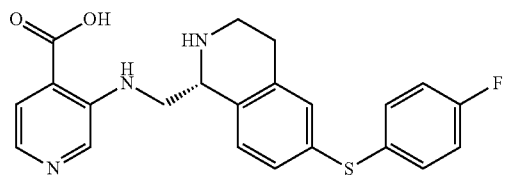 [SMILES: O=C(O)c1ccncc1NC[C@@H]1NCCc2cc(Sc3ccc(F)cc3)ccc21]

(R)-3-(((6-((4-fluorophenyl)thio)-1,2,3,4-
tetrahydroisoquinolin-1-yl)methyl)amino)
isonicotinic acid TABLE 2-continued

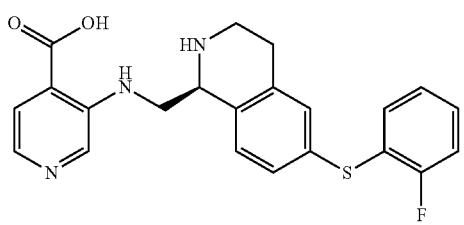 [SMILES: O=C(O)c1ccncc1NC[C@H]1NCCc2cc(Sc3ccccc3F)ccc21]

(S)-3-(((6-((2-fluorophenyl)thio)-1,2,3,4-
tetrahydroisoquinolin-1-yl)methyl)amino)
isonicotinic acid

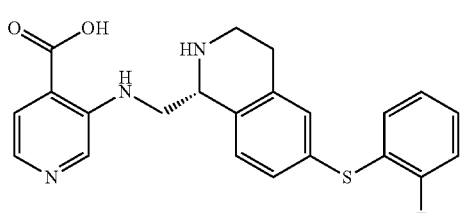

(R)-3-(((6-((2-fluorophenyl)thio)-1,2,3,4-
tetrahydroisoquinolin-1-yl)methyl)amino)
isonicotinic acid

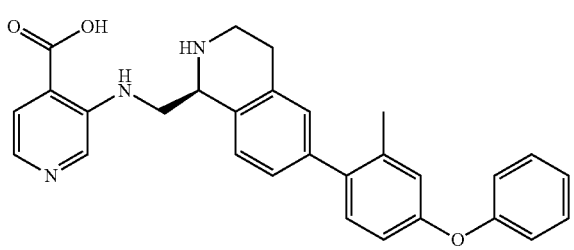 [SMILES: Cc1cc(Oc2ccccc2)ccc1-c1ccc2c(c1)CCN[C@@H]2CNc1cnccc1C(=O)O]

(S)-3-(((6-(2-methyl-4-phenoxyphenyl)-1,2,3,4-
tetrahydroisoquinolin-1-yl)methyl)amino)
isonicotinic acid

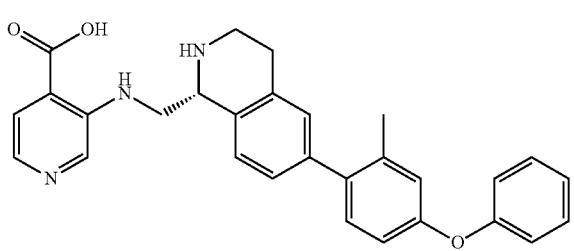 [SMILES: Cc1cc(Oc2ccccc2)ccc1-c1ccc2c(c1)CCN[C@H]2CNc1cnccc1C(=O)O]

(R)-3-(((6-(2-methyl-4-phenoxyphenyl)-1,2,3,4-
tetrahydroisoquinolin-1-yl)methyl)amino)
isonicotinic acid

(S)-3-(((5-(2,4-difluorophenyl)isoindolin-1-yl)
methyl)amino)isonicotinic acid

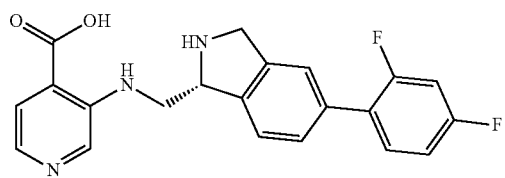 [SMILES: O=C(O)c1ccncc1NC[C@@H]1NCc2cc(-c3ccc(F)cc3F)ccc21]

(R)-3-(((5-(2,4-difluorophenyl)isoindolin-1-yl)methyl)amino)isonicotinic acid

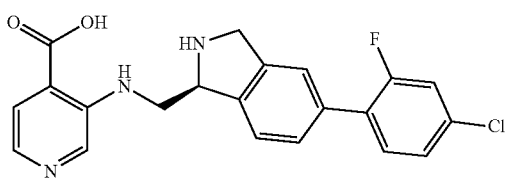 [SMILES: O=C(O)c1ccncc1NC[C@H]1NCc2cc(-c3ccc(Cl)cc3F)ccc21]

(S)-3-(((5-(4-chloro-2-fluorophenyl)isoindolin-1-yl)methyl)amino)isonicotinic acid

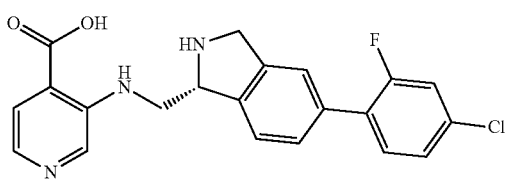 [SMILES: O=C(O)c1ccncc1NC[C@@H]1NCc2cc(-c3ccc(Cl)cc3F)ccc21]

(R)-3-(((5-(4-chloro-2-fluorophenyl)isoindolin-1-yl)methyl)amino)isonicotinic acid

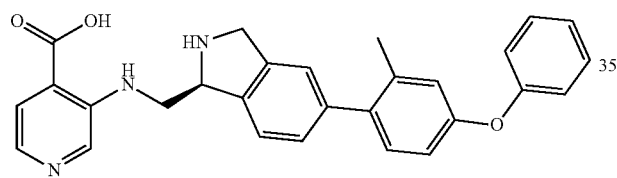

(S)-3-(((5-(2-methyl-4-phenoxyphenyl)isoindolin-1-yl)methyl)amino)isonicotinic acid

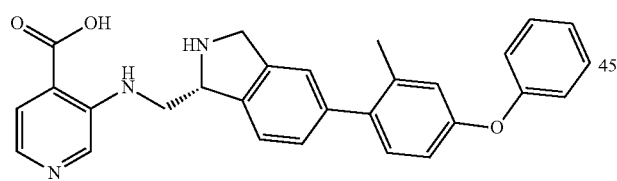

(R)-3-(((5-(2-methyl-4-phenoxyphenyl)isoindolin-1-yl)methyl)amino)isonicotinic acid

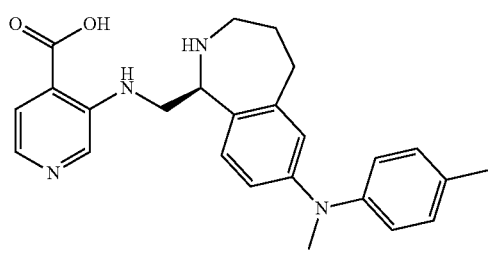 [SMILES: Cc1ccc(N(C)c2ccc3c(c2)CCCN[C@@H]3CNc2cnccc2C(=O)O)cc1]

(S)-3-(((7-(methyl(p-tolyl)amino)-2,3,4,5-tetrahydro-1H-benzo[c]azepin-1-yl)methyl)amino)isonicotinic acid

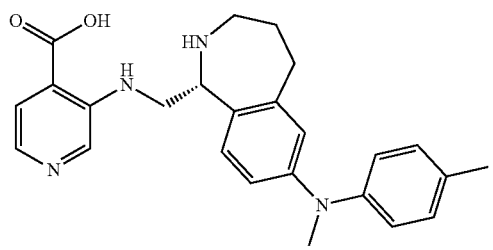 [SMILES: Cc1ccc(N(C)c2ccc3c(c2)CCCN[C@H]3CNc2cnccc2C(=O)O)cc1]

(R)-3-(((7-(methyl(p-tolyl)amino)-2,3,4,5-tetrahydro-1H-benzo[c]azepin-1-yl)methyl)amino)isonicotinic acid

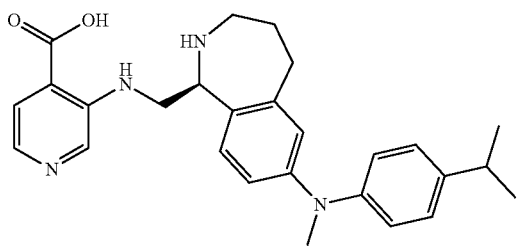 [SMILES: CC(C)c1ccc(N(C)c2ccc3c(c2)CCCN[C@@H]3CNc2cnccc2C(=O)O)cc1]

(S)-3-(((7-((4-isopropylphenyl)(methyl)amino)-2,3,4,5-tetrahydro-1H-benzo[c]azepin-1-yl)methyl)amino)isonicotinic acid

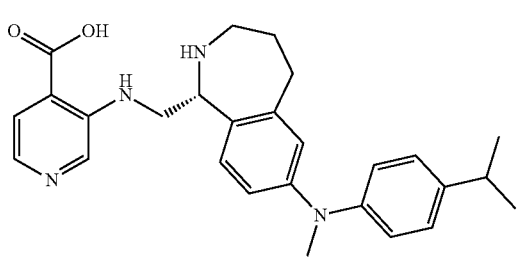 [SMILES: CC(C)c1ccc(N(C)c2ccc3c(c2)CCCN[C@H]3CNc2cnccc2C(=O)O)cc1]

(R)-3-(((7-((4-isopropylphenyl)(methyl)amino)-2,3,4,5-tetrahydro-1H-benzo[c]azepin-1-yl)methyl)amino)isonicotinic acid

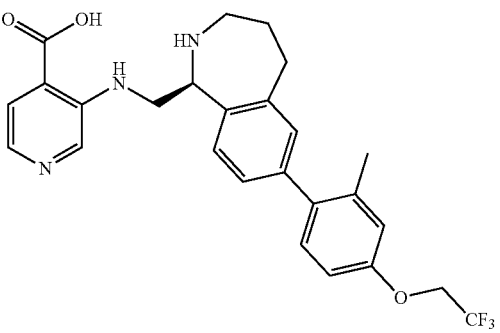 [SMILES: Cc1cc(OCC(F)(F)F)ccc1-c1ccc2c(c1)CCCN[C@@H]2CNc1cnccc1C(=O)O]

(S)-3-(((7-(2-methyl-4-(2,2,2-trifluoroethoxy)phenyl)-2,3,4,5-tetrahydro-1H-benzo[c]azepin-1-yl)methyl)amino)isonicotinic acid TABLE 2-continued

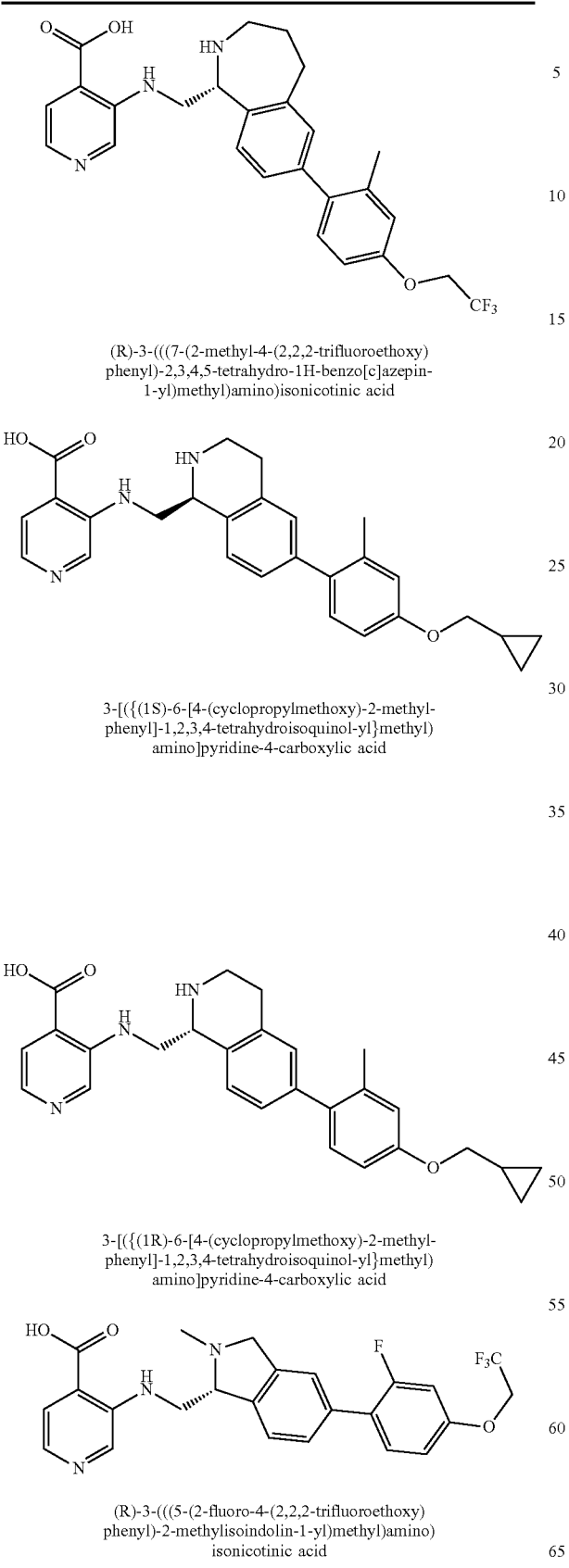

(R)-3-(((7-(2-methyl-4-(2,2,2-trifluoroethoxy)
phenyl)-2,3,4,5-tetrahydro-1H-benzo[c]azepin-
1-yl)methyl)amino)isonicotinic acid 3-[({(1S)-6-[4-(cyclopropylmethoxy)-2-methyl-
phenyl]-1,2,3,4-tetrahydroisoquinol-yl}methyl)
amino]pyridine-4-carboxylic acid 3-[({(1R)-6-[4-(cyclopropylmethoxy)-2-methyl-
phenyl]-1,2,3,4-tetrahydroisoquinol-yl}methyl)
amino]pyridine-4-carboxylic acid (R)-3-(((5-(2-fluoro-4-(2,2,2-trifluoroethoxy)
phenyl)-2-methylisoindolin-1-yl)methyl)amino)
isonicotinic acid TABLE 2-continued

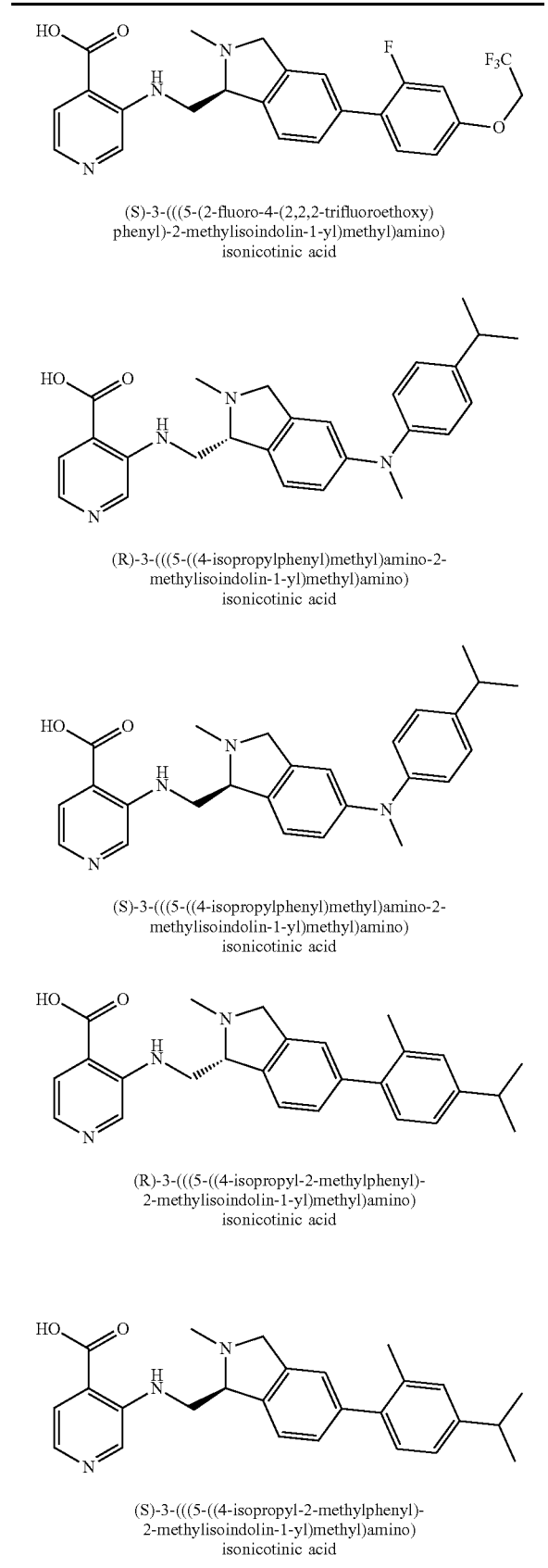

(S)-3-(((5-(2-fluoro-4-(2,2,2-trifluoroethoxy)
phenyl)-2-methylisoindolin-1-yl)methyl)amino)
isonicotinic acid (R)-3-(((5-((4-isopropylphenyl)methyl)amino-2-
methylisoindolin-1-yl)methyl)amino)
isonicotinic acid (S)-3-(((5-((4-isopropylphenyl)methyl)amino-2-
methylisoindolin-1-yl)methyl)amino)
isonicotinic acid (R)-3-(((5-((4-isopropyl-2-methylphenyl)-
2-methylisoindolin-1-yl)methyl)amino)
isonicotinic acid (S)-3-(((5-((4-isopropyl-2-methylphenyl)-
2-methylisoindolin-1-yl)methyl)amino)
isonicotinic acid TABLE 2-continued

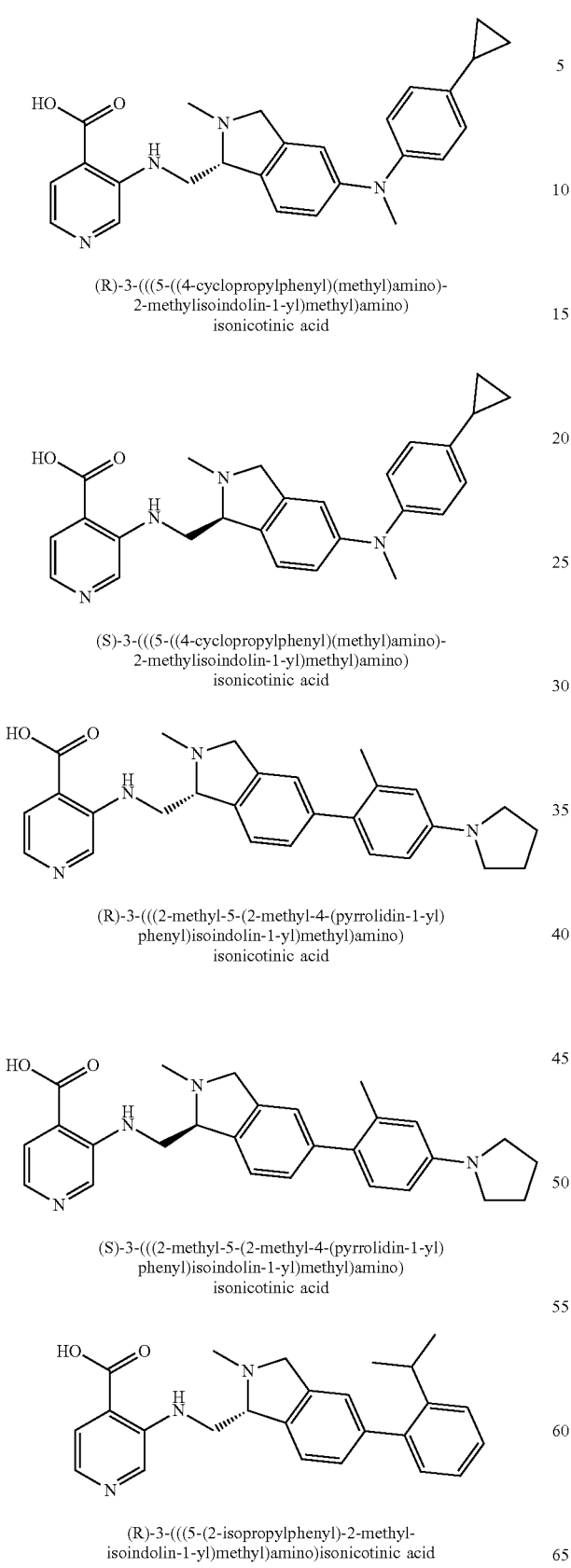

(R)-3-(((5-((4-cyclopropylphenyl)(methyl)amino)-
2-methylisoindolin-1-yl)methyl)amino)
isonicotinic acid (S)-3-(((5-((4-cyclopropylphenyl)(methyl)amino)-
2-methylisoindolin-1-yl)methyl)amino)
isonicotinic acid (R)-3-(((2-methyl-5-(2-methyl-4-(pyrrolidin-1-yl)
phenyl)isoindolin-1-yl)methyl)amino)
isonicotinic acid (S)-3-(((2-methyl-5-(2-methyl-4-(pyrrolidin-1-yl)
phenyl)isoindolin-1-yl)methyl)amino)
isonicotinic acid (R)-3-(((5-(2-isopropylphenyl)-2-methyl-
isoindolin-1-yl)methyl)amino)isonicotinic acid TABLE 2-continued

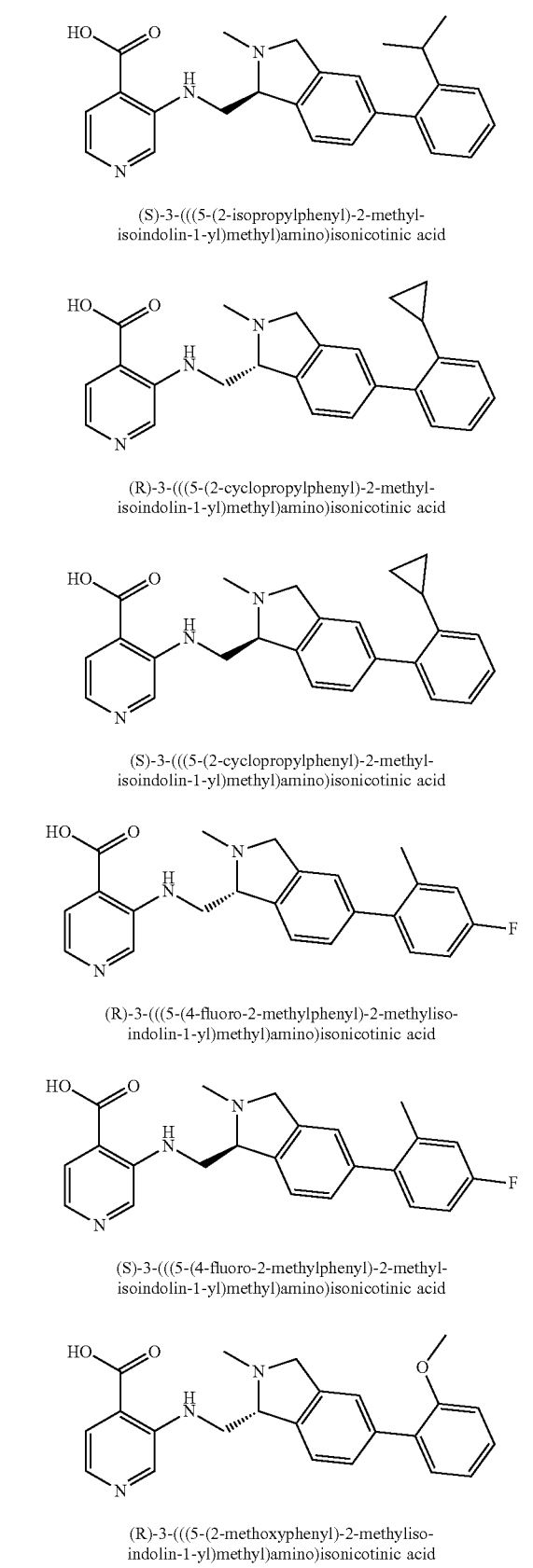

(S)-3-(((5-(2-isopropylphenyl)-2-methyl-
isoindolin-1-yl)methyl)amino)isonicotinic acid (R)-3-(((5-(2-cyclopropylphenyl)-2-methyl-
isoindolin-1-yl)methyl)amino)isonicotinic acid (S)-3-(((5-(2-cyclopropylphenyl)-2-methyl-
isoindolin-1-yl)methyl)amino)isonicotinic acid (R)-3-(((5-(4-fluoro-2-methylphenyl)-2-methyliso-
indolin-1-yl)methyl)amino)isonicotinic acid (S)-3-(((5-(4-fluoro-2-methylphenyl)-2-methyl-
isoindolin-1-yl)methyl)amino)isonicotinic acid (R)-3-(((5-(2-methoxyphenyl)-2-methyliso-
indolin-1-yl)methyl)amino)isonicotinic acid TABLE 2-continued

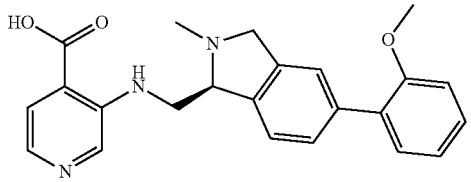 [SMILES: COc1ccccc1-c1ccc2c(c1)CN(C)[C@@H]2CNc1cnccc1C(=O)O]

(S)-3-(((5-(2-methoxyphenyl)-2-methyliso-
indolin-1-yl)methyl)amino)isonicotinic acid

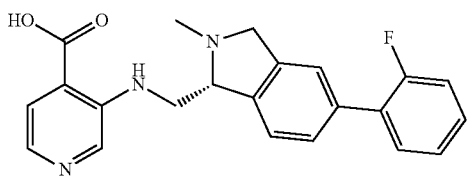 [SMILES: CN1Cc2cc(-c3ccccc3F)ccc2[C@@H]1CNc1cnccc1C(=O)O]

(R)-3-(((5-(2-fluorophenyl)-2-methyliso-indolin-
1-yl)methyl)amino)isonicotinic acid

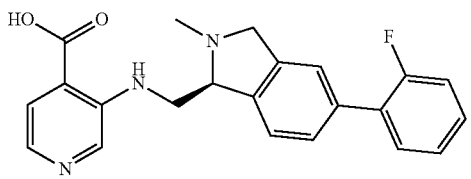 [SMILES: CN1Cc2cc(-c3ccccc3F)ccc2[C@H]1CNc1cnccc1C(=O)O]

(S)-3-(((5-(2-fluorophenyl)-2-methyliso-indolin-
1-yl)methyl)amino)isonicotinic acid

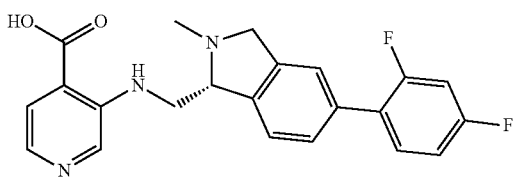 [SMILES: CN1Cc2cc(-c3ccc(F)cc3F)ccc2[C@@H]1CNc1cnccc1C(=O)O]

(R)-3-(((5-(2,4-difluorophenyl)-2-methyliso-
indolin-1-yl)methyl)amino)isonicotinic acid

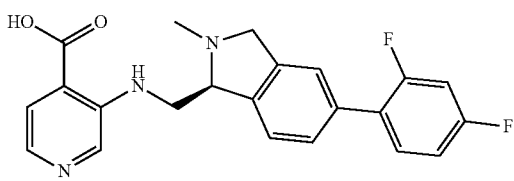 [SMILES: CN1Cc2cc(-c3ccc(F)cc3F)ccc2[C@H]1CNc1cnccc1C(=O)O]

(S)-3-(((5-(2,4-difluorophenyl)-2-methyliso-
indolin-1-yl)methyl)amino)isonicotinic acid

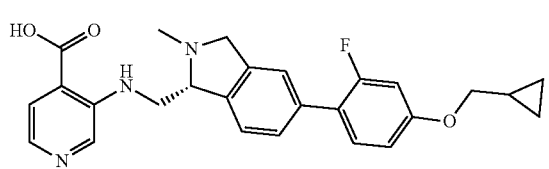 [SMILES: CN1Cc2cc(-c3ccc(OCC4CC4)cc3F)ccc2[C@@H]1CNc1cnccc1C(=O)O]

(R)-3-(((5-(4-cyclopropylmethoxy)-2-fluoro-
phenyl)-2-methylisoindolin-1-yl)methyl)amino)
isonicotinic acid TABLE 2-continued

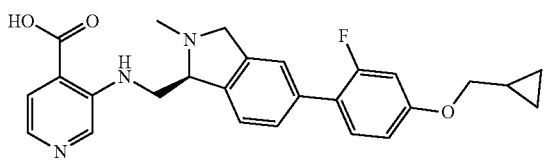 [SMILES: CN1Cc2cc(-c3ccc(OCC4CC4)cc3F)ccc2[C@H]1CNc1cnccc1C(=O)O]

(S)-3-(((5-(4-cyclopropylmethoxy)-2-fluoro-
phenyl)-2-methylisoindolin-1-yl)methyl)amino)
isonicotinic acid

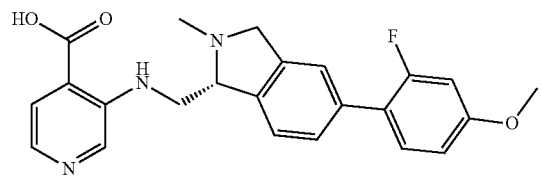 [SMILES: COc1ccc(-c2ccc3c(c2)CN(C)[C@H]3CNc2cnccc2C(=O)O)c(F)c1]

(R)-3-(((5-(2-fluoro-4-methoxyphenyl)-2-methyl-
isoindolin-1-yl)methyl)amino)isonicotinic acid

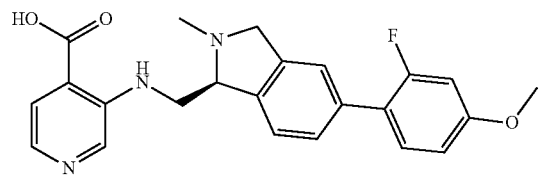 [SMILES: COc1ccc(-c2ccc3c(c2)CN(C)[C@@H]3CNc2cnccc2C(=O)O)c(F)c1]

(S)-3-(((5-(2-fluoro-4-methoxyphenyl)-2-methyl-
isoindolin-1-yl)methyl)amino)isonicotinic acid

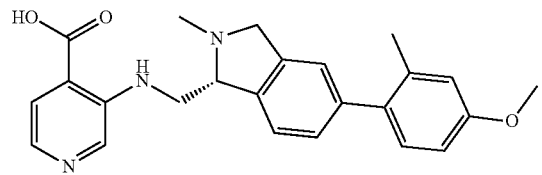 [SMILES: COc1ccc(-c2ccc3c(c2)CN(C)[C@H]3CNc2cnccc2C(=O)O)c(C)c1]

(R)-3-(((5-(4-methoxyphenyl-2-methylphenyl)-
2-methylisoindolin-1-yl)methyl)amino)
isonicotinic acid

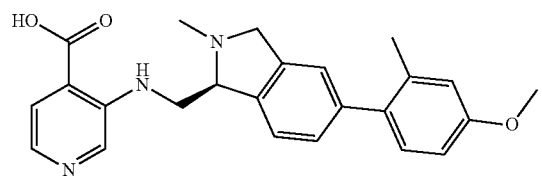 [SMILES: COc1ccc(-c2ccc3c(c2)CN(C)[C@@H]3CNc2cnccc2C(=O)O)c(C)c1]

(S)-3-(((5-(4-methoxyphenyl-2-methylphenyl)-
2-methylisoindolin-1-yl)methyl)amino)
isonicotinic acid

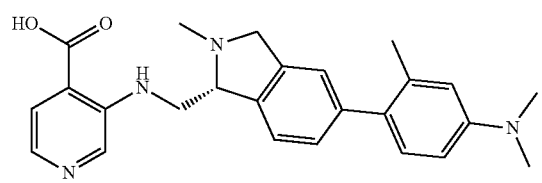 [SMILES: Cc1cc(N(C)C)ccc1-c1ccc2c(c1)CN(C)[C@H]2CNc1cnccc1C(=O)O]

(R)-3-(((5-(4-(dimethylamino)-2-methylphenyl)-
2-methylisoindolin-1-yl)methyl)amino)
isonicotinic acid TABLE 2-continued

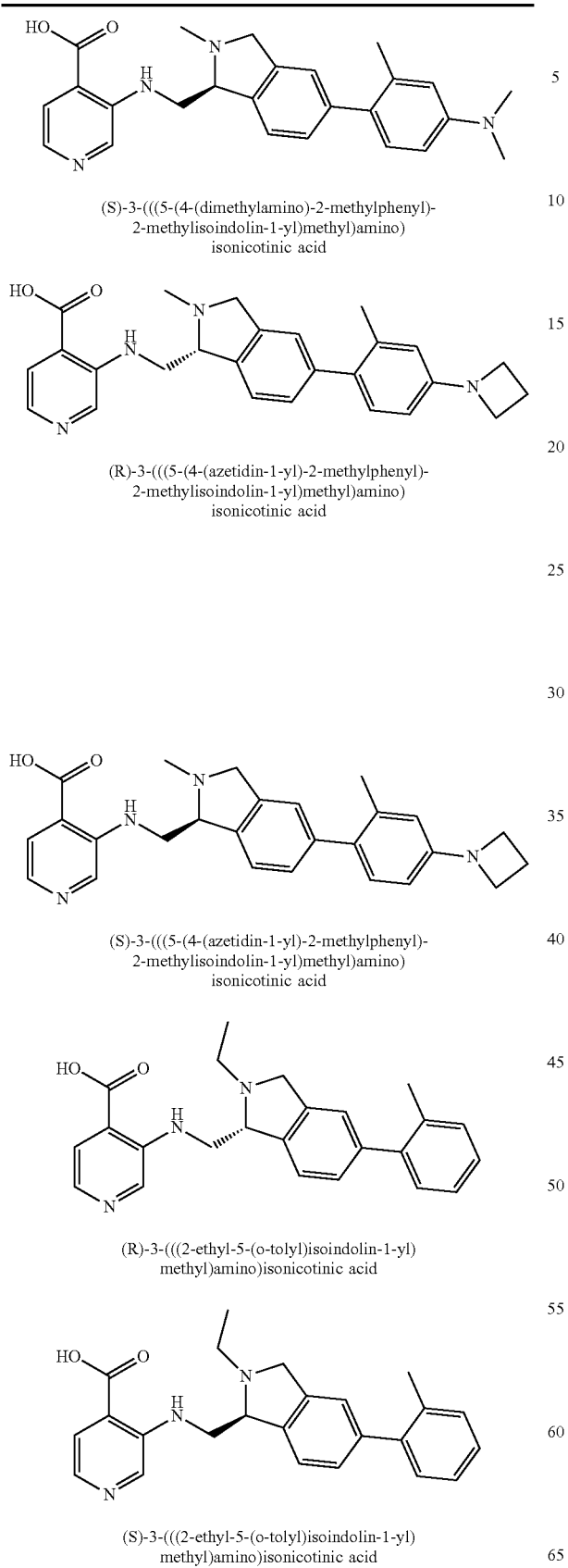

(S)-3-(((5-(4-(dimethylamino)-2-methylphenyl)-
2-methylisoindolin-1-yl)methyl)amino)
isonicotinic acid (R)-3-(((5-(4-(azetidin-1-yl)-2-methylphenyl)-
2-methylisoindolin-1-yl)methyl)amino)
isonicotinic acid (S)-3-(((5-(4-(azetidin-1-yl)-2-methylphenyl)-
2-methylisoindolin-1-yl)methyl)amino)
isonicotinic acid (R)-3-(((2-ethyl-5-(o-tolyl)isoindolin-1-yl)
methyl)amino)isonicotinic acid (S)-3-(((2-ethyl-5-(o-tolyl)isoindolin-1-yl)
methyl)amino)isonicotinic acid TABLE 2-continued

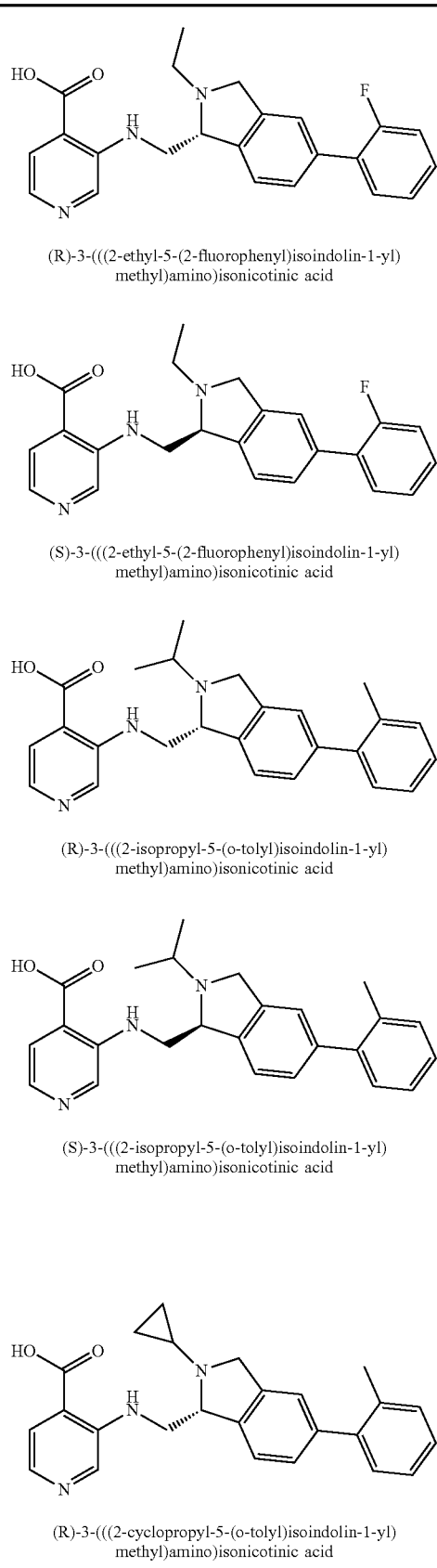

(R)-3-(((2-ethyl-5-(2-fluorophenyl)isoindolin-1-yl)
methyl)amino)isonicotinic acid (S)-3-(((2-ethyl-5-(2-fluorophenyl)isoindolin-1-yl)
methyl)amino)isonicotinic acid (R)-3-(((2-isopropyl-5-(o-tolyl)isoindolin-1-yl)
methyl)amino)isonicotinic acid (S)-3-(((2-isopropyl-5-(o-tolyl)isoindolin-1-yl)
methyl)amino)isonicotinic acid (R)-3-(((2-cyclopropyl-5-(o-tolyl)isoindolin-1-yl)
methyl)amino)isonicotinic acid TABLE 2-continued

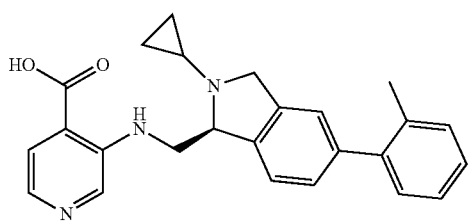 [SMILES: Cc1ccccc1-c1ccc2c(c1)CN(C1CC1)[C@@H]2CNc1cnccc1C(=O)O]

(S)-3-(((2-cyclopropyl-5-(o-tolyl)isoindolin-1-yl)
methyl)amino)isonicotinic acid

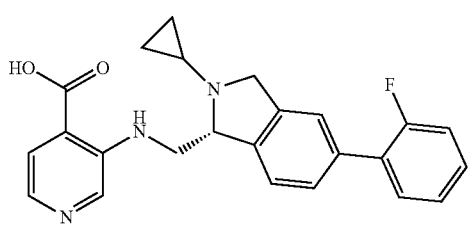 [SMILES: O=C(O)c1ccncc1NC[C@H]1c2ccc(-c3ccccc3F)cc2CN1C1CC1]

(R)-3-(((2-cyclopropyl-5-(2-fluorophenyl)
isoindolin-1-yl)methyl)amino)isonicotinic acid

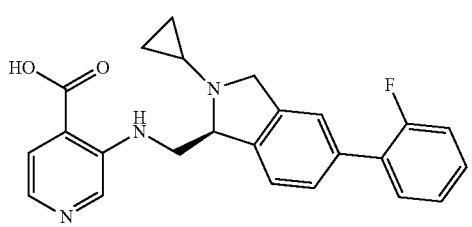 [SMILES: O=C(O)c1ccncc1NC[C@@H]1c2ccc(-c3ccccc3F)cc2CN1C1CC1]

(S)-3-(((2-cyclopropyl-5-(2-fluorophenyl)
isoindolin-1-yl)methyl)amino)isonicotinic acid

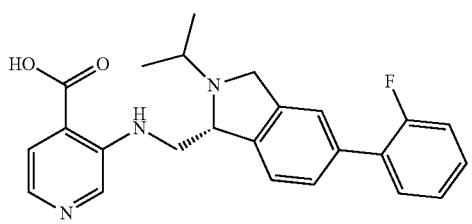

(R)-3-(((5-(2-fluorophenyl)-2-isopropyliso-
indolin-1-yl)methyl)amino)isonicotinic acid

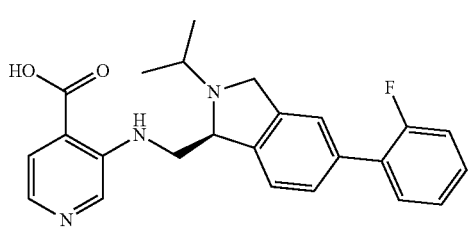 [SMILES: CC(C)N1Cc2cc(-c3ccccc3F)ccc2[C@H]1CNc1cnccc1C(=O)O]

(S)-3-(((5-(2-fluorophenyl)-2-isopropyliso-
indolin-1-yl)methyl)amino)isonicotinic acid TABLE 2-continued

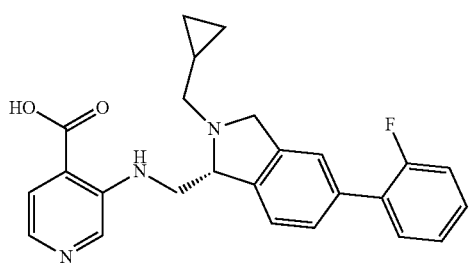 [SMILES: O=C(O)c1ccncc1NC[C@H]1c2ccc(-c3ccccc3F)cc2CN1CC1CC1]

(R)-3-(((2-(cyclopropylmethyl)-5-(2-fluorophenyl)
isoindolin-1-yl)methyl)amino)isonicotinic acid

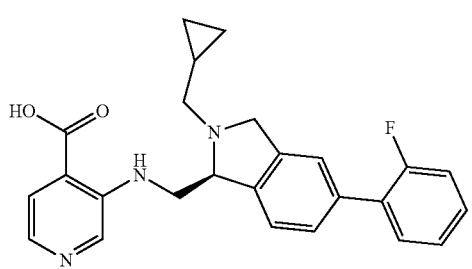 [SMILES: O=C(O)c1ccncc1NC[C@@H]1c2ccc(-c3ccccc3F)cc2CN1CC1CC1]

(S)-3-(((2-(cyclopropylmethyl)-5-(2-fluorophenyl)
isoindolin-1-yl)methyl)amino)isonicotinic acid

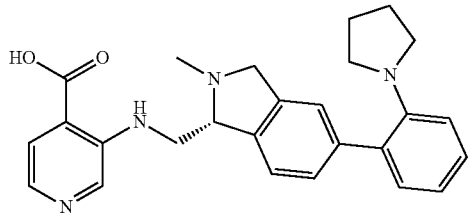 [SMILES: CN1Cc2cc(-c3ccccc3N3CCCC3)ccc2[C@@H]1CNc1cnccc1C(=O)O]

(R)-3-(((2-methyl-5-(2-pyrrolidin-1-yl)phenyl)
isoindolin-1-yl)methyl)amino)isonicotinic acid

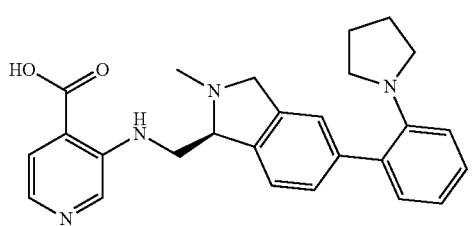 [SMILES: CN1Cc2cc(-c3ccccc3N3CCCC3)ccc2[C@H]1CNc1cnccc1C(=O)O]

(S)-3-(((2-methyl-5-(2-pyrrolidin-1-yl)phenyl)
isoindolin-1-yl)methyl)amino)isonicotinic acid

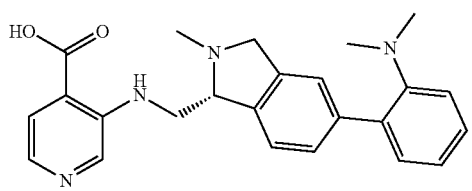 [SMILES: CN(C)c1ccccc1-c1ccc2c(c1)CN(C)[C@H]2CNc1cnccc1C(=O)O]

(R)-3-(((5-(2-dimethylamino)phenyl)isoindolin-
1-yl)methyl)amino)isonicotinic acid TABLE 2-continued

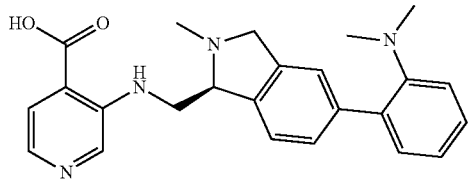 [SMILES: CN(C)c1ccccc1-c1ccc2c(c1)CN(C)[C@@H]2CNc1cnccc1C(=O)O]

(S)-3-(((5-(2-dimethylamino)phenyl)isoindolin-1-yl)methyl)amino)isonicotinic acid

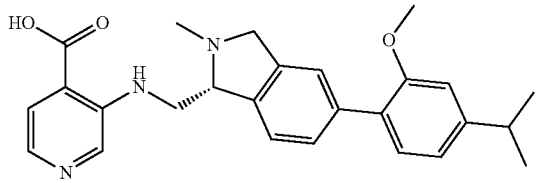 [SMILES: COc1cc(C(C)C)ccc1-c1ccc2c(c1)CN(C)[C@H]2CNc1cnccc1C(=O)O]

(R)-3-(((5-(4-isopropyl-2-methoxyphenyl)-2-methylisoindolin-1-yl)methyl)amino)
isonicotinic acid

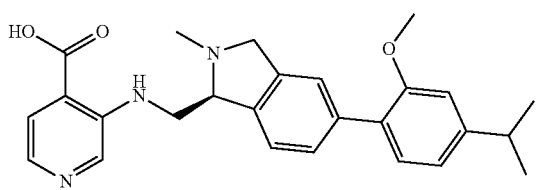 [SMILES: COc1cc(C(C)C)ccc1-c1ccc2c(c1)CN(C)[C@@H]2CNc1cnccc1C(=O)O]

(S)-3-(((5-(4-isopropyl-2-methoxyphenyl)-2-methylisoindolin-1-yl)methyl)amino)
isonicotinic acid

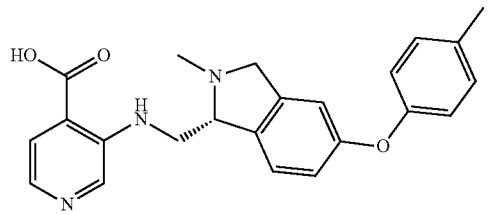 [SMILES: Cc1ccc(Oc2ccc3c(c2)CN(C)[C@H]3CNc2cnccc2C(=O)O)cc1]

(R)-3-(((2-methyl-5-(p-tolyloxy)isoindolin-1-yl)methyl)amino)isonicotinic acid

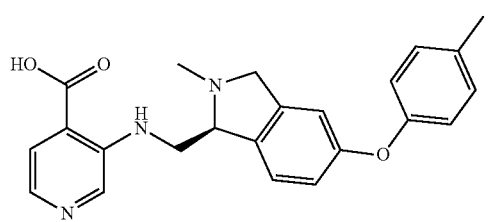 [SMILES: Cc1ccc(Oc2ccc3c(c2)CN(C)[C@@H]3CNc2cnccc2C(=O)O)cc1]

(S)-3-(((2-methyl-5-(p-tolyloxy)isoindolin-1-yl)methyl)amino)isonicotinic acid

TABLE 2-continued

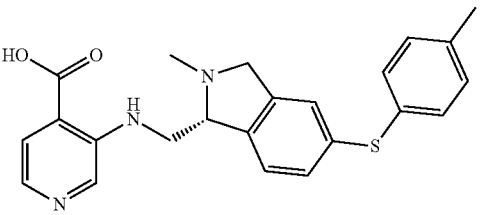 [SMILES: Cc1ccc(Sc2ccc3c(c2)CN(C)[C@H]3CNc2cnccc2C(=O)O)cc1]

(R)-3-(((2-methyl-5-(p-tolylthio)isoindolin-1-yl)methyl)amino)isonicotinic acid

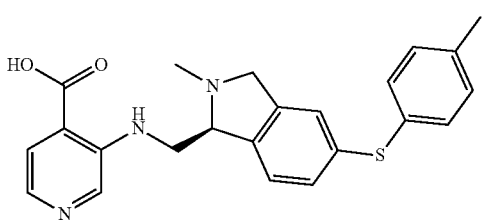 [SMILES: Cc1ccc(Sc2ccc3c(c2)CN(C)[C@@H]3CNc2cnccc2C(=O)O)cc1]

(S)-3-(((2-methyl-5-(p-tolylthio)isoindolin-1-yl)methyl)amino)isonicotinic acid

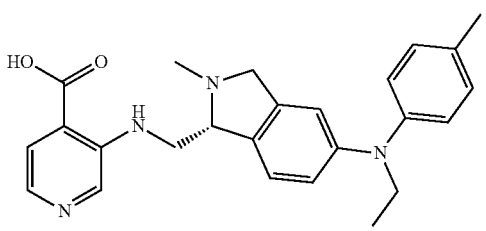 [SMILES: CCN(c1ccc(C)cc1)c1ccc2c(c1)CN(C)[C@H]2CNc1cnccc1C(=O)O]

(R)-3-(((5-(ethyl(p-tolyl)amino)-2-methyliso-indolin-1-yl)methyl)amino)isonicotinic acid

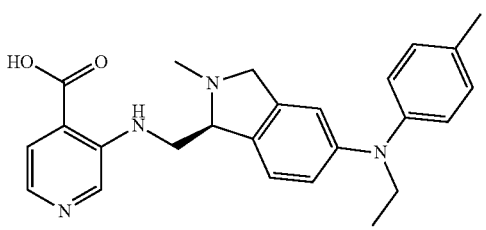 [SMILES: CCN(c1ccc(C)cc1)c1ccc2c(c1)CN(C)[C@@H]2CNc1cnccc1C(=O)O]

(S)-3-(((5-(ethyl(p-tolyl)amino)-2-methyliso-indolin-1-yl)methyl)amino)isonicotinic acid

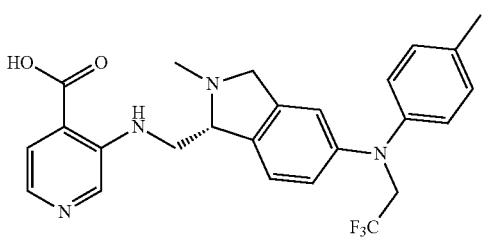 [SMILES: Cc1ccc(N(CC(F)(F)F)c2ccc3c(c2)CN(C)[C@H]3CNc2cnccc2C(=O)O)cc1]

(R)-3-(((2-methyl-5-(p-tolyl(2,2,2-trifluoro-ethyl)amino)isoindolin-1-yl)methyl)amino)
isonicotinic acid TABLE 2-continued

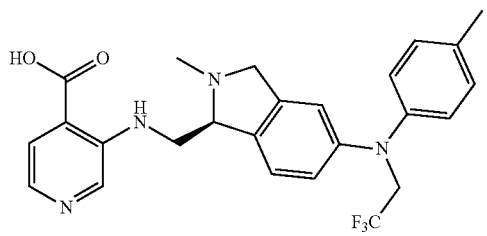 [SMILES: Cc1ccc(N(CC(F)(F)F)c2ccc3c(c2)CN(C)[C@@H]3CNc2cnccc2C(=O)O)cc1]

(S)-3-(((2-methyl-5-(p-tolyl(2,2,2-trifluoro-
ethyl)amino)isoindolin-1-yl)methyl)amino)
isonicotinic acid

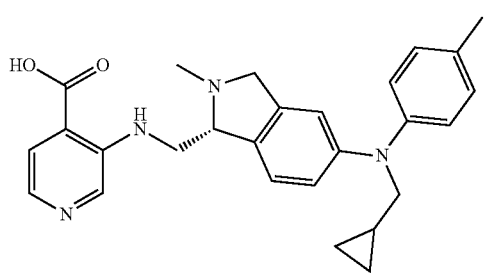 [SMILES: Cc1ccc(N(CC2CC2)c2ccc3c(c2)CN(C)[C@H]3CNc2cnccc2C(=O)O)cc1]

(R)-3-(((5-(cyclopropylmethyl)(p-tolyl)amino)-2-
methylisoindolin-1-yl)methyl)amino)
isonicotinic acid

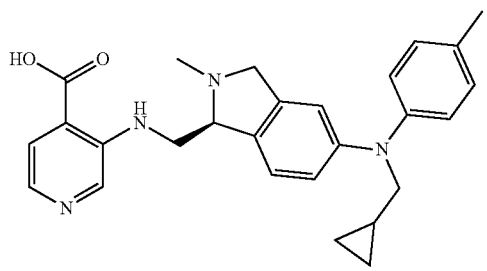 [SMILES: Cc1ccc(N(CC2CC2)c2ccc3c(c2)CN(C)[C@@H]3CNc2cnccc2C(=O)O)cc1]

(S)-3-(((5-(cyclopropylmethyl)(p-tolyl)amino)-2-
methylisoindolin-1-yl)methyl)amino)
isonicotinic acid

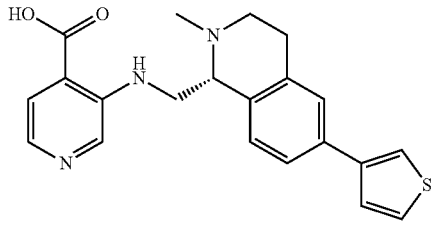 [SMILES: CN1CCc2cc(-c3ccsc3)ccc2[C@@H]1CNc1cnccc1C(=O)O]

(R)-3-(((2-methyl-6-(thiophen-3-yl)-1,2,3,4-
tetrahydroisoquinolin-1-yl)methyl)amino)
isonicotinic acid

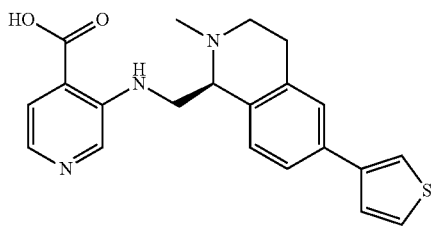 [SMILES: CN1CCc2cc(-c3ccsc3)ccc2[C@H]1CNc1cnccc1C(=O)O]

(S)-3-(((2-methyl-6-(thiophen-3-yl)-1,2,3,4-
tetrahydroisoquinolin-1-yl)methyl)amino)
isonicotinic acid TABLE 2-continued

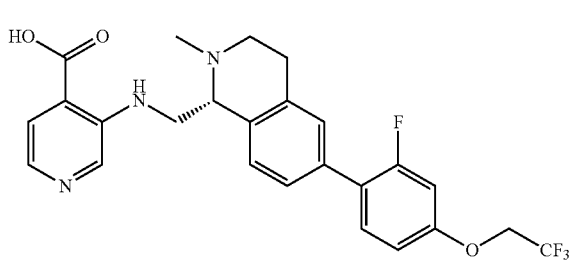 [SMILES: CN1CCc2cc(-c3ccc(OCC(F)(F)F)cc3F)ccc2[C@@H]1CNc1cnccc1C(=O)O]

(R)-3-(((6-(2-fluoro-4-(2,2,2-trifluroethoxy)
phenyl)-2-methyl)-1,2,3,4-tetrahydroiso-quinolin-
1-yl)methyl)amino)isonicotinic acid

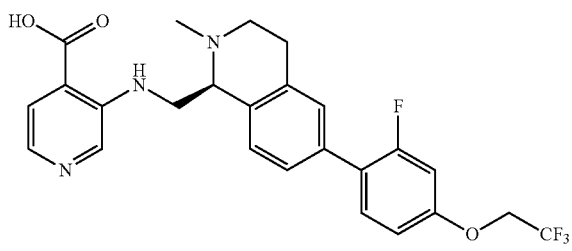 [SMILES: CN1CCc2cc(-c3ccc(OCC(F)(F)F)cc3F)ccc2[C@H]1CNc1cnccc1C(=O)O]

(S)-3-(((6-(2-fluoro-4-(2,2,2-trifluroethoxy)
phenyl)-2-methyl)-1,2,3,4-tetrahydroiso-quinolin-
1-yl)methyl)amino)isonicotinic acid

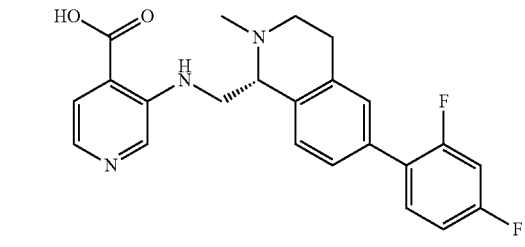 [SMILES: CN1CCc2cc(-c3ccc(F)cc3F)ccc2[C@@H]1CNc1cnccc1C(=O)O]

(R)-3-(((6-(2,4-difluorophenyl)-2-methyl-1,2,3,4-
tetrahydroisoquinolin-1-yl)methyl)amino)
isonicotinic acid

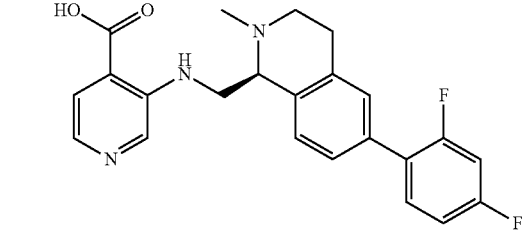 [SMILES: CN1CCc2cc(-c3ccc(F)cc3F)ccc2[C@H]1CNc1cnccc1C(=O)O]

(S)-3-(((6-(2,4-difluorophenyl)-2-methyl-1,2,3,4-
tetrahydroisoquinolin-1-yl)methyl)amino)
isonicotinic acid

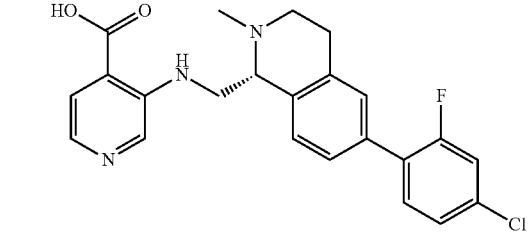 [SMILES: CN1CCc2cc(-c3ccc(Cl)cc3F)ccc2[C@@H]1CNc1cnccc1C(=O)O]

(R)-3-(((6-(4-chloro-2-fluorophenyl)-2-methyl-
1,2,3,4-tetrahydroisoquinolin-1-yl)methyl)amino)
isonicotinic acid TABLE 2-continued

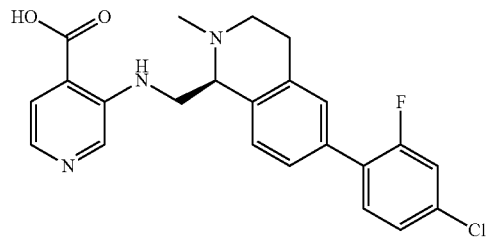 [SMILES: CN1CCc2cc(-c3ccc(Cl)cc3F)ccc2[C@H]1CNc1cnccc1C(=O)O]

(S)-3-(((6-(4-chloro-2-fluorophenyl)-2-methyl-
1,2,3,4-tetrahydroisoquinolin-1-yl)methyl)amino)
isonicotinic acid

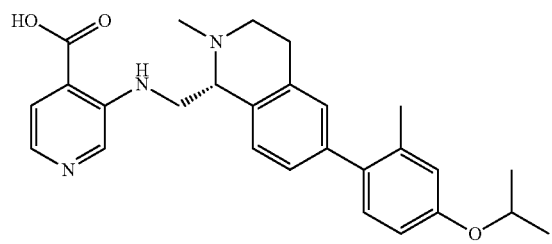 [SMILES: Cc1cc(OC(C)C)ccc1-c1ccc2c(c1)CCN(C)[C@H]2CNc1cnccc1C(=O)O]

(R)-3-(((6-(4-isopropoxy-2-methylphenyl)-2-
methyl-1,2,3,4-tetrahydroisoquinolin-1-yl)
methyl)amino)isonicotinic acid

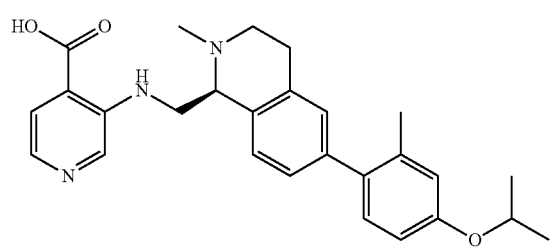

(S)-3-(((6-(4-isopropoxy-2-methylphenyl)-2-
methyl-1,2,3,4-tetrahydroisoquinolin-1-yl)
methyl)amino)isonicotinic acid

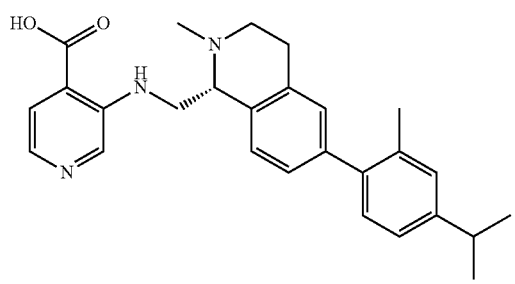 [SMILES: Cc1cc(C(C)C)ccc1-c1ccc2c(c1)CCN(C)[C@H]2CNc1cnccc1C(=O)O]

(R)-3-(((6-(4-isopropyl-2-methylphenyl)-2-methyl-
1,2,3,4-tetrahydroisoquinolin-1-yl)methyl)amino)
isonicotinic acid TABLE 2-continued

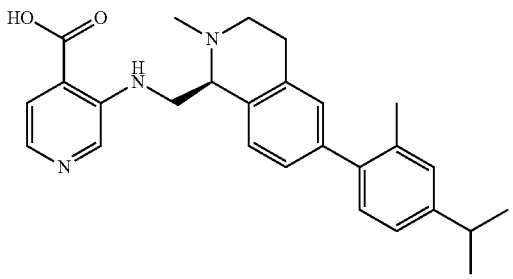 [SMILES: Cc1cc(C(C)C)ccc1-c1ccc2c(c1)CCN(C)[C@@H]2CNc1cnccc1C(=O)O]

(S)-3-(((6-(4-isopropyl-2-methylphenyl)-2-methyl-
1,2,3,4-tetrahydroisoquinolin-1-yl)methyl)amino)
isonicotinic acid

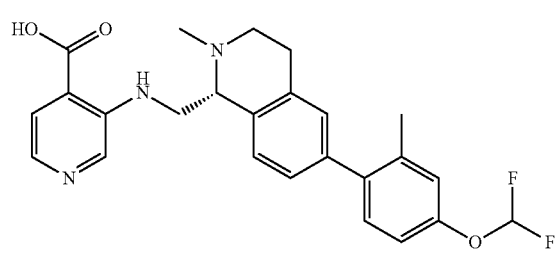 [SMILES: Cc1cc(OC(F)F)ccc1-c1ccc2c(c1)CCN(C)[C@H]2CNc1cnccc1C(=O)O]

(R)-3-(((6-(4-(difluoromethoxy)-2-methylphenyl)-
2-methyl-1,2,3,4-tetrahydro-isoquinolin-1-yl)
methyl)amino)isonicotinic acid

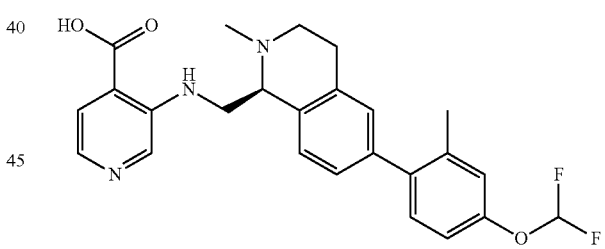

(S)-3-(((6-(4-(difluoromethoxy)-2-methylphenyl)-
2-methyl-1,2,3,4-tetrahydro-isoquinolin-1-yl)
methyl)amino)isonicotinic acid

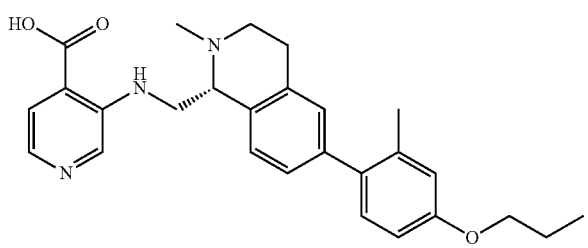 [SMILES: CCCOc1ccc(-c2ccc3c(c2)CCN(C)[C@H]3CNc2cnccc2C(=O)O)c(C)c1]

(R)-3-(((2-methyl-6-(2-methyl-4-propoxyphenyl)-
1,2,3,4-tetrahydroisoquinolin-1-yl)methyl)amino)
isonicotinic acid TABLE 2-continued

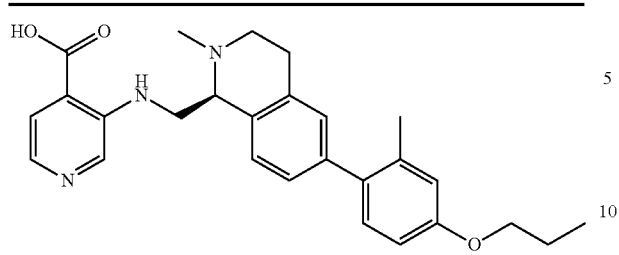

(S)-3-(((2-methyl-6-(2-methyl-4-propoxyphenyl)-
1,2,3,4-tetrahydroisoquinolin-1-yl)methyl)amino)
isonicotinic acid

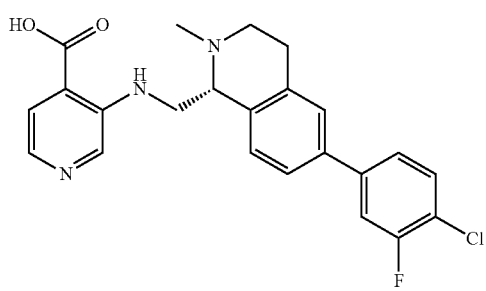 [SMILES: CN1CCc2cc(-c3ccc(Cl)c(F)c3)ccc2[C@@H]1CNc1cnccc1C(=O)O]

(R)-3-(((6-(4-chloro-3-fluorophenyl)-2-methyl-
1,2,3,4-tetrahydroisoquinolin-1-yl)methyl)amino)
isonicotinic acid

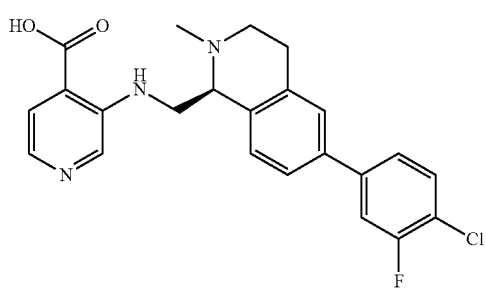 [SMILES: CN1CCc2cc(-c3ccc(Cl)c(F)c3)ccc2[C@H]1CNc1cnccc1C(=O)O]

(S)-3-(((6-(4-chloro-3-fluorophenyl)-2-methyl-
1,2,3,4-tetrahydroisoquinolin-1-yl)methyl)amino)
isonicotinic acid

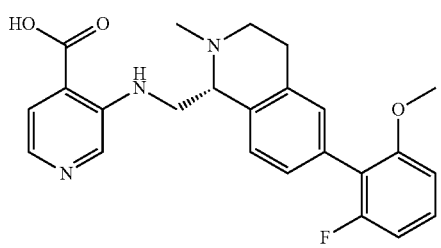 [SMILES: COc1cccc(F)c1-c1ccc2c(c1)CCN(C)[C@H]2CNc1cnccc1C(=O)O]

(R)-3-(((6-(2-fluoro-6-methoxyphenyl)-2-methyl-
1,2,3,4-tetrahydroisoquinolin-1-yl)methyl)amino)
isonicotinic acid TABLE 2-continued

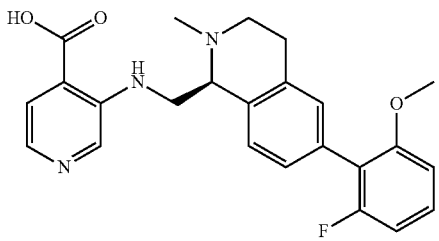 [SMILES: COc1cccc(F)c1-c1ccc2c(c1)CCN(C)[C@@H]2CNc1cnccc1C(=O)O]

(S)-3-(((6-(2-fluoro-6-methoxyphenyl)-2-methyl-
1,2,3,4-tetrahydroisoquinolin-1-yl)methyl)amino)
isonicotinic acid

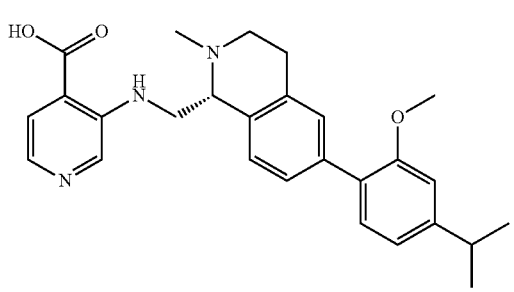 [SMILES: COc1cc(C(C)C)ccc1-c1ccc2c(c1)CCN(C)[C@H]2CNc1cnccc1C(=O)O]

(R)-3-(((6-(4-isopropyl-2-methoxyphenyl)-2-
methyl-1,2,3,4-tetrahydroisoquinolin-1-yl)methyl)
amino)isonicotinic acid

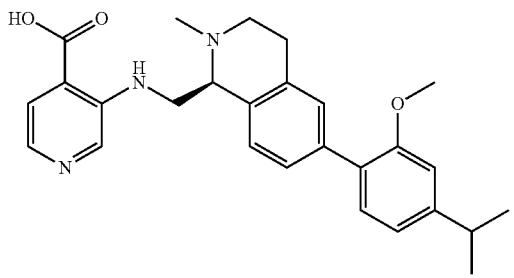 [SMILES: COc1cc(C(C)C)ccc1-c1ccc2c(c1)CCN(C)[C@@H]2CNc1cnccc1C(=O)O]

(S)-3-(((6-(4-isopropyl-2-methoxyphenyl)-2-
methyl-1,2,3,4-tetrahydroisoquinolin-1-yl)methyl)
amino)isonicotinic acid

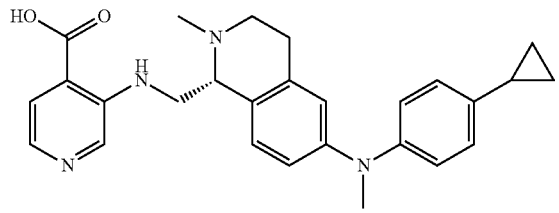 [SMILES: CN(c1ccc(C2CC2)cc1)c1ccc2c(c1)CCN(C)[C@H]2CNc1cnccc1C(=O)O]

(R)-3-(((6-(4-cyclopropylphenyl)(methyl)amino)-
2-methyl-1,2,3,4-tetrahydroiso-quinolin-1-yl)
methyl)amino)isonicotinic acid

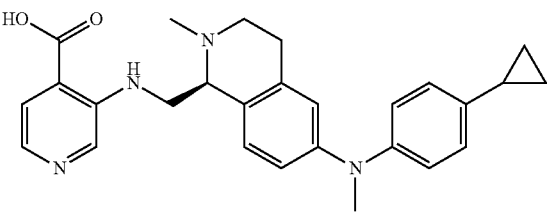 [SMILES: CN(c1ccc(C2CC2)cc1)c1ccc2c(c1)CCN(C)[C@@H]2CNc1cnccc1C(=O)O]

(S)-3-(((6-(4-cyclopropylphenyl)(methyl)amino)-
2-methyl-1,2,3,4-tetrahydroiso-quinolin-1-yl)
methyl)amino)isonicotinic acid

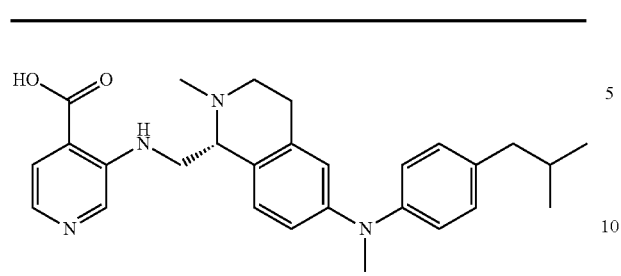

(R)-3-(((6-(4-isobutylphenyl)(methyl)amino)-2-methyl-1,2,3,4-tetrahydro-isoquinolin-1-yl)methyl)amino)isonicotinic acid

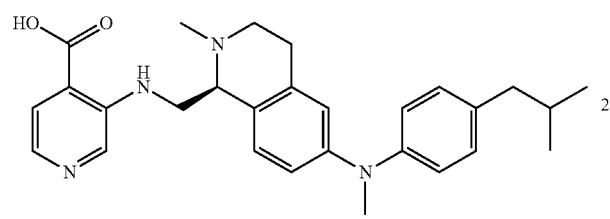

(S)-3-(((6-(4-isobutylphenyl)(methyl)amino)-2-methyl-1,2,3,4-tetrahydro-isoquinolin-1-yl)methyl)amino)isonicotinic acid

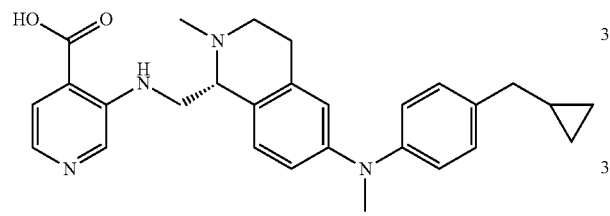

(R)-3-(((6-(4-cyclopropylmethyl)phenyl)(methyl)amino)-2-methyl-1,2,3,4-tetrahydroisoquinolin-1-yl)methyl)amino)isonicotinic acid

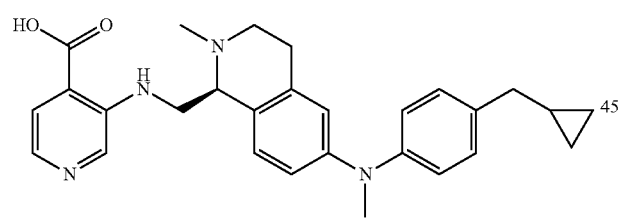

(S)-3-(((6-(4-cyclopropylmethyl)phenyl)(methyl)amino)-2-methyl-1,2,3,4-tetrahydroisoquinolin-1-yl)methyl)amino)isonicotinic acid

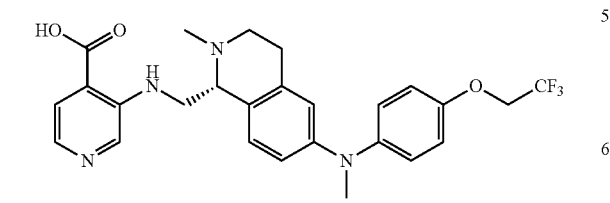

(R)-3-(((2-methyl-6-(methyl(4-(2,2,2-trifluoroethoxy)phenyl)amino)-1,2,3,4,-tetrahydroisoquinolin-1-yl)methyl)amino)isonicotinic acid

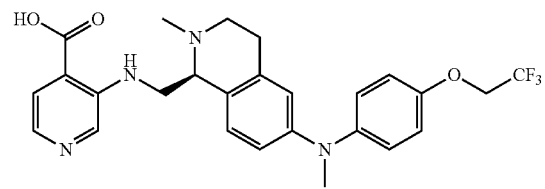 [SMILES: CN(c1ccc(OCC(F)(F)F)cc1)c1ccc2c(c1)CCN(C)[C@@H]2CNc1cnccc1C(=O)O]

(S)-3-(((2-methyl-6-(methyl(4-(2,2,2-trifluoroethoxy)phenyl)amino)-1,2,3,4,-tetrahydroisoquinolin-1-yl)methyl)amino)isonicotinic acid

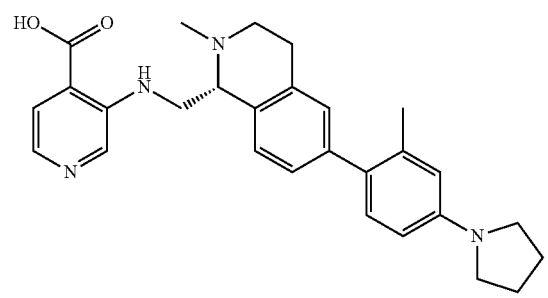 [SMILES: Cc1cc(N2CCCC2)ccc1-c1ccc2c(c1)CCN(C)[C@H]2CNc1cnccc1C(=O)O]

(R)-3-(((2-methyl-6-(2-methyl-4-(pyrrolidin-1-yl)phenyl)-1,2,3,4-tetrahydroisoquinolin-1-yl)methyl)amino)isonicotinic acid

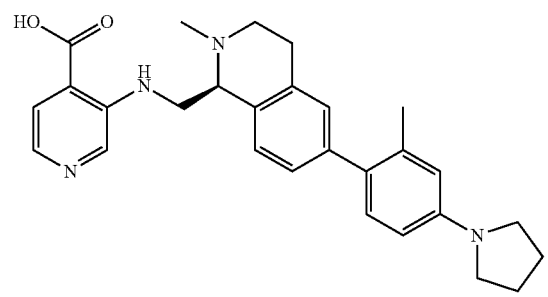 [SMILES: Cc1cc(N2CCCC2)ccc1-c1ccc2c(c1)CCN(C)[C@@H]2CNc1cnccc1C(=O)O]

(S)-3-(((2-methyl-6-(2-methyl-4-(pyrrolidin-1-yl)phenyl)-1,2,3,4-tetrahydroisoquinolin-1-yl)methyl)amino)isonicotinic acid

(R)-3-(((6-(4-isopropoxyphenyl)(methyl)amino)-2-methyl-1,2,3,4-tetrahydro-isoquinolin-1-yl)methyl)amino)isonicotinic acid

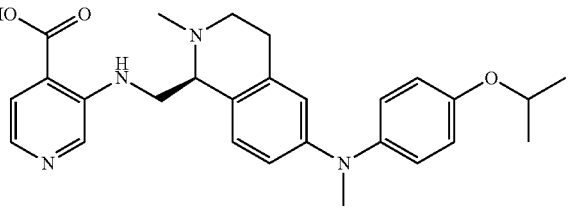

(S)-3-(((6-(4-isopropoxyphenyl)(methyl)amino)-2-methyl-1,2,3,4-tetrahydro-isoquinolin-1-yl)methyl)amino)isonicotinic acid TABLE 2-continued

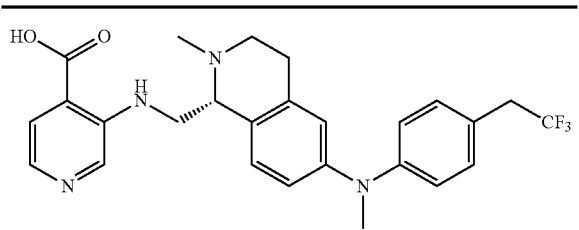

(R)-3-(((2-methyl-6-(methyl(4-(2,2,2-trifluroethyl)
phenyl)amino)-1,2,3,4,-tetrahydroisoquinolin-1-yl)
methyl)amino)isonicotinic acid

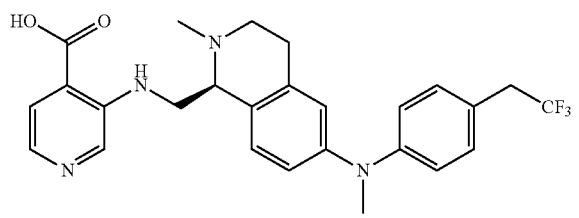 [SMILES: CN(c1ccc(CC(F)(F)F)cc1)c1ccc2c(c1)CCN(C)[C@@H]2CNc1cnccc1C(=O)O]

(S)-3-(((2-methyl-6-(methyl(4-(2,2,2-trifluroethyl)
phenyl)amino)-1,2,3,4,-tetrahydroisoquinolin-1-yl)
methyl)amino)isonicotinic acid

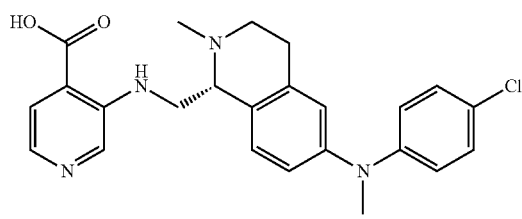 [SMILES: CN(c1ccc(Cl)cc1)c1ccc2c(c1)CCN(C)[C@H]2CNc1cnccc1C(=O)O]

(R)-3-(((6-((4-chlorophenyl)(methyl)amino)-2-
methyl-1,2,3,4-tetrahydroisoquinolin-1-yl)methyl)
amino)isonicotinic acid

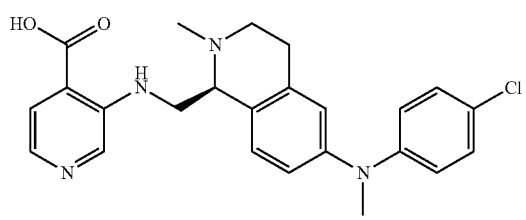 [SMILES: CN(c1ccc(Cl)cc1)c1ccc2c(c1)CCN(C)[C@@H]2CNc1cnccc1C(=O)O]

(S)-3-(((6-((4-chlorophenyl)(methyl)amino)-2-
methyl-1,2,3,4-tetrahydroisoquinolin-1-yl)methyl)
amino)isonicotinic acid

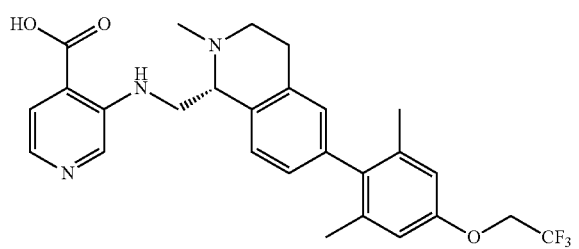 [SMILES: Cc1cc(OCC(F)(F)F)cc(C)c1-c1ccc2c(c1)CCN(C)[C@H]2CNc1cnccc1C(=O)O]

(R)-3-(((6-(2,6-dimethyl-4-(2,2,2-trifluroethoxy)
phenyl)-2-methyl-1,2,3,4-tetrahydroisoquinolin-
1-yl)methyl)amino)isonicotinic acid TABLE 2-continued

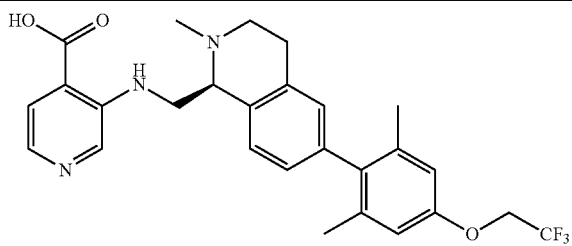

(S)-3-(((6-(2,6-dimethyl-4-(2,2,2-trifluroethoxy)
phenyl)-2-methyl-1,2,3,4-tetrahydroisoquinolin-
1-yl)methyl)amino)isonicotinic acid

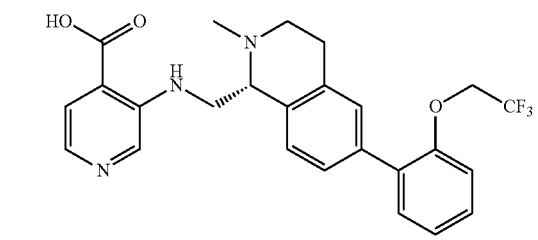 [SMILES: CN1CCc2cc(-c3ccccc3OCC(F)(F)F)ccc2[C@@H]1CNc1cnccc1C(=O)O]

(R)-3-(((6-(2-methyl-6-(2-(2,2,2-trifluroethoxy)
phenyl)-1,2,3,4-tetrahydroisoquinolin-1-yl)methyl)
amino)isonicotinic acid

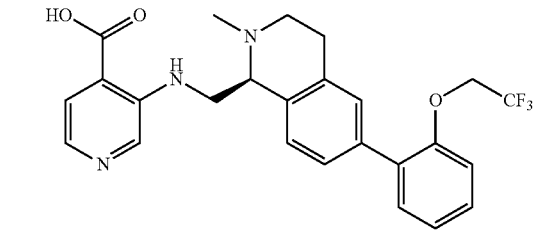 [SMILES: CN1CCc2cc(-c3ccccc3OCC(F)(F)F)ccc2[C@H]1CNc1cnccc1C(=O)O]

(S)-3-(((6-(2-methyl-6-(2-(2,2,2-trifluroethoxy)
phenyl)-1,2,3,4-tetrahydroisoquinolin-1-yl)
methyl)amino)isonicotinic acid

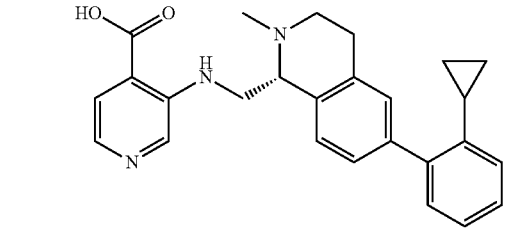 [SMILES: CN1CCc2cc(-c3ccccc3C3CC3)ccc2[C@@H]1CNc1cnccc1C(=O)O]

(R)-3-(((6-(2-cyclopropylphenyl)-2-methyl-
1,2,3,4-tetrahydroisoquinolin-1-yl)methyl)amino)
isonicotinic acid

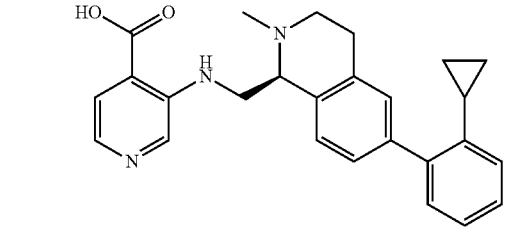 [SMILES: CN1CCc2cc(-c3ccccc3C3CC3)ccc2[C@H]1CNc1cnccc1C(=O)O]

(S)-3-(((6-(2-cyclopropylphenyl)-2-methyl-
1,2,3,4-tetrahydroisoquinolin-1-yl)methyl)amino)
isonicotinic acid

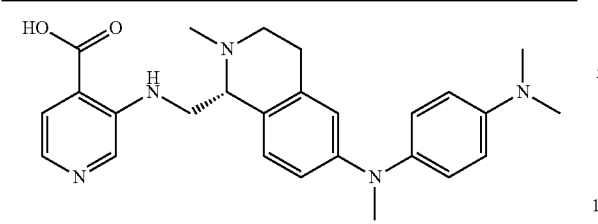

(R)-3-(((6-(4-dimethylamino)phenyl)(methyl)amino)-2-methyl-1,2,3,4-tetrahydroisoquinolin-1-yl)methyl)amino)isonicotinic acid

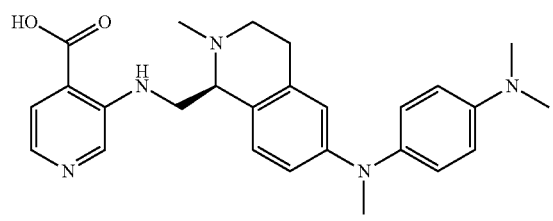 [SMILES: CN(C)c1ccc(N(C)c2ccc3c(c2)CCN(C)[C@@H]3CNc2cnccc2C(=O)O)cc1]

(S)-3-(((6-(4-dimethylamino)phenyl)(methyl)amino)-2-methyl-1,2,3,4-tetrahydroisoquinolin-1-yl)methyl)amino)isonicotinic acid

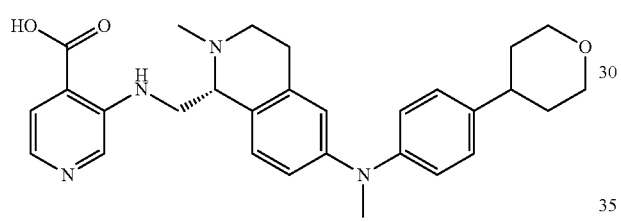

(R)-3-(((2-methyl-6-(methyl(4-(tetrahydro-2H-pyran-4-yl)phenyl)amino)-1,2,3,4-tetrahydroisoquinolin-1-yl)methyl)amino)isonicotinic acid

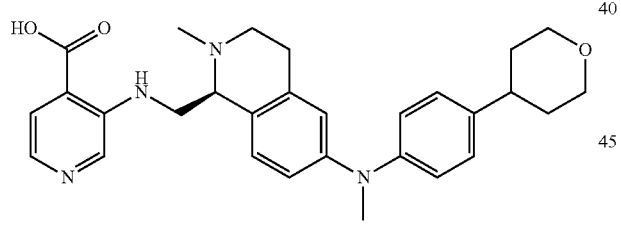

(S)-3-(((2-methyl-6-(methyl(4-(tetrahydro-2H-pyran-4-yl)phenyl)amino)-1,2,3,4-tetrahydroisoquinolin-1-yl)methyl)amino)isonicotinic acid

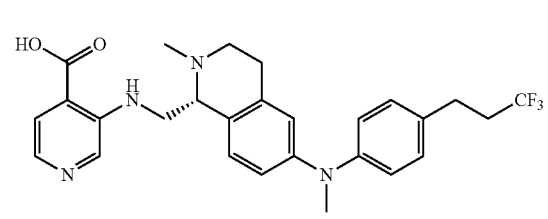 [SMILES: CN(c1ccc(CCC(F)(F)F)cc1)c1ccc2c(c1)CCN(C)[C@H]2CNc1cnccc1C(=O)O]

(R)-3-(((2-methyl-6-(methyl(4-(3,3,3-trifluoropropyl)phenyl)amino)-1,2,3,4-tetrahydroisoquinolin-1-yl)methyl)amino)isonicotinic acid

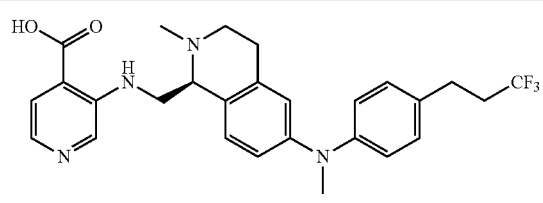 [SMILES: CN(c1ccc(CCC(F)(F)F)cc1)c1ccc2c(c1)CCN(C)[C@@H]2CNc1cnccc1C(=O)O]

(S)-3-(((2-methyl-6-(methyl(4-(3,3,3-trifluoropropyl)phenyl)amino)-1,2,3,4-tetrahydroisoquinolin-1-yl)methyl)amino)isonicotinic acid

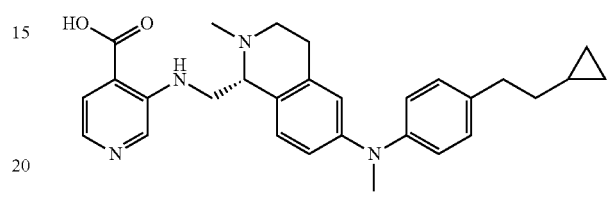

(R)-3-(((6-(4-(2-cyclopropylethyl)phenyl)(methyl)amino)-2-methyl-1,2,3,4-tetrahydroisoquinolin-1-yl)methyl)amino)isonicotinic acid

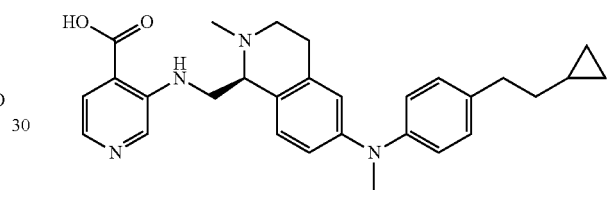

(S)-3-(((6-(4-(2-cyclopropylethyl)phenyl)(methyl)amino)-2-methyl-1,2,3,4-tetrahydroisoquinolin-1-yl)methyl)amino)isonicotinic acid

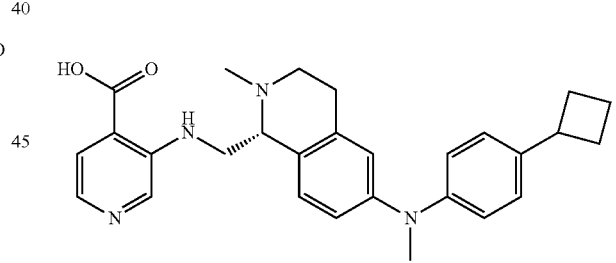

(R)-3-(((6-((4-cyclobutylphenyl)(methyl)amino)-2-methyl-1,2,3,4-tetrahydroisoquinolin-1-yl)methyl)amino)isonicotinic acid

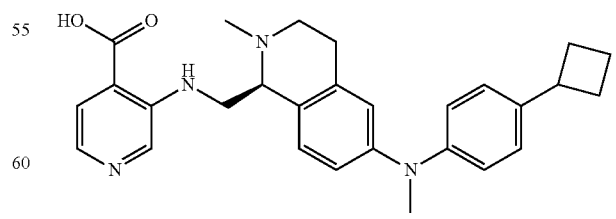

(S)-3-(((6-((4-cyclobutylphenyl)(methyl)amino)-2-methyl-1,2,3,4-tetrahydroisoquinolin-1-yl)methyl)amino)isonicotinic acid TABLE 2-continued

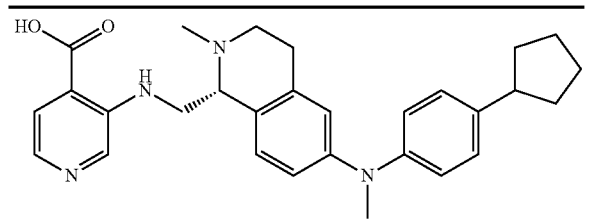

(R)-3-(((6-((4-cyclopentylphenyl)(methyl)amino)-
2-methyl-1,2,3,4-tetrahydroisoquinolin-1-yl)
methyl)amino)isonicotinic acid

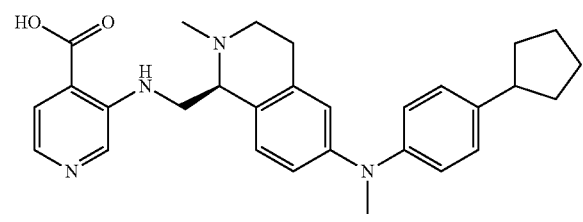 [SMILES: CN(c1ccc(C2CCCC2)cc1)c1ccc2c(c1)CCN(C)[C@@H]2CNc1cnccc1C(=O)O]

(S)-3-(((6-((4-cyclopentylphenyl)(methyl)amino)-
2-methyl-1,2,3,4-tetrahydroisoquinolin-1-yl)
methyl)amino)isonicotinic acid

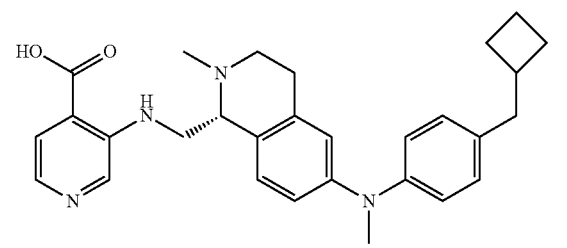 [SMILES: CN(c1ccc(CC2CCC2)cc1)c1ccc2c(c1)CCN(C)[C@H]2CNc1cnccc1C(=O)O]

(R)-3-(((6-((4-cyclobutylmethyl)phenyl)
(methyl)amino)-2-methyl-1,2,3,4-tetrahydro-
isoquinolin-1-yl)methyl)amino)isonicotinic acid

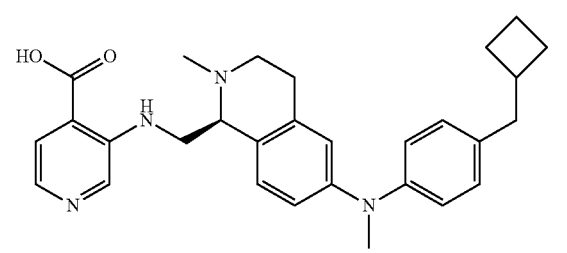 [SMILES: CN(c1ccc(CC2CCC2)cc1)c1ccc2c(c1)CCN(C)[C@@H]2CNc1cnccc1C(=O)O]

(S)-3-(((6-((4-cyclobutylmethyl)phenyl)
(methyl)amino)-2-methyl-1,2,3,4-tetrahydro-
isoquinolin-1-yl)methyl)amino)isonicotinic acid

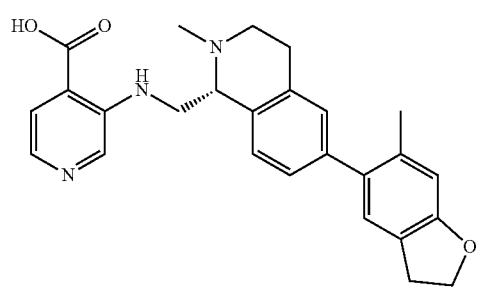 [SMILES: Cc1cc2c(cc1-c1ccc3c(c1)CCN(C)[C@H]3CNc1cnccc1C(=O)O)CCO2]

(R)-3-(((2-methyl-6-(6-methyl-2,3-dihydrobenzo-
furan-5-yl)-1,2,3,4-tetrahydroisoquinolin-1-yl)
methyl)amino)isonicotinic acid

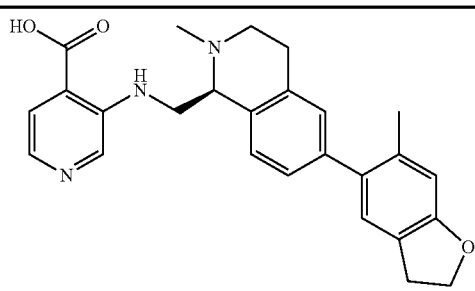

(S)-3-(((2-methyl-6-(6-methyl-2,3-dihydrobenzo-
furan-5-yl)-1,2,3,4-tetrahydroisoquinolin-1-yl)
methyl)amino)isonicotinic acid

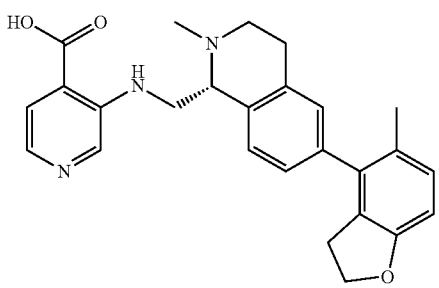 [SMILES: Cc1ccc2c(c1-c1ccc3c(c1)CCN(C)[C@H]3CNc1cnccc1C(=O)O)CCO2]

(R)-3-(((2-methyl-6-(5-methyl-2,3-dihydro-
benzofuran-4-yl)-1,2,3,4-tetrahydroiso-quinolin-1-
yl)methyl)amino)isonicotinic acid

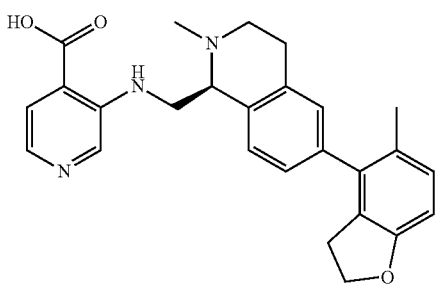 [SMILES: Cc1ccc2c(c1-c1ccc3c(c1)CCN(C)[C@@H]3CNc1cnccc1C(=O)O)CCO2]

(S)-3-(((2-methyl-6-(5-methyl-2,3-dihydro-
benzofuran-4-yl)-1,2,3,4-tetrahydroiso-quinolin-1-
yl)methyl)amino)isonicotinic acid

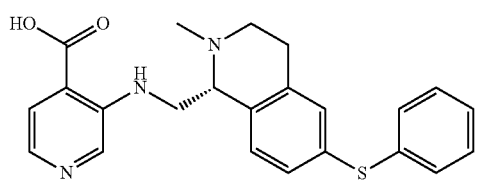 [SMILES: CN1CCc2cc(Sc3ccccc3)ccc2[C@@H]1CNc1cnccc1C(=O)O]

(R)-3-(((2-methyl-6-(phenylthio)-1,2,3,4-
tetrahydroisoquinolin-1-yl)methyl)amino)
isonicotinic acid

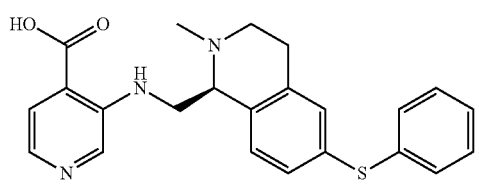 [SMILES: CN1CCc2cc(Sc3ccccc3)ccc2[C@H]1CNc1cnccc1C(=O)O]

(S)-3-(((2-methyl-6-(phenylthio)-1,2,3,4-
tetrahydroisoquinolin-1-yl)methyl)amino)
isonicotinic acid Preparation of the Substituted Pyridine Derivative Compounds The compounds used in the reactions described herein are made according to organic synthesis techniques known to those skilled in this art, starting from commercially available chemicals and/or from compounds described in the chemical literature. Commercially available chemicals are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Co. (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Methods known to one of ordinary skill in the art are identified through various reference books and databases. Numerous suitable reference books and treatises that detail the synthesis of reactants useful in the preparation of compounds described herein, or provide references to articles that describe the preparation, are well known to those of skill in the art. See, e.g., SYNTH. ORG. CHEM. (John Wiley & Sons, Inc., New York); Sandler et al., ORG. FUNCT. GROUP PREP. (2nd Ed., Academic Press, New York, 1983); House, MOD. SYNTH. REACT. (2nd Ed., W. A. Benjamin, Inc., Menlo Park, Calif., 1972); Gilchrist, HETEROCYCL. CHEM. (2nd Ed., John Wiley & Sons, New York, 1992); March, ADV. ORG. CHEM: REACT., MECH. & STR. (4th Ed., Wiley-Intersci., New York, 1992); Fuhrhop & Penzlin, ORG. SYNTH: CONCEPTS, METHS., STARTING MATER., 2ND, REVIS. & ENLARGED ED. (John Wiley & Sons, 1994); Hoffman, ORG. CHEM., INTERMED. TEXT (Oxford Univ. Press, 1996); Larock, COMPR. ORG. TRANSFORM.: GUIDE TO FUNCT. GROUP PREP. (2nd Ed., Wiley-VCH, 1999); MOD. CARBONYL CHEM. (Otera, ed., Wiley-VCH, 2000); Patai, PATAI'S 1992 GUIDE TO CHEM. FUNCT. GROUPS (Intersci., 1992); Solomons, ORG. CHEM. (7th Ed., John Wiley & Sons 2000); Stowell, INTERMED. ORG. CHEM. (2nd Ed. Wiley-Intersci. 1993); INDUS. ORG. CHEM.: STARTING MATER. & INTERMED.: AN ULLMANN'S ENCYCLO., in 8 vol. (John Wiley & Sons, 1999); ORG. REACT., in over 55 vol. (John Wiley & Sons, 1942-2000); CHEM. FUNCT. GROUPS, in 73 vol. (John Wiley & Sons).

Specific and analogous reactants may also be identified through the indices of known chemicals, such as those prepared by the Chemical Abstract Service of the American Chemical Society (Washington, D.C.), which are available in most public and university libraries, as well as through on-line databases. Chemicals that are known but not commercially available in catalogs can usually be prepared by custom chemical synthesis houses, and many of the standard chemical supply houses provide custom synthesis services.

Substituted pyridine derivative compounds of the present embodiments can be prepared by general synthetic routes, for example, as described herein according to Schemes 1-3.

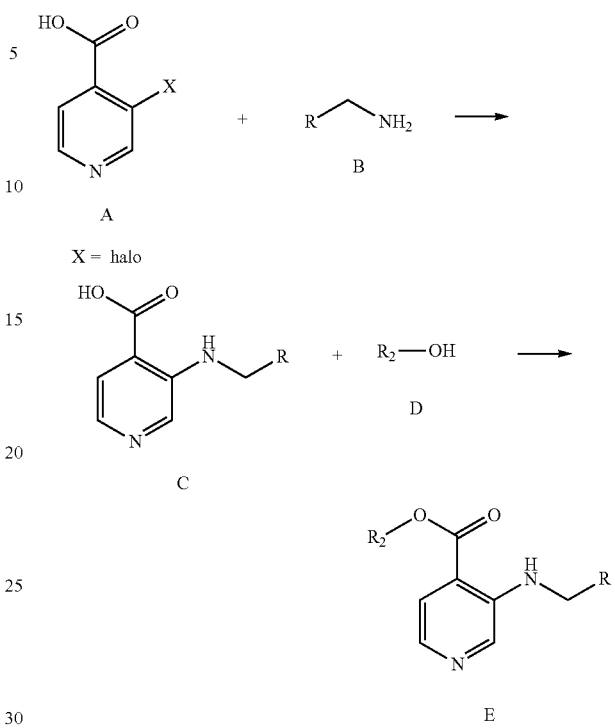

Referring to Scheme 1, above, compound A and an amine compound B are mixed and treated under a variety of conditions to form compound C. For example, the mixture of compound A and amine B can be subjected to microwave irradiation in an appropriate solvent, at temperatures ranging from 120° C. to 172° C. The ester compound E can be prepared from compound C and alcohol D using a coupling reagent, such as HATU, in the presence of base.

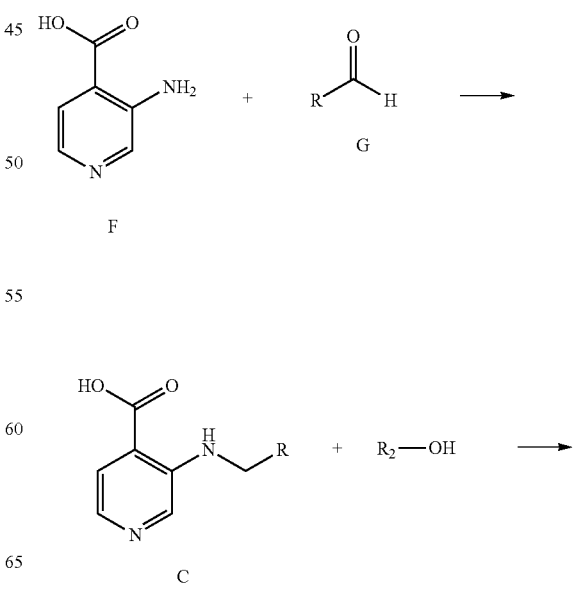

109

-continued

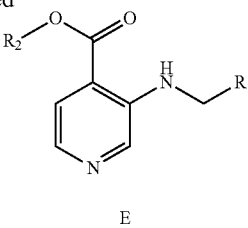

E

Referring to Scheme 2, above, compound F and aldehyde compound G are mixed and treated under reductive amination conditions to form compound C. The ester compound E can be prepared from compound C and alcohol D using a coupling reagent, such as HATU, in the presence of base.

Scheme 3

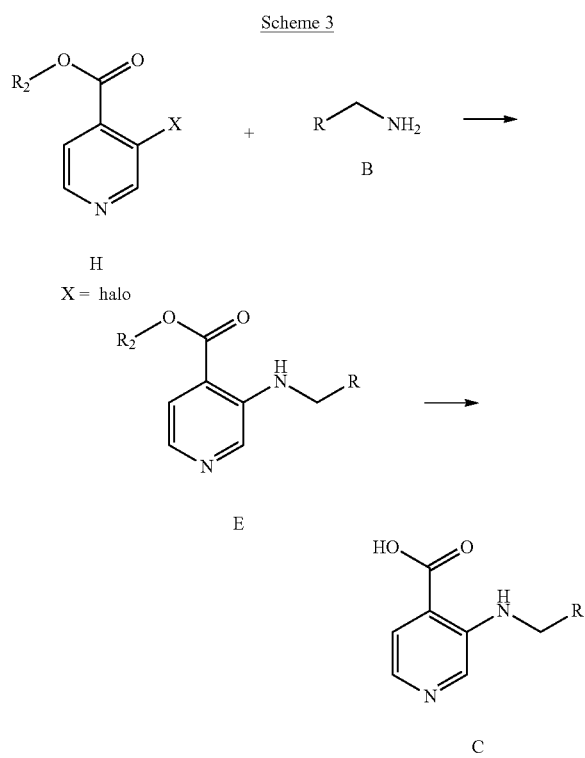

Referring to Scheme 3, compound H and amine compound B are mixed and treated under a variety of conditions to form compound E. For example, the mixture of compound H and amine B can be subjected to a Buchwald reaction under microwave irradiation in an appropriate solvent, at temperatures ranging from 100° C. to 120° C. The ester compound E can be hydrolyzed to give compound C, using basic conditions such as 1N aq. NaOH.

Pharmaceutical Compositions

In certain embodiments, a substituted pyridine derivative compound as described herein may be administered as a pure chemical (i.e., compound or salt thereof). In other embodiments, a substituted pyridine derivative compound described herein is combined with a pharmaceutically suitable or acceptable excipient or carrier (also referred to herein as a physiologically suitable or acceptable excipient or carrier) selected on the basis of a chosen route of administration and standard pharmaceutical practice. See, e.g., REMINGTON: SCI. & PRACT. PHARM. (Gennaro, 21st Ed. Mack Pub. Co., Easton, Pa., 2005).

110

Accordingly, at least one embodiment provides a pharmaceutical composition comprising at least one substituted pyridine derivative compound or a stereoisomer, prodrug, pharmaceutically acceptable salt, hydrate, solvate, or N-oxide thereof, and at least one pharmaceutically acceptable excipient. One embodiment provides a pharmaceutical composition comprising a pharmaceutically acceptable excipient, and a compound of Formula 1, Formula 2, Formula 3, Formula 4, or a tautomer, stereoisomer, geometric isomer, N-oxide, or pharmaceutically acceptable salt of these compounds. Another embodiment provides a pharmaceutical composition comprising at least one substituted pyridine derivative compound or a stereoisomer, prodrug, pharmaceutically acceptable salt, hydrate, solvate, or N-oxide thereof, and at least one pharmaceutically acceptable excipient, and further comprises at least one other active agent, such as a therapeutic or prophylactic agent. Typically, an excipient is acceptable or suitable if it is compatible with the other components of the composition (e.g., active agents or excipients) and not deleterious to the recipient (e.g., the subject or patient) of the composition.

In certain embodiments, the substituted pyridine derivative compound as described by Formula 1, Formula 2, Formula 3, or Formula 4 is substantially pure, in that it contains less than about 5%, or less than about 1%, or less than about 0.1%, of other organic small molecules, such as contaminating intermediates or by-products that are created, for example, during compound synthesis.

Pharmaceutical compositions may be administered in a manner appropriate to the disease to be treated (or prevented) as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses may generally be determined using experimental models and/or clinical trials. The optimal dose may depend upon the body mass, weight, or blood volume of the patient.

The dose of a pharmaceutical composition comprising at least one substituted pyridine derivative compound as described herein may differ, depending upon the patient's (e.g., human) condition; that is, the stage of the disease, general health status, age, and other factors that a physician or other person skilled in the medical art will use to determine dose.

Accordingly, some embodiments provide an oral dosage form comprising the compound of Formula 1, the compound of Formula 2, the compound of Formula 3, or the compound of Formula 4. Suitable oral dosage forms include, for example, tablets, pills, sachets, or capsules of hard or soft gelatin, methylcellulose or of another suitable materials easily dissolved in the digestive tract. Suitable nontoxic solid carriers can be used which include, for example, pharmaceutical grades of mannitol, lactose, starch, magnesium stearate, sodium saccharin, talcum, cellulose, glucose, sucrose, magnesium carbonate, and the like. See, e.g., Remington, 2005.

For the substituted pyridine derivative compounds described herein oral doses typically range from about 1.0 mg to about 1000 mg, one to four times, or more, per day.

A related embodiment provides a pharmaceutical formulation, for example a diluted version of the pharmaceutical composition or the compound of Formula 1, the compound of Formula 2, the compound of Formula 3 or the compound of Formula 4; wherein the diluent is suitable for intravenous infusion of the diluted pharmaceutical composition or the compound of Formula 1, the compound of Formula 2, the compound of Formula 3, or the compound of Formula 4. An example pharmaceutical formulation comprises the pharmaceutical composition or compound of Formula 2 and saline or dextrose as a diluent.

Histone Demethylases

In each mammalian cell, about 2 meters of linear DNA is packaged tightly enough to fit inside the roughly 10 μm diameter cell nucleus, yet still ensure appropriate access for required gene expression. The basic package unit, a nucleosome, comprises a segment of DNA wound in sequence around eight histone protein cores. These nucleosomes, in turn, are folded through a series of successively higher ordered chromatin structures that form the chromosome. Because histones are the major protein component of chromatin, histone modification, for example, by methylation, acetylation, demethylation, or deacetylation, has profound effects on chromatin structure. Several classes of enzymes are known that modify histones at various sites.

More specifically, histones can be modified (post-translation) by acetylation, methylation, phosphorylation, or ubiquitination. Methylation is catalyzed by histone methyltransferases that transfer methyl groups from S-adenosyl methionine to histones. Specific methylation targets include amino groups in lysine residues and the guanidino groups of arginines, by carboxymethylation of aspartate, glutamate, or of the C-terminus of the protein. Histone methylation is known to participate in a diverse range of biological processes including heterochromatin formation, X-chromosome inactivation, and transcriptional regulation. Histone methylation, then, is a characterized modification of the "histone code," that along with DNA methylation provides an epigenetic code. See Lachner et al., 116 J. Cell Sci. 2117 (2003); Margueron et al., 15 Curr. Opin. Genet. Devel. 163 (2005).

Methylated lysines are perhaps the best understood marks of the histone code, yet this code remains complex because each of the four standard histones can be simultaneously modified at multiple different sites with multiple different modifications. There are four histone families, and, for example histone H3 contains nineteen lysines known to be independently methylated: each can be un-, mono-, di- or tri-methylated. The patterns of histone lysine methylation have been standardized and refer to the histone family, K (standard abbreviation of lysine), the position residue methylated, and the number of methyl groups added (e.g., "me3" means three methyl groups); accordingly H3K4me3 means trimethylation of lysine 4 on histone H3. Unlike acetylation, which generally correlates with transcriptional activation, whether histone methylation leads to transcription activation or repression depends on the particular site of methylation and the degree of methylation (e.g., whether a particular histone lysine residue is mono-, di-, or tri-methylated). In general, methylation of histone H3K9, H3K27, and H4K20 is associated with transcriptional repression; conversely, demethylation of H3K4 is correlated with silencing of the genomic region. Methylation of lysines H3K4, H3K36, and H3K79 is generally associated with transctiptional activation; and tri- and di-methylation of H3K4 (H3K4me3 and H3K4me2, respectively) generally marks the transcriptional start sites of actively transcribed genes, whereas monomethylation of H3K4 (H3K4me) is associated with enhancer sequences.

A "demethylase" or "protein demethylase," in the context of the present embodiments, is an enzyme that removes at least one methyl group from an amino acid side chain of histones, e.g., act as a histone H3 or H4 demethylase. For example, a H3 demethylase may demethylate one or more of H3K4, H3K9, H3K27, H3K36, or H3K79. Alternately, a H4 demethylase may demethylate H4K20. Demethylases can demethylate mono-, di- or a tri-methylated substrate, and can act on a methylated core histone substrate, a mononucleosome substrate, a dinucleosome substrate, or an nucleosome substrate, peptide substrate, or chromatin (e.g., in a cell-based assay). Aptly named, lysine specific demethylase 1 (LSD1/KDM1) was the first lysine-specific histone demethylase discovered, and this enzyme demethylates both mono- and di-methylated H3K4 and H3K9, using flavin as a cofactor.

A second class of histone demethylases containing a Jumonji C (JmjC) domain was confirmed using a formaldehyde release assay and H3K36; this class was named "JmjC domain containing histone demethylase 1" (JHDM1/KDM2A). Additional JmjC domain-containing proteins were identified subsequently, and they can be phylogenetically clustered into seven subfamilies: JHDM1, JHDM2, JHDM3, JMJD2, JARID, PHF2/PHF8, UTX/UTY, and JmjC domain only.

JMJD2 Family

The JMJD2 jumonji proteins are histone-demethylases that demethylate tri- and di-methylated H3K9, and were the first identified histone tri-methyl demethylase. In particular, ectopic expression of JMJD2 family members dramatically decreases levels of H3K9me3 and H3K9me2, and increases levels of H3K9me; which delocalizes Heterochromatin Protein 1 (HP1) and reduces overall levels of heterochromatin in vivo. Members of the JMJD2 subfamily of jumonji proteins include JMJD2C and its homologues JMJD2A, JMJD2B, JMJD2D, and JMJD2E. Common structural features found in the JMJD2 subfamily of Jumonji proteins include the JmjN, JmjC, PHD and Tdr sequences.

JMJD2C, also known as GASC1 and KDM4C, is known to demethylate H3K9me3 and H3K36me3. Histone demethylation by JMJD2C occurs via a hydroxylation reaction dependent on iron and α-ketoglutarate, wherein oxidative decarboxylation of α-ketoglutarate by JMJD2C produces carbon dioxide, succinate, and ferryl and ferryl subsequently hydroxylates methylated lysine H3K9, releasing formaldehyde. JMJD2C is known to modulate regulation of adipogenesis by the nuclear receptor PPARγ and is known to be involved in regulation of self-renewal in embryonic stem cells.

JARID Family

JARID proteins in the JARID1 subfamily include JARID1A, JARID1B, JARID1C, and JARID1D proteins, and the JARID2 subfamily, as well as homologues thereof. Further descriptions and listings of JARID proteins can be found elsewhere. See Klose et al., 7 Nat. Rev. Genet. 715 (2006). The JARID1 family proteins contain several conserved domains: JmjN, ARID, JmjC, PHD, and a C5HC2 zing finger.

JARID1A, also called KDM5A or RBP2, was found initially as a binding partner of retinoblastoma (Rb) protein. JARID1A was subsequently found to function as a demethylase of H3K4me3 and H3K4me2, and has been found to promote cell growth, while inhibiting senescence and differentiation. For instance, abrogation of JARID1A from mouse cells inhibits cell growth, induces senescence and differentiation, and causes loss of pluripotency of embryonic stem cells in vitro. JARID1A has been found to be overexpressed in gastric cancer and the loss of JARID1A has been found to reduce tumorigenesis in a mouse cancer model. Additionally, studies have demonstrated that loss of the retinoblastome binding protein 2 (RBP2) histone demethylase suppresses tumorigenesis in mice lacking Rb1 or Men1, indicating that RBP2-inhibitory drugs might have anticancer activity. Lin et al., 108 PNAS 13379 (2011).

JARID1B, also referred to as KDM5B and PLU1, was found originally in experiments regarding genes regulated by the HER2 tyrosine kinase. Consistently, research has shown that JARID1B is expressed in breast cancer cell lines, while restriction of JARID1B has been found in normal adult tissues with the exception of the testis. JARID1B is also apparently up-regulated in prostate cancers, but has more limited expression in benign prostate; and is also up-regulated in bladder cancer and lung cancer (both SCLC and NSCLC). In addition, 90% of invasive ductal carcinomas express JARID1B. Finally, JARID1B has been found to repress tumor suppressor genes such as BRCA1, CAV1, and 14-3-3σ; and knockdown of JARID1B increases the levels of trimethylated H3K4 at these genes.

UTX/UTY Family

UTX/UTY family includes KDM6A, KDM6B, and UTY. KDM6A (also called UTX) and KDM6B (also called JMJD3), act on H3K27me2 and H3K27me3 and are important for development, whereas the substrate and role of UTY remains to be elucidated. Both KDM6A (UTX) and KDM6B (JMJD3) have demonstrated tumor-supressive characteristics by functioning as antagonists against the oncogenic polycomb group (PcG) proteins. PcG proteins are important repressive histone marks that catalyze the tri- and di-methylation of H3K27. PcG genes have been characterized as oncogenes that are frequently overexpressed or amplified in cancer.

Accordingly, at least one embodiment provides a method for inhibiting a histone-demethylase enzyme comprising contacting the enzyme with a substituted pyridine derivative compound as disclosed herein. In a specific embodiment, the histone-demethylase enzyme comprises a JmjC domain. Another embodiment provides a method for inhibiting a histone-demethylase enzyme comprising contacting the enzyme with a substituted pyridine derivative compound as disclosed herein, wherein the histone-demethylase enzyme is JARID1A, JARID1B, JMJD2C, or JMJD3. In one embodiment, a method for inhibiting the histone-demethylase enzyme JMJD3 comprises contacting the JMJD3 enzyme with a substituted pyridine derivative compound as disclosed herein. In another embodiment, a method for inhibiting the histone-demethylase enzyme JMJD2C comprises contacting the JMJD2C enzyme with a substituted pyridine derivative compound as disclosed herein.

Methods of Treatment

Disclosed herein are methods of modulating demethylation in a cell or in a subject, either generally or with respect to one or more specific target genes. Demethylation can be modulated to control a variety of cellular functions, including without limitation: differentiation; proliferation; apoptosis; tumorigenesis, leukemogenesis or other oncogenic transformation events; hair loss; or sexual differentiation. For example, particular embodiments herein provide a method of treating a disease regulated by histone methylation or demethylation in a subject in need thereof by modulating the activity of at least one demethylase comprising a JmjC domain. In a specific embodiment, the histone demethylase is a JHDM protein.

Another aspect of the present embodiments provides methods of treating cancer or neoplastic disease comprising administering at least one compound described herein to a patient in need thereof. In a further aspect of a method for treating cancer in a patient, the cancer is prostate cancer, breast cancer, bladder cancer, lung cancer, or melanoma. In particular embodiments, the neoplastic disease is multiple endocrine neoplasia type 1. In a particular embodiment, the cancer is retinoblastoma. An embodiment provides a method of treating cancer in a patient in need thereof comprising administering to the patient a compound of Formula 1, or a pharmaceutical composition comprising a compound of Formula 1. Another embodiment provides a method of treating cancer in a patient in need thereof comprising administering to the patient a compound of Formula 2, or a pharmaceutical composition comprising a compound of Formula 2. Another embodiment provides a method of treating cancer in a patient in need thereof comprising administering to the patient a compound of Formula 3, or a pharmaceutical composition comprising a compound of Formula 3. Another embodiment provides a method of treating cancer in a patient in need thereof comprising administering to the patient a compound of Formula 4, or a pharmaceutical composition comprising a compound of Formula 4.

In an additional aspect of the present embodiments provides a method of inhibiting the growth of a tumor or tumor or neoplastic cells comprising exposing (e.g., contacting) the tumor or cells with at least one compound described herein. In a particular embodiment, the tumor is characterized by a loss of retinoblastoma gene (RB1) function. In a particular embodiment, the tumor is characterized by a loss of multiple endocrine neoplasia type 1 gene (Men1) function. In an embodiment, a method for inhibiting the growth of a tumor or tumor cells comprises exposing the tumor to a compound of Formula 1, a composition comprising a compound of Formula 1, or pharmaceutically composition comprising a compound of Formula 1. In an embodiment, a method for inhibiting the growth of a tumor or tumor cells comprises exposing the tumor to a compound of Formula 2, a composition comprising a compound of Formula 2, or pharmaceutically composition comprising a compound of Formula 2. In an embodiment, a method for inhibiting the growth of a tumor or tumor cells comprises exposing the tumor to a compound of Formula 3, a composition comprising a compound of Formula 3, or pharmaceutically composition comprising a compound of Formula 3. In an embodiment, a method for inhibiting the growth of a tumor or tumor cells comprises exposing the tumor to a compound of Formula 4, a composition comprising a compound of Formula 4, or pharmaceutically composition comprising a compound of Formula 4.

Another aspect of the present embodiments provides use of at least one compound described herein as a medicament or for making a medicament for treating cancer or neoplastic disease. The cancer or neoplastic disease for which the medicament is manufactured may be prostate cancer, breast cancer, bladder cancer, lung cancer, melanoma, retinoblastoma, or multiple endocrine neoplasia type 1. At least one embodiment provides a use a compound of Formula 1 or composition comprising a compound of Formula 1. Another embodiment provides a use a compound of Formula 2 or composition comprising a compound of Formula 2. Another embodiment provides a use a compound of Formula 3 or composition comprising a compound of Formula 3. Yet another embodiment provides a use a compound of Formula 4 or composition comprising a compound of Formula 4.

Other embodiments and uses will be apparent to one skilled in the art, in light of this Specification. The following examples are provided merely as illustrative of various embodiments and shall not be construed to limit the invention in any way.

EXAMPLES

I. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling constants, J are reported in Hertz. For proton spectra the solvent peak was used as the reference peak.

Preparation of common intermediate 6-bromo-1-[(4-methoxycarbonyl-pyridin-3-ylamino)-methyl]-3,4-dihydro-1H-isoquinoline-2-carboxylic acid tert-butyl ester was performed according to the following outline:

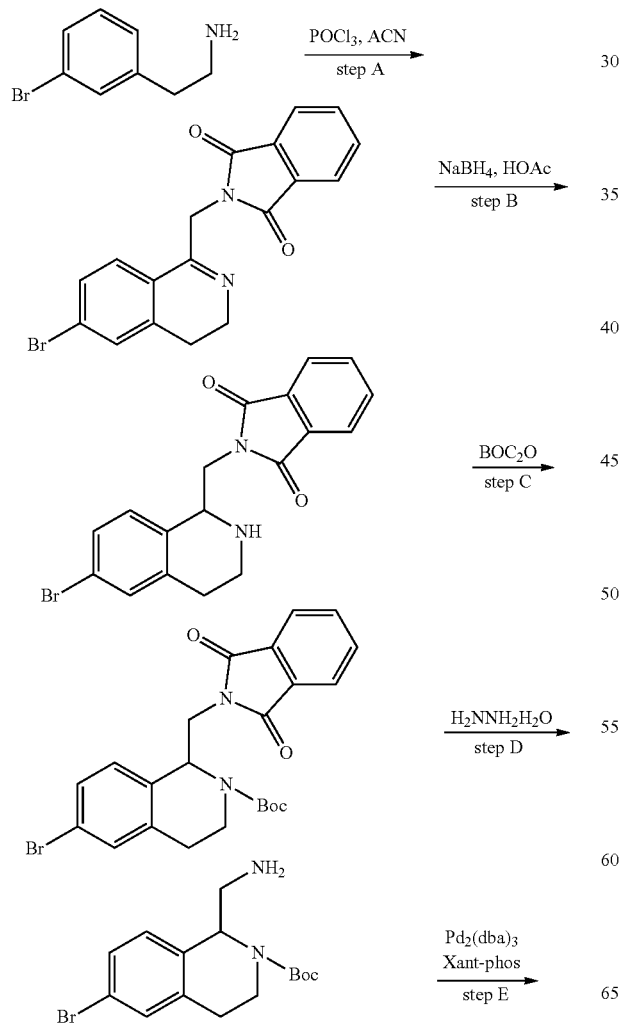

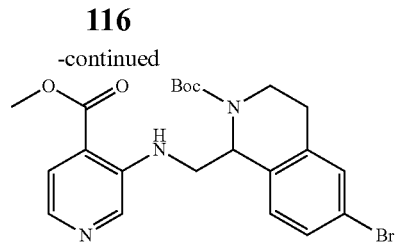

Step A: 2-(6-Bromo-3,4-dihydro-isoquinolin-1-ylmethyl)-isoindole-1,3-dione

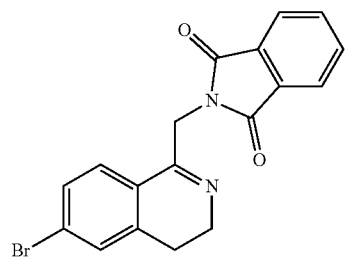 [SMILES: O=C1c2ccccc2C(=O)N1CC1=NCCc2cc(Br)ccc21]

To a solution of (1,3-dioxo-1,3-dihydro-isoindol-2-yl)-acetic acid (1 g, 4.87 mmol) in CH$_3$CN (25 mL) was added 2-(3-bromo-phenyl)-ethylamine (1.08 g, 5.36 mmol) and POCl$_3$ (3.0 g, 19.8 mmol). The reaction mixture was refluxed overnight. The solution was concentrated in vacuo, and the residue was neutralized with aqueous NaHCO$_3$. The aqueous phase was extracted with DCM, and the organic layers were dried with Na$_2$SO$_4$ and concentrated in vacuo. The residue was purified by flash column chromatography (EA:PE=1:1) to obtain title compound (0.6 g, 35%).

Step B: 2-(6-Bromo-1,2,3,4-tetrahydro-isoquinolin-1-ylmethyl)-isoindole-1,3-dione

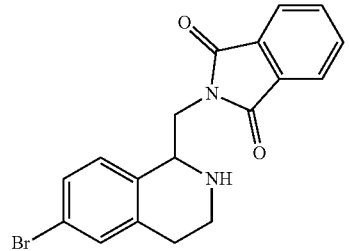 [SMILES: O=C1c2ccccc2C(=O)N1CC1NCCc2cc(Br)ccc21]

To a mixture of 2-(6-bromo-3,4-dihydro-isoquinolin-1-ylmethyl)-isoindole-1,3-dione (400 mg, 1.08 mmol) in AcOH (10 mL) was added NaBH$_4$ (85 mg, 2.16 mmol) portionwise at 0° C. (9.5 g, 61.4 mmol). The reaction mixture was stirred at ambient temperature ("temp") overnight. The reaction mixture was neutralized with aq. NaHCO$_3$ and extracted with DCM. The organic layers were dried with Na$_2$SO$_4$ and concentrated in vacuo to afford the title crude compound (400 mg, 100%), which was used directly in the next step without further purification.

Step C: 6-Bromo-1-(1,3-dioxo-1,3-dihydro-isoindol-2-ylmethyl)-3,4-dihydro-1H-isoquinoline-2-carboxylic Acid tert-butyl ester

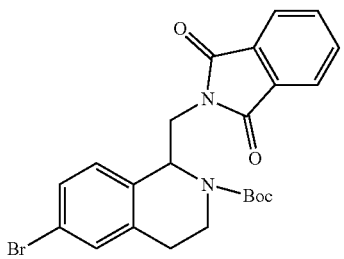 [SMILES: CC(C)(C)OC(=O)N1CCc2cc(Br)ccc2C1CN1C(=O)c2ccccc2C1=O]

To a solution of 2-(6-bromo-1, 2, 3, 4-tetrahydro-isoquinolin-1-ylmethyl)isoindole-1,3-dione (8.0 g, 21.6 mmol) in DCM (50 mL) was added (Boc)$_2$O (5.7 g, 25.9 mmol) and DIEA (5.9 g, 43.2 mmol). The reaction mixture was stirred at ambient temp for 2 hr. Aqueous NH$_4$Cl was added, and the organic layers were collected and concentrated in vacuo. The residue was purified by flash column chromatography (EA:PE=1:1) to afford the title compound (4.5 g, 45%).

Step D: 1-Aminomethyl-6-bromo-3,4-dihydro-1H-isoquinoline-2-carboxylic Acid tert-butyl ester

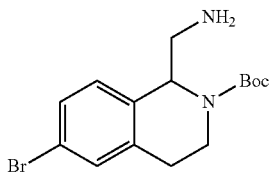 [SMILES: CC(C)(C)OC(=O)N1CCc2cc(Br)ccc2C1CN]

To a solution of 6-bromo-1-(1,3-dioxo-1,3-dihydroisoindol-2-ylmethyl)-3,4-dihydro-1H-isoquinoline-2-carboxylic acid tert-butyl ester (4.5 g, 9.6 mmol) in CH$_3$CN (50 mL) was added H$_2$NNH$_2$.H$_2$O (2.7 g, 96 mmol), and the reaction mixture was refluxed overnight. Upon reaction completion, the mixture was concentrated in vacuo. The resulting residue was taken up in DCM, and the organic layers were successively washed with water and brine, dried with Na$_2$SO$_4$, and concentrated in vacuo. The residue was purified by purified by flash column chromatography (DCM:MeOH=1:1) to afford the title compound (2.5 g, 76%).

Step E: 6-Bromo-1-[(4-methoxycarbonyl-pyridin-3-ylamino)-methyl]-3,4-dihydro-1H-isoquinoline-2-carboxylic Acid tert-butyl ester

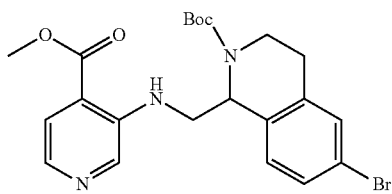 [SMILES: COC(=O)c1ccncc1NCC1c2ccc(Br)cc2CCN1C(=O)OC(C)(C)C]

To a solution of 1-aminomethyl-6-bromo-3,4-dihydro-1H-isoquinoline-2-carboxylic acid tert-butyl ester (2.5 g, 7.35 mmol) in toluene under N$_2$ atmosphere was added 3-bromoisonicotinic acid methyl ester (1.98 g, 8.82 mmol), Pd$_2$(dba)$_3$ (340 mg, 0.37 mmol), Xant-phos (260 mg, 0.45 mmol) and Cs$_2$CO$_3$ (3.36 g, 10.3 mmol). The reaction mixture refluxed overnight. Upon completion, the reaction mixture was filtered, and the filtrate was concentrated in vacuo. The resulting residue was purified by flash column chromatography (EA:PE=1:4) to afford the title compound (1.8 g, 51.4%).

Step R: (R)-6-Bromo-1-[(4-methoxycarbonyl-pyridin-3-ylamino)-methyl]-3,4-dihydro-1H-isoquinoline-2-carboxylic Acid tert-butyl ester, and (S)-6-Bromo-1-[(4-methoxycarbonyl-pyridin-3-ylamino)-methyl]-3,4-dihydro-1H-isoquinoline-2-carboxylic Acid tert-butyl ester

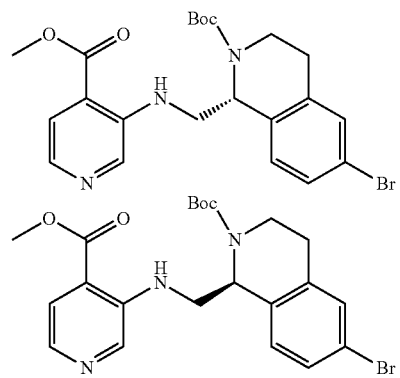

To a solution of 1-aminomethyl-6-bromo-3,4-dihydro-1H-isoquinoline-2-carboxylic acid tert-butyl ester (2.5 g, 7.35 mmol) in toluene under N$_2$ was added 3-bromo-isonicotinic acid methyl ester (1.98 g, 8.82 mmol), Pd$_2$(dba)$_3$ (340 mg, 0.37 mmol), Xant-phos (260 mg, 0.45 mmol) and Cs$_2$CO$_3$ (3.36 g, 10.3 mmol). The reaction mixture was refluxed overnight. Upon completion, the reaction mixture was filtered, and the filtrate was concentrated in vacuo. The resulting residue was purified by flash column chromatography (EA:PE=1:4) to afford the title compound (1.8 g, 51.4%). NMR (400 MHz, CDCl$_3$): δ 1.34-1.49 (d, 9H), 2.74-2.31 (m, 2H), 3.21-3.37 (m, 1H), 3.52-3.66 (m, 2H), 3.89 (s, 3H), 3.96-4.28 (m, 1H), 5.31-5.47 (m, 1H), 7.06 (d, J=10.8 Hz, 1H), 7.34-7.37 (m, 2H), 7.61-7.67 (m, 2H), 7.93-7.97 (m, 1H), 8.34-8.64 (m, 1H). [M+H] Calc'd for C$_{22}$H$_{26}$BrN$_3$O$_4$: 476; Found: 476. Optionally the racemic compound was subjected to chiral separation: Column, Superchiral S-OD, 0.46 cm I.D.*25 cm L; mobile phase: CO$_2$/IPA/DE, A=75/25/0.05; flow rate ("F"): 2.5 mL/min; wave length ("W"): UV 245 nm; temperature ("T"): 35° C.; retention time ("RT"): 4.014 min, 4.241 min.

Step S: tert-butyl (R)-1-(((4-(methoxycarbonyl)pyridin-3-yl)amino)methyl)-6-(o-tolyl)-3,4-dihydroisoquinoline-2(1H)-carboxylate, and tert-butyl (S)-1-(((4-(methoxycarbonyl)pyridin-3-yl)amino)methyl)-6-(o-tolyl)-3,4-dihydroisoquinoline-2(1H)-carboxylate

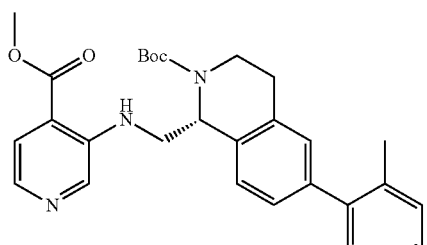

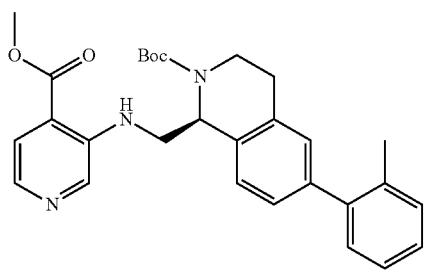

Suzuki coupling of the enantiomers were carried out as follows: To a solution of (R)-6-bromo-1-[(4-methoxycarbonylpyridin-3-ylamino)methyl]-3,4-dihydro-1H-isoquinoline-2-carboxylic acid tert-butyl ester or (S)-6-Bromo-1-[(4-methoxycarbonylpyridin-3-ylamino)methyl]-3,4-dihydro-1H-isoquinoline-2-carboxylic acid tert-butyl ester (350 mg, 0.74 mmol) in toluene (30 mL) under $N_2$ atmosphere was added 2-methylphenylboronic acid (150 mg, 1.1 mmol), Pd(PPh$_3$)$_4$ (43 mg, 0.04 mmol), and Cs$_2$CO$_3$ (720 mg, 2.2 mmol). The reaction mixture refluxed overnight. Upon completion, the reaction mixture was taken up in EA, and the combined organic layers were successively washed with water, brine, dried with Na$_2$SO$_4$, and concentrated in vacuo. The resulting residue was purified by flash column chromatography (EA:PE=1:3) to afford the title compound (350 mg, 83%). [M+H] Calc'd for C$_{29}$H$_{33}$N$_3$O$_4$, 488; Found, 488.

Example 1A and Example 1B: 3-[({(1S)-6-[methyl(4-methylphenyl)amino]-1,2,3,4-tetrahydroisoquinolyl}methyl)amino]pyridine-4-carboxylic Acid; and 3-[({(1R)-6-[methyl(4-methylphenyl)amino]-1,2,3,4-tetrahydroisoquinolyl}methyl)amino] pyridine-4-carboxylic Acid Step F: 1-[(4-Methoxycarbonyl-pyridin-3-ylamino)-methyl]-6-(methyl-p-tolyl-amino)-3,4-dihydro-1H-isoquinoline-2-carboxylic Acid tert-butyl ester

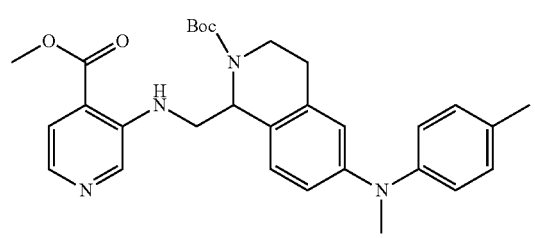

To a solution of 6-bromo-1-[(4-methoxycarbonyl-pyridin-3-ylamino)-methyl]-3,4-dihydro-1H-isoquinoline-2-carboxylic acid tert-butyl ester (110 mg, 0.23 mmol) in toluene (30 mL) under $N_2$ atmosphere was added N-methyl-p-tolylamine (34 mg, 0.28 mmol), Pd$_2$(dba)$_3$ (11 mg, 0.012 mmol), Xant-phos (20 mg, 0.035 mmol) and Cs$_2$CO$_3$ (105 mg, 0.32 mmol). The reaction mixture was allowed to reflux overnight. Upon completion, the reaction mixture was taken up in EA, and the combined organic layers were successively washed with water and brine, dried with Na$_2$SO$_4$, and concentrated in vacuo. The resulting residue was purified by flash column chromatography (EA:PE=1:4) to afford (90 mg, 75%) the title compound. Chiral separation using prep-HPLC (Chiralpak IA 5 um 4.6*250 mm, Phase:Hex:IPA=70:30, F: 1.0 mL/min; W: 230 nm; T: 30° C.) afforded two optically active compounds:
3-[({(1S)-6-[methyl(4-tolyl)amino]-1,2,3,4-tetrahydroisoquinolyl}methyl)amino] pyridine-4-carboxylic acid; and 3-[({(1R)-6-[methyl(4-tolyl)amino]-1,2,3,4-tetrahydroisoquinolyl}methyl)amino]pyridine-4-carboxylic acid:

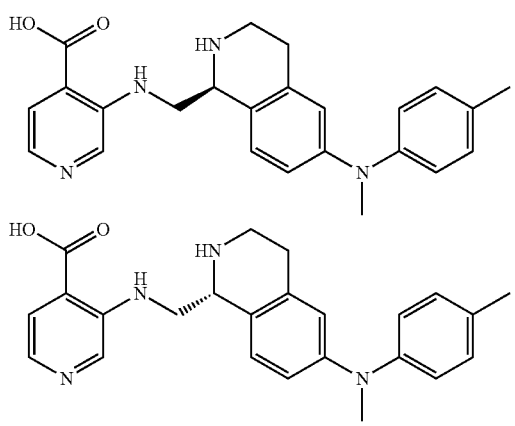

Hydrolysis and de-protection of Boc of each of the enantiomers were carried out as follows: To a solution of 1-[(4-methoxycarbonyl-pyridin-3-ylamino)-methyl]-6-

(methyl-p-tolyl-amino)-3,4-dihydro-1H-isoquinoline-2-carboxylic acid tert-butyl ester (80 mg, 0.155 mmol) in THF/H₂O (1:1, 10 mL) was added LiOH.H₂O (16 mg, 0.62 mmol). The mixture was stirred overnight at ambient temp. Upon completion, the reaction mixture was concentrated in vacuo and the residue was adjusted to pH 3 with HCl (2N). The aqueous layers were extracted with EA (thrice) and the combined organic layers were dried with Na₂SO₄ and concentrated in vacuo. The residue was dissolved in DCM (10 mL) followed by TFA (1 mL). The reaction mixture was stirred for 2 hr and concentrated in vacuo, affording the title compound (65% to 80% yields). The analytical data for the two enantiomers are identical. ¹H NMR (400 MHz, Methanol-d₄): δ 2.32 (s, 3H), 3.00-3.07 (m, 2H), 3.29 (s, 3H), 3.33-3.39 (m, 1H), 3.57-3.64 (m, 1H), 3.85-3.93 (m, 1H), 4.04-4.10 (m, 1H), 4.78-4.81 (m, 1H), 6.68-6.75 (m, 2H), 7.02 (d, J=10.8 Hz, 2H), 7.16-7.22 (m, 3H), 8.02 (d, J=7.6 Hz, 1H), 8.12 (d, J=7.6 Hz, 1H), 8.43 (s, 1H). [M+H] Calc'd for $C_{24}H_{26}N_4O_2$: 403; Found: 403.

Example 2A and Example 2B: 3-[({(1S)-6-[2-methyl-4-(2,2,2-trifluoroethoxy)phenyl]-1,2,3,4-tetrahydroisoquinolyl}methyl)amino]pyridine-4-carboxylic Acid; and 3-[({(1R)-6-[2-methyl-4-(2,2,2-trifluoroethoxy)phenyl]-1,2,3,4-tetrahydroisoquinolyl}methyl)amino]pyridine-4-carboxylic Acid Step G: 1-[(4-Methoxycarbonyl-pyridin-3-ylamino)-methyl]-6-[2-methyl-4-(2,2,2-trifluoro-ethoxy)-phenyl]-3,4-dihydro-1H-isoquinoline-2-carboxylic Acid tert-butyl ester

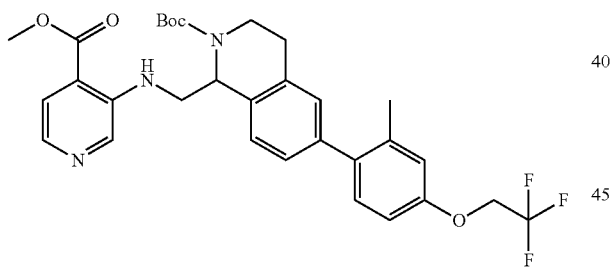

To a solution of 6-bromo-1-[(4-methoxycarbonyl-pyridin-3-ylamino)-methyl]-3,4-dihydro-1H-isoquinoline-2-carboxylic acid tert-butyl ester (400 mg, 0.84 mmol) in toluene (30 mL) under N₂ atmosphere was added 2,2,2-trifluoro-1-[3-methyl-4-(4,4,5,5-tetramethyl (1,3,2-dioxaborolan-2-yl)) phenoxy]ethane (400 mg, 1.26 mmol), Pd(PPh₃)₄ (50 mg, 0.043 mmol), and Cs₂CO₃ (825 mg, 2.53 mmol). The reaction mixture was refluxed overnight. Upon completion, the reaction mixture was taken up in EA, and the combined organic layers successively washed with water and brine, dried with Na₂SO₄, and concentrated in vacuo. The resulting residue was purified by flash column chromatography (EA:PE=1:4) to afford the title compound (380 mg, 78%). Chiral separation using prep-HPLC (Chiralpak IA 5 um 4.6*250 mm, Phase: Hex:EtOH=80:20, F: 1.0 mL/min, W: 230 nm, T: 30° C.) afforded two optically active compounds:

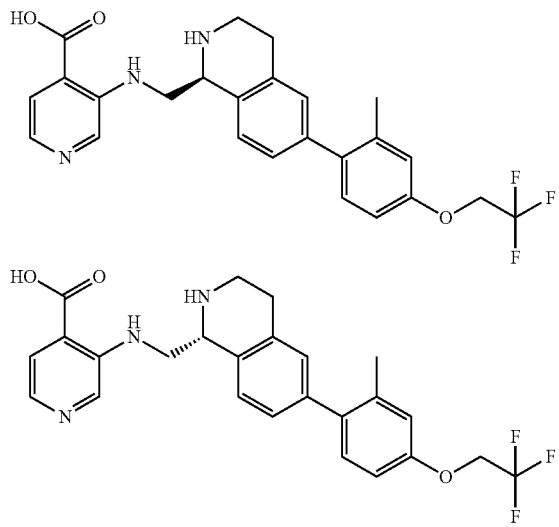

The title compounds were prepared in 85 to 88% yield according to the procedure of Example 1A. ¹H NMR (400 MHz, Methanol-d₄): δ 2.23 (s, 3H), 3.17-3.23 (m, 2H), 3.29-3.31 (m, 1H), 3.43-3.52 (m, 1H), 3.67-3.73 (m, 1H), 4.14-4.20 (m, 1H), 4.50-4.59 (m, 2H), 4.98-5.02 (m, 1H), 6.87-6.95 (m, 2H), 7.14 (d, J=10.8 Hz, 1H), 7.25-7.28 (m, 2H), 7.51 (d, J=10.8 Hz, 1H), 7.97-8.00 (m, 2H), 8.44 (s, 1H). [M+H] Calc'd for $C_{25}H_{24}F_3N_3O_3$: 472; Found: 472.

Example 3A and Example 3B: 3-{[(((1S)-6-{methyl [4-(methylethyl)phenyl]amino}-1,2,3,4-tetrahydroisoquinolyl)methyl]amino}pyridine-4-carboxylic Acid; and 3-{[(((1R)-6-{methyl[4-(methylethyl)phenyl]amino}-1,2,3,4-tetrahydroisoquinolyl)methyl] amino}pyridine-4-carboxylic Acid

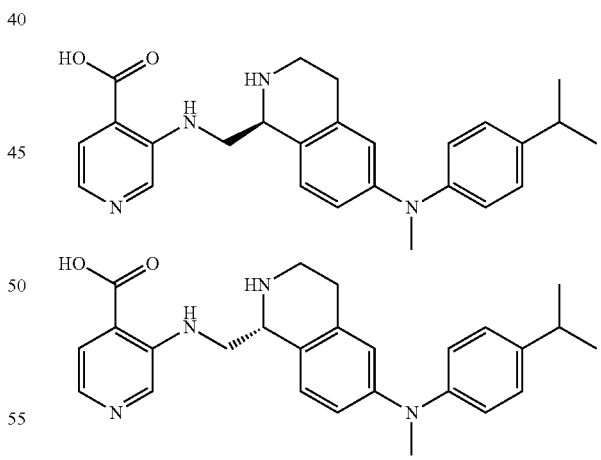

The title compounds were prepared in 80% yield according to the procedure of Example 1A. ¹H NMR (400 MHz, Methanol-d₄): δ 1.25 (d, J=7.2 Hz, 6H), 2.87-3.06 (m, 3H), 3.29 (s, 3H), 3.34-3.40 (m, 1H), 3.59-3.65 (m, 1H), 3.81-3.87 (m, 1H), 4.02-4.07 (m, 1H), 4.79-4.85 (m, 1H), 6.70 (d, J=2.4 Hz, 1H), 6.76-6.79 (m, 1H), 7.06 (d, J=8.4 Hz, 2H), 7.21-7.25 (m, 3H), 7.90 (d, J=4.8 Hz, 1H), 7.97 (d, J=3.2 Hz, 1H), 8.34 (s, 1H). [M+H] Calc'd for $C_{26}H_{30}N_4O_2$: 431; Found: 431.

Example 4A and Example 4B: 3-[({(1S)-6-[4-(cyclopropylmethoxy)-2-methylphenyl]-1,2,3,4-tetrahydroisoquinolyl}methyl)amino]pyridine-4-carboxylic Acid; and 3-[({(1R)-6-[4-(cyclopropylmethoxy)-2-methylphenyl]-1,2,3,4-tetrahydroisoquinolyl}methyl)amino]pyridine-4-carboxylic Acid

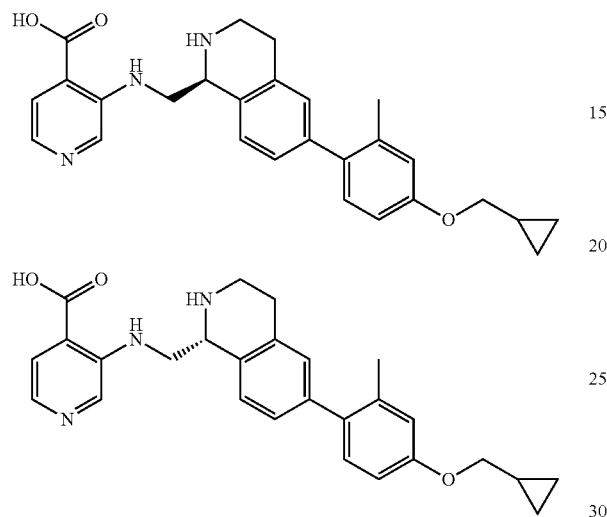

The title compounds were prepared in 72 to 75% yield according to the procedure of Example 1A. NMR (400 MHz, Methanol-$d_4$): δ 0.34-0.38 (m, 2H), 0.59-0.65 (m, 2H), 1.23-1.29 (m, 1H), 2.20 (s, 3H), 3.16-3.30 (m, 2H), 3.42-3.50 (m, 1H), 3.67-3.72 (m, 1H), 3.81 (d, J=4.8 Hz, 2H), 3.90-3.98 (m, 1H), 4.12-4.18 (m, 1H), 4.92-5.00 (m, 1H), 6.76-6.82 (m, 2H), 7.07 (d, J=10.4 Hz, 1H), 7.23-7.29 (m, 2H), 7.49 (d, J=10.4 Hz, 1H), 7.90 (d, J=6.8 Hz, 1H), 7.99 (J=7.2 Hz, 1H), 8.41 (s, 1H). [M+H] Calc'd for $C_{27}H_{29}N_3O_3$, 444; Found, 444.

Preparation of common intermediate methyl 3-[({(1S)-2-[(tert-butyl)oxycarbonyl]-5-bromoisoindolinyl}methyl)amino]pyridine-4-carboxylate and methyl 3-[({(1R)-2-[(tert-butyl) oxycarbonyl]-5-bromoisoindolinyl}methyl)amino]pyridine-4-carboxylate was achieved according to the following outline:

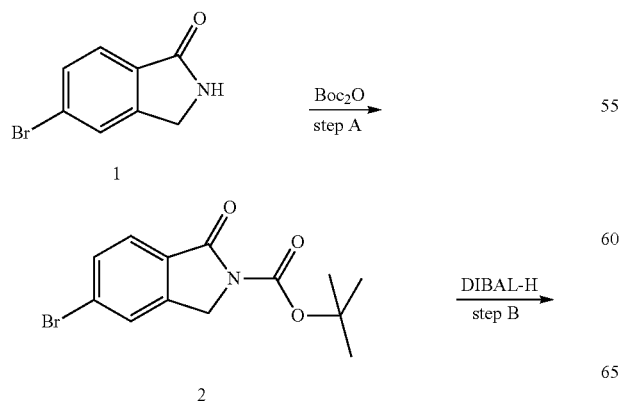

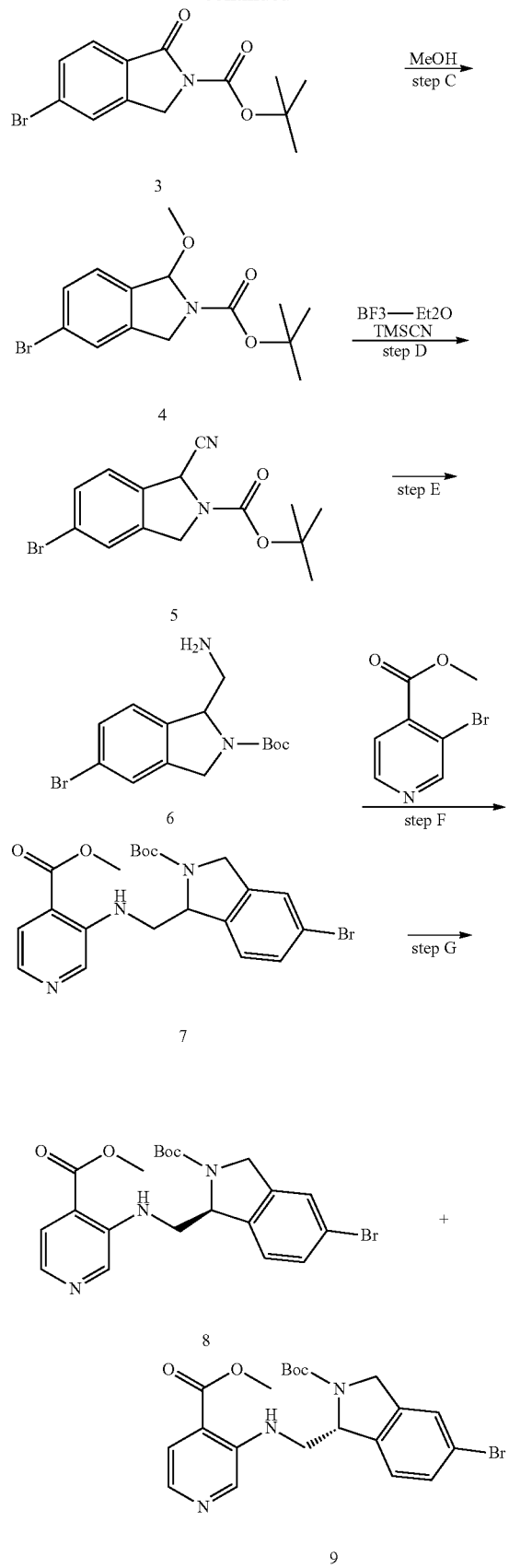

Step A:
5-Bromo-1-oxo-1,3-dihydro-isoindole-2-carboxylic Acid tert-butyl ester

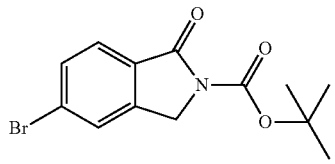 [SMILES: CC(C)(C)OC(=O)N1Cc2cc(Br)ccc2C1=O]

To a solution of 5-bromo-2,3-dihydro-isoindol-1-one (10.0 g, 47.4 mmol) in THF (100 mL) was added a solution of (Boc)$_2$O (20.6 g, 94.5 mmol), and DMAP (0.57 g, 4.6 mmol). The reaction mixture was stirred at ambient temp overnight. Upon completion, the reaction mixture was concentrated in vacuo, and the residue was purified by flash column chromatography (EA:PE=1:10) to afford the title compound (13 g, 88%).

Step B: 5-Bromo-1-hydroxy-1,3-dihydro-isoindole-2-carboxylic Acid tert-butyl ester

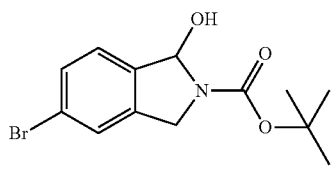 [SMILES: CC(C)(C)OC(=O)N1Cc2cc(Br)ccc2C1O]

To a solution of 5-bromo-1-oxo-1,3-dihydro-isoindole-2-carboxylic acid tert-butyl ester (5.0 g, 16.0 mmol) in anhydrous THF (10 mL) at −78° C. under argon was added a 1.5 M solution of diisobutylaluminum hydride in hexane (16 mL, 24.0 mmol) dropwise. The reaction mixture was stirred at −78° C. for 2 hr. The reaction was quenched with saturated aqueous sodium acetate (50 mL) and allowed to warm to room temp. A 3:1 mixture of diethyl ether and saturated aqueous ammonium chloride (320 mL) was added and the resulting mixture was stirred at room temp until a suspension formed. The solid was filtered under reduced pressure and washed with diethyl ether (twice, 50 mL). The organic layers were collected, and the aqueous layer was extracted with diethyl ether (thrice, 100 mL). The combined organic layers were successively washed with water (50 mL) and brine (50 mL), dried over sodium sulfate, filtered, and concentrated in vacuo. The crude solid were used in the next step without further purification.

Step C: 5-Bromo-1-methoxy-1,3-dihydro-isoindole-2-carboxylic Acid tert-butyl ester

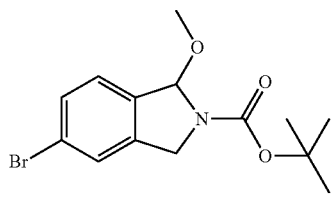 [SMILES: COC1c2ccc(Br)cc2CN1C(=O)OC(C)(C)C]

To a solution of the 5-bromo-1-hydroxy-1,3-dihydro-isoindole-2-carboxylic acid tert-butyl ester in MeOH (50 mL) was added pyridinium p-toluensulfonate (500 mg, 1.9 mmol). The reaction mixture was stirred at room temp for 2 hr and then quenched with triethylamine (2.4 g, 23.7 mmol). The reaction was concentrated in vacuo to give the title compound, which was used in the next step without further purification.

Step D:
5-Bromo-1-cyano-1,3-dihydro-isoindole-2-carboxylic Acid tert-butyl ester

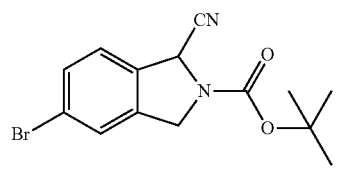 [SMILES: CC(C)(C)OC(=O)N1Cc2cc(Br)ccc2C1C#N]

To a solution of crude 5-bromo-1-methoxy-1,3-dihydro-isoindole-2-carboxylic acid tert-butyl ester in anhydrous CH$_2$Cl$_2$ (50 mL) was added trimethylsilyl cyanide (TMSCN, 3.0 mL, 24.1 mmol), and boron trifluoride-diethyl etherate (3.0 mL, 24.1 mmol) at −78° C. under argon. The reaction mixture was stirred at −78° C. for 1 hr, and then quenched with saturated NaHCO$_3$ (50 mL). The resulting mixture was allowed to warm to room temp and stirred for 2 hr. The biphasic solution was partitioned and the aqueous phase was extracted with CH$_2$Cl$_2$ (3×40 mL). The combined organic layers were dried over magnesium sulfate, filtered, and concentrated in vacuo. The resulting residue was purified by flash chromatography (EA:PE=1:30) to afford the title compound as a white solid (3 g, 58%). $^1$H NMR (300 MHz, CDCl$_3$): δ 1.57 (s, 9H), 4.72 (s, 2H), 5.70 (s, 1H), 7.29-7.37 (m, 1H), 7.50-7.54 (m, 2H).

Step E: 1-Aminomethyl-5-bromo-1,3-dihydroisoindole-2-carboxylic Acid tert-butyl ester

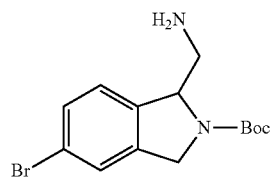

To a solution of the 5-bromo-1-cyano-1,3-dihydroisoindole-2-carboxylic acid tert-butyl ester (1.2 g, 3.7 mmol) in EtOH (20 mL) was added Raney Ni (100 mg in 2 mL water). The reaction mixture was stirred overnight under H$_2$ at ambient temp. The reaction mixture was filtered through Celite, and the filtrate was concentrated in vacuo to provide the title compound (1.2 g, 100%).

Step F: 5-Bromo-1-[(2-methoxycarbonyl-phenylamino)-methyl]-1,3-dihydro-isoindole-2-carboxylic Acid tert-butyl ester

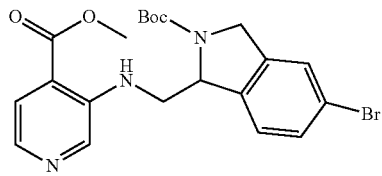 [SMILES: COC(=O)c1ccncc1NCC1c2ccc(Br)cc2CN1C(=O)OC(C)(C)C]

To a solution of 1-aminomethyl-5-bromo-1,3-dihydro-isoindole-2-carboxylic acid tert-butyl ester (1.2 g, 3.68 mmol) in toluene under $N_2$ atmosphere was added 3-bromoisonicotinic acid methyl ester (0.87 g, 4.02 mmol), $Pd_2(dba)_3$ (169 mg, 0.18 mmol), Xant-phos (319 mg, 0.55 mmol), and $Cs_2CO_3$ (1.68 g, 5.15 mmol). The reaction mixture was stirred at reflux overnight. Upon completion, the reaction was concentrated in vacuo, and residue was purified by flash chromatography (EA:PE=1:2) to afford the title compound (0.4 g, 19%).

Step G: methyl 3-[({(1S)-2-[(tert-butyl)oxycarbonyl]-5-bromoisoindolinyl}methyl) amino]pyridine-4-carboxylate and methyl 3-[({(1R)-2-[(tert-butyl)oxycarbonyl]-5-bromoisoindolinyl}methyl)amino]pyridine-4-carboxylate

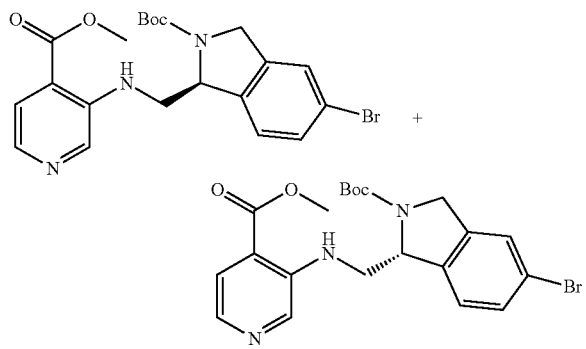

Chiral separation using prep-SFC (Superchiral S-OZ 5 ul 4.6*250 mm, $CO_2$:IPA:DEA=60:40:0.05, F: 2.5 mL/min, W: 254 nm, T: 35° C.) afforded two optically active compounds (2.46 min and 3.13 min).

Example 5A and Example 5B: 3-[({(1S)-5-[methyl(4-methylphenyl)amino]isoindolinyl} methyl)amino]pyridine-4-carboxylic Acid; and 3-[({(1R)-5-[methyl(4-methylphenyl)amino]isoindolinyl}methyl)amino]pyridine-4-carboxylic Acid

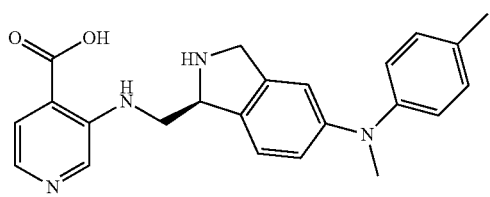

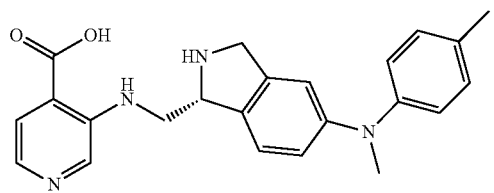

To a solution of methyl 3-[({2-[(tert-butyl)oxycarbonyl]-5-bromoisoindolinyl}methyl) amino]pyridine-4-carboxylate (50 mg, 0.11 mmol) in toluene (10 mL) under $N_2$ atmosphere was added N-methyl-p-tolyl-amine (26 mg, 0.21 mmol), $Pd_2(dba)_3$ (5 mg, 0.005 mmol), Xant-phos (9 mg, 0.015 mmol), and $Cs_2CO_3$ (49 mg, 0.15 mmol). The reaction mixture was refluxed overnight. Upon completion, the reaction mixture was taken up in EA and successively washed with water and brine, dried over $Na_2SO_4$, and concentrated in vacuo. The residue was purified by flash chromatography (EA:PE=1:2) to afford methyl 3-[({2-[(tert-butyl)oxycarbonyl]-5-[methyl (4-methylphenyl) amino] isoindolinyl}methyl)amino]pyridine-4-carboxylate (50 mg, 92%) as oil.

To the solution of methyl 3-[({2-[(tert-butyl) oxycarbonyl]-5-[methyl (4-methyl-phenyl)amino] isoindolinyl}methyl)amino]pyridine-4-carboxylate (50 mg, 0.099 mmol) in THF/$H_2O$ (1:1,10 mL) was added LiOH.$H_2O$ (16 mg, 0.62 mmol). The mixture was stirred at ambient temp overnight. The reaction was concentrated in vacuo and the pH adjusted to ~pH 3 with HCl (2N). The aqueous layers were extracted with EA (thrice), and the combined organic layers were dried with $Na_2SO_4$ and concentrated in vacuo. The residue was dissolved in DCM (10 mL) followed by dropwise addition of TFA (1 mL) and allowed to stir at ambient temp for 2 hr. Upon completion, the reaction mixture was concentrated in vacuo to afford the title compounds (68 to 84%). The analytical data for the two enantiomers are identical. $^1$H NMR (400 MHz, Methanol-$d_4$): δ 2.33 (s, 3H), 3.25 (s, 3H), 3.84-3.91 (m, 1H), 4.02-4.08 (m, 1H), 4.46-4.62 (m, 2H), 5.19-5.22 (m, 1H), 6.78-6.81 (m, 2H), 7.01 (d, J=8.4 Hz, 2H), 7.18 (d, J=8.1 Hz, 2H), 7.27 (d, J=8.1 Hz, 1H), 7.97-8.07 (m, 2H), 8.38 (s, 1H). [M+H] Calc'd for $C_{23}H_{24}N_4O_2$: 403; Found: 403.

Example 6A and Example 6B: 3-{[((1S)-5-{methyl[4-(methylethyl)phenyl]amino}isoindolinyl) methyl]amino}pyridine-4-carboxylic Acid; and 3-{[((1R)-5-{methyl[4-(methylethyl)phenyl]amino} isoindolinyl)methyl]amino}pyridine-4-carboxylic Acid

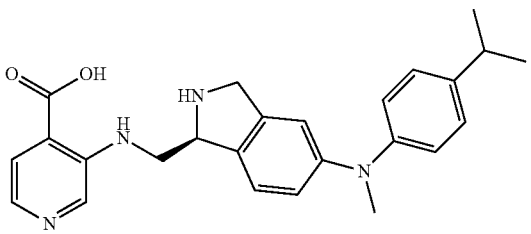

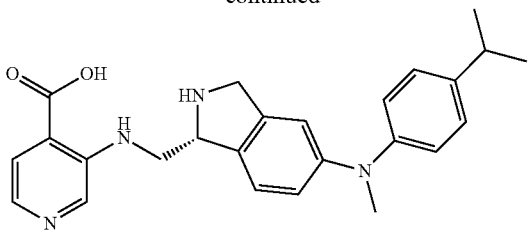

The title compounds were prepared in 44 to 58% yield according to the procedure of Example 5A. $^1$H NMR (300 MHz, Methanol-$d_4$): δ 1.25 (d, J=6.6 Hz, 6H), 2.88-2.92 (m, 1H), 3.26 (s, 3H), 3.85-3.88 (m, 1H), 4.00-4.02 (m, 1H), 4.45-4.57 (m, 2H), 5.17-5.20 (m, 1H), 6.80-6.83 (m, 2H), 7.05 (d, J=8.4 Hz, 2H), 7.22-7.30 (m, 3H), 7.93-7.95 (m, 2H), 8.33 (s, 1H). [M+H] Calc'd for $C_{25}H_{28}N_4O_2$, 416; Found, 416.

Example 7A and 7B: 3-[({(1S)-5-[2-methyl-4-(2,2,2-trifluoroethoxy)phenyl]isoindolinyl}methyl)amino]pyridine-4-carboxylic Acid; and 3-[({(1R)-5-[2-methyl-4-(2,2,2-trifluoroethoxy) phenyl]isoindolinyl}methyl)amino]pyridine-4-carboxylic Acid

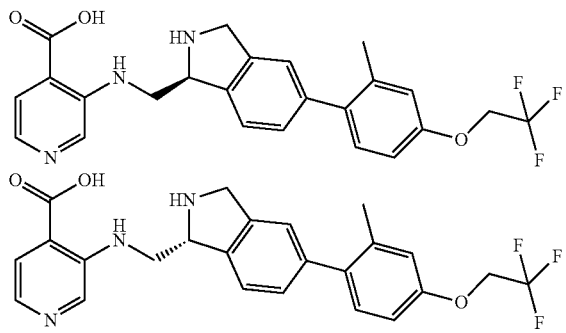

To a solution of methyl 3-[({2-[(tert-butyl) oxycarbonyl]-5-bromoisoindolinyl}methyl) amino]pyridine-4-carboxylate (50 mg, 0.11 mmol) in toluene (10 mL) under $N_2$ atmosphere was added 2,2,2-trifluoro-1-[3-methyl-4-(4,4,5,5-tetramethyl(1,3,2-dioxaborolan-2-yl))phenoxy] ethane (68 mg, 0.21 mmol), Pd(PPh$_3$)$_4$, (12 mg, 0.01 mmol), and Cs$_2$CO$_3$ (106 mg, 0.32 mmol). The reaction mixture refluxed overnight. Upon completion, the reaction mixture was taken up in EA and successively washed with water and brine, dried over Na$_2$SO$_4$, and concentrated in vacuo. The residue was purified by flash chromatography (EA:PE=1:2) to afford methyl 3-[({2-[(tert-butyl) oxycarbonyl]-5-[2-methyl-4-(2,2,2-trifluoroethoxy)-phenyl]isoindolinyl}methyl)amino]pyridine-4-carboxylate (80%) as oil.

To the solution of methyl 3-[({2-[(tert-butyl)oxycarbonyl]-5-[2-methyl-4-(2,2,2-trifluoroethoxy)phenyl]isoindolinyl}methyl)-amino]pyridine-4-carboxylate (50 mg, 0.087 mmol) in THF/H$_2$O (1:1, 10 mL) was added LiOH.H$_2$O (16 mg, 0.62 mmol). The mixture was stirred overnight at ambient temp. The reaction was concentrated in vacuo, and the pH adjusted to ~pH 3 with HCl (2N). The aqueous layers were extracted thrice with EA, and the combined organic layers were dried with Na$_2$SO$_4$ and concentrated in vacuo. The residue was dissolved in DCM (10 mL) followed by dropwise addition of TFA (1 mL) and the reaction mixture stirred at ambient temp for 2 hr. Upon completion, the reaction mixture was concentrated in vacuo to afford the title compound (66 to 76%). $^1$H NMR (400 MHz, Methanol-$d_4$): δ 2.20 (s, 3H), 4.00-4.02 (m, 1H), 4.13-4.15 (m, 1H), 4.50-4.56 (m, 2H), 4.64-4.74 (m, 2H), 5.37-5.40 (m, 1H), 6.88-6.95 (m, 2H), 7.13 (d, J=8.4 Hz, 1H), 7.34-7.37 (m, 2H), 7.58 (d, J=9.9 Hz, 1H), 7.97-8.04 (m, 2H), 8.43 (s, 1H). [M+H] Calc'd for $C_{24}H_{22}F_3N_3O_3$: 457; Found: 457.

Example 8A and Example 8B: (R)-3-(((6-(o-tolyl)-1,2,3,4-tetrahydroisoquinolin-1-yl)methyl) amino) isonicotinic Acid, and (S)-3-(((6-(o-tolyl)-1,2,3,4-tetrahydroisoquinolin-1-yl)methyl) amino) isonicotinic Acid

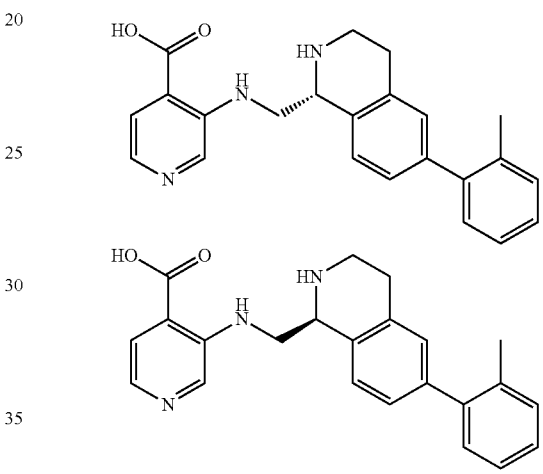

Hydrolysis and de-protection of Boc of each of the enantiomers were carried out as follows: To a solution of tert-butyl (R)-1-(((4-(methoxycarbonyl)pyridin-3-yl)amino)methyl)-6-(o-tolyl)-3,4-dihydroisoquinoline-2(1H)-carboxylate or (S)-1-(((4-(methoxycarbonyl)pyridin-3-yl)amino)methyl)-6-(o-tolyl)-3,4-dihydroisoquinoline-2(1H)-carboxylate (90 mg, 0.18 mmol) in THF/H$_2$O (1:1, 10 mL) was added LiOH.H$_2$O (24 mg, 0.55 mmol). The mixture was stirred overnight at ambient temp. Upon completion, the reaction mixture was concentrated in vacuo and the residue was adjusted to pH~3 with HCl (2N). The aqueous layers were extracted with EA (3×5 mL) and the combined organic layers were dried with Na$_2$SO$_4$ and concentrated in vacuo. The residue was dissolved in DCM (10 mL) followed by TFA (1 mL). The reaction mixture was stirred for 2 hr and concentrated in vacuo affording the title compound (70 mg, 75%). NMR (400 MHz, Methanol-$d_4$): δ 2.23 (s, 3H), 3.18-3.24 (m, 2H), 3.47-3.60 (m, 1H), 3.69-3.74 (m, 1H), 3.97-4.03 (m, 1H), 4.16-4.20 (m, 1H), 5.01-5.03 (m, 1H), 7.15-7.30 (m, 6H), 7.53 (d, J=10.8 Hz, 1H), 8.04-8.07 (m, 2H), 8.49 (s, 1H). [M+H] Calc'd for $C_{23}H_{23}N_3O_2$: 374; Found: 374.

Example 9A and Example 9B: (R)-3-(((6-(2-ethylphenyl)-1,2,3,4-tetrahydroisoquinolin-1-yl) methyl) amino)isonicotinic Acid, and (S)-3-(((6-(2-ethylphenyl)-1,2,3,4-tetrahydroisoquinolin-1-yl) methyl) amino)isonicotinic Acid

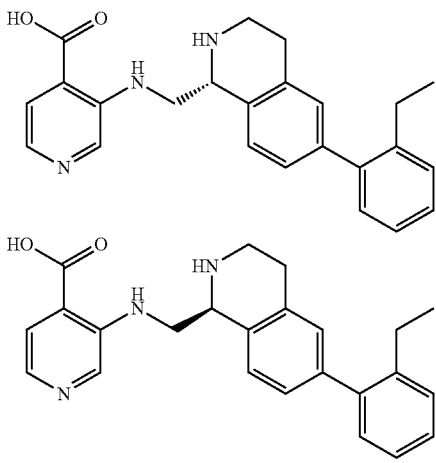

Each of the title compounds were prepared up to 80% yield according to the procedure of Example 8A and 8B. NMR (400 MHz, Methanol-d$_4$): δ 1.05 (t, J=7.6 Hz, 3H), 2.57 (q, J=7.6 Hz, 2H), 3.15-3.23 (m, 2H), 3.45-3.52 (m, 1H), 3.69-3.75 (m, 1H), 3.99-4.05 (m, 1H), 4.18-4.23 (m, 1H), 5.03-5.06 (m, 1H), 7.11-7.32 (m, 6H), 7.52 (d, J=8.4 Hz, 1H), 8.06 (d, J=5.2 Hz, 1H), 8.16 (d, J=5.2 Hz, 1H), 8.54 (s, 1H). [M+H] Calc'd for C$_{24}$H$_{25}$N$_3$O$_2$: 388; Found: 388.

Step T: tert-butyl (R)-6-((4-ethylphenyl)(methyl)amino)-1-(((4-(methoxycarbonyl) pyridin-3-yl)amino)methyl)-3,4-dihydroisoquinoline-2(1H)-carboxylate; and tert-butyl (S)-6-((4-ethylphenyl)(methyl)amino)-1-(((4-(methoxycarbonyl)pyridin-3-yl)amino) methyl)-3,4-dihydroisoquinoline-2(1H)-carboxylate

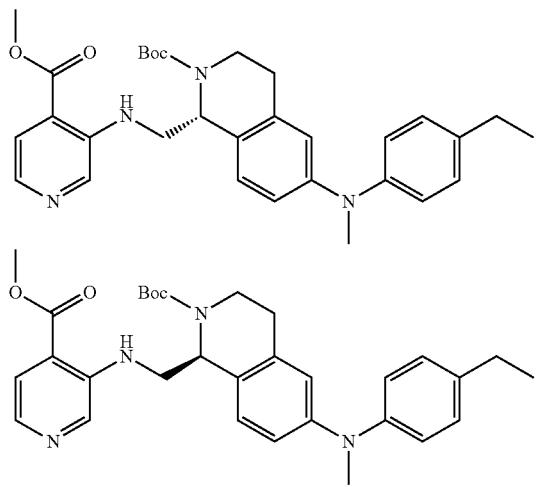

Buchwald reactions of the enantiomers were carried out as follows: To a solution of (R)-6-bromo-1-[(4-methoxycarbonyl-pyridin-3-ylamino)-methyl]-3,4-dihydro-1H-isoquinoline-2-carboxylic acid tert-butyl ester (80 mg, 0.17 mmol) in toluene (30 mL) under N$_2$ atmosphere was added 4-ethyl-N-methylaniline (27 mg, 0.20 mmol), Pd$_2$(dba)$_3$ (8 mg, 0.01 mmol), Xant-phos (6 mg, 0.01 mmol) and Cs$_2$CO$_3$ (80 mg, 0.24 mmol). The reaction mixture was refluxed overnight. Upon completion, the reaction mixture was taken up in EA and the combined organic layers were successively washed with water and brine, dried over Na$_2$SO$_4$, and concentrated in vacuo. The resulting residue was purified by flash column chromatography (EA:PE=1:3) to afford (40 mg, 44%) the title compound. [M+H] Calc'd for C$_{31}$H$_{38}$N$_4$O$_4$: 531; Found: 531.

Example 10A and Example 10B: (R)-3-(((6-((4-ethylphenyl)(methyl)amino)-1,2,3,4-tetrahydroisoquinolin-1-yl)methyl)amino)isonicotinic Acid, and (S)-3-(((6-((4-ethylphenyl) (methyl)amino)-1,2,3,4-tetrahydroisoquinolin-1-yl)methyl)amino)isonicotinic Acid

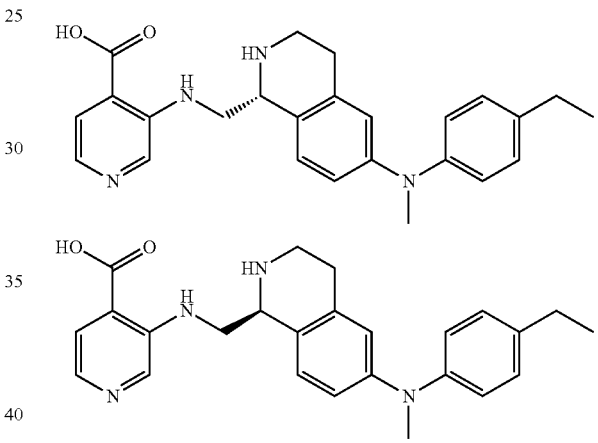

Each of the title compounds was prepared up to 50% yield according to the procedure of Example 8A and 8B. NMR (400 MHz, Methanol-d$_4$): δ 1.24 (t, J=7.2 Hz, 3H), 2.65 (q, J=7.2 Hz, 2H), 2.96-3.12 (m, 2H), 3.29 (s, 3H), 3.34-3.41 (m, 1H), 3.59-3.65 (m, 1H), 3.85-3.91 (m, 1H), 4.05-4.09 (m, 1H), 4.82-4.93 (m, 1H), 6.69-6.77 (m, 2H), 7.04 (d, J=8.4 Hz, 2H), 7.20-7.22 (m, 3H), 8.01-8.10 (m, 2H), 8.42-8.50 (m, 1H). [M+H] Calc'd for C$_{25}$H$_{28}$N$_4$O$_2$: 417; Found: 417.

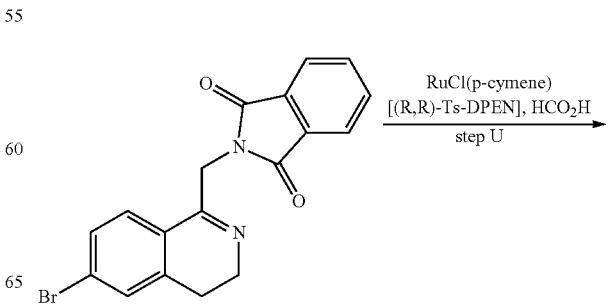

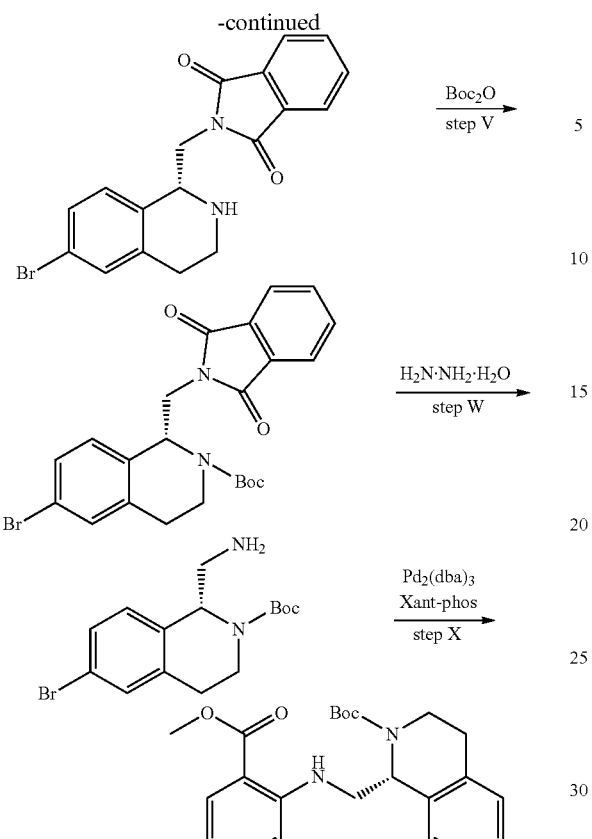

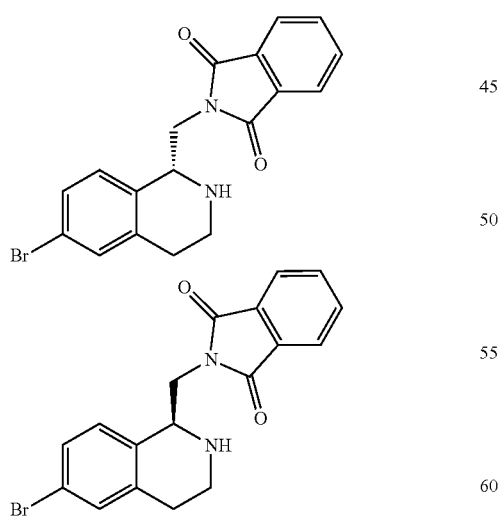

To a solution of 2-(6-bromo-3,4-dihydro-isoquinolin-1-yl-methyl)-isoindole-1,3-dione (111.1 g, 301 mmol) in DMF (500 mL) was added RuCl(p-cymene) [(R,R)-Ts-DPEN] or RuCl(p-cymene) [(S,S)-Ts-DPEN] (19.2 g, 30.1 mmol) at room temp. A mixture of HCO$_2$H (100 mL) and TEA (40 mL) was added dropwise at 0° C. The mixture was stirred at ambient temp for 4 hr. Upon completion, the solution was diluted with H$_2$O, and the pH was adjusted with Na$_2$CO$_3$ to ~pH 10. The solution was extracted thrice with DCM (800 mL). The organic layers were successively washed with H$_2$O, brine, dried over Na$_2$SO$_4$, and concentrated in vacuo. The residue was purified by flash column chromatography (EA:PE=1:4 to 1:1) to afford the title compound (82.0 g, 73.4%) as a white solid. [M+H] Calc'd for C$_{18}$H$_{15}$BrN$_2$O$_2$: 371; Found: 371.

Step V: (R)-6-bromo-1-(1,3-dioxo-1,3-dihydro-isoindol-2-ylmethyl)-3,4-dihydro-1H-isoquinoline-2-carboxylic Acid tert-butyl ester, and (S)-6-Bromo-1-(1,3-dioxo-1,3-dihydro-isoindol-2-ylmethyl)-3,4-dihydro-1H-isoquinoline-2-carboxylic Acid tert-butyl ester

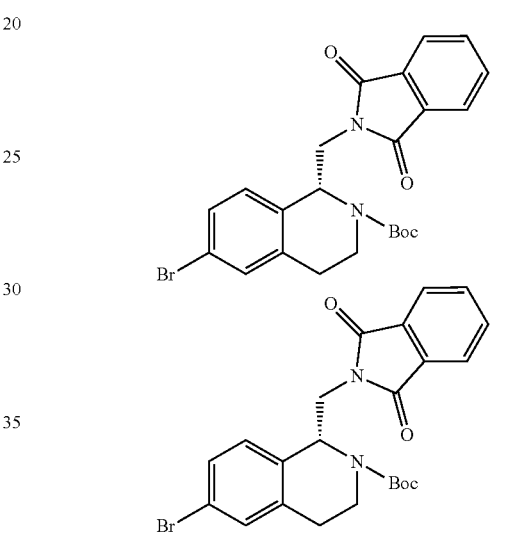

To a solution of 2-(6-bromo-1,2,3,4-tetrahydro-isoquinolin-1-ylmethyl)-isoindole-1,3-dione (82.0 g, 221 mmol) in DCM (800 mL) was added (Boc)$_2$O (57.8 g, 265 mmol) and DIEA (57.0 g, 442 mmol). The reaction mixture was stirred at ambient temp for 6 hr. Aqueous NH$_4$Cl was added, and the organic layer was concentrated in vacuo. The residue was purified by flash column chromatography (EA:PE=1:10 to 1:5) to afford the title compound (93 g, 93.6%) as a white solid. [M+H] Calc'd for C$_{23}$H$_{23}$BrN$_2$O$_4$: 471; Found: 471.

Step W: (R)-1-Aminomethyl-6-bromo-3,4-dihydro-1H-isoquinoline-2-carboxylic Acid tert-butyl ester, and (S)-1-Aminomethyl-6-bromo-3,4-dihydro-1H-isoquinoline-2-carboxylic Acid tert-butyl ester

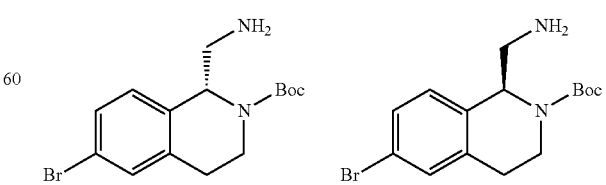

To a solution of (R)-6-bromo-1-(1,3-dioxo-1,3-dihydroisoindol-2-ylmethyl)-3,4-dihydro-1H-isoquinoline-2- carboxylic acid tert-butyl ester or (S)-6-bromo-1-(1,3-di-oxo-1,3-dihydroisoindol-2-ylmethyl)-3,4-dihydro-1H-isoquinoline-2-carboxylic acid tert-butyl ester (55 g, 117 mmol) in CH₃CN (500 mL) was added H₂NNH₂.H₂O (117 g, 2.34 mol); the reaction mixture was refluxed for 6 hr. Upon reaction completion, the mixture was concentrated in vacuo. The resulting residue was dissolved in DCM, and successively washed with water, brine, dried over Na₂SO₄, and concentrated in vacuo to afford the title compound (39.7 g, 100%) as pink oil. [M+H] Calc'd for $C_{15}H_{21}BrN_2O_2$: 341; Found, 341.

Step X: (R)-6-Bromo-1-[(4-methoxycarbonyl-pyridin-3-ylamino)-methyl]-3,4-dihydro-1H-isoquinoline-2-carboxylic Acid tert-butyl ester; and (S)-6-Bromo-1-[(4-methoxycarbonyl-pyridin-3-ylamino)-methyl]-3,4-dihydro-1H-isoquinoline-2-carboxylic Acid tert-butyl ester

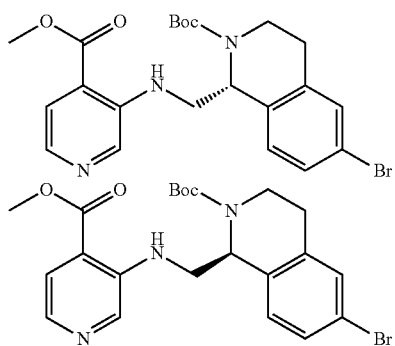

A mixture of (R)-1-aminomethyl-6-bromo-3,4-dihydro-1H-isoquinoline-2-carboxylic acid tert-butyl ester or (S)-1-aminomethyl-6-bromo-3,4-dihydro-1H-isoquinoline-2-carboxylic acid tert-butyl ester (39.7 g, 117 mmol), 3-bromo-isonicotinic acid methyl ester (30.3 g, 140 mmol), Pd₂(dba)₃ (5.38 g, 5.84 mmol), Xant-phos (4.05 g, 7.01 mmol) and Cs₂CO₃ (53.3 g, 163 mmol) in toluene (300 mL) was stirred overnight at 120° C. under N₂ atmosphere. Upon completion, the reaction mixture was filtered, and the filtrate was concentrated in vacuo. The resulting residue was purified by flash column chromatography (EA:PE=1:20 to 1:4) to afford the title compound (28.0 g, 50.1%) as a yellow solid. [M+H] Calc'd for $C_{22}H_{26}BrN_3O_4$: 476; Found: 476.

Step Y: (R)-1-[(4-methoxycarbonyl-pyridin-3-ylamino)-methyl]-6-(methyl-p-tolyl-amino)-3,4-dihydro-1H-isoquinoline-2-carboxylic Acid tert-butyl ester, and (S)-1-[(4-methoxycarbonyl-pyridin-3-ylamino)-methyl]-6-(methyl-p-tolyl-amino)-3,4-dihydro-1H-isoquinoline-2-carboxylic Acid tert-butyl ester

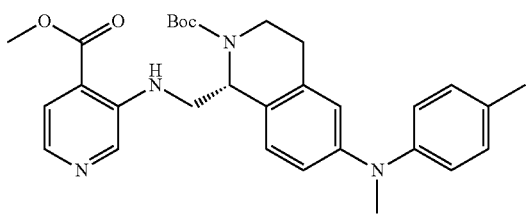

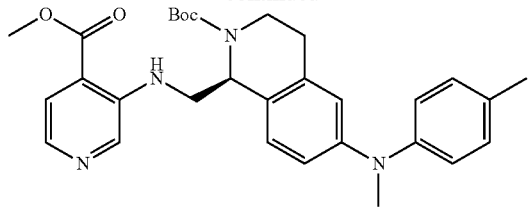

A mixture of (R)-6-bromo-1-[(4-methoxycarbonyl-pyridin-3-ylamino)-methyl]-3,4-dihydro-1H-isoquinoline-2-carboxylic acid tert-butyl ester or (S)-6-bromo-1-[(4-methoxycarbonyl-pyridin-3-ylamino)-methyl]-3,4-dihydro-1H-isoquinoline-2-carboxylic acid tert-butyl ester (4.0 g, 8.40 mmol), N-methyl-p-tolyl-amine (1.22 g, 10.1 mmol), Pd2(dba)3 (387 mg, 0.42 mmol), Xant-phos (729 mg, 1.26 mmol) and Cs2CO3 (3.83 g, 11.8 mmol) in toluene (80 mL) stirred overnight at 120° C. under N₂ atmosphere. Upon completion, the reaction mixture was filtered, and the filtrate was concentrated in vacuo. The resulting residue was purified by flash column chromatography (EA:PE=1:10 to 1:5) to afford the title compound (3.16 g, 72.8%) as yellow oil. [M+H] Calc'd for $C_{30}H_{36}N_4O_4$: 517; Found: 517.

Step Z: Methyl (R)-3-(((6-(methyl(p-tolyl)amino)-1,2,3,4-tetrahydroisoquinolin-1-yl) methyl)amino) isonicotinate, and methyl (S)-3-(((6-(methyl(p-tolyl) amino)-1,2,3,4-tetra-hydroisoquinolin-1-yl)methyl) amino)isonicotinate

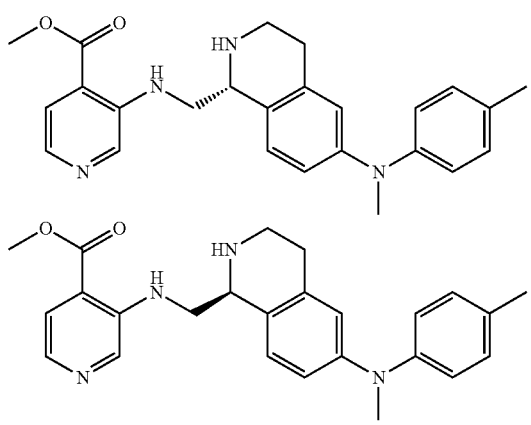

To a solution of (R)-1-[(4-methoxycarbonyl-pyridin-3-ylamino)-methyl]-6-(methyl-p-tolyl-amino)-3,4-dihydro-1H-isoquinoline-2-carboxylic acid tert-butyl ester or (S)-1-[(4-methoxycarbonyl-pyridin-3-ylamino)-methyl]-6-(methyl-p-tolyl-amino)-3,4-dihydro-1H-isoquinoline-2-carboxylic acid tert-butyl ester (3.16 g, 6.11 mmol) in DCM (30 mL) was added TFA (10 mL) at ambient temp and stirred for 2 hr. Upon completion, the resulting solution was concentrated in vacuo. The residue was neutralized with saturated NaHCO₃ and extracted thrice with EA (100 mL). The organic layers were successively washed with brine, dried over Na₂SO₄ and concentrated in vacuo to afford the title compound (2.54 g, 99.6%) as yellow oil. [M+H] Calc'd for $C_{25}H_{28}N_4O_2$: 417; Found: 417.

Step A1: Methyl (R)-3-(((2-methyl-6-(methyl(p-tolyl)amino)-1,2,3,4-tetrahydroisoquinolin-1-yl)methyl)amino)isonicotinate, and methyl (S)-3-(((2-methyl-6-(methyl(p-tolyl)amino)-1,2,3,4-tetrahydroisoquinolin-1-yl)methyl)amino)isonicotinate

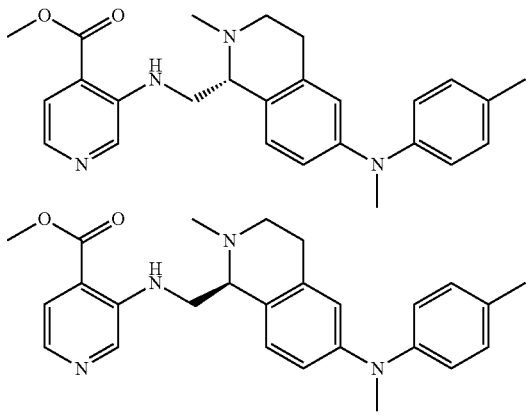

To a solution of (R)-3-{[6-(methyl-p-tolyl-amino)-1,2,3,4-tetrahydroisoquinolin-1-yl-methyl]amino}isonicotinic acid methyl ester or (S)-3-{[6-(methyl-p-tolyl-amino)-1,2,3,4-tetrahydroisoquinolin-1-yl-methyl]amino}isonicotinic acid methyl ester (2.54 g, 6.11 mmol) and DIEA (1.58 g, 12.2 mmol) in DMSO was added a solution of $CH_3I$ (865 mg, 6.11 mmol) in DMSO (50 mL) dropwise. The mixture was stirred at ambient temp for 2 hr. Upon completion, the solution was diluted with $H_2O$ and extracted with DCM (100 mL). The organic layers were successively washed with $H_2O$ (thrice with 80 mL), brine, dried over $Na_2SO_4$, and concentrated in vacuo. The resulting residue was purified by flash column chromatography (MeOH:DCM=1:40) to afford the title compound (1.4 g, 53.2%) as yellow oil. [M+H] Calc'd for $C_{26}H_{30}N_4O_2$: 431; Found: 431.

Example 11A and Example 11B: (R)-3-(((2-methyl-6-(methyl(p-tolyl)amino)-1,2,3,4-tetrahydroisoquinolin-1-yl)methyl)amino)isonicotinic Acid, and (S)-3-(((2-methyl-6-(methyl(p-tolyl)amino)-1,2,3,4-tetrahydroisoquinolin-1-yl)methyl)amino)isonicotinic Acid

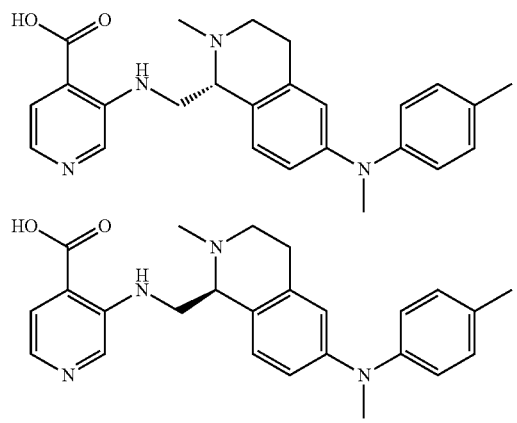

A mixture of (R)-3-{[2-methyl-6-(methyl-p-tolyl-amino)-1,2,3,4-tetrahydroisoquinolin-1-ylmethyl]amino}isonicotinic acid methyl ester or (S)-3-{[2-methyl-6-(methyl-p-tolyl-amino)-1,2,3,4-tetrahydroisoquinolin-1-ylmethyl]amino}isonicotinic acid methyl ester (1.4 g, 3.25 mmol) and $LiOH \cdot H_2O$ (410 mg, 9.74 mmol) in $THF/H_2O$ (20 mL) was stirred overnight at room temp. Upon completion, the volume of the reaction mixture was reduced in vacuo and the pH adjusted with HCl (1N) to ~pH 7. The precipitate was filtered and the filter cake dried in vacuo to afford the title compound (1.05 g, 77.8%) as a yellow solid. [M+H] Calc'd for $C_{25}H_{28}N_4O_2$: 417; Found: 417.

NMR (400 MHz, $CD_3OD$): δ 8.07 (s, 1H), 7.82 (d, J=4.8 Hz, 1H), 7.69 (d, J=4.8 Hz, 1H), 7.15-7.12 (m, 3H), 7.00-6.97 (m, 2H), 6.74 (d, J=8.4 Hz, 1H), 6.65 (s, 1H), 4.41 (t, J=5.6 Hz, 1H), 3.76 (d, J=6.0 Hz, 2H), 3.67-3.63 (m, 1H), 3.24-3.18 (m, 4H), 3.01-2.98 (m, 2H), 2.87 (s, 3H), 2.31 (s, 3H).

Step B1. tert-butyl (R)-1-(((4-(methoxycarbonyl)pyridin-3-yl)amino)methyl)-6-(o-tolyl)-3,4-dihydroisoquinoline-2(1H)-carboxylate; and tert-butyl (S)-1-(((4-(methoxycarbonyl) pyridin-3-yl)amino)methyl)-6-(o-tolyl)-3,4-dihydroisoquinoline-2(1H)-carboxylate

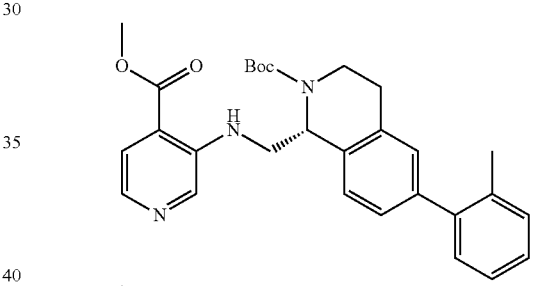

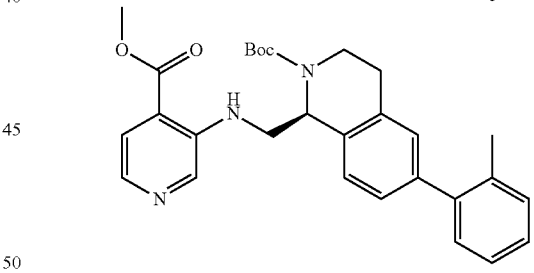

Suzuki coupling of the enantiomers were carried out as follows: A mixture of (R)-6-bromo-1-[(4-methoxycarbonyl-pyridin-3-ylamino)methyl]-3,4-dihydro-1H-isoquinoline-2-carboxylic acid tert-butyl ester or (S)-6-bromo-1-[(4-methoxycarbonyl-pyridin-3-ylamino) methyl]-3,4-dihydro-1H-isoquinoline-2-carboxylic acid tert-butyl ester (900 mg, 1.89 mmol), 2-methyl-phenylboronic acid (311 mg, 2.29 mmol), $Pd(PPh_3)_4$ (108 mg, 0.095 mmol) and $Cs_2CO_3$ (1.85 g, 5.67 mmol) in toluene (40 mL) stirred overnight at 120° C. under $N_2$ atmosphere. Upon completion, the reaction mixture was filtered, and the filtrate concentrated in vacuo. The resulting residue was purified by flash column chromatography (EA:PE=1:10 to 1:5) to afford the title compound (921 mg, 99.8%) as yellow oil. [M+H] Calc'd for $C_{29}H_{33}N_3O_4$: 488; Found: 488.

Example 12A and Example 12B: (R)-3-(((2-methyl-6-(o-tolyl)-1,2,3,4-tetrahydroisoquinolin-1-yl) methyl)amino)isonicotinic Acid, and (S)-3-(((2-methyl-6-(o-tolyl)-1,2,3,4-tetrahydroisoquinolin-1-yl) methyl)amino)isonicotinic Acid

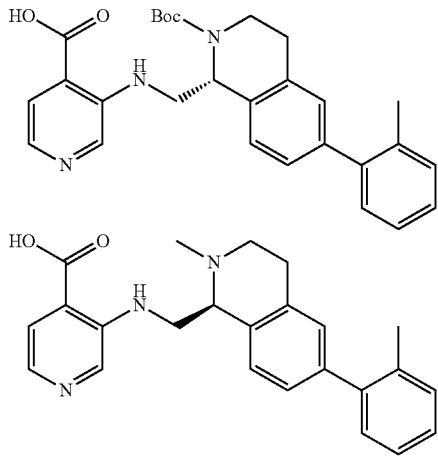

Each of the title compounds was prepared according to the procedure for Example 8A and Example 8B. NMR (400 MHz, DMSO-d6) δ 8.26 (s, 1H), 7.77 (d, J=5.2 Hz, 1H), 7.49 (d, J=4.8 Hz, 1H), 7.35 (d, J=8.0 Hz, 1H), 7.27-7.19 (m, 3H), 7.16-7.10 (m, 1H), 7.08 (d, J=1.6 Hz, 1H), 7.05 (s, 1H), 3.82-3.81 (m, 1H), 3.71-3.61 (m, 2H), 3.16-3.11 (m, 1H), 2.88-2.82 (m, 2H), 2.70-2.65 (m, 1H), 2.50 (s, 3H), 2.19 (s, 3H). [M+H] Calc'd for $C_{24}H_{25}N_3O_2$: 388; Found: 388.

Example 13A and Example 13B: (R)-3-(((6-((4-ethylphenyl)(methyl)amino)-2-methyl-1,2,3,4-tetrahydroisoquinolin-1-yl)methyl)amino)isonicotinic Acid, and (S)-3-(((6-((4-ethylphenyl)(methyl)amino)-2-methyl-1,2,3,4-tetrahydroisoquinolin-1-yl)methyl)amino)isonicotinic Acid

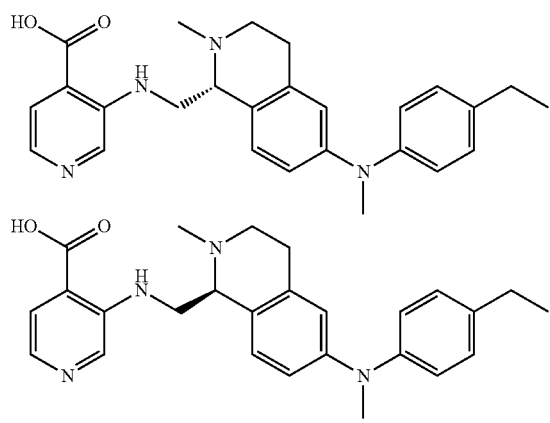

Each of the title compounds was prepared in 86% yield according to the procedure for Example 11A and Example 11B. NMR (400 MHz, CD₃OD): δ 8.06 (s, 1H), 7.81 (d, J=4.8 Hz, 1H), 7.69 (d, J=4.8 Hz, 1H), 7.17-7.12 (m, 3H), 7.01-6.99 (m, 2H), 6.75 (d, J=8.4 Hz, 1H), 6.66 (s, 1H), 4.42-4.39 (m, 1H), 3.77 (d, J=5.2 Hz, 2H), 3.66-3.62 (m, 1H), 3.26-3.18 (m, 4H), 3.00-2.98 (m, 2H), 2.86 (s, 3H), 2.62 (q, J=7.6 Hz, 2H), 1.22 (t, J=7.6 Hz, 3H). [M+H] Calc'd for $C_{26}H_{30}N_4O_2$: 431; Found: 431.

Example 14A and Example 14B: (R)-3-(((2-methyl-6-(methyl(4-propylphenyl)amino)-1,2,3,4-tetrahydroisoquinolin-1-yl)methyl)amino)isonicotinic Acid, and (S)-3-(((2-methyl-6-(methyl(4-propylphenyl) amino)-1,2,3,4-tetrahydroisoquinolin-1-yl)methyl) amino)isonicotinic Acid

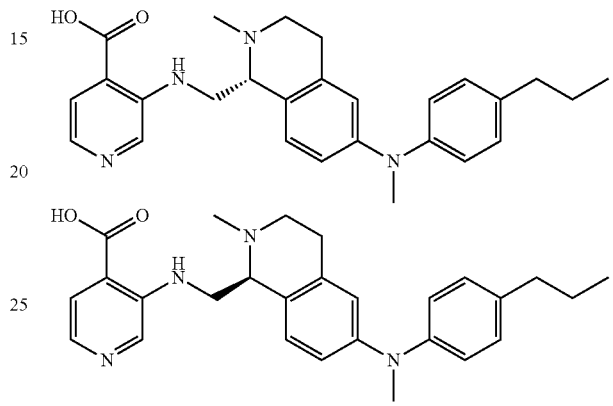

Each of the title compounds was prepared according to the procedure for Example 11A and Example 11B. NMR (400 MHz, CD₃OD) δ 8.10 (s, 1H), 7.86 (d, J=5.2 Hz, 1H), 7.70 (d, J=4.8 Hz, 1H), 7.17-7.14 (m, 3H), 7.02 (d, J=8.0 Hz, 2H), 6.78-6.75 (m, 1H), 6.68 (d, J=2.0 Hz, 1H), 4.57-4.54 (m, 1H), 3.82-3.81 (m, 2H), 3.76-3.73 (m, 1H), 3.33-3.30 (m, 1H), 3.25 (s, 3H), 3.06-3.03 (m, 2H), 2.94 (s, 3H), 2.59-2.55 (m, 2H), 1.67-1.61 (m, 2H), 0.97-0.93 (m, 2H). [M+H] Calc'd for $C_{27}H_{32}N_4O_2$: 445; Found: 445.

Example 15A and Example 15B: (R)-3-(((6-(2-ethylphenyl)-2-methyl-1,2,3,4-tetrahydroisoquinolin-1-yl)methyl)amino)isonicontinic Acid, and (S)-3-(((6-(2-ethylphenyl)-2-methyl-1,2,3,4-tetrahydroisoquinolin-1-yl)methyl)amino) isonicotinic Acid

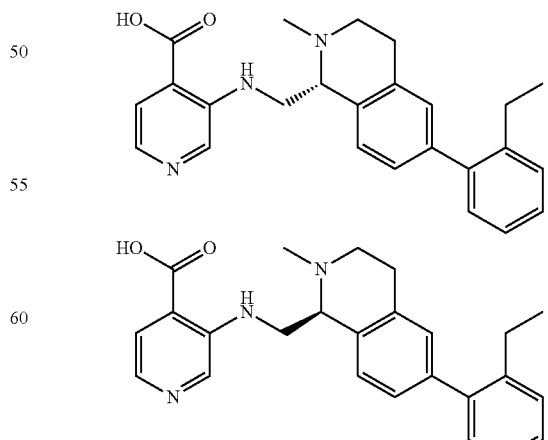

Each of the title compounds was prepared up to 66% yield according to the procedure for Example 12A and Example 12B. NMR (400 MHz, CD$_3$OD): δ 8.22 (s, 1H), 7.75 (d, J=4.8 Hz, 1H), 7.49 (d, J=4.8 Hz, 1H), 7.36-7.26 (m, 3H), 7.23-7.18 (m, 1H), 7.11 (d, J=7.2 Hz, 1H), 7.05 (d, J=8.0 Hz, 1H), 7.01 (s, 1H), 3.80 (t, J=4.0 Hz, 1H), 3.66-3.61 (m, 2H), 3.16-3.10 (m, 1H), 2.88-2.81 (m, 2H), 2.69-2.64 (m, 1H), 2.53-2.48 (m, 2H), 2.48 (s, 3H), 1.01 (t, J=7.6 Hz, 3H). LCMS: [M+H] Calc'd for C$_{25}$H$_{27}$N$_3$O$_2$: 402; Found: 402.

Example 16A and Example 16B: (R)-3-(((6-(2-iso-propylphenyl)-2-methyl-1,2,3,4-tetrahydroisoquinolin-1-yl)methyl)amino)isonicotinic Acid, and (S)-3-(((6-(2-isopropylphenyl)-2-methyl-1,2,3,4-tetrahydroisoquinolin-1-yl)methyl)amino) isonicotinic Acid

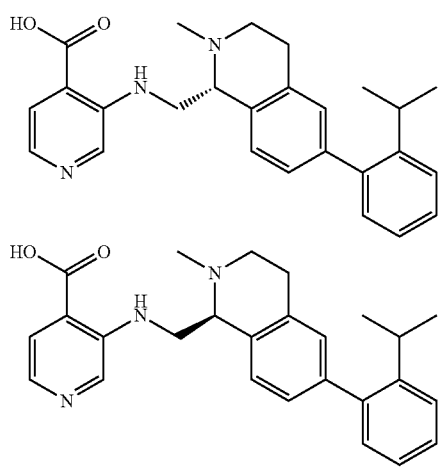 [SMILES: CC(C)c1ccccc1-c1ccc2c(c1)CCN(C)[C@H]2CNc1cnccc1C(=O)O ; CC(C)c1ccccc1-c1ccc2c(c1)CCN(C)[C@@H]2CNc1cnccc1C(=O)O]

Each of the title compounds were prepared up to 42% yield according to the procedure for Example 12A and Example 12B. NMR (400 MHz, DMSO-d6): δ 8.25 (s, 1H), 7.75 (d, J=5.2 Hz, 1H), 7.48 (d, J=4.8 Hz, 1H), 7.40-7.29 (m, 3H), 7.18 (m, 1H), 7.08 (d, J=6.4 Hz, 1H), 7.01 (m, 2H), 3.80 (t, J=4.0 Hz, 1H), 3.67-3.65 (m, 2H), 3.14-3.11 (m, 1H), 2.94-2.81 (m, 3H), 2.67-2.66 (m, 1H), 2.51 (s, 3H), 1.08 (m, 6H). LCMS: [M+H] Calc'd for C$_{26}$H$_{29}$N$_3$O$_2$: 416; Found: 416.

Example 17A and Example 17B: (R)-3-(((6-(2,6-dimethylphenyl)-2-methyl-1,2,3,4-tetrahydroisoquinolin-1-yl)methyl)amino)isonicotinic Acid, and (S)-3-(((6-(2,6-dimethylphenyl)-2-methyl-1,2,3,4-tetrahydroisoquinolin-1-yl)methyl)amino) isonicotinic Acid

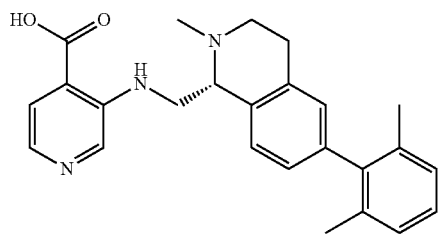

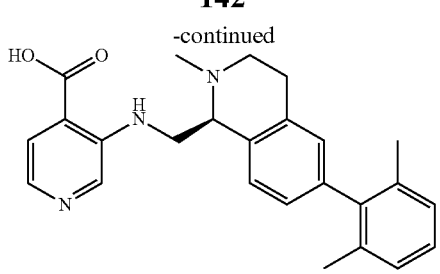

Each of the title compounds was prepared according to the procedure for Example 12A and Example 12B. NMR (400 MHz, DMSO-d6): δ 8.25 (s, 1H), 7.74 (d, J=4.8 Hz, 1H), 7.45 (d, J=5.2 Hz, 1H), 7.35 (d, J=7.6 Hz, 1H), 7.15-7.05 (m, 3H), 6.86-6.84 (m, 2H), 3.81 (s, 1H), 3.70-3.66 (m, 2H), 3.12-3.09 (m, 1H), 2.86-2.78 (m, 2H), 2.67-2.65 (m, 1H), 2.50 (s, 3H), 1.96 (s, 3H), 1.84 (s, 3H). [M+H] Calc'd for C$_{25}$H$_{27}$N$_3$O$_2$: 402; Found: 402.

Step C1: tert-butyl (R)-5-bromo-1-(((4-(methoxycarbonyl)pyridin-3-yl)amino)methyl)isoindoline-2-carboxylate; and tert-butyl (S)-5-bromo-1-(((4-(methoxycarbonyl)pyridin-3-yl) amino)methyl) isoindoline-2-carboxylate

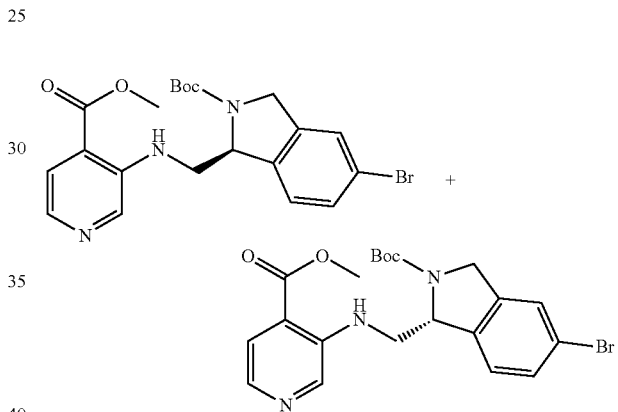

Chiral separation using prep-SFC (Superchiral S-OZ 5 μl 4.6*250 mm, CO$_2$:IPA:DEA=60:40:0.05, F: 2.5 mL/min, W: 254 nm, T: 35° C.) afforded two optically active compounds (2.46 min and 3.13 min). NMR (CDCl3, 400 MHz): δ 8.44 (s, 1H), 7.95-7.88 (m, 1H), 7.62-7.55 (m, 1H), 747-7.36 (m, 3H), 7.20-7.10 (m, 1H), 5.29-5.19 (m, 1H), 4.85-4.48 (m, 2H), 3.92-3.90 (m, 4H), 3.80-3.77 (m, 1H), 1.54 (s, 9H,). LCMS: [M+H] Calc'd for C$_{21}$H$_{24}$BrN$_3$O$_4$: 462; Found: 462.

Step D1: 3-[({(1S)-5-[methyl(4-methylphenyl) amino]isoindolinyl}methyl)amino] pyridine-4-carboxylic Acid, and 3-[({(1R)-5-[methyl(4-methylphenyl)amino] isoindolinyl}methyl) amino] pyridine-4-carboxylic Acid

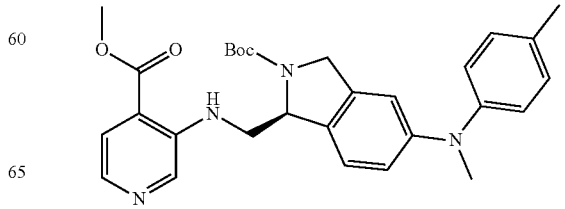

-continued

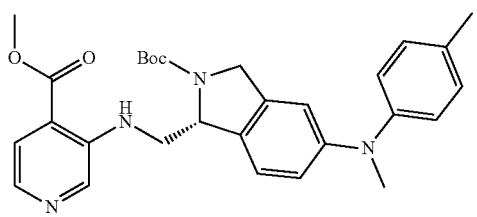

To a solution of methyl 3-[({2-[(tert-butyl)oxycarbonyl]-5-bromoisoindolinyl}methyl) amino] pyridine-4-carboxylate (4.5 g, 9.72 mmol) in toluene (100 mL) under $N_2$ atmosphere was added N-methyl-p-tolyl-amine (1.4 g, 11.66 mmol), $Pd_2(dba)_3$ (450 mg, 0.5 mmol), Xant-phos (840 mg, 1.5 mmol), and $Cs_2CO_3$ (4.5 g, 13.6 mmol). The reaction mixture was refluxed overnight. Upon completion, the reaction mixture was taken up in EA and successively washed with water and brine, dried over $Na_2SO_4$, and concentrated in vacuo. The residue was purified by flash chromatography (EA:PE=1:4) to afford methyl 3-[({2-[(tert-butyl)oxycarbonyl]-5-[methyl (4-methyl phenyl)amino] isoindolinyl}methyl)amino]pyridine-4-carboxylate (2.6 g, 54%) as oil. LCMS: [M+H] Calc'd for $C_{29}H_{34}N_4O_4$: 503; Found: 503.

Example 18A and Example 18B: (R)-3-(((2-methyl-5-(methyl(p-tolyl)amino)isoindolin-1-yl) methyl)amino)isonicotinic Acid, and (S)-3-(((2-methyl-5-(methyl(p-tolyl)amino)isoindolin-1-yl) methyl)amino)isonicotinic Acid

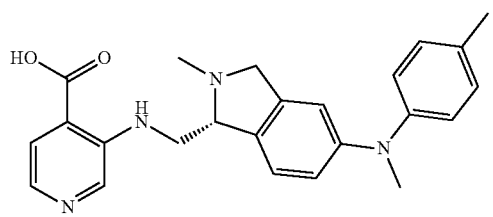

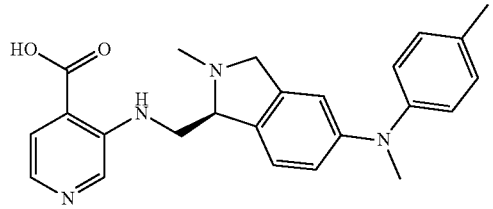

Each of the title compounds was prepared up to 65% yield according to the procedure for Example 11A and 11B. NMR (400 MHz, CD3OD): δ 8.49 (s, 1H), 8.30 (d, J=6.0 Hz, 1H), 8.06 (d, J=6.0 Hz, 1H), 7.27-7.19 (m, 3H), 7.04 (d, J=8.4 Hz, 2H), 6.83-6.79 (m, 2H), 5.10-5.09 (m, 1H), 4.94-4.89 (m, 1H), 4.45-4.42 (m, 1H), 4.17-4.00 (m, 2H), 3.27 (s, 3H), 3.14 (s, 3H), 2.33 (s, 3H). LCMS: [M+H] Calc'd for $C_{24}H_{26}N_4O_2$: 403; Found: 403.

Example 19A and Example 19B: (R)-3-(((5-((4-ethylphenyl)(methyl)amino)-2-methylisoindolin-1-yl)methyl)amino)isonicotinic Acid, and (S)-3-(((5-((4-ethylphenyl)(methyl)amino)-2-methylisoindolin-1-yl)methyl)amino)isonicotinic Acid

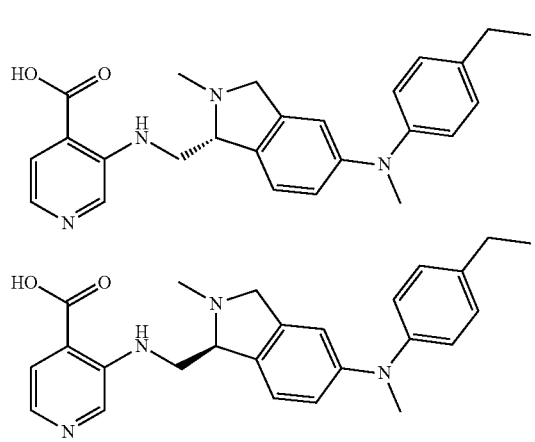

Each of the title compounds was prepared up to 87% yield according to the procedure for Example 18A and 18B. NMR (400 MHz, CD3OD): δ 8.35 (s, 1H), 8.01-7.97 (m, 2H), 7.28-7.21 (m, 3H), 7.06 (d, J=8.4 Hz, 2H), 6.85-6.78 (m, 2H), 5.07-5.05 (m, 1H), 4.90-4.85 (m, 1H), 4.47-4.41 (m, 1H), 4.14-4.09 (m, 1H), 3.98-3.95 (m, 1H), 3.27 (s, 3H), 3.14 (s, 3H), 2.64 (q, J=7.2 Hz, 1H), 1.24 (t, J=7.2 Hz, 3H). LCMS: [M+H] Calc'd for $C_{25}H_{28}N_4O_2$: 417; Found: 417.

Example 20A and Example 20B: (R)-3-(((2-methyl-5-(methyl(4-propylphenyl)amino)isoindolin-1-yl) methyl)amino)isonicotinic Acid, and (S)-3-(((2-methyl-5-(methyl(4-propyl-phenyl)amino)isoindolin-1-yl)methyl)amino)isonicotinic Acid

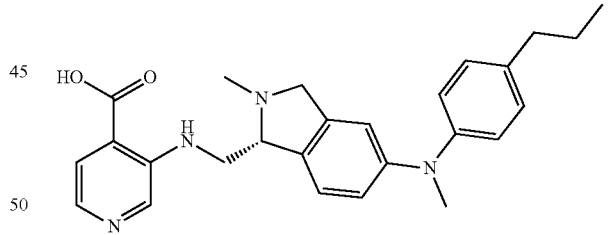

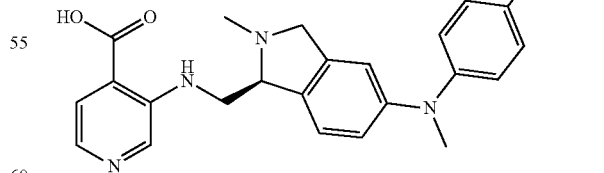

Each of the title compounds was prepared up to 60% yield according to the procedure for Example 18A and 18B. NMR (400 MHz, CD3OD): δ 8.34 (s, 1H), 8.02-7.97 (m, 2H), 7.27-7.19 (m, 3H), 7.06-7.03 (m, 2H), 6.84-6.78 (m, 2H), 5.07-5.04 (m, 1H), 4.90-4.85 (m, 1H), 4.44-4.40 (m, 1H), 4.13-4.09 (m, 1H), 3.98-3.93 (m, 1H), 3.27 (s, 3H), 3.13 (s, 3H), 2.58 (t, J=7.2 Hz, 2H), 1.69-1.59 (m, 2H), 0.95 (t, J=7.2 Hz, 3H). LCMS: [M+H] Calc'd for $C_{26}H_{30}N_4O_2$: 431; Found: 431.

Step E1: tert-butyl (R)-1-(((4-(methoxycarbonyl) pyridin-3-yl)amino)methyl)-5-(o-tolyl)isoindoline-2-carboxylate; and tert-butyl (S)-1-(((4-(methoxycarbonyl)pyridin-3-yl)amino)methyl)-5-(o-tolyl) isoindoline-2-carboxylate

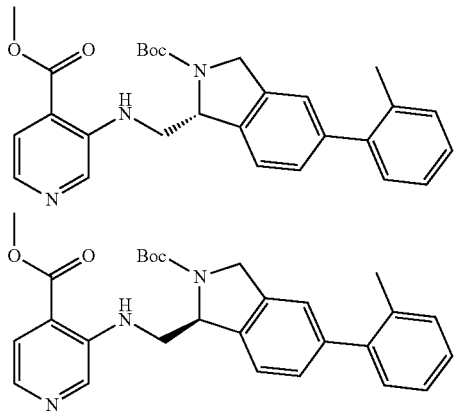

A mixture of tert-butyl (1R)-5-bromo-1-({[4-(methoxycarbonyl)(3-pyridyl)]amino} methyl)isoindoline-2-carboxylate (200 mg, 0.43 mmol), 2-methylphenylboronic Acid (118 mg, 0.86 mmol), Pd(PPh$_3$)$_4$ (25 mg, 0.02 mmol) and Cs$_2$CO$_3$ (420 mg, 1.29 mmol) in toluene (40 mL) stirred overnight at 120° C. under N$_2$. Upon completion, the reaction mixture was filtered, and the filtrate concentrated in vacuo. The resulting residue was purified by flash column chromatography (EA:PE=1:3) to afford the title compound (130 mg, 65%) as yellow oil. [M+H] Calc'd for $C_{28}H_{31}N_3O_4$: 474; Found: 474.

Example 21A and Example 21B: (R)-3-(((2-methyl-5-(o-tolyl)isoindolin-1-yl)methyl)amino) isonicotinic Acid; and (S)-3-(((2-methyl-5-(o-tolyl)isoindolin-1-yl)methyl)amino) isonicotinic Acid

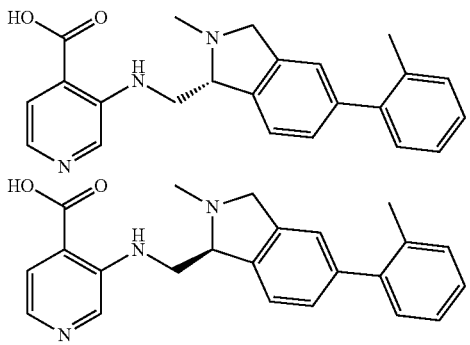

Each of the title compounds was prepared up to 60% yield according to the procedure for Example 12A and 12B. NMR (400 MHz, CD3OD): δ 8.19 (s, 1H), 8.80 (d, J=5.2 Hz, 1H), 7.71 (d, J=4.8 Hz, 1H), 7.55 (d, J=7.6 Hz, 1H), 7.30-7.12 (m, 6H), 5.07-5.04 (m, 1H), 4.90-4.85 (m, 1H), 4.28-4.25 (m, 1H), 4.11-4.07 (m, 1H), 3.96-3.92 (m, 1H), 3.01 (s, 3H), 2.18 (s, 3H). LCMS: [M+H] Calc'd for $C_{23}H_{23}N_3O_2$: 374; Found: 374.

Example 22A and Example 22B: (R)-3-(((5-(2-ethylphenyl)-2-methylisoindolin-1-yl)methyl) amino) isonicotinic Acid; and (S)-3-(((5-(2-ethylphenyl)-2-methylisoindolin-1-yl)methyl)amino) isonicotinic Acid

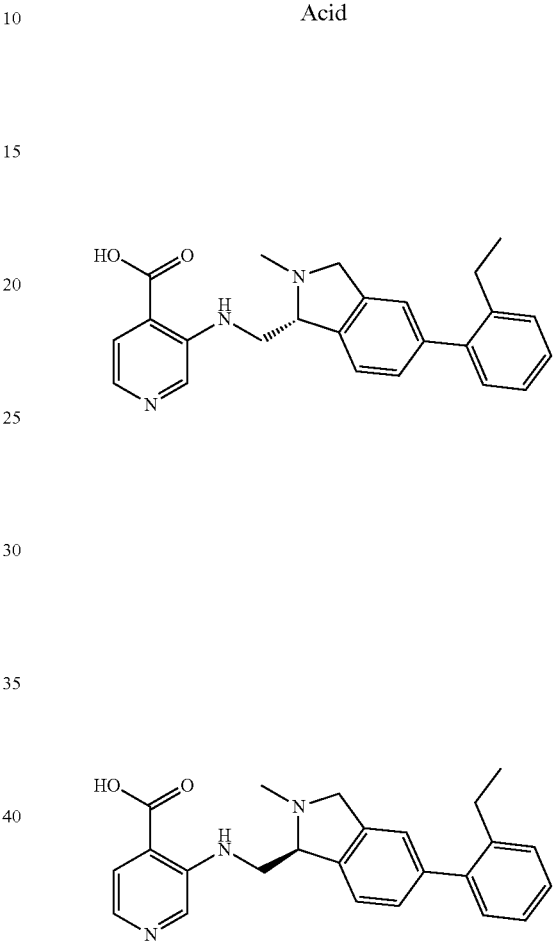

Each of the title compounds was prepared up to 47% yield according to the procedure for Example 21A and 21B. NMR (400 MHz, CD$_3$OD): δ 8.25 (s, 1H), 7.86 (d, J=5.2 Hz, 1H), 7.77 (d, J=5.2 Hz, 1H), 7.57 (d, J=7.6 Hz, 1H), 7.34-7.29 (m, 4H), 7.23-7.20 (m, 1H), 7.11 (d, J=7.6 Hz, 1H), 5.10-5.03 (m, 2H), 4.44 (d, J=14.4 Hz, 1H), 4.18-4.14 (m, 1H), 4.04-3.99 (m, 1H), 3.11 (s, 3H), 2.53 (q, J=7.6 Hz, 2H), 1.03 (t, J=7.6 Hz, 3H). LCMS: [M+H] Calc'd for $C_{24}H_{25}N_3O_2$: 388; Found: 388.

Additional embodiments of a compound of Formula 2 are shown in Table 3 ("Example" refers to a Chemical Synthesis Example prepared according to the "Example preparation" example as described above):

TABLE 3

| Example | Compound IUPAC name | Example preparation | H¹ NMR and MS |
|---|---|---|---|
| 23A and 23B | 3-({[(1R)-6-(thiophen-3-yl)-1,2,3,4-tetrahydroisoquinolin-1-yl]methyl}amino)pyridine-4-carboxylic acid; and 3-({[(1S)-6-(thiophen-3-yl)-1,2,3,4-tetrahydroisoquinolin-1-yl]methyl}amino)pyridine-4-carboxylic acid 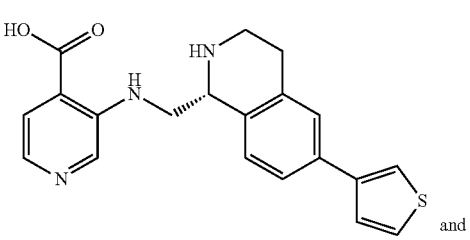 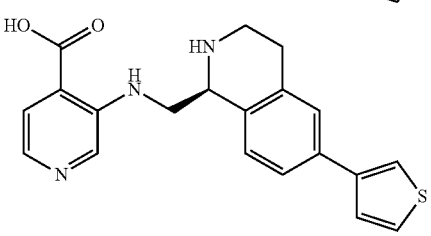 and | 2A and 2B | NMR (400 MHz, CD$_3$OD + DMSO-d6): δ 3.14-3.23 (2H, m), 3.37-3.42 (1H, m), 3.61-3.66 (1H, m), 3.91-3.97 (1H, m), 4.13-4.18 (1H, m), 4.91-4.94 (1H, m), 7.52-7.69 (5H, m), 7.83(1H, t, J = 1.6 Hz), 7.92 (1H, d, J = 5.2 Hz), 8.03(1H, d, J = 5.2 Hz), 8.97 (1H s). [M + H] Calc'd for C$_{20}$H$_{19}$N$_3$O$_2$S: 366; Found: 366. |
| 24A and 24B | 3-({[(1R)-6-[2-fluoro-4-(2,2,2-trifluoroethoxy)phenyl]-1,2,3,4-tetrahydroisoquinolin-1-yl]methyl}amino)pyridine-4-carboxylic acid; and 3-({[(1S)-6-[2-fluoro-4-(2,2,2-trifluoroethoxy)phenyl]-1,2,3,4-tetrahydroisoquinolin-1-yl]methyl}amino)pyridine-4-carboxylic acid 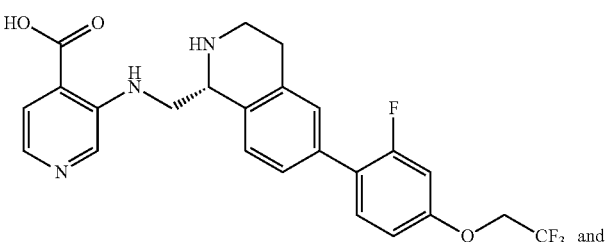 and 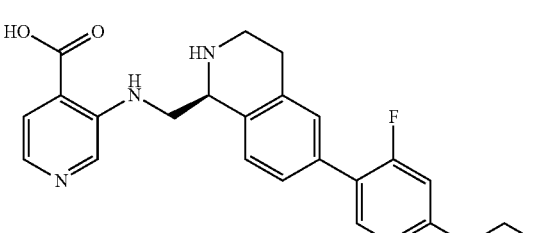 | 2A and 2B | NMR (400 MHz, CD$_3$OD): δ 3.14-3.25 (2H, m), 3.42-3.49 (1H, m), 3.66-3.73 (1H, m), 3.93-4.00 (1H, m), 4.14-4.19 (1H, m), 4.57-4.65 (2H, m), 4.99-5.01 (1H, m), 6.92-6.97 (2H, m), 7.43-7.56 (4H, m), 8.02 (2H, s), 8.49 (1H, s). [M + H] Calc'd for C$_{24}$H$_{21}$F$_4$N$_3$O$_3$, 476; Found, 476. |

TABLE 3-continued

| Example | Compound IUPAC name | Example preparation | H¹ NMR and MS |
|---|---|---|---|
| 25A and 25B | 3-({[(1R)-6-(2,4-difluorophenyl)-1,2,3,4-tetrahydroisoquinolin-1-yl]methyl}amino)pyridine-4-carboxylic acid; and 3-({[(1S)-6-(2,4-difluorophenyl)-1,2,3,4-tetrahydroisoquinolin-1-yl]methyl}amino)pyridine-4-carboxylic acid | 2A and 2B | NMR (400 MHz, CD$_3$OD): δ 3.20-3.29 (2H, m), 3.46-3.49 (1H, m), 3.68-3.73 (1H, m), 3.92-3.96 (1H, m), 4.13-4.17 (1H, m), 4.96-5.01 (1H, m), 7.05-7.09 (2H, m), 7.48-7.57 (4H, m), 7.93 (1H, d, J = 5.2 Hz), 7.99 (1H, d, J = 5.2 Hz), 8.42 (1H, s). [M + H] Calc'd for C$_{22}$H$_{19}$F$_2$N$_3$O$_2$: 396; Found: 396. |
| 26A and 26B | (R)-3-(((6-(4-chloro-2-fluorophenyl)-1,2,3,4-tetrahydroisoquinolin-1-yl)methyl)amino)isonicotinic acid; and (S)-3-(((6-(4-chloro-2-fluorophenyl)-1,2,3,4-tetrahydroisoquinolin-1-yl)methyl)amino)isonicotinic acid | 2A and 2B | NMR (400 MHz, CD$_3$OD): δ 3.20-3.28 (2H, m), 3.45-3.51 (1H, m), 3.69-3.73 (1H, m), 3.95-4.02 (1H, m), 4.16-4.20 (1H, m), 5.02-5.04 (1H, m), 7.30-7.34 (1H, m), 7.48-7.58 (2H, m), 8.05 (4H, m), 8.05 (1H, d, J = 4.8 Hz), 8.12 (1H, d, J = 4.8 Hz ), 8.51 (1H, s). [M + H] Calc'd for C$_{22}$H$_{19}$ClFN$_3$O$_2$: 412; Found: 412. |

| Example | Compound IUPAC name | Example preparation | H¹ NMR and MS |
|---|---|---|---|
| 27A and 27B | (R)-3-(((6-(4-isopropoxy-2-methylphenyl)-1,2,3,4-tetrahydroisoquinolin-1-yl)methyl)amino)isonicotinic acid; and (S)-3-(((6-(4-isopropoxy-2-methylphenyl)-1,2,3,4-tetrahydroisoquinolin-1-yl)methyl)amino)isonicotinic acid 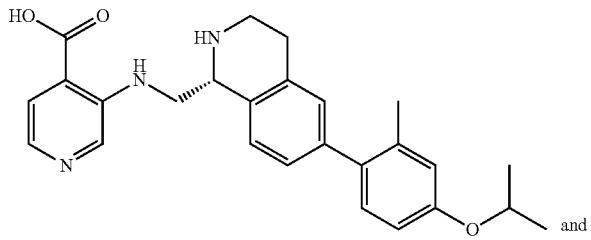 [SMILES: Cc1cc(OC(C)C)ccc1-c1ccc2c(c1)CCN[C@H]2CNc1cnccc1C(=O)O] and 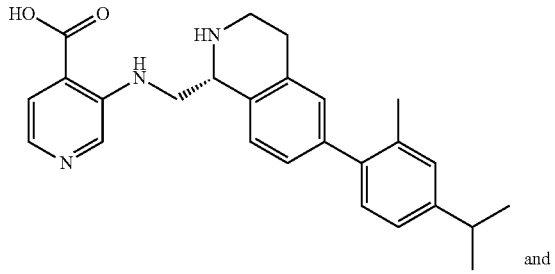 | 8A and 8B | NMR (400 MHz, CD$_3$OD): δ 1.32 (6H, d, J = 8.0 Hz) 2.21 (3H, s), 3.16-3.21 (2H, m), 3.44-3.49 (1H, m), 3.67-3.73 (1H, m), 3.90-4.00 (1H, m), 4.15-4.20 (1H, m), 4.60-4.64 (1H, m), 5.02-5.04 (1H, m), 6.76-6.81 (2H, m), 6.90 (1H, d, J = 11.2 Hz), 7.24-7.28 (2H, m), 7.49 (1H, d, J = 10.4 Hz), 8.02 (2H, s), 8.47 (1H, s). [M + H] Calc'd for C$_{26}$H$_{29}$N$_3$O$_3$: 432; Found: 432. |
| 28A and 28B | (R)-3-(((6-(4-isopropyl-2-methylphenyl)-1,2,3,4-tetra-hydroisoquinolin-1-yl)methyl)amino)isonicotinic acid; and (S)-3-(((6-(4-isopropyl-2-methylphenyl)-1,2,3,4-tetra-hydroisoquinolin-1-yl)methyl)amino)isonicotinic acid 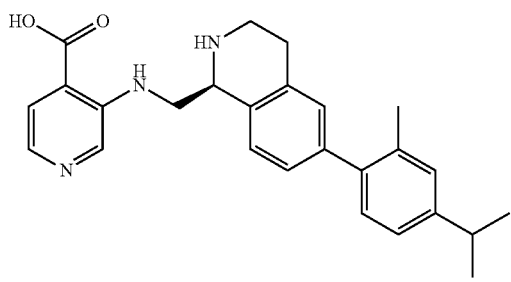 [SMILES: Cc1cc(C(C)C)ccc1-c1ccc2c(c1)CCN[C@@H]2CNc1cnccc1C(=O)O] and | 8A and 8B | NMR (400 MHz, CD$_3$OD): δ 1.27 (6H, d, J = 9.2 Hz) 2.22 (3H, s), 2.85-2.95 (1H, m), 3.16-3.27 (2H, m), 3.43-3.52 (1H, m), 3.67-3.71 (1H, m), 3.95-4.00 (1H, m), 4.15-4.22 (1H, m), 4.95-5.04 (1H, m), 7.07-7.14 (3H, m), 7.25-7.29 (2H, m), 7.51 (1H, d, J = 10.8 Hz), 8.03-8.05 (2H, m), 8.48 (1H, s). [M + H] Calc'd for C$_{26}$H$_{29}$N$_3$O$_2$: 416; Found: 416. |

| Example | Compound IUPAC name | Example preparation | H¹ NMR and MS |
|---|---|---|---|
| 29A and 29B | (R)-3-(((6-(4-(difluoromethoxy)-2-methylphenyl)-1,2,3,4-tetrahydroisoquinolin-1-yl)methyl)amino)isonicotinic acid; and (S)-3-(((6-(4-(difluoromethoxy)-2-methylphenyl)-1,2,3,4-tetrahydroisoquinolin-1-yl)methyl)amino)isonicotinic acid<br />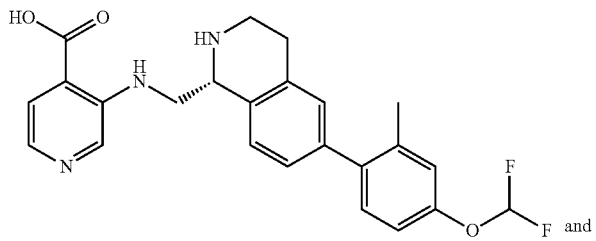 [SMILES: Cc1cc(OC(F)F)ccc1-c1ccc2c(c1)CCN[C@H]2CNc1cnccc1C(=O)O] and 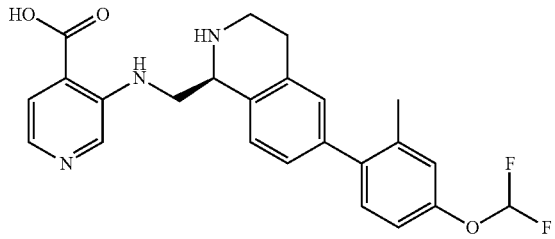 [SMILES: Cc1cc(OC(F)F)ccc1-c1ccc2c(c1)CCN[C@@H]2CNc1cnccc1C(=O)O] | 8A and 8B | NMR (400 MHz, CD₃OD): δ 2.21 (3H, s), 3.16-3.26 (2H, m), 3.44-3.52 (1H, m), 3.67-3.73 (1H, m), 3.90-4.00 (1H, m), 4.14-4.20 (1H, m), 4.93-5.03 (1H, m), 6.85 (1H, t, J = 13.6 Hz), 7.01-7.09 (2H, m), 7.19-7.29 (3H, m), 7.55 (1H, d, J = 10.8 Hz), 8.01-8.08 (2H, m), 8.50 (1H, s). [M + H] Calc'd for C₂₄H₂₃F₂N₃O₃: 440; Found: 440. |
| 30A and 30B | (R)-3-(((6-(2-methyl-4-propoxyphenyl)-1,2,3,4-tetrahydroisoquinolin-1-yl)methyl)amino)isonicotinic acid; and (S)-3-(((6-(2-methyl-4-propoxyphenyl)-1,2,3,4-tetrahydro-isoquinolin-1-yl)methyl)amino)isonicotinic acid<br />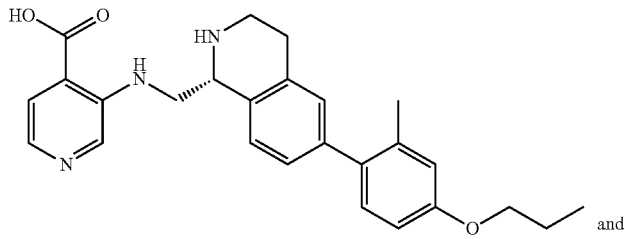 [SMILES: CCCOc1ccc(-c2ccc3c(c2)CCN[C@H]3CNc2cnccc2C(=O)O)c(C)c1] and 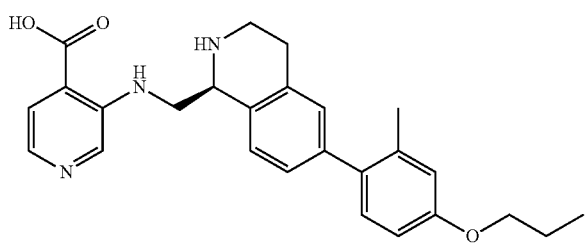 [SMILES: CCCOc1ccc(-c2ccc3c(c2)CCN[C@@H]3CNc2cnccc2C(=O)O)c(C)c1] | 8A and 8B | NMR (400 MHz, CD₃OD): δ 1.06 (3H, t, J = 10.4 Hz) 1.74-1.86 (2H, m), 2.21 (3H, s), 3.16-3.25 (2H, m), 3.44-3.49 (1H, m), 3.67-3.73 (1H, m), 3.88-4.00 (3H, m), 4.15-4.20 (1H, m), 4.88-5.01 (1H, m), 6.77-6.81 (2H, m), 7.08 (1H, d, J = 11.2 Hz), 7.24-7.28 (2H, m), 7.47-7.51 (1H, m), 8.00 (2H, s), 8.48 (1H, s). [M + H] Calc'd for C₂₆H₂₉N₃O₃: 432; Found: 432. |

TABLE 3-continued

| Example | Compound IUPAC name | Example preparation | H¹ NMR and MS |
|---|---|---|---|

31A and 31B  (R)-3-(((6-(4-chloro-3-fluorophenyl)-1,2,3,4-tetrahydro-isoquinolin-1-yl)methyl)amino)isonicotinic acid; and (S)-3-(((6-(4-chloro-3-fluorophenyl)-1,2,3,4-tetrahydroiso-quinolin-1-yl)methyl)amino)isonicotinic acid

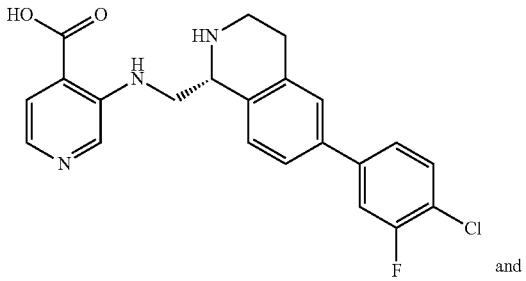 [SMILES: O=C(O)c1ccncc1NC[C@@H]1NCCc2cc(-c3ccc(Cl)c(F)c3)ccc21]

and

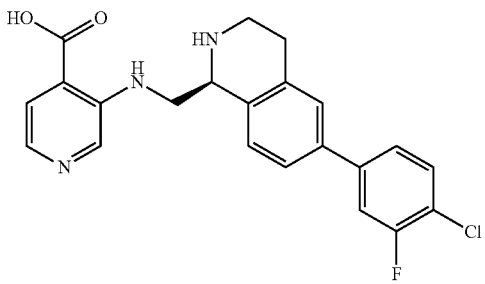 [SMILES: O=C(O)c1ccncc1NC[C@H]1NCCc2cc(-c3ccc(Cl)c(F)c3)ccc21]

8A and 8B  NMR (400 MHz, CD$_3$OD): δ 3.20-3.27 (2H, m), 3.45-3.49 (1H, m), 3.67-3.73 (1H, m), 3.90-3.96 (1H, m), 4.12-4.19 (1H, m), 4.98-5.02 (1H, m), 7.46-7.64 (6H, m), 7.95-8.01 (2H, m), 8.43 (1H, s). [M + H] Calc'd for C$_{22}$H$_{19}$ClFN$_3$O$_2$, 412; Found, 412.

32A and 32B  (R)-3-(((6-(2-fluoro-6-methoxyphenyl)-1,2,3,4-tetrahydro-isoquinolin-1-yl)methyl)amino)isonicotinic acid; and (S)-3-(((6-(2-fluoro-6-methoxyphenyl)-1,2,3,4-tetrahydroiso-quinolin-1-yl)methyl)amino) isonicotinic acid

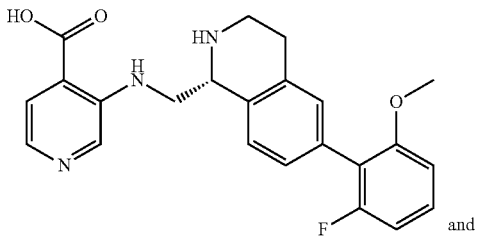 [SMILES: COc1cccc(F)c1-c1ccc2c(c1)CCN[C@H]2CNc1cnccc1C(=O)O]

and

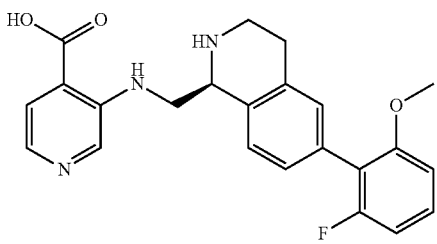 [SMILES: COc1cccc(F)c1-c1ccc2c(c1)CCN[C@@H]2CNc1cnccc1C(=O)O]

8A and 8B  NMR (400 MHz, CD$_3$OD): δ 3.17-3.22 (2H, m), 3.45-3.49 (1H, m), 3.69-3.76 (4H, m), 3.95-4.03 (1H, m), 4.16-4.22 (1H, m), 4.99-5.04 (1H, m), 6.80 (1H, t, J = 12.0 Hz),6.91 (1H, d, J = 11.2 Hz),7.29-7.35 (3H, m), 7.51 (1H, d, J = 10.8 Hz),8.06 (1H, d, J = 7.6 Hz), 8.17 (1H, d, J = 7.6 Hz), 8.53 (1H, s). [M + H] Calc'd: 408; Found: 408.

TABLE 3-continued

| Example Compound IUPAC name | Example preparation | H¹ NMR and MS |
|---|---|---|
| 33A and 33B (R)-3-(((6-(4-(3,4-dihydroquinolin-1(2H)-yl)phenyl)-1,2,3,4-tetrahydroisoquinolin-1-yl)methyl)amino) isonicotinic acid; and (S)-3-(((6-(4-(3,4-dihydroquinolin-1(2H)-yl)phenyl)-1,2,3,4-tetrahydroisoquinolin-1-yl)methyl)amino)isonicotinic acid 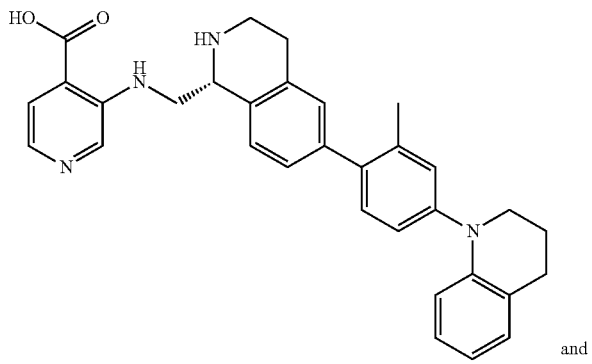 and 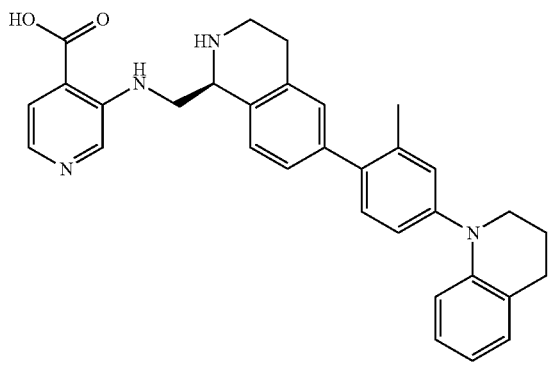 | 8A and 8B | NMR (400 MHz, CD₃OD): δ 1.96-2.04 (2H, m), 2.78-2.82 (2H, m), 3.07-3.18 (2H, m), 3.39-3.48 (1H, m), 3.61-3.73 (3H, m), 4.01-4.08 (1H, m), 4.17-4.23 (1H, m), 4.96-5.01 (1H, m), 6.73-6.80 (2H, m), 6.90-6.95 (1H, m), 7.05-7.18 (3H, m), 7.39-7.42 (1H, m), 8.12 (1H, d, J = 7.6 Hz), 8.35-8.39 (1H, m), 8.68 (1H, s). [M + H] Calc'd for $C_{25}H_{26}N_4O_2$: 415; Found: 415. |

| Example | Compound IUPAC name | Example preparation | H¹ NMR and MS |
|---|---|---|---|
| 34A and 34B | (R)-3-(((6-(4-(3,4-dihydroisoquinolin-2(1H)-yl)phenyl)-1,2,3,4-tetrahydroisoquinolin-1-yl)methyl)amino isonicotinic acid; and (S)-3-(((6-(4-(3,4-dihydro-isoquinolin-2(1H)-yl)phenyl)-1,2,3,4-tetrahydro-isoquinolin-1-yl) methyl)amino)isonicotinic acid 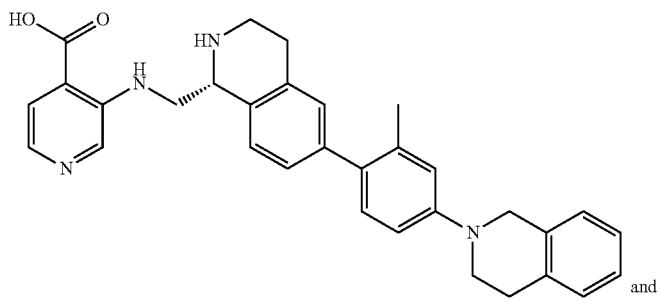 and 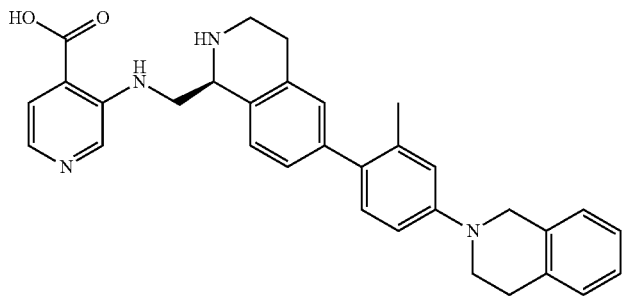 | 8A and 8B | NMR (400 MHz, CD$_3$OD): δ 3.35-3.42 (3H, m) 3.48-3.52 (1H, m), 3.71-3.77 (1H, m), 4.03-4.14 (4H, m), 4.23-4.28 (1H, m), 4.82-4.86 (2H, m), 5.12-5.13 (1H, m), 7.25-7.34 (4H, m), 7.67-7.81 (3H, m), 8.14 (1H, d, J = 7.6 Hz), 8.38 (1H, d, J = 7.6 Hz), 8.77 (1H, s). [M + H] Calc'd for C$_{25}$H$_{26}$N$_4$O$_2$: 415; Found: 415. |
| 35A and 35B | (R)-3-(((6-(4-isopropyl-2-methoxyphenyl)-1,2,3,4-tetra-hydroisoquinolin-1-yl)methyl)amino)isonicotinic acid; and (S)-3-(((6-(4-isopropyl-2-methoxyphenyl)-1,2,3,4-tetra-hydroisoquinolin-1-yl)methyl)amino) isonicotinic acid 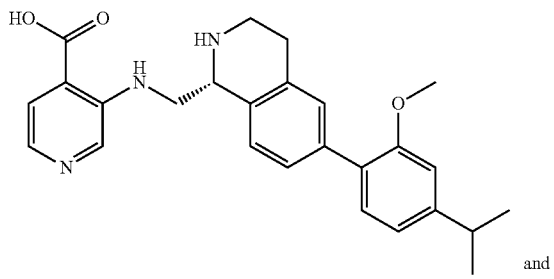 [SMILES: COc1cc(C(C)C)ccc1-c1ccc2c(c1)CCN[C@H]2CNc1cnccc1C(=O)O] and 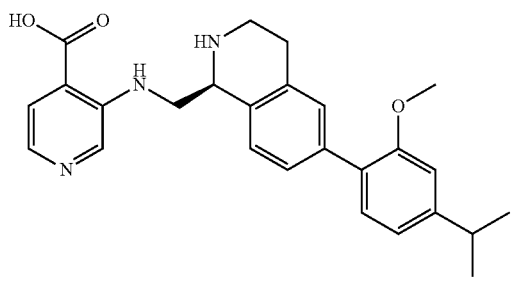 [SMILES: COc1cc(C(C)C)ccc1-c1ccc2c(c1)CCN[C@@H]2CNc1cnccc1C(=O)O] | 8A and 8B | NMR (400 MHz, CD$_3$OD): δ 1.19 (6H, d, J = 6.8 Hz), 2.83-2.86 (1H, m), 3.08-3.32 (2H, m), 3.35-3.37 (1H, m), 3.58-3.61 (1H, m), 3.69 (3H, s), 3.86-3.89 (1H, m), 4.04-4.07 (1H, m), 4.87-4.89 (1H, m), 6.80-6.84 (2H, m), 7.09 (1H, d, J = 7.6 Hz), 7.31-7.36 (3H, m), 7.95-7.97 (2H, m), 8.47 (1H, s). [M + H] Calc'd for C$_{26}$H$_{29}$N$_3$O$_3$: 432; Found: 432. |

TABLE 3-continued

| Example | Compound IUPAC name | Example preparation | H¹ NMR and MS |
|---|---|---|---|
| 36A and 36B | (R)-3-(((6-(4-(indolin-1-yl)phenyl)-1,2,3,4-tetrahydroiso-quinolin-1-yl)methyl)amino)isonicotinic acid; and (S)-3-(((6-(4-(indolin-1-yl)phenyl)-1,2,3,4-tetrahydroisoquinolin-1-yl)methyl)amino)isonicotinic acid | 8A and 8B | NMR (400 MHz, CD$_3$OD): δ 2.25 (3H, s), 3.06-3.18 (4H, m), 3.40-3.46 (1H, m), 3.64-3.70 (1H, m), 3.88-3.94 (3H, m), 4.00-4.14 (1H, m), 4.83-4.90 (1H, m), 6.87 (1H, d, J = 8.0 Hz), 7.01-7.08 (3H, m), 7.18-7.20 (1H, m), 7.37-7.42 (1H, m), 8.03 (1H, d, J = 5.2 Hz), 8.13 (1H, d, J = 5.2 Hz), 8.46 (1H, s). [M + H] Calc'd for C$_{25}$H$_{26}$N$_4$O$_2$: 415; Found: 415. |
| 37A and 37B | (R)-3-(((6-((4-cyclopropylphenyl)(methyl)amino)-1,2,3,4-tetrahydroisoquinolin-1-yl)methyl)amino) isonicotinic acid; and (S)-3-(((6-((4-cyclopropylphenyl)(methyl)amino)-1,2,3,4-tetrahydroisoquinolin-1-yl) methyl)amino) isonicotinic acid | 10A and 10B | NMR (400 MHz, CD$_3$OD): δ 0.64-0.68 (2H, m), 0.93-0.98 (2H, m), 1.88-1.92 (1H, m), 3.00-3.07 (2H, m), 3.25 (3H, s), 3.34-3.39 (1H, m), 3.60-3.63 (1H, m), 3.86-3.91 (1H, m), 4.05-4.09 (1H, m), 4.82-4.84 (1H, m), 6.68-6.75 (2H, m), 7.02 (2H, d, J = 8.4 Hz), 7.08 (2H, d, J = 8.4 Hz), 7.21 (1H, J = 9.2 Hz), 8.02 (1H, d, J = 5.2 Hz), 8.09 (1H, d, J = 5.2 Hz), 8.42 (1H, s). [M + H] Calc'd for C$_{26}$H$_{28}$N$_4$O$_2$: 429; Found: 429. |

TABLE 3-continued

| Example | Compound IUPAC name | Example preparation | H¹ NMR and MS |
|---|---|---|---|
| 38A and 38B | (R)-3-(((6-(methyl(4-propylphenyl)amino)-1,2,3,4-tetra-hydroisoquinolin-1-yl)methyl)amino)isonicotinic acid; and (S)-3-(((6-(methyl(4-propylphenyl)amino)-1,2,3,4-tetra-hydroisoquinolin-1-yl)methyl)amino)isonicotinic acid 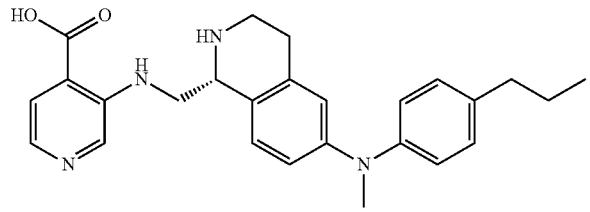 and 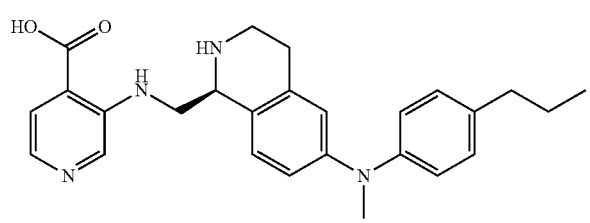 [SMILES: CCCc1ccc(N(C)c2ccc3c(c2)CCN[C@@H]3CNc2cnccc2C(=O)O)cc1] | 10A and 10B | NMR (400 MHz, CD$_3$OD): δ 0.97 (3H, t, J = 9.6 Hz), 1.52-1.70 (2H, m), 2.57-2.62 (2H, m), 3.02-3.09 (2H, m), 3.25 (3H, s), 3.34-3.42 (1H, m), 3.60-3.66 (1H, m), 3.86-3.94 (1H, m), 4.06-4.12 (1H, m), 4.84-4.94 (1H, m), 6.72-6.79 (2H, m), 7.06 (2H, d, J = 10.8 Hz), 7.18-7.25 (3H, m), 8.04 (1H, d, J = 6.2 Hz), 8.12 (1H, d, J = 6.8 Hz), 8.45 (1H, s). [M + H] Calc'd for C$_{26}$H$_{30}$N$_4$O$_2$: 431; Found: 431. |
| 39A and 39B | (R)-3-(((6-((4-isobutylphenyl)(methyl)amino)-1,2,3,4-tetrahydroisoquinolin-1-yl)methyl)amino)isonicotinic acid; and (S)-3-(((6-((4-isobutylphenyl)(methyl)amino)-1,2,3,4-tetrahydroisoquinolin-1-yl)methyl)amino)isonicotinic acid 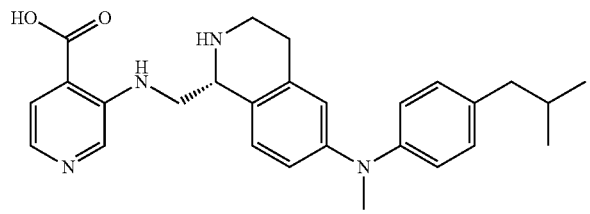 and 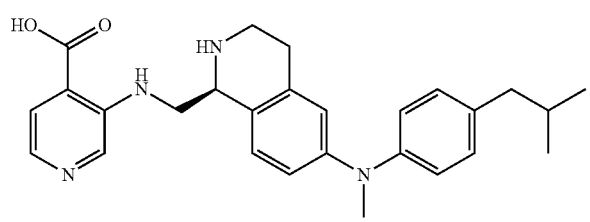 [SMILES: CC(C)Cc1ccc(N(C)c2ccc3c(c2)CCN[C@@H]3CNc2cnccc2C(=O)O)cc1] | 10A and 10B | NMR (400 MHz, CD$_3$OD): δ 0.94 (6H, d, J = 6.8 Hz), 1.85-1.91 (1H, m), 2.49 (2H, d, J = 6.8 Hz), 3.03-3.10 (2H, m), 3.25 (3H, s), 3.34-3.38 (1H, m), 3.62-3.66 (1H, m), 3.89-3.95 (1H, m), 4.08-4.12 (1H, m), 4.85-4.88 (1H, m), 6.73-6.79 (2H, m), 7.06 (2H, d, J = 8.4 Hz), 7.17 (2H, d, J = 8.4 Hz), 7.22-7.25 (1H, m), 8.05 (1H, d, J = 5.2 Hz), 8.14 (1H, d, J = 5.2 Hz), 8.47 (1H, s). [M + H] Calc'd for C$_{27}$H$_{32}$N$_4$O$_2$: 445; Found: 445. |

| Example | Compound IUPAC name | Example preparation | H¹ NMR and MS |
|---|---|---|---|
| 40A and 40B | (R)-3-(((6-((4-hexylphenyl)(methyl)amino)-1,2,3,4-tetra-hydroisoquinolin-1-yl)methyl)amino)isonicotinic acid; and (S)-3-(((6-((4-hexylphenyl)(methyl)amino)-1,2,3,4-tetra-hydroisoquinolin-1-yl)methyl)amino) isonicotinic acid 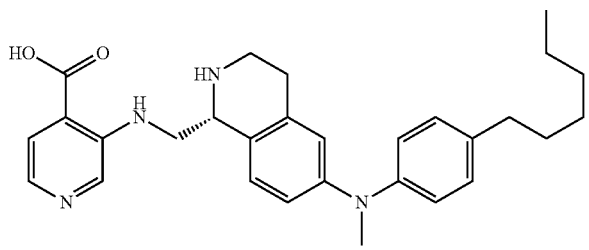 and 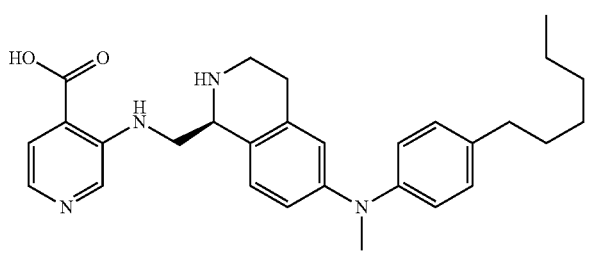 [SMILES: CCCCCCc1ccc(N(C)c2ccc3c(c2)CCN[C@@H]3CNc2cnccc2C(=O)O)cc1] | 10A and 10B | NMR (400 MHz, CD$_3$OD): δ 0.90 (3H, t, J = 7.2 Hz), 1.29-1.37 (6H, m), 1.58-1.65 (2H, m), 2.60 (2H, t, J = 7.2 Hz), 2.98-3.08 (2H, m), 3.25 (3H, s), 3.34-3.38 (1H, m), 3.59-3.65 (1H, m), 3.86-3.92 (1H, m), 4.05-4.10 (1H, m), 4.82-4.89 (1H, m), 6.69-6.76 (2H, m), 7.04 (2H, d, J = 8.4 Hz), 7.17-7.22 (3H, m), 8.02 (1H, d, J = 5.2 Hz), 8.11 (1H, d, J = 5.2 Hz), 8.43 (1H, s). [M + H] Calc'd for C$_{29}$H$_{36}$N$_4$O$_2$: 473; Found: 473. |
| 41A and 41B | (R)-3-(((6-((4-(cyclopropylmethyl)phenyl)(methyl) amino)-1,2,3,4-tetrahydroisoquinolin-1-yl)methyl) amino)isonico-tinic acid; and (S)-3-(((6-((4-(cyclo-propylmethyl)phenyl) (methyl)amino)-1,2,3,4-tetra-hydroisoquinolin-1-yl)methyl) amino)isonicotinic acid 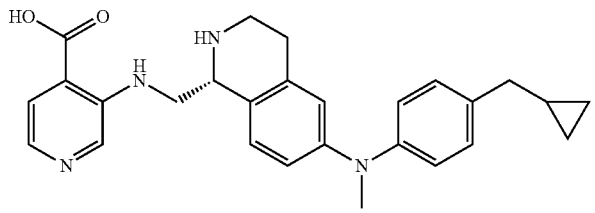 and 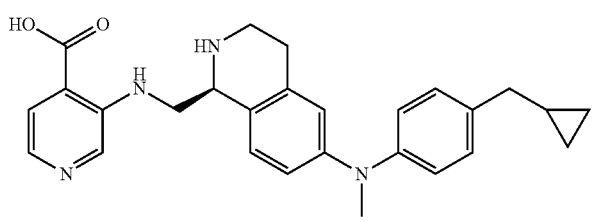 [SMILES: CN(c1ccc(CC2CC2)cc1)c1ccc2c(c1)CCN[C@@H]2CNc1cnccc1C(=O)O] | 10A and 10B | NMR (400 MHz, CD$_3$OD): δ 0.19-0.23 (2H, m), 0.50-0.54 (2H, m), 0.97-1.00 (1H, m) 2.53 (2H, d, J = 6.8 Hz), 3.01-3.08 (2H, m), 3.25 (3H, s), 3.36-3.41 (1H, m), 3.60-3.63 (1H, m), 3.86-3.92 (1H, m), 4.05-4.09 (1H, m), 4.85-4.93 (1H, m), 6.70-6.77 (2H, m), 7.05 (2H, d, J = 8.4 Hz), 7.21-7.26 (3H, m), 8.02 (1H, d, J = 5.2 Hz), 8.11 (1H, d, J = 5.2 Hz), 8.44 (1H, s). [M + H] Calc'd for C$_{27}$H$_{30}$N$_4$O$_2$, 443; Found: 443. |

| Example | Compound IUPAC name | Example preparation | H¹ NMR and MS |
|---|---|---|---|
| 42A and 42B | (R)-3-(((6-(methyl(4-(2,2,2-trifluoroethoxy)phenyl) amino)-1,2,3,4-tetrahydroisoquinolin-1-yl)methyl) amino)isonicotinic acid; and (S)-3-(((6-(methyl(4-(2,2,2-trifluoro-ethoxy)phenyl)amino)-1,2,3,4-tetrahydro-methyl)amino)isonicotinic acid isoquinolin-1-yl) | 10A and 10B | NMR (400 MHz, CD$_3$OD): δ 3.00-3.07 (2H, m), 3.25 (3H, s), 3.36-3.41 (1H, m), 3.58-3.63 (1H, m), 3.87-3.89 (1H, m), 4.03-4.06 (1H, m), 4.50-4.56 (2H, m), 4.80-4.84 (1H, m), 6.64-6.72 (3H, m), 7.02-7.06 (2H, m), 7.11-7.14 (2H, m), 7.99 (2H, s), 8.36 (1H, s). [M + H] Calc'd for C$_{25}$H$_{25}$F$_3$N$_4$O$_3$: 487; Found: 487. |
| 43A and 43B | (R)-3-(((6-(2-methyl-4-(pyrrolidin-1-yl)phenyl)-1,2,3,4-tetrahydroisoquinolin-1-yl)methyl)amino)isonicotinic acid; and (S)-3-(((6-(2-methyl-4-(pyrrolidin-1-yl) phenyl)-1,2,3,4-tetrahydroisoquinolin-1-yl)methyl) amino)isonicotinic acid | 8A and 8B | NMR (400 MHz, CD$_3$OD): δ 2.17-2.21 (4H, m), 2.28 (3H, s), 3.19-3.23 (2H, m), 3.46-3.49 (1H, m), 3.58-3.61 (4H, m), 3.70-3.74 (1H, m), 4.01-4.07 (1H, m), 4.20-4.25 (1H, m), 5.04-5.08 (1H, m), 7.05-7.08 (2H, m), 7.22-7.29 (3H, m), 7.53 (1H, d, J = 8.0 Hz), 8.09 (1H, d, J = 5.2 Hz), 8.30 (1H, d, J = 5.2 Hz), 8.62 (1H, s). [M + H] Calc'd for C$_{27}$H$_{30}$N$_4$O$_2$: 443; Found: 443. |

TABLE 3-continued

| Example | Compound IUPAC name | Example preparation | H¹ NMR and MS |
|---|---|---|---|
| 44A and 44B | (R)-3-(((6-((4-isopropoxyphenyl)(methyl)amino)-1,2,3,4-tetrahydroisoquinolin-1-yl)methyl)amino)isonicotinic acid; and (S)-3-(((6-((4-isopropoxyphenyl)(methyl)amino)-1,2,3,4-tetrahydroisoquinolin-1-yl)methyl)amino)isonicotinic acid<br />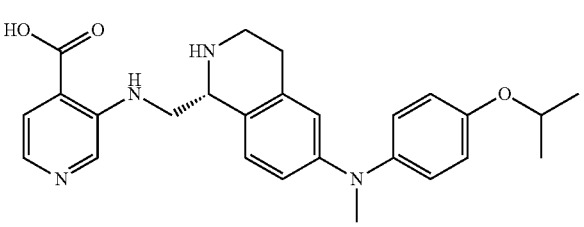<br />and<br />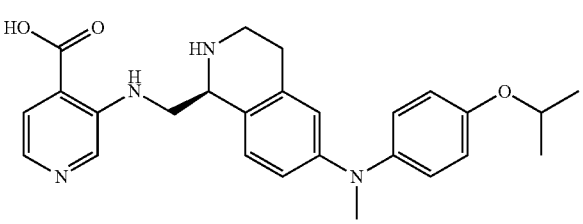 [SMILES: CC(C)Oc1ccc(N(C)c2ccc3c(c2)CCN[C@@H]3CNc2cnccc2C(=O)O)cc1] | 10A and 10B | NMR (400 MHz, CD$_3$OD): δ 1.31 (6H, d, J = 6.0 Hz), 2.97-3.12 (2H, m), 3.22 (3H, s), 3.34-3.40 (1H, m), 3.59-3.64 (1H, m), 3.95-4.00 (1H, m), 4.10-4.15 (1H, m), 4.50-4.54 (1H, m), 4.91-4.95 (1H, m), 6.61-6.64 (2H, m), 6.91-6.93 (2H, m), 7.04-7.08 (2H, m), 7.19-7.21 (1H, m), 8.08 (1H, d, J = 5.6 Hz), 8.34 (1H, d, J = 5.6 Hz), 8.59 (1H, s). [M + H] Calc'd for C$_{26}$H$_{30}$N$_4$O$_3$: 447; Found: 447. |
| 45A and 45B | (R)-3-(((6-(methyl(4-(2,2,2-trifluoroethyl)phenyl)amino)-1,2,3,4-tetrahydroisoquinolin-1-yl)methyl)amino) isonicotinic acid; and (S)-3-(((6-(methyl(4-(2,2,2-trifluoro-ethyl)phenyl)amino)-1,2,3,4-tetrahydroisoquinolin-1-yl) methyl)amino)isonicotinic acid<br />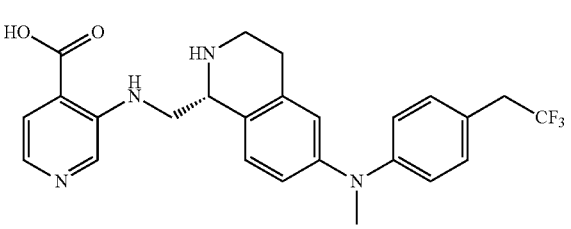<br />and<br />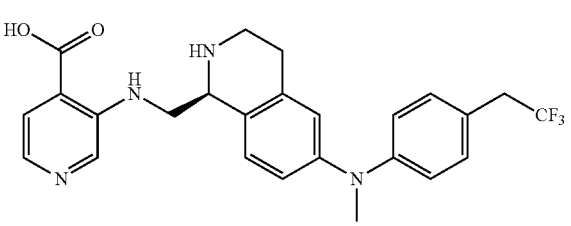 [SMILES: CN(c1ccc(CC(F)(F)F)cc1)c1ccc2c(c1)CCN[C@@H]2CNc1cnccc1C(=O)O] | 10A and 10B | NMR (400 MHz, CD$_3$OD): δ 3.04-3.10 (2H, m), 3.22 (3H, s), 3.37-3.48 (3H, m), 3.62-3.66 (1H, m), 3.87-3.93 (1H, m), 4.06-4.11 (1H, m), 4.85-4.89 (1H, m), 6.86-6.92 (2H, m), 7.07-7.10 (2H, m), 7.27-7.30 (3H, m), 8.01-8.07 (2H, m), 8.42 (1H, s). [M + H] Calc'd for C$_{25}$H$_{25}$F$_3$N$_4$O$_2$, 471; Found, 471. |

| Example | Compound IUPAC name | Example preparation | H¹ NMR and MS |
|---|---|---|---|
| 46A and 46B | (R)-3-(((6-((4-chlorophenyl)(methyl)amino)-1,2,3,4-tetrahydroisoquinolin-1-yl)methyl)amino)isonicotinic acid; and (S)-3-(((6-((4-chlorophenyl)(methyl)amino)-1,2,3,4-tetra-hydroisoquinolin-1-yl)methyl)amino) isonicotinic acid 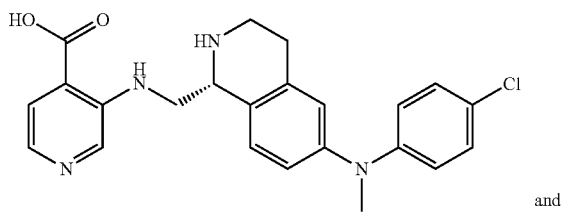 [SMILES: CN(c1ccc(Cl)cc1)c1ccc2c(c1)CCN[C@H]2CNc1cnccc1C(=O)O] and 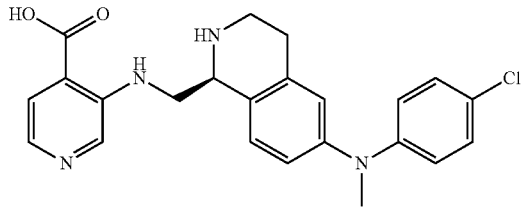 [SMILES: CN(c1ccc(Cl)cc1)c1ccc2c(c1)CCN[C@@H]2CNc1cnccc1C(=O)O] | 10A and 10B | NMR (400 MHz, CD$_3$OD): δ 3.04-3.10 3.37-3.43 (1H, m), s), 3.61-3.66 (1H, m), 3.87-3.93 (1H, m), 4.06-4.11 (1H, m), 4.90-4.95 (1H, m), 6.85-6.92 (2H, m), 7.03-7.06 (2H, m), 7.27-7.31 (3H, m), 8.01-8.07 (2H, m), 8.42 (1H, s). [M + H] Calc'd for C$_{23}$H$_{23}$ClN$_4$O$_2$, 423; Found: 423. |
| 47A and 47B | (R)-3-(((6-(2-ethylphenyl)-1,2,3,4-tetrahydroisoquinolin-1-yl)methyl)amino)isonicotinic acid; and (S)-3-(((6-(2-ethyl-phenyl)-1,2,3,4-tetrahydroisoquinolin-1-yl)methyl) amino) isonicotinic acid 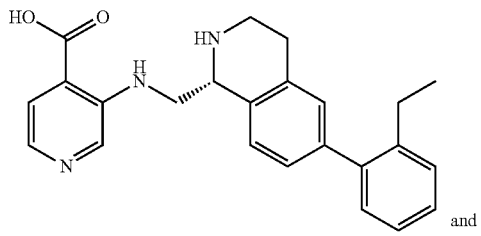 [SMILES: CCc1ccccc1-c1ccc2c(c1)CCN[C@H]2CNc1cnccc1C(=O)O] and 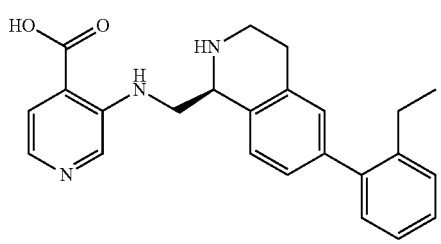 [SMILES: CCc1ccccc1-c1ccc2c(c1)CCN[C@@H]2CNc1cnccc1C(=O)O] | 8A and 8B | NMR (400 MHz, CD$_3$OD): δ 1.05 (3H, t, J = 7.6 Hz), 2.57 (2H, q, J = 7.6 Hz), 3.15-3.23 (2H, m), 3.45-3.52 (1H, m), 3.69-3.75 (1H, m), 3.99-4.05 (1H, m), 4.18-4.23 (1H, m), 5.03-5.06 (1H, m), 7.11-7.32 (6H, m), 7.52 (1H, d, J = 8.4 Hz), 8.06 (1H, d, J = 5.2 Hz), 8.16 (1H, d, J = 5.2 Hz), 8.54 (1H, s). [M + H] Calc'd for C$_{24}$H$_{25}$N$_3$O$_2$: 388; Found: 388. |

TABLE 3-continued

| Example | Compound IUPAC name | Example preparation | H¹ NMR and MS |
|---|---|---|---|
| 48A and 48B | (R)-3-(((6-(2-isopropylphenyl)-1,2,3,4-tetrahydroiso-quinolin-1-yl)methyl)amino)isonicotinic acid; and (S)-3-(((6-(2-isopropylphenyl)-1,2,3,4-tetrahydroisoquinolin-1-yl)methyl)amino)isonicotinic acid 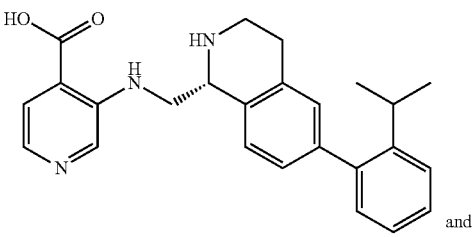 [SMILES: CC(C)c1ccccc1-c1ccc2c(c1)CCN[C@H]2CNc1cnccc1C(=O)O] and 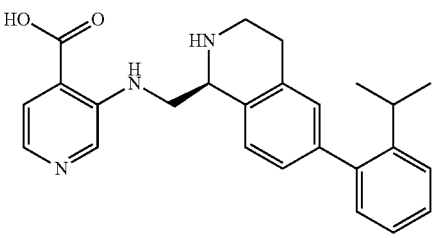 [SMILES: CC(C)c1ccccc1-c1ccc2c(c1)CCN[C@@H]2CNc1cnccc1C(=O)O] | 8A and 8B | NMR (400 MHz, CD$_3$OD): δ 1.16 (6H, d, J = 8.4 Hz), 2.95-3.04 (1H, m), 3.19-3.25 (2H, m), 3.45-3.54 (1H, m), 3.70-3.78 (1H, m), 3.96-4.05 (1H, m), 4.18-4.25 (1H, m), 5.03-5.08 (1H, m), 7.10-7.44 (6H, m), 7.54 (1H, d, J = 10.4 Hz), 8.06 (1H, d, J = 7.2 Hz), 8.11 (1H, d, J = 7.2 Hz), 8.54 (1H, s). [M + H] Calc'd for C$_{25}$H$_{27}$N$_3$O$_2$: 402; Found: 402. |
| 49A and 49B | (R)-3-(((6-(2,6-dimethyl-4-(2,2,2-trifluoroethoxy)phenyl)-1,2,3,4-tetrahydroisoquinolin-1-yl)methyl)amino)isonicotinic acid; and (S)-3-(((6-(2,6-dimethyl-4-(2,2,2-trifluoro-ethoxy)phenyl)-1,2,3,4-tetrahydroiso-quinolin-1-yl)methyl) amino)isonicotinic acid 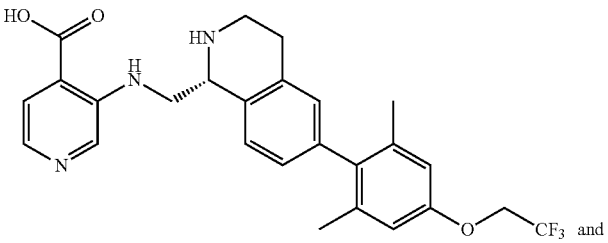 [SMILES: Cc1cc(OCC(F)(F)F)cc(C)c1-c1ccc2c(c1)CCN[C@H]2CNc1cnccc1C(=O)O] and 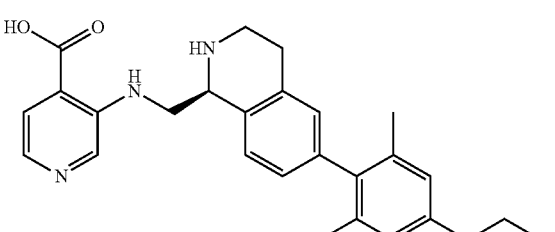 | 8A and 8B | NMR (400 MHz, CD$_3$OD): δ 1.99 (3H, s), 2.01 (3H, s), 2.95-3.04 (2H, m), 3.46-3.54 (1H, m), 3.69-3.76 (1H, m), 3.96-4.05 (1H, m), 4.16-4.23 (1H, m), 4.49-4.57 (2H, m), 5.00-5.05 (1H, m), 6.78 (2H, s), 7.11-7.14 (2H, m), 7.57 (1H, d, J = 10.8 Hz), 7.95 (1H, d, J = 6.8 Hz), 8.00 (1H, d, J = 7.2 Hz), 8.45 (1H, s). [M + H] Calc'd for C$_{26}$H$_{26}$F$_3$N$_3$O$_3$, 486; Found, 486. |

| Example | Compound IUPAC name | Example preparation | H¹ NMR and MS |
|---|---|---|---|
| 50A and 50B | (R)-3-(((6-(2-(2,2,2-trifluoroethoxy)phenyl)-1,2,3,4-tetra-hydroisoquinolin-1-yl)methyl)amino)isonicotinic acid; and (S)-3-(((6-(2-(2,2,2-trifluoroethoxy)phenyl)-1,2,3,4-tetra-hydroisoquinolin-1-yl)methyl)amino)isonicotinic acid<br>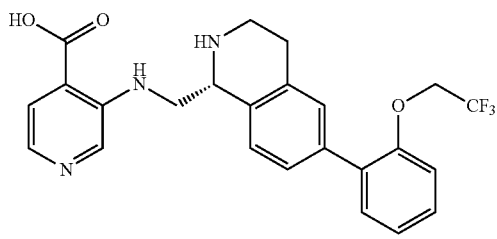 and 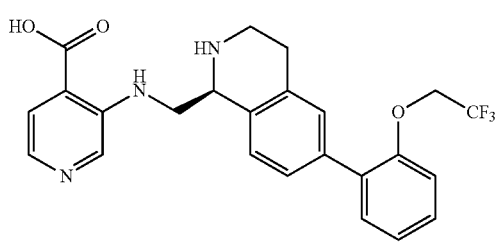 [SMILES: O=C(O)c1ccncc1NC[C@H]1NCCc2cc(-c3ccccc3OCC(F)(F)F)ccc21] | 8A and 8B | NMR (400 MHz, CD$_3$OD): δ 3.18-3.24 (2H, m) 345-3 .51 (1H, m), 3.96-4.02 (1H, m), 4.17-4.22 (1H, m), 4.51 (2H, dd, J = 8.4 & 17.2 Hz), 5.02 (1H, dd, J = 4.4 & 10.2 Hz), 7.12-7.16 (2H, m), 7.36-7.40 (2H, m), 7.48-7.54 (3H, m), 8.05 (1H, d, J = 5.6 Hz), 8.15 (1H, d, J = 6.0 Hz), 8.54 (1H, s). [M + H] Calc'd for C$_{24}$H$_{22}$F$_3$N$_3$O$_3$: 458; Found: 458. |
| 51A and 51B | (R)-3-(((6-(2,6-dimethylphenyl)-1,2,3,4-tetrahydroiso-quinohn-1-yl)methyl)amino)isonicotinic acid; and (S)-3-(((6-(2,6-dimethylphenyl)-1,2,3,4-tetrahydroisoquinolin-1-yl)methyl)amino)isonicotinic acid<br>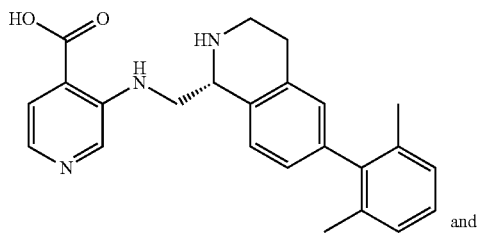 [SMILES: Cc1cccc(C)c1-c1ccc2c(c1)CCN[C@H]2CNc1cnccc1C(=O)O] and 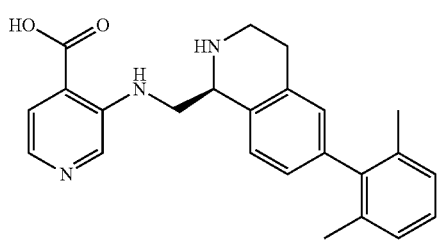 [SMILES: Cc1cccc(C)c1-c1ccc2c(c1)CCN[C@@H]2CNc1cnccc1C(=O)O] | 8A and 8B | NMR (400 MHz, CD$_3$OD): δ 1.97 3.18-3.24 (2H, m), 3.47-3.53 (1H, m), 3.69-3.76 (1H, m), 4.00-4.06 (1H, m), 4.18-4.22(1H, m), 5.02-5.06 (1H, m), 7.08-7.17 (5H, m), 7.56 (1H, d, J = 8.0 Hz), 8.02-8.07 (2H, m), 8.50 (1H, s). [M + H] Calc'd for C$_{24}$H$_{25}$N$_3$O$_2$: 388; Found: 388 |

TABLE 3-continued

| Example | Compound IUPAC name | Example preparation | H¹ NMR and MS |
|---|---|---|---|
| 52A and 52B | (R)-3-(((6-(2-cyclopropylphenyl)-1,2,3,4-tetrahydroiso-quinolin-1-yl)methyl)amino)isonicotinic acid; and (S)-3-4(6-(2-cyclopropylphenyl)-1,2,3,4-tetrahydroiso-quinolin-1-yl)methyl)amino)isonicotinic acid 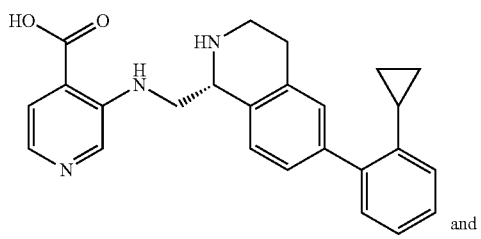 [SMILES: O=C(O)c1ccncc1NC[C@@H]1NCCc2cc(-c3ccccc3C3CC3)ccc21] and 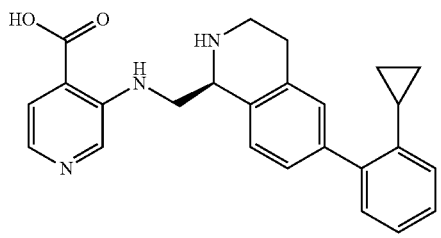 [SMILES: O=C(O)c1ccncc1NC[C@H]1NCCc2cc(-c3ccccc3C3CC3)ccc21] | 8A and 8B | NMR (400 MHz, MeOD): δ 0.66-0.69 (2H, m), 0.79-0.82 (2H, m), 1.79-1.83 (1H, m), 3.20-3.30 (2H, m), 3.48-3.51 (1H, m), 3.70-3.74 (1H, m), 3.97-4.03 (1H, m), 4.16-4.21 (1H, m), 5.01-5.04 (1H, m), 6.98 (1H, d, J = 8.0 Hz), 7.15-7.22 (2H, m), 7.25-7.29 (1H, m), 7.37-7.41 (2H, m), 7.52 (1H, d, J = 8.0 Hz), 8.02-8.06 (2H, m), 8.48 (1H, s). [M + H] Calc'd for $C_{25}H_{25}N_3O_2$: 400; Found 400. |
| 53A and 53B | (R)-3-(((6-((4-(dimethylamino)phenyl)(methyl)amino)-1,2,3,4-tetrahydroisoquinolin-1-yl)methyl)amino)iso-nicotinic acid; and (S)-3-(((6-((4-(dimethylamino)phenyl)(methyl)amino)-1,2,3,4-tetrahydroisoquinolin-1-yl)methyl)amino)isonicotinic acid 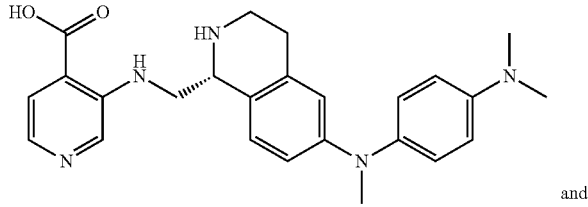 [SMILES: CN(C)c1ccc(N(C)c2ccc3c(c2)CCN[C@H]3CNc2cnccc2C(=O)O)cc1] and 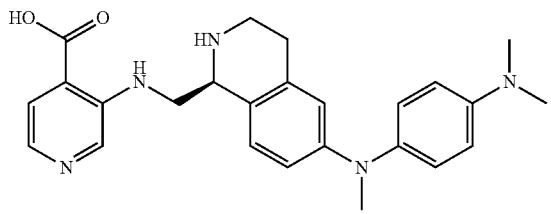 [SMILES: CN(C)c1ccc(N(C)c2ccc3c(c2)CCN[C@@H]3CNc2cnccc2C(=O)O)cc1] | 10A and 10B | NMR (400 MHz, MeOD): δ 3.07-3.11 (2H, m), 3.26 (6H, s), 3.34 (3H, s), 3.40-3.47 (1H, m), 3.65-3.69 (1H, m), 3.96-4.04 (1H, m), 4.05-4.20 (1H, m), 4.98-5.06 (1H, m), 7.07-7.11 (4H, m), 7.44-7.50 (3H, m), 8.11 (1H, d, J = 5.6 Hz), 8.35 (1H, d, J = 5.2 Hz), 8.61 (1H, s). [M + H] Calc'd for $C_{25}H_{29}N_5O_2$: 432; Found: 432 |

TABLE 3-continued

| Example | Compound IUPAC name | Example preparation | H¹ NMR and MS |
|---|---|---|---|
| 54A and 54B | (R)-3-(((6-((4-cyclohexylphenyl)(methyl)amino)-1,2,3,4-tetrahydroisoquinolin-1-yl)methyl)amino)isonicotinic acid; and (S)-3-(((6-((4-cyclohexylphenyl)(methyl)amino)-1,2,3,4-tetrahydroisoquinolin-1-yl)methyl)amino)isonicotinic acid | 10A and 10B | NMR (400 MHz, MeOD): δ 1.27-1.50 (5H, m), 1.75-1.87 (5H, m), 2.48-2.53 (1H, m), 2.98-3.07 (2H, m), 3.10 (3H, s), 3.34-3.40 (1H, m), 3.58-3.62 (1H, m), 3.81-3.86 (1H, m), 4.02-4.06 (1H, m), 4.78-4.85 (1H, m), 6.69-6.78 (2H, m), 7.05 (2H, d, J = 10.0 Hz), 7.20-7.23 (3H, m), 7.87 (1H, d, J = 5.2 Hz), 7.96 (1H, d, J = 5.2 Hz), 8.33 (1H, s). [M + H] Calc'd for $C_{29}H_{34}N_4O_2$: 471; Found: 471. |
| 55A and 55B | (R)-3-(((6-(methyl(4-(tetrahydro-2H-pyran-4-yl)phenyl)amino)-1,2,3,4-tetrahydroisoquinolin-1-yl)methyl)amino)isonicotinic acid; and (S)-3-(((6-(methyl(4-(tetrahydro-2H-pyran-4-yl)phenyl)amino)-1,2,3,4-tetrahydroisoquinolin-1-yl)methyl)amino) isonicotinic acid | 10A and 10B | NMR (400 MHz, MeOD): δ 1.75-1.83 (4H, m), 2.80-2.84 (1H, m), 3.05-3.08 (2H, m), 3.28 (3H, s), 3.53-3.56 (1H, m), 3.57-3.64 (3H, m), 3.90-3.93 (1H, m), 4.04-4.08 (3H, m), 4.83-4.85 (1H, m), 6.74-6.81 (2H, m), 7.10 (2H, d, J = 11.6 Hz), 7.11-7.28 (3H, m), 8.03-8.07 (2H, m), 8.42 (1H, s). [M + H] Calc'd for $C_{28}H_{32}N_4O_3$: 473; Found: 473. |

TABLE 3-continued

| Example | Compound IUPAC name | Example preparation | H¹ NMR and MS |
|---|---|---|---|
| 56A | (R)-3-(((6-(methyl(4-(3,3,3-trifluoropropyl)phenyl)amino)-1,2,3,4-tetrahydroisoquinolin-1-yl)methyl)amino)isonicotinic acid; and (S)-3-(((6-(methyl(4-(3,3,3-trifluoropropyl)phenyl)amino)-1,2,3,4-tetrahydroisoquinolin-1-yl)methyl)amino) isonicotinic acid 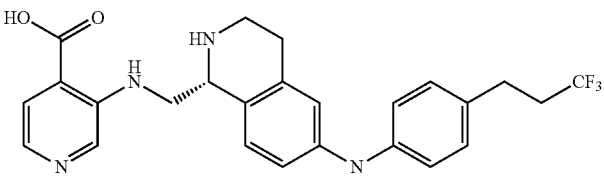 and 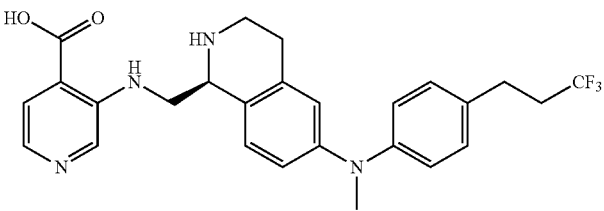 [SMILES: CN(c1ccc(CCC(F)(F)F)cc1)c1ccc2c(c1)CCN[C@@H]2CNc1cnccc1C(=O)O] | 10A and 10B | NMR (400 MHz, MeOD): δ 2.43-2.50 (2H, m), 2.84-2.89 (2H, m), 3.02-3.08 (2H, m), 3.28 (3H, s), 3.36-3.41 (1H, m), 3.61-3.65 (1H, m), 3.88-3.92 (1H, m), 4.05-4.10 (1H, m), 4.83-4.85 (1H, m), 6.75-6.82 (2H, m), 7.07 (2H, d, J = 8.0 Hz), 7.23-7.25 (3H, m), 8.01-8.08 (2H, m), 8.42 (1H, s). [M + H] Calc'd for $C_{26}H_{27}F_3N_4O_2$: 485; Found: 485. |
| 57A and 57B | (R)-3-(((6-((4-(2-cyclopropylethyl)phenyl)(methyl)amino)-1,2,3,4-tetrahydroisoquinolin-1-yl)methyl)amino)isonicotinic acid; and (S)-3-(((6-((4-(2-cyclopropylethyl)phenyl)(methyl)amino)-1,2,3,4-tetrahydroisoquinolin-1-yl) methyl)amino)isonicotinic acid 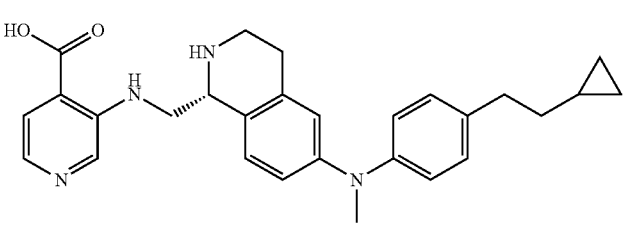 and 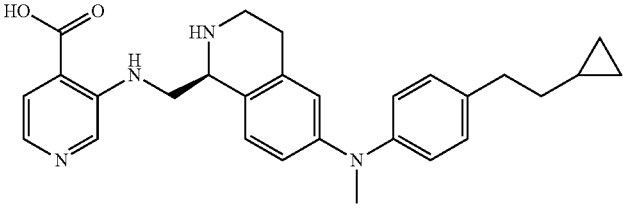 [SMILES: CN(c1ccc(CCC2CC2)cc1)c1ccc2c(c1)CCN[C@@H]2CNc1cnccc1C(=O)O] | 10A and 10B | NMR (400 MHz, DMSO-d6): δ 0.01-0.08 (2H, m), 0.40-0.45 (2H, m), 0.69-0.75 (m, 1H), 1.48-1.54 (m, 2H), 2.70 (2H, t, J = 8.0 Hz), 3.02-3.06 (2H, m), 3.27 (3H, s), 3.33-3.39 (1H, m), 3.60-3.63 (1H, m), 3.80-3.86 (1H, m), 4.02-4.06 (1H, m), 4.79-4.88 (1H, m), 6.69 (1H, d, J = 2.4 Hz), 6.76 (1H, dd, J = 8.4, 2.4 Hz), 7.04 (2H, d, J = 8.4 Hz), 7.19-7.23 (3H, m), 7.87 (1H, d, J = 5.2 Hz), 7.96 (1H, d, J = 5.2 Hz), 8.33 (1H, s). [M + H] Calc'd for $C_{28}H_{32}N_4O_2$: 457; Found: 457. |

TABLE 3-continued

| Example | Compound IUPAC name | Example preparation | H¹ NMR and MS |
|---|---|---|---|
| 58A and 58B | (R)-3-(((6-((4-cyclobutylphenyl)(methyl)amino)-1,2,3,4-tetrahydroisoquinolin-1-yl)methyl)amino)isonicotinic acid; and (S)-3-(((6-((4-cyclobutylphenyl)(methyl)amino)-1,2,3,4-tetrahydroisoquinolin-1-yl)methyl)amino)isonicotinic acid | 10A and 10B | NMR (400 MHz, DMSO-d6): δ 1.78-2.12 (4H, m), 2.24-2.33 (2H, m), 2.90-2.94 (2H, m), 3.23 (3H, s), 3.23-3.25 (1H, m), 3.37-3.53 (2H, m), 3.76-3.80 (1H, m), 3.99-4.03 (1H, m), 4.73-4.76 (1H, m), 6.74-6.78 (2H, m), 7.03 (2H, d, J = 8.2 Hz), 7.21 (2H, d, J = 8.2 Hz), 7.31 (1H, d, J = 8.0 Hz), 7.68 (1H, d, J = 5.2 Hz), 7.80 (1H, s), 7.96 (1H, d, J = 5.2 Hz), 8.51 (1H, s), 8.89 (1H, br), 9.39 (1H, br). [M + H] Calc'd for C₂₇H₃₀N₄O₂: 443; Found: 443. |
| 59A and 59B | (R)-3-(((6-((4-cyclopentylphenyl)(methyl)amino)-1,2,3,4-tetrahydroisoquinolin-1-yl)methyl)amino)isonicotinic acid; and (S)-3-(((6-((4-cyclopentylphenyl)(methyl)amino)-1,2,3,4-tetrahydroisoquinolin-1-yl)methyl)amino)isonicotinic acid | 10A and 10B | NMR (400 MHz, CD₃OD): δ 1.59-1.62 (2H, m), 1.72-1.76 (2H, m), 1.82-1.85 (2H, m), 2.06-2.08 (2H, m), 2.98-3.08 (3H, m), 3.26 (3H, s), 3.35-3.41 (1H, m), 3.58-3.65 (1H, m), 3.85-3.91 (1H, m), 4.04-4.09 (1H, m), 4.82-4.85 (1H, m), 6.70 (1H, s), 6.75 (1H, dd, J = 2.4 Hz, 8.4 Hz), 7.05 (2H, d, J = 8.8 Hz), 7.21-7.26 (3H, m), 8.00-8.05 (2H, m), 8.40 (1H, s). [M + H] Calc'd for C₂₈H₃₂N₄O₂: 457; Found: 457 |

TABLE 3-continued

| Example | Compound IUPAC name | Example preparation | H¹ NMR and MS |
|---|---|---|---|
| 60A and 60B | (R)-3-(((6-((4-(cyclobutylmethyl)phenyl)(methyl)amino)-1,2,3,4-tetrahydroisoquinolin-1-yl)methyl)amino)isonicotinic acid; and (S)-3-(((6-((4-(cyclobutylmethyl)phenyl)(methyl)amino)-1,2,3,4-tetrahydroisoquinolin-1-yl)methyl) amino)isonicotinic acid 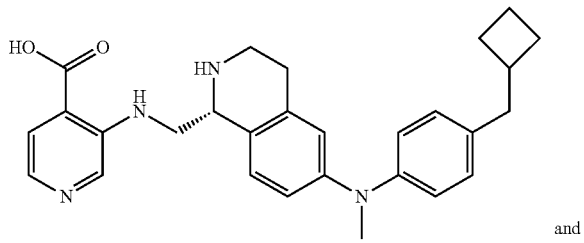 [SMILES: CN(c1ccc(CC2CCC2)cc1)c1ccc2c(c1)CCN[C@H]2CNc1cnccc1C(=O)O] and 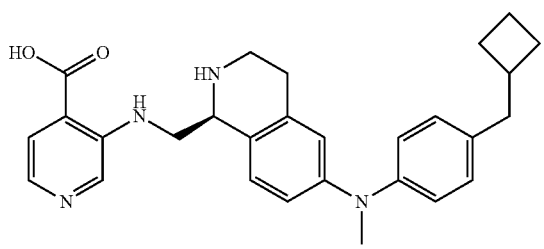 [SMILES: CN(c1ccc(CC2CCC2)cc1)c1ccc2c(c1)CCN[C@@H]2CNc1cnccc1C(=O)O] | 10A and 10B | NMR (400 MHz, DMSO-d6): δ 1.67-1.82 (4H, m), 1.99-2.08 (2H, m), 2.54-5.56 (1H, m), 2.64-2.67 (m, 2H), 2.92-2.94 (m, 2H), 3.22 (3H, s), 3.26-3.28 (1H, m), 3.51-3.53 (1H, m), 3.76-3.78 (1H, m), 3.98-4.02 (1H, m), 4.74-4.76 (1H, m), 6.74-6.76 (2H, m), 7.00 (2H, d, J = 8.2 Hz), 7.13 (2H, d, J = 8.2 Hz), 7.30 (1H, d, J = 8.0 Hz), 7.68 (1H, d, J = 5.2 Hz), 7.80 (1H, s), 7.96 (1H, d, J = 5.2 Hz), 8.50 (1H, s), 8.78 (1H, br), 9.27 (1H, br). [M + H] Calc'd for $C_{28}H_{32}N_4O_2$: 457; Found: 457. |
| 61A and 61B | (R)-3-(((6-(6-methyl-2,3-dihydrobenzofuran-5-yl)-1,2,3,4-tetrahydroisoquinolin-1-yl)methyl)amino) isonicotinic acid; and (S)-3-(((6-(6-methyl-2,3-dihydrobenzofuran-5-yl)-1,2,3,4-tetrahydroisoquinolin-1-yl) methyl)amino) isonicotinic acid 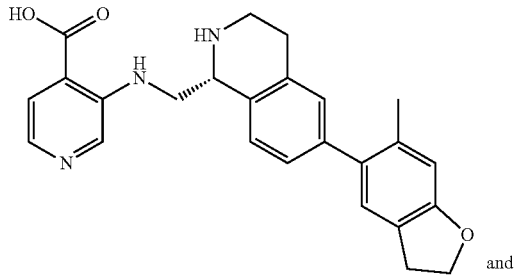 [SMILES: Cc1cc2c(cc1-c1ccc3c(c1)CCN[C@H]3CNc1cnccc1C(=O)O)CCO2] and 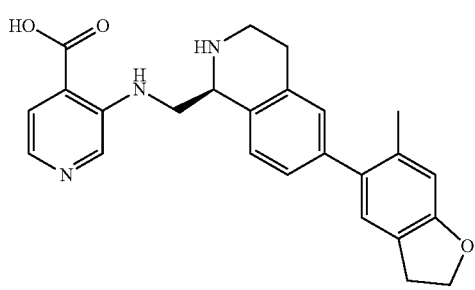 [SMILES: Cc1cc2c(cc1-c1ccc3c(c1)CCN[C@@H]3CNc1cnccc1C(=O)O)CCO2] | 8A and 8B | NMR (400 MHz, MeOD): δ 2.16 (3H, s), 3.16-3.24 (4H, m) 3.45-3.52 (1H, m), 3.69-3.74 (1H, m), 4.03-4.09 (1H, m), 4.19-4.23 (1H, m), 4.53-4.57 (2H, m), 5.04-5.14 (1H, m), 6.65 (1H, d, J = 8.0 Hz), 7.00 (1H, d, J = 8.0 Hz), 7.21-7.23 (2H, m), 7.48 (1H, d, J = 7.6 Hz), 8.11 (1H, d, J = 6.0 Hz), 8.36 (1H, d, J = 5.6 Hz), 8.61 (1H, s). [M + H] Calc'd for $C_{25}H_{25}N_3O_3$: 416; Found: 416. |

| Example | Compound IUPAC name | Example preparation | H¹ NMR and MS |
|---|---|---|---|
| 62A and 62B | (R)-3-(((6-(5-methyl-2,3-dihydrobenzofuran-4-yl)-1,2,3,4-tetrahydroisoquinolin-1-yl)methyl)amino) isonicotinic acid; and (S)-3-(((6-(5-methyl-2,3-dihydro-benzofuran-4-yl)-1,2,3,4-tetrahydroisoquinolin-1-yl) methyl)amino) isonicotinic acid 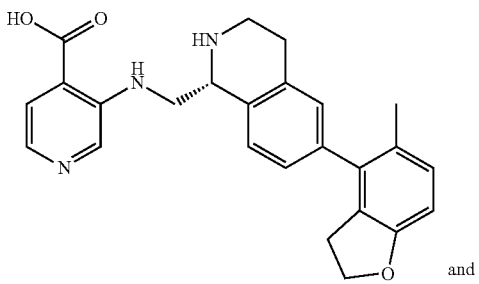 [SMILES: Cc1ccc2c(c1-c1ccc3c(c1)CCN[C@H]3CNc1cnccc1C(=O)O)CCO2] and 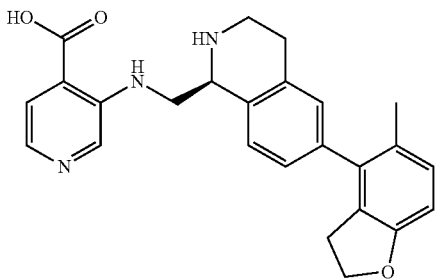 [SMILES: Cc1ccc2c(c1-c1ccc3c(c1)CCN[C@@H]3CNc1cnccc1C(=O)O)CCO2] | 8A and 8B | NMR (400 MHz, MeOD): δ 2.03 (3H, s), 2.88-2.92 (2H, m), 3.19-3.24 (2H, m), 3.47-3.50 (1H, m), 3.70-3.73 (1H, m), 3.96-4.02 (1H, m), 4.15-4.19 (1H, m), 4.44-4.49 (2H, m), 4.99-5.03 (1H, m), 6.63 (1H, d, J = 8.0 Hz), 7.00 (1H, d, J = 8.0 Hz), 7.21-7.23 (2H, m), 7.54 (1H, d, J = 8.0 Hz), 7.97-8.01 (2H, m), 8.44 (1H, s). [M + H] Calc'd for C$_{25}$H$_{25}$N$_3$O$_3$: 416; Found: 416. |
| 63A and 63B | (R)-3-(((5-(2-fluoro-4-(2,2,2-trifluoroethoxy)phenyl)iso-indolin-1-yl)methyl)amino)isonicotinic acid; and (S)-3-(((5-(2-fluoro-4-(2,2,2-trifluoroethoxy)phenyl)iso-indolin-1-yl)methyl)amino)isonicotinic acid 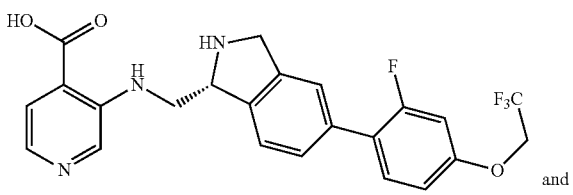 [SMILES: O=C(O)c1ccncc1NC[C@@H]1NCc2cc(-c3ccc(OCC(F)(F)F)cc3F)ccc21] and 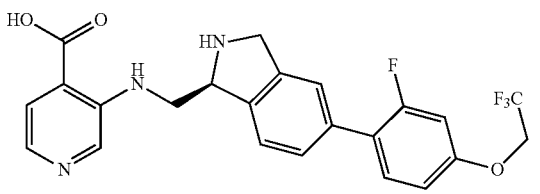 [SMILES: O=C(O)c1ccncc1NC[C@H]1NCc2cc(-c3ccc(OCC(F)(F)F)cc3F)ccc21] | 7A and 7B | NMR (300 MHz, CD$_3$OD): δ 3.88-3.96 (1H, m), 4.12-4.18 (1H, m), 4.58-4.89 (4H, m), 5.35-5.38 (1H, m), 6.94-6.98 (2H, m), 7.43-7.49 (1H, m), 7.64-7.56 (3H, m), 7.86-7.94 (2H, m), 8.36 (1H, s). [M + H] Calc'd for C$_{23}$H$_{19}$F$_4$N$_3$O$_3$: 462; Found: 462. |

TABLE 3-continued

| Example | Compound IUPAC name | Example preparation H¹ NMR and MS |
|---|---|---|
| 64A and 64B | (R)-3-(((5-(o-tolyl)isoindolin-1-yl)methyl)amino)isonicotinic acid; and (S)-3-(((5-(o-tolyl)isoindolin-1-yl)methyl)amino)isonicotinic acid 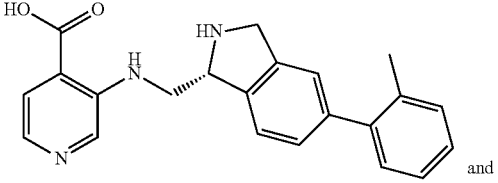 and  | 8A and 8B NMR (300 MHz, CD$_3$OD): δ 2.20 (3H, s), 4.00-4.06 (1H, m), 4.16-4.22 (1H, m), 4.64-4.81 (2H, m), 5.40-5.43 (1H, m), 7.14-7.39 (6H, m), 7.61 (1H, d, J = 7.8 Hz), 8.02 (1H, d, J = 5.4 Hz), 8.13 (1H, t, J = 5.4 Hz), 8.50 (s, 1H). [M + H] Calc'd for C$_{22}$H$_{21}$N$_3$O$_2$: 360; Found: 360. |
| 65A and 65B | (R)-3-(((5-((4-isopropylphenyl)(methyl)amino)isoindolin-1-yl)methyl)amino)isonicotinic acid; and (S)-3-(((5-((4-isopropylphenyl)(methyl)amino)isoindolin-1-yl)methyl) amino)isonicotinic acid 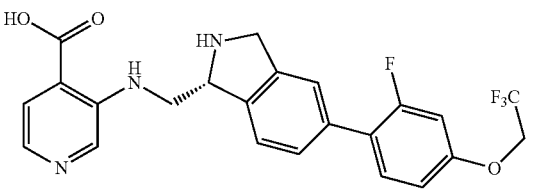 and 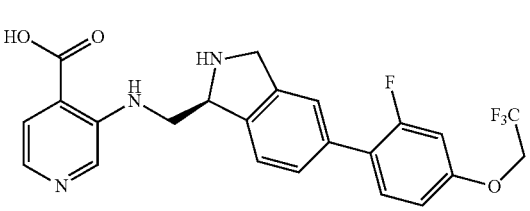 [SMILES: O=C(O)c1ccncc1NC[C@H]1NCc2cc(-c3ccc(OCC(F)(F)F)cc3F)ccc21] | 7A and 7B NMR (300 MHz, CD$_3$OD): δ 1.25 (6H, d, J = 6.6 Hz), 2.88-2.92 (1H, m), 3.26 (3H, s), 3.85-3.88 (1H, m), 4.00-4.02 (1H, m), 4.45-4.57 (2H, m), 5.17-5.20 (1H, m), 6.80-6.83 (2H, m), 7.05 (2H, d, J = 8.4 Hz), 7.22-7.30 (3H, m), 7.93-7.95 (2H, m), 8.33 (1H, s). [M + H] Calc'd for C$_{25}$H$_{28}$N$_4$O$_2$: 417; Found: 417. |
| 66A and 66B | (R)-3-(((5-(4-isopropyl-2-methylphenyl)isoindolin-1-yl)methyl)amino)isonicotinic acid; and (S)-3-(((5-(4-isopropyl-2-methylphenyl)isoindolin-1-yl)methyl)amino) isonicotinic acid 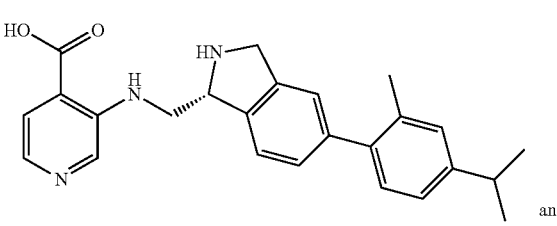 and 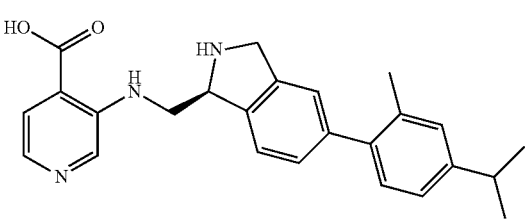 [SMILES: Cc1cc(C(C)C)ccc1-c1ccc2c(c1)CN[C@@H]2CNc1cnccc1C(=O)O] | 7A and 7B NMR (400 MHz, MeOD): δ 0.88 (6H, d, J = 9.2 Hz), 2.16 (3H, s), 2.87-2.91 (1H, m), 3.93-3.99 (1H, m), 4.13-4.16 (1H, m), 4.64-4.77 (2H, m), 5.35-5.36 (1H, m), 7.05-7.13 (3H, m), 7.34-7.36 (2H, m), 7.57-7.59 (1H, m), 7.91-7.95 (2H, m), 8.40 (1H, s). [M + H] Calc'd for C$_{25}$H$_{27}$N$_3$O$_2$: 402; Found: 402. |

TABLE 3-continued

| Example | Compound IUPAC name | Example preparation | H¹ NMR and MS |
|---|---|---|---|
| 67A and 67B | (R)-3-(((5-((4-cyclopropylphenyl)(methyl)amino)isoindolin-1-yl)methyl)amino)isonicotinic acid; and (S)-3-(((5-((4-cyclopropylphenyl)(methyl)amino)isoindolin-1-yl)methyl)amino)isonicotinic acid 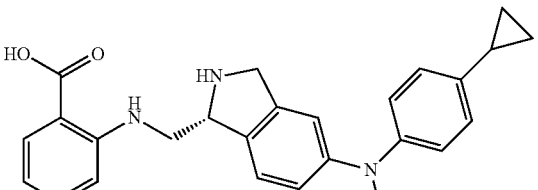 | 5A and 5B | NMR (400 MHz, MeOD): δ 0.63-0.67 (2H, m), 0.93-0.98 (2H, m), 1.88-1.92 (1H, m), 3.25 (3H, s), 3.81-3.86 (1H, m), 4.01-4.05 (1H, m), 4.46-4.60 (2H, m), 5.17-5.20 (1H, m), 6.78-6.82 (2H, m), 7.00 (2H, d, J = 8.4 Hz), 7.07 (2H, d, J = 8.8 Hz), 7.27 (1H, d, J = 8.0 Hz), 7.93 (2H, s), 8.32 (1H, s). [M + H] Calc'd for $C_{25}H_{26}N_4O_2$: 415; Found: 415. |
| 68A and 68B | (R)-3-(((5-((4-ethylphenyl)(methyl)amino)isoindolin-1-yl)methyl)amino)isonicotinic acid; and (S)-3-(((5-((4-ethylphenyl)(methyl)amino)isoindolin-1-yl)methyl) amino) isonicotinic acid 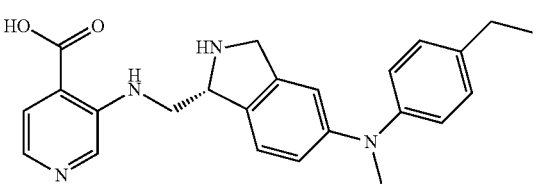 | 5A and 5B | NMR (400 MHz, MeOD): δ 1.24 (3H, t, J = 8.0 Hz), 2.63 (2H, q, J = 8.0 Hz), 3.26 (3H, s), 3.81-3.86 (1H, m), 4.00-4.05 (1H, m), 4.46-4.60 (2H, m), 5.17-5.19 (1H, m), 6.79-6.83 (2H, m), 7.03 (2H, d, J = 8.4 Hz), 7.21 (2H, d, J = 8.8 Hz), 7.28 (1H, d, J = 8.4 Hz), 7.89-7.94 (2H, m), 8.30 (1H, s). [M + H] Calc'd for $C_{25}H_{23}F_3N_2O_4$: 473; Found: 473. |
| 69A and 69B | (R)-3-(((5-(methyl(4-propylphenyl)amino)isoindolin-1-yl)methyl)amino)isonicotinic acid; and (S)-3-(((5-(methyl (4-propylphenyl)amino)isoindolin-1-yl)methyl)amino) isonicotinic acid 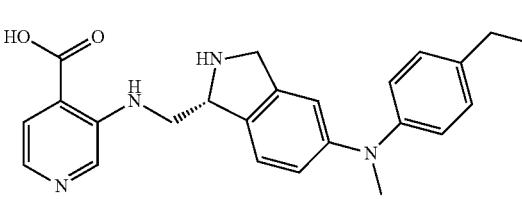 | 5A and 5B | NMR (400 MHz, MeOD): δ 0.95 (3H, t, J = 8.0 Hz), 1.61-1.67 (2H, m), 2.56-2.60 (2H, m), 3.26 (3H, s), 3.80-3.85 (1H, m), 4.00-4.05 (1H, m), 4.46-4.61 (2H, m), 5.16-5.19 (1H, m), 6.80-6.83 (2H, m), 7.03 (2H, d, J = 8.0 Hz), 7.19 (2H, d, J = 8.0 Hz), 7.28 (1H, d, J = 8.0 Hz), 7.86-7.92 (2H, m), 8.28 (1H, s). [M + H] Calc'd for $C_{25}H_{28}N_4O_2$: 417; Found: 417. |

TABLE 3-continued

| Example | Compound IUPAC name | Example preparation H¹ NMR and MS |
|---|---|---|
| 70A and 70B | (R)-3-(((5-(2-methyl-4-(pyrrolidin-1-yl)phenyl)iso-indolin-1-yl)methyl)amino)isonicotinic acid; and (S)-3-(((5-(2-methyl-4-(pyrrolidin-1-yl)phenyl)isoindolin-1-yl) methyl) amino)isonicotinic acid 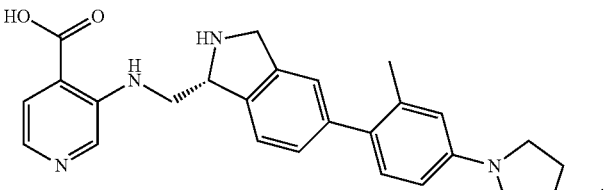 and 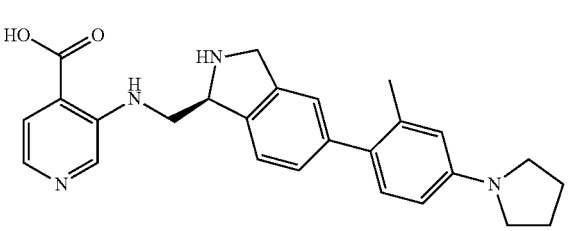 [SMILES: Cc1cc(N2CCCC2)ccc1-c1ccc2c(c1)CN[C@@H]2CNc1cnccc1C(=O)O] | 7A and 7B NMR (400 MHz, MeOD): δ 2.06-2.11 (4H, m), 2.21 (3H, s), 3.40-3.42 (4H, m), 3.98-4.03 (1H, m), 4.15-4.19 (1H, m), 4.64-4.78 (2H, m), 5.38-5.40 (1H, m), 6.70-6.73 (2H, m), 7.08 (1H, d, J = 8.0 Hz), 7.34-7.36 (2H, m), 7.56 (1H, d, J = 8.4 Hz), 8.02 (1H, s), 8.16-8.18 (1H,m), 8.50 (1H, s). [M + H] Calc'd for $C_{26}H_{28}N_4O_2$: 429; Found: 429. |
| 71A and 71B | (R)-3-(((5-(2-ethylphenyl)isoindolin-1-yl)methyl)amino) isonicotinic acid; and (S)-3-(((5-(2-ethylphenyl)iso-indolin-1-yl)methyl)amino)isonicotinic acid 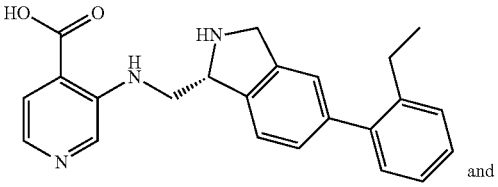 [SMILES: CCc1ccccc1-c1ccc2c(c1)CN[C@H]2CNc1cnccc1C(=O)O] and 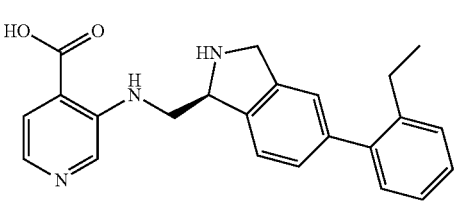 [SMILES: CCc1ccccc1-c1ccc2c(c1)CN[C@@H]2CNc1cnccc1C(=O)O] | 7A and 7B NMR (300 MHz, MeOD): δ 1.04 (3H, t, J = 7.5 Hz), 2.54 (2H, q, J = 7.5 Hz), 3.99-4.06 (1H, m), 4.15-4.22 (1H, m), 4.67-4.82 (2H, m), 5.40-5.43 (1H, m), 7.12 (1H, d, J = 7.5 Hz), 7.22-7.26 (1H, m), 7.32-7.38 (4H, m), 7.62 (1H, d, J = 7.8 Hz), 8.00-8.08 (2H, m), 8.47 (1H, s). [M + H] Calc'd for $C_{23}H_{23}N_3O_2$: 374; Found: 374. |
| 72A and 72B | (R)-3-(((5-(2-isopropylphenyl)isoindolin-1-yl)methyl) amino)isonicotinic acid; and (S)-3-(((5-(2-isopropyl phenyl)isoindolin-1-yl)methyl)amino)isonicotinic acid 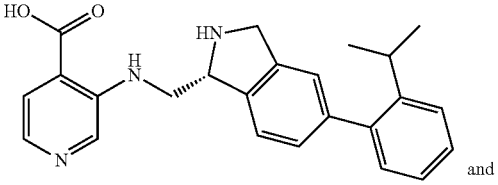 [SMILES: CC(C)c1ccccc1-c1ccc2c(c1)CN[C@H]2CNc1cnccc1C(=O)O] and 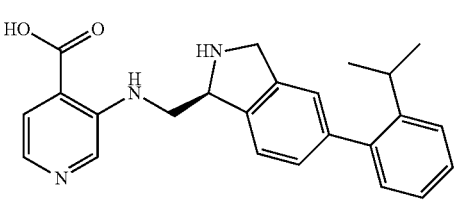 [SMILES: CC(C)c1ccccc1-c1ccc2c(c1)CN[C@@H]2CNc1cnccc1C(=O)O] | 7A and 7B NMR (400 MHz, MeOD): δ 1.12 (6H, d, J = 4.4 Hz), 2.86-5.89 (1H, m), 3.99-4.03 (1H, m), 4.13-4.17 (1H, m), 4.66-4.79 (2H, m), 5.36-5.39 (1H, m), 7.60 (1H, d, J = 8.0 Hz), 7.17-7.21 (1H, m), 7.31-7.41 (4H, m), 7.60 (1H, d, J = 7.6 Hz), 7.93-7.96 (2H, m), 8.40 (1H, s). [M + H] Calc'd $C_{24}H_{25}N_3O_2$: 388; Found: 388. |

TABLE 3-continued

| Example Compound IUPAC name | Example preparation | $H^1$ NMR and MS |
|---|---|---|
| 73A (R)-3-(((5-(2-cyclopropylphenyl)isoindolin-1-yl)methyl) and 73B amino)isonicotinic acid; and (S)-3-(((5-(2-cyclopropyl phenyl)isoindolin-1-yl)methyl)amino)isonicotinic acid | 7A and 7B | NMR (300 MHz, MeOD): δ 0.64-0.69 (2H, m), 0.77-0.84 (2H, m), 1.70-1.74 (1H, m), 3.99-4.06 (1H, m), 4.15-4.21 (1H, m), 4.67-4.82 (2H, m), 5.39-5.42 (1H, m), 7.00 (1H, d, J = 7.2 Hz), 7.14-7.31 (3H, m), 7.48-7.49 (2H, m), 7.61-7.64 (1H, m), 7.96-8.01 (2H, m), 8.43 (1H, s). [M + H] Calc'd for $C_{24}H_{23}N_3O_2$: 386; Found: 386 |

II. Biological Evaluation

Example 1A: In Vitro Enzyme Inhibition Assay for JMJD2C Activity

This assay determines the ability of a test compound to inhibit JMJD2C demethylase activity. Baculovirus expressed JMJD2C (GenBank Accession #BC143571, AA 2-372) was purchased from BPS Bioscience (Cat#50105).

JMJD2C Assay

The ability of test compounds to inhibit the activity of JMJD2C was determined in 384-well plate format under the following reaction conditions: 0.3 nM JMJD2C, 300 nM H3K9me3-biotin labeled peptide (Anaspec cat #64360), 2 μM alpha-ketoglutaric acid in assay buffer of 50 mM HEPES, pH7.3, 0.005% Brij35, 0.5 mM TCEP, 0.2 mg/ml BSA, 50 μM sodium L-ascorbate, and 2 μM ammonium iron(II) sulfate. Reaction product was determined quantitatively by TR-FRET after the addition of detection reagent Phycolink Streptavidin-allophycocyanin (Prozyme) and Europium-anti-di-methylated histone H3 lysine 9 (H3K9me2) antibody (PerkinElmer) in the presence of 5 mM EDTA in LANCE detection buffer (PerkinElmer) at a final concentration of 50 nM and 1 nM, respectively.

The assay reaction was initiated by the following: 2 μl of the mixture of 900 nM H3K9me3-biotin labeled peptide and 6 μM alpha-ketoglutaric acid with 2 μl of 11-point serial diluted inhibitor in 3% DMSO were added to each well of the plate, followed by the addition of 2 μl of 0.9 nM JMJD2C to initiate the reaction. The reaction mixture was incubated at RT for 30 min, and terminated by the addition of 6 μl of 5 mM EDTA in LANCE detection buffer containing 100 nM Phycolink Streptavidin-allophycocyanin and 2 nM Europium-anti-H3K9me2 antibody. Plates were read by EnVisionMultilabel Reader in TR-FRET mode (excitation at 320 nm, emission at 615 nm and 665 nm) after 1 hr incubation at RT. A ratio was calculated (665/615) for each well and fitted to determine inhibition constant ($IC_{50}$).

Example 1B: In Vitro Enzyme Inhibition Assay for JMJD3 Activity

This assay determines the ability of a test compound to inhibit JMJD3 demethylase activity. Baculovirus expressed JMJD3 (GenBank Accession #NM-001080424, AA1043-end) was purchased from BPS Bioscience (Cat#50115).

JMJD3 Assay

The enzymatic assay of JMJD3 activity is based upon Time Resolved-Fluorescence Resonance Energy Transfer (TR-FRET) detection. The ability of test compounds to inhibit the activity of JMJD3 was determined in 384-well plate format under the following reaction conditions: 5 nM JMJD3, 250 nM H3K27me3-biotin labeled peptide (Anaspec cat #64367), 0.4 to 2 μM α-ketoglutaric acid in assay buffer of 50 mM HEPES, pH7.3, 0.005% Brij35, 0.5 mM TCEP, 0.2 mg/ml BSA, 50 μM sodium L-ascorbate, and 5 μM ammonium iron(II) sulfate. Reaction product was determined quantitatively by TR-FRET after the addition of detection reagent Phycolink Streptavidin-allophycocyanin (Prozyme) and Europium-anti-H3K27me2 antibody (PerkinElmer) in the presence of 5 mM EDTA in LANCE detection buffer (PerkinElmer) at a final concentration of 50 nM and 1 nM, respectively.

The assay reaction was initiated by the following: 2 μM of the mixture of 750 nM H3K27me3-biotin labeled peptide and 1.2 to 6 μM alpha-ketoglutaric acid with 2 μL of 11-point serial diluted inhibitor in 3% DMSO were added to each well of plate, followed by the addition of 2 μl of 15 nM JMJD3 to initiate the reaction. The reaction mixture was incubated at RT for 30 min, and terminated by the addition of 6 μL of 5 mM EDTA in LANCE detection buffer containing 100 nM Phycolink Streptavidin-allophycocyanin and 2 nM Europium-anti-H3K27me2 antibody. Plates were read by EnVisionMultilabel Reader in TR-FRET mode (excitation at 320 nm, emission at 615 nm and 665 nm) after 1 hr incubation at RT. A ratio from the readout of 665/615 was calculated for each well and fitted to determine inhibition constant ($IC_{50}$).

Example 1C: In Vitro Enzyme Inhibition Assay for Jarid1B Activity

Jarid1B Assay

The ability of test compounds to inhibit the activity of Jarid1B was determined in 384-well plate format under the following reaction conditions: 0.8 nM Jarid1B, 300 nM H3K4me3-biotin labeled peptide (Anaspec cat #64357), 2 µM alpha-ketoglutaric acid in assay buffer of 50 mM HEPES, pH7.3, 0.005% Brij35, 0.5 mM TCEP, 0.2 mg/ml BSA, 50 µM sodium L-ascorbate, and 2 µM ammonium iron(II) sulfate. Reaction product was determined quantitatively by TR-FRET after the addition of detection reagent Phycolink Streptavidin-allophycocyanin (Prozyme) and Europium-anti-H3K4me or -H3K4me2 antibody (PerkinElmer) in the presence of 5 mM EDTA in LANCE detection buffer (PerkinElmer) at a final concentration of 25 nM and 1 nM, respectively.

The assay reaction was initiated by the following: 2 µl of the mixture of 900 nM H3K4me3-biotin labeled peptide and 6 µM alpha-ketoglutaric acid with 2 µl of 11-point serial diluted inhibitor in 3% DMSO was added to each well of the plate, followed by the addition of 2 µl of 2.4 nM Jarid1B to initiate the reaction. The reaction mixture was incubated at RT for 30 min, and terminated by the addition of 6 µl of 5 mM EDTA in LANCE detection buffer containing 50 nM Phycolink Streptavidin-allophycocyanin and 2 nM Europium-anti-H3K4me/H3K4me2 antibody. Plates were read by EnVisionMultilabel Reader in TR-FRET mode (excitation at 320 nm, emission at 615 nm and 665 nm) after 1 hr incubation at RT. A ratio was calculated (665/615) for each well and fitted to determine inhibition constant ($IC_{50}$).

The ability of the compounds disclosed herein to inhibit demethylase activity was quantified and the respective $IC_{50}$ value was determined. Tables 4 and 5 provide $IC_{50}$ values of various compounds disclosed herein ("Example" refers to the chemical synthesis example as above):

TABLE 4

| Example | Name | JMJD2C IC50 (nM) | JMJD3 IC50 (nM) | Jarid1b IC50 (nM) |
|---|---|---|---|---|
| 1A and 1B | 3-[({(1S)-6-[methyl(4-methylphenyl)amino]-1,2,3,4-tetrahydroisoquinolyl}methyl)amino]pyridine-4-carboxylic acid; and 3-[({(1R)-6-[methyl(4-methylphenyl)amino]-1,2,3,4-tetrahydroisoquinolyl}methyl)amino]pyridine-4-carboxylic acid | B/B* | B/B | A/A |
| 2A and 2B | 3-[({(1S)-6-[2-methyl-4-(2,2,2-trifluoroethoxy)phenyl]-1,2,3,4-tetrahydroisoquinolyl}methyl)amino]pyridine-4-carboxylic acid; and 3-[({(1R)-6-[2-methyl-4-(2,2,2-trifluoroethoxy)phenyl]-1,2,3,4-tetrahydroisoquinolyl}methyl)amino]pyridine-4-carboxylic acid | C/C | C/C | A/A |
| 3A and 3B | 3-{[((1S)-6-{methyl[4-(methylethyl)phenyl]amino}-1,2,3,4-tetrahydroisoquinolyl)methyl]amino}pyridine-4-carboxylic acid; and 3-{[((1R)-6-{methyl[4-(methylethyl)phenyl]amino}-1,2,3,4-tetrahydroisoquinolyl)methyl]amino}pyridine-4-carboxylic acid | B/B | C/B | A/A |
| 4A and 4B | 3-[({(1S)-6-[4-(cyclopropylmethoxy)-2-methylphenyl]-1,2,3,4-tetrahydroisoquinolyl}methyl)amino]pyridine-4-carboxylic acid; and 3-[({(1R)-6-[4-(cyclopropylmethoxy)-2-methylphenyl]-1,2,3,4-tetrahydroisoquinolyl}methyl)amino]pyridine-4-carboxylic acid | C/C | C/D | A/A |
| 5A and 5B | 3-[({(1S)-5-[methyl(4-methylphenyl)amino]isoindolinyl}methyl)amino]pyridine-4-carboxylic acid; and 3-[({(1R)-5-[methyl(4-methylphenyl)amino]isoindolinyl}methyl)amino]pyridine-4-carboxylic acid | C/B | B/B | A/A |
| 6A and 6B | 3-{[((1S)-5-{methyl[4-(methylethyl)phenyl]amino}isoindolinyl)methyl]amino}pyridine-4-carboxylic acid; and 3-{[((1R)-5-{methyl[4-(methylethyl)phenyl]amino}isoindolinyl)methyl]amino}pyridine-4-carboxylic acid | C/C | C/D | A/A |
| 7A and 7B | 3-[({(1S)-5-[2-methyl-4-(2,2,2-trifluoroethoxy)phenyl]isoindolinyl}methyl)amino]pyridine-4-carboxylic acid; and 3-[({(1R)-5-[2-methyl-4-(2,2,2-trifluoroethoxy)phenyl]isoindolinyl}methyl)amino]pyridine-4-carboxylic acid | C/C | B/C | A/A |

*Biochemical assay $IC_{50}$ data are designated within the following ranges: A: ≤100 nM; B: >100 nM to ≤1000 nM; C: >1000 nM to ≤10,000 nM; D: >10,000 nM

TABLE 5

| Example | Compound Name | JMJD2C $IC_{50}$ (nM) | JMJD3 $IC_{50}$ (nM) | Jarid1b $IC_{50}$ (nM) |
|---|---|---|---|---|
| 1A and 1B | 3-[({(1S)-6-[methyl(4-methylphenyl)amino]-1,2,3,4-tetra-hydroisoquinolyl}methyl)amino]pyridine-4-carboxylic acid; and 3-[({(1R)-6-[methyl(4-methylphenyl)amino]-1,2,3,4-tetrahydroisoquinolyl} methyl)amino] pyridine-4-carboxylic acid | B* | C | A |

TABLE 5-continued

| Example | Compound Name | JMJD2C IC$_{50}$ (nM) | JMJD3 IC$_{50}$ (nM) | Jarid1b IC$_{50}$ (nM) |
|---|---|---|---|---|
| 2A and 2B | 3-[({(1S)-6-[2-methyl-4-(2,2,2-trifluoroethoxy)phenyl]-1,2,3,4-tetrahydroisoquinolyl}methyl)amino]pyridine-4-carboxylic acid; and 3-[({(1R)-6-[2-methyl-4-(2,2,2-trifluoroethoxy)phenyl]-1,2,3,4-tetrahydroisoquinolyl}methyl)amino]pyridine-4-carboxylic acid | C | C | A |
| 3A and 3B | 3-{[((1S)-6-{methyl[4-(methylethyl)phenyl]amino}-1,2,3,4-tetrahydroisoquinolyl)methyl]amino}pyridine-4-carboxylic acid; and 3-{[((1R)-6-{methyl[4-(methylethyl)phenyl]amino}-1,2,3,4-tetrahydroisoquinolyl)methyl]amino}pyridine-4-carboxylic acid | B | B | A |
| 4A and 4B | 3-[({(1S)-6-[4-(cyclopropylmethoxy)-2-methylphenyl]-1,2,3,4-tetrahydroisoquinolyl}methyl)amino]pyridine-4-carboxylic acid; and 3-[({(1R)-6-[4-(cyclopropylmethoxy)-2-methylphenyl]-1,2,3,4-tetrahydroisoquinolyl}methyl) amino]pyridine-4-carboxylic acid | B | D | A |
| 5A and 5B | 3-[({(1S)-5-[methyl(4-methylphenyl)amino]isoindolinyl}methyl)amino]pyridine-4-carboxylic acid; and 3-[({(1R)-5-[methyl(4-methylphenyl)amino]isoindolinyl} methyl)amino]pyridine-4-carboxylic acid | C | C | A |
| 6A and 6B | 3-{[((1S)-5-{methyl[4-(methylethyl)phenyl]amino} isoindolinyl)methyl]amino}pyridine-4-carboxylic acid; and 3-{[((1R)-5-{methyl[4-(methylethyl)phenyl]amino} isoindolinyl)methyl]amino}pyridine-4-carboxylic acid | C | C | A |
| 7A and 7B | 3-[({(1S)-5-[2-methyl-4-(2,2,2-trifluoroethoxy)phenyl] isoindolinyl}methyl)amino]pyridine-4-carboxylic acid; and 3-[({(1R)-5-[2-methyl-4-(2,2,2-trifluoroethoxy) phenyl] isoindolinyl}methyl)amino]pyridine-4-carboxylic acid | C | C | A |
| 8A and 8B | (R)-3-(((6-(o-tolyl)-1,2,3,4-tetrahydroisoquinolin-1-yl) methyl)amino)isonicotinic acid; and (S)-3-(((6-(o-tolyl)-1,2,3,4-tetrahydroisoquinolin-1-yl)methyl)amino) isonicotinic acid | C | C | A |
| 9A and 9B | (R)-3-(((6-(2-ethylphenyl)-1,2,3,4-tetrahydroisoquinolin-1-yl)methyl)amino)isonicotinic acid; and (S)-3-(((6-(2-ethylphenyl)-1,2,3,4-tetrahydroisoquinolin-1-yl) methyl)amino) isonicotinic acid | C | C | A |
| 10A and 10B | (R)-3-(((6-((4-ethylphenyl)(methyl)amino)-1,2,3,4-tetrahydroisoquinolin-1-yl)methyl)amino)isonicotinic acid; and (S)-3-(((6-((4-ethylphenyl)(methyl)amino)-1,2,3,4-tetra-hydroisoquinolin-1-yl)methyl)amino) isonicotinic acid. | C | C | A |
| 11A and 11B | (R)-3-(((2-methyl-6-(methyl(p-tolyl)amino)-1,2,3,4-tetra-hydroisoquinolin-1-yl)methyl)amino)isonicotinic acid; and (S)-3-(((2-methyl-6-(methyl(p-tolyl)amino)-1,2,3,4-tetra-hydroisoquinolin-1-yl)methyl)amino) isonicotinic acid | B | C | A |
| 12A and 12B | (R)-3-(((2-methyl-6-(o-tolyl)-1,2,3,4-tetrahydroisoquinolin-1-yl)methyl)amino)isonicotinic acid; and (S)-3-(((2-methyl-6-(o-tolyl)-1,2,3,4-tetrahydroisoquinolin-1-yl)methyl)amino)isonicotinic acid | C | C | A |
| 13A and 13B | (R)-3-(((6-((4-ethylphenyl)(methyl)amino)-2-methyl-1,2,3,4-tetrahydroisoquinolin-1-yl) methyl)amino)isonico-tinic acid; and (S)-3-(((6-((4-ethylphenyl)(methyl)amino)-2-methyl-1,2,3,4-tetrahydroisoquinolin-1-yl) methyl)amino)isonicotinic acid | B | C | A |
| 14A and 14B | (R)-3-(((2-methyl-6-(methyl(4-propylphenyl)amino)-1,2,3,4-tetrahydroisoquinolin-1-yl)methyl)amino) isonicotinic acid; and (S)-3-(((2-methyl-6-(methyl(4-propylphenyl)amino)-1,2,3,4-tetrahydroisoquinolin-1-yl) methyl)amino)isonicotinic acid | C | C | A |
| 15A and 15B | (R)-3-(((6-(2-ethylphenyl)-2-methyl-1,2,3,4-tetrahydro-isoquinolin-1-yl)methyl)amino)isonicotinic acid; and (S)-3-(((6-(2-ethylphenyl)-2-methyl-1,2,3,4-tetrahydro-isoquinolin-1-yl)methyl)amino) isonicotinic acid | B | C | A |
| 16A and 16B | (R)-3-(((6-(2-isopropylphenyl)-2-methyl-1,2,3,4-tetra-hydroisoquinolin-1-yl)methyl)amino)isonicotinic acid; and (S)-3-(((6-(2-isopropylphenyl)-2-methyl-1,2,3,4-tetrahydroisoquinolin-1-yl)methyl)amino) isonicotinic acid | C | — | A |
| 17A and 17B | (R)-3-(((6-(2,6-dimethylphenyl)-2-methyl-1,2,3,4-tetra-hydroisoquinolin-1-yl)methyl)amino)isonicotinic acid; and (S)-3-(((6-(2,6-dimethylphenyl)-2-methyl-1,2,3,4-tetra-hydroisoquinolin-1-yl)methyl)amino) isonicotinic acid | C | — | A |

TABLE 5-continued

| Example | Compound Name | JMJD2C IC$_{50}$ (nM) | JMJD3 IC$_{50}$ (nM) | Jarid1b IC$_{50}$ (nM) |
|---|---|---|---|---|
| 18A and 18B | (R)-3-(((2-methyl-5-(methyl(p-tolyl)amino)iso-indolin-1-yl)methyl)amino)isonicotinic acid; and (S)-3-(((2-methyl-5-(methyl(p-tolyl)amino)isoindolin-1-yl)methyl)amino)isonicotinic acid | B | C | A |
| 19A and 19B | (R)-3-(((5-((4-ethylphenyl)(methyl)amino)-2-methyl-isoindolin-1-yl)methyl)amino)isonicotinic acid; and (S)-3-(((5-((4-ethylphenyl)(methyl)amino)-2-methylisoindolin-1-yl)methyl)amino)isonicotinic acid | B | C | A |
| 20A and 20B | (R)-3-(((2-methyl-5-(methyl(4-propylphenyl)amino)iso-indolin-1-yl)methyl)amino)isonicotinic acid; and (S)-3-(((2-methyl-5-(methyl(4-propylphenyl)amino)isoindolin-1-yl)methyl)amino)isonicotinic acid | B | C | A |
| 21A and 21B | (R)-3-(((2-methyl-5-(o-tolyl)isoindolin-1-yl)methyl) amino) isonicotinic acid; and (S)-3-(((2-methyl-5-(o-tolyl)iso-indolin-1-yl)methyl)amino) isonicotinic acid | B | C | A |
| 22A and 22B | (R)-3-(((5-(2-ethylphenyl)-2-methylisoindolin-1-yl) methyl)amino)isonicotinic acid; and (S)-3-(((5-(2-ethylphenyl)-2-methylisoindolin-1-yl) methyl)amino) isonicotinic acid | B | C | A |

*Biochemical assay IC$_{50}$ data are designated within the following ranges: A: ≤100 nM; B: >100 nM to ≤1000 nM; C: >1000 nM to ≤10,000 nM; D: >10,000 nM.

Example 2: In Vitro Cell-Based Assay

The Jurkat (T-ALL) cell line proliferation assay (Cell-MTS Assay) is a colorimetric cellular assay to assess the ability of KDM small molecule inhibitors to effect the proliferation of the established human acute T cell leukemia cancer cell line Jurkat.

This Cell-MTS assay is a 7-day plate-based colorimetric assay which quantifies the amount of newly generated NADH in the presence and absence of test compound. These NADH levels are used as a proxy for the quantification of cancer cell proliferation.

Assay Method

The established cancer cell line Jurkat with a verified p53 mutation were purchased from *American Type Culture Collection* (ATCC) and routinely passaged according to ATCC published protocols. For routine assay these cells were seeded at a density of 10,000 cells per 96-well. 24 hr after plating, cells received an 11-point dilution of test compound with final concentration ranges from 10 μM to 0.15 nM. Cells were incubated in the presence of compound for 168 hr at 37° C., 5% CO$_2$. At the end of this compound incubation period, 80 μl of media is removed and 20 μL of CellTiter 96® AQueous Non-Radioactive Cell Proliferation Assay solution (Promega) is added. The cells were incubated until the OD$_{490}$ reached >0.6. IC$_{50}$ values are calculated using the IDBS XLfit software package and include background subtracted OD490 values and normalization to DMSO controls. Cellular proliferation IC$_{50}$ values are uploaded and archived using the Chem Biography Platform.

Table 6 provides the cellular IC$_{50}$ values of various compounds disclosed herein:

TABLE 6

| Example | Cellular IC50 (μM) |
|---|---|
| 1A and 1B | A/ND |
| 2A and 2B | B/B |
| 3A and 3B | A/ND |
| 4A and 4B | ND/ND |
| 5A and 5B | ND/ND |

TABLE 6-continued

| Example | Cellular IC50 (μM) |
|---|---|
| 6A and 6B | ND/ND |
| 7A and 7B | ND/ND |

*Biochemical assay IC50 data are designated within the following ranges: A: ≤0.10 μM; B: >0.10 μM to ≤1.0 μM; C: >1.0 μM to ≤10 μM; D: >10 μM; ND: not determined Table 7 provides IC$_{50}$ values of various compounds disclosed herein, tested in cellular human esophageal squamous cell carcinoma KYSE-150 cells:

TABLE 7

| Example | Cellular IC$_{50}$ (μM) |
|---|---|
| 1A and 1B | C |
| 2A and 2B | D |
| 3A and 3B | A |
| 4A and 4B | B |
| 5A and 5B | C |
| 6A and 6B | B |
| 7A and 7B | B |
| 8A and 8B | B |
| 9A and 9B | B |
| 10A and 10B | B |
| 11A and 11B | A |
| 12A and 12B | A |
| 13A and 13B | A |
| 14A and 14B | A |
| 15A and 15B | — |
| 16A and 16B | — |
| 17A and 17B | — |
| 18A and 18B | A |
| 19A and 19B | A |
| 20A and 20B | A |
| 21A and 21B | A |
| 22A and 22B | A |

Cellular assay IC$_{50}$ data are designated within the following ranges: A: ≤0.10 μM; B: >0.10 μM to ≤1.0 μM; C: >1.0 μM to ≤10 μM; D: >10 μM.

Example 3: In Vivo Xenograph Study

Time release pellets containing 0.72 mg 1743 Estradiol are subcutaneously implanted into nu/nu mice. MCF-7 cells are grown in RPMI containing 10% FBS at 5% CO$_2$, 37° C. Cells are spun down and re-suspended in 50% serum free RPMI and 50% Matrigel at 1×10$^7$ cells/mL. MCF-7 cells are subcutaneously injected (100 μL/animal) on the right flank 2-3 days post pellet implantation and tumor volume (length× width$^2$/2) is monitored bi-weekly. When tumors reach an average volume of ~200 mm³ animals are randomized and treatment is started. Animals are treated with vehicle or test compound daily for 4 weeks. Tumor volume and body weight are monitored bi-weekly throughout the study. At the conclusion of the treatment period, plasma and tumor samples are taken for pharmacokinetic and pharmacodynamic analyses, respectively.

III. Preparation of Pharmaceutical Dosage Forms

Example 1: Oral Tablet

A tablet is prepared by mixing 48% by weigh of at least one compound of Formula 1, Formula 2, Formula 3 or Formula 4; 45% by weight of microcrystalline cellulose; 5% by weight of low-substituted hydroxypropyl cellulose; and 2% by weight of magnesium stearate. Tablets are prepared by direct compression. The total weight of the compressed tablets is maintained at 250-500 mg.

We claim:

1. A compound having the structure of Formula 1:

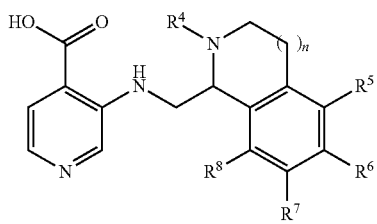

Formula 1 wherein a compound of Formula 1 includes isomers and pharmaceutically acceptable salts thereof, and wherein:

n is 0 or 1;

$R^4$ is hydrogen or optionally substituted $C_1$-$C_6$ alkyl;

$R^6$ is hydrogen or X—Y, wherein

X is a bond, O, S, N(R), C(O), N(R)C(O), C(O)N(R), or optionally substituted $C_1$-$C_3$ alkyl, wherein R is hydrogen or optionally substituted $C_1$-$C_6$ alkyl, and Y is optionally substituted alkyl, cycloalkyl, heterocyclyl, aryl, or heteroaryl; and $R^5$, $R^7$, and $R^8$ are each independently selected from hydrogen, halogen, hydroxyl, cyanyl, N($R^1$)($R^2$), or optionally substituted $C_1$-$C_6$ alkyl, $C_1$-$C_6$ alkynyl, $C_1$-$C_6$ alkenyl, $C_1$-$C_6$ alkoxy, $C_3$-$C_7$ carbocyclyl, $C_3$-$C_7$ carbocyclyloxy, $C_4$-$C_{12}$ carbocyclylalkyl, $C_4$-$C_{12}$ carbocyclylalkoxy, $C_6$-$C_{10}$ aryl, $C_6$-$C_{10}$ aryloxy, $C_6$-$C_{10}$ aryl-S, $C_6$-$C_{10}$ aryl-SO$_2$, $C_7$-$C_{14}$ aralkoxy, heteroaryl, heteroaryloxy, heterocyclyl, heterocyclyloxy, heterocyclylalkyl, heterocyclylalkoxy or heteroaryl-S, wherein $R^1$ is hydrogen or optionally substituted $C_1$-$C_6$ alkyl, and $R^2$ is optionally substituted alkyl, aryl, heteroaryl, heterocyclyl, cycloalkyl, cycloalkylalkyl, aryl-CO, heteroaryl-CO, cycloalkyl-CO, or alkyl-CO.

2. The compound of claim 1, wherein n is 0 or 1, and $R^4$ is methyl.

3. A pharmaceutical composition comprising the compound of claim 1.

4. A compound of Formula 2:

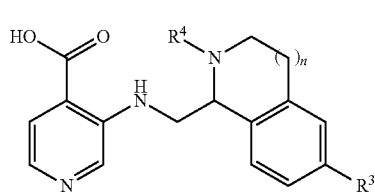

Formula 2 wherein a compound of Formula 2 includes isomers and pharmaceutically acceptable salts thereof, and wherein:

n is 0 or 1;

$R^4$ is hydrogen or optionally substituted $C_1$-$C_6$ alkyl; and $R^3$ is N(R)($R^9$), N(R)C(O), C(O)N(R), or optionally substituted $C_3$-$C_7$ carbocyclyl, $C_3$-$C_7$ carbocyclyloxy, $C_4$-$C_{12}$ carbocyclylalkyl, $C_4$-$C_{12}$ carbocyclylalkoxy, $C_6$-$C_{10}$ aryl, $C_6$-$C_{10}$ aryloxy, $C_6$-$C_{10}$ aryl-S, $C_6$-$C_{10}$ aryl-SO$_2$, $C_7$-$C_{14}$ aralkoxy, $C_1$-$C_6$ alkoxy, heteroaryl, heteroaryloxy, heterocyclyl, heterocyclyloxy, heterocyclylalkyl, heterocyclylalkoxy or heteroaryl-S, wherein R is hydrogen or optionally substituted $C_1$-$C_6$ alkyl, and $R^9$ is optionally substituted $C_3$-$C_7$ carbocyclyl, $C_3$-$C_7$ carbocyclyloxy, $C_1$-$C_6$ alkoxy, $C_4$-$C_{12}$ carbocyclylalkyl, $C_4$-$C_{12}$ carbocyclylalkoxy, $C_6$-$C_{10}$ aryl, $C_6$-$C_{10}$ aryloxy, $C_6$-$C_{10}$ aryl-S, $C_6$-$C_{10}$ aryl-SO$_2$, $C_7$-$C_{14}$ aralkoxy, heteroaryl, heteroaryloxy, heterocyclyl, heterocyclyloxy, heterocyclylalkyl, heterocyclylalkoxy or heteroaryl-S.

5. The compound of claim 4, wherein n is 0 or 1.

6. The compound of claim 4, wherein $R^4$ is hydrogen or methyl.

7. The compound of claim 4, wherein $R^3$ is N(R)($R^9$), and wherein R is methyl.

8. The compound of claim 7, wherein $R^9$ is optionally substituted $C_6$-$C_{10}$ aryl selected from optionally substituted halophenyl, alkylphenyl, haloalkylphenyl, halo(alkyloxy)phenyl, or haloalkyloxyphenyl.

9. The compound of claim 7, wherein $R^9$ is optionally substituted chlorophenyl, difluorophenyl, chlorofluorophenyl, (trifluoroethyl)phenyl, (trifluoropropyl)-phenyl, methylphenyl (tolyl), dimethylphenyl, ethylphenyl, propylphenyl, butylphenyl, pentylphenyl, hexylphenyl, (cyclopropylethyl)phenyl, cyclopropylphenyl, cyclobutylphenyl, cyclopentylphenyl, cyclohexylphenyl, (cyclobutylmethyl)phenyl, propoxyphenyl, (propylmethoxy)phenyl, (trifluoroethoxy)phenyl, (trifluoroethoxy)fluorophenyl, (trifluoroethoxy)dimethylphenyl, (propoxy)methylphenyl, (difluoromethoxy)methylphenyl, (quinolinyl)methylphenyl, (dihydroquinolinyl)methylphenyl, indolinylphenyl, dimethylaminophenyl, pyranylphenyl, methyldihydrobenzofuranyl, (indolinyl)methylphenyl, (pyrrolidinyl)methylphenyl, or thiole.

10. The compound of claim 4, wherein $R^3$ is optionally substituted $C_6$-$C_{10}$ aryl, selected from optionally substituted flurophenyl, methylphenyl, ethylphenyl, propylphenyl, butylphenyl, cycloalkoxyphenyl, cycloalkoxymethylphenyl, or (cyclopropylmethoxy)methylphenyl.

11. The compound of claim 4, wherein $R^3$ is optionally substituted $C_6$-$C_{10}$ aryl-S, heterocyclyl, heteroaryl, or $C_4$-$C_{12}$ carbocyclylalkoxy.

12. The compound of claim 4, wherein $R^3$ is optionally substituted chlorophenyl, fluorophenyl, difluorophenyl, chlorofluorophenyl, (trifluoroethyl)phenyl, (trifluoropropyl)phenyl, methylphenyl ("tolyl"), dimethylphenyl, ethylphenyl, propylphenyl, butylphenyl, pentylphenyl, hexylphenyl, cyclopropylphenyl, cyclobutylphenyl, cyclopentylphenyl, cyclohexylphenyl, (cyclopropylethyl)phenyl, (cyclobutylmethyl)phenyl, methoxyphenyl, ethoxyphenyl, propoxyphenyl, (cyclopropylmethoxy)phenyl, (trifluoroethoxy)phenyl, (methoxy)fluorophenyl, (trifluoroethoxy)fluorophenyl, (trifluoroethoxy)methylphenyl, (trifluoroethoxy)dimethylphenyl, (difluoromethoxy)methylphenyl, (propoxy)methylphenyl, (quinolinyl)methylphenyl, (dihydroquinolinyl)methylphenyl, (dihydroisoquinolinyl)methylphenyl, indolinylphenyl, dimethylaminophenyl, pyranylphenyl, methyldihydrobenzofuranyl, (indolinyl)methylphenyl, (pyrrolidinyl)methylphenyl, or thiole.

13. A pharmaceutical composition comprising at least one pharmaceutically acceptable excipient and a compound of claim 4.

14. A compound having the structure of Formula 3:

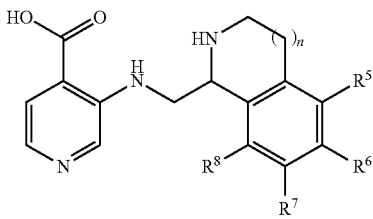

Formula 3 wherein the compound of Formula 3 includes isomers and pharmaceutically acceptable salts thereof, and wherein:

n is 0 or 1;

$R^6$ is X—Y, wherein
- X is a bond, O, S, N(R), C(O), N(R)C(O), C(O)N(R), or optionally substituted $C_1$-$C_3$ alkyl, wherein R is hydrogen or optionally substituted $C_1$-$C_6$ alkyl, and
- Y is optionally substituted $C_1$-$C_6$ alkyl, cycloalkyl, $C_3$-$C_7$ carbocyclyl, $C_1$-$C_6$ alkoxy, $C_3$-$C_7$ carbocyclyloxy, $C_4$-$C_{12}$ carbocyclylalkyl, $C_4$-$C_{12}$ carbocyclylalkoxy, $C_6$-$C_{10}$ aryl, $C_6$-$C_{10}$ aryloxy, $C_6$-$C_{10}$ aryl-S, $C_6$-$C_{10}$ aryl-SO$_2$, $C_7$-$C_{14}$ aralkoxy, heteroaryl, heteroaryloxy, heterocyclyl, heterocyclyloxy, heterocyclylalkyl, heterocyclylalkoxy or heteroaryl-S; and $R^5$, $R^7$, and $R^8$ are each independently selected from hydrogen, halogen, hydroxyl, cyanyl, or N($R^1$)($R^2$), or optionally substituted $C_1$-$C_6$ alkyl, $C_1$-$C_6$ alkynyl, $C_1$-$C_6$ alkenyl, $C_1$-$C_6$ alkoxy, $C_3$-$C_7$ carbocyclyl, $C_3$-$C_7$ carbocyclyloxy, $C_4$-$C_{12}$ carbocyclylalkyl, $C_4$-$C_{12}$ carbocyclylalkoxy, $C_6$-$C_{10}$ aryl, $C_6$-$C_{10}$ aryloxy, $C_6$-$C_{10}$ aryl-S, $C_6$-$C_{10}$ aryl-SO$_2$, $C_7$-$C_{14}$ aralkoxy, heteroaryl, heteroaryloxy, heterocyclyl, heterocyclyloxy, heterocyclylalkyl, heterocyclylalkoxy, or heteroaryl-S, in which
$R^1$ is hydrogen or optionally substituted $C_1$-$C_6$ alkyl, and
$R^2$ is optionally substituted alkyl, aryl, heteroaryl, heterocyclyl, cycloalkyl, cycloalkylalkyl, aryl-CO, heteroaryl-CO, cycloalkyl-CO, or alkyl-CO.

15. A pharmaceutical composition comprising at least one pharmaceutically acceptable excipient and the compound of claim 14.

16. A compound of Formula 4:

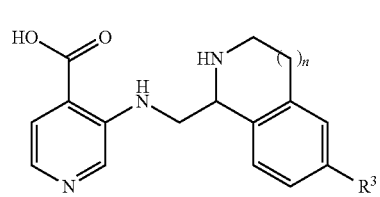

Formula 4 wherein a compound of Formula 4 includes isomers and pharmaceutically acceptable salts thereof, and wherein:

n is 0 or 1; and $R^3$ is N(R)($R^9$), N(R)C(O), C(O)N(R), or optionally substituted $C_3$-$C_7$ carbocyclyl, $C_3$-$C_7$ carbocyclyloxy, $C_4$-$C_{12}$ carbocyclylalkyl, $C_4$-$C_{12}$ carbocyclylalkoxy, $C_6$-$C_{10}$ aryl, $C_6$-$C_{10}$ aryloxy, $C_6$-$C_{10}$ aryl-S, $C_6$-$C_{10}$ aryl-SO$_2$, $C_7$-$C_{14}$ aralkoxy, heteroaryl, heteroaryloxy, heterocyclyl, heterocyclyloxy, heterocyclylalkyl, heterocyclylalkoxy, or heteroaryl-S, wherein
R is hydrogen or optionally substituted $C_1$-$C_6$ alkyl, and
$R^9$ is optionally substituted $C_3$-$C_7$ carbocyclyl, $C_3$-$C_7$ carbocyclyloxy, $C_4$-$C_{12}$ carbocyclylalkyl, $C_4$-$C_{12}$ carbocyclylalkoxy, $C_6$-$C_{10}$ aryl, $C_6$-$C_{10}$ aryloxy, $C_6$-$C_{10}$ aryl-S, $C_7$-$C_{14}$ aralkoxy, heteroaryl, heteroaryloxy, heterocyclyl, heterocyclyloxy, heterocyclylalkyl, heterocyclylalkoxy, $C_6$-$C_{10}$ aryl-SO$_2$, or heteroaryl-S.

17. A pharmaceutical composition comprising at least one pharmaceutically acceptable excipient and the compound of claim 16.

* * * * *